United States Patent
Ni et al.

(10) Patent No.: US 7,078,186 B2
(45) Date of Patent: Jul. 18, 2006

(54) APOPTOSIS RELATED POLYNUCLEOTIDES, POLYPEPTIDES, AND ANTIBODIES

(75) Inventors: Jian Ni, Germantown, MD (US); Paul E. Young, Gaithersburg, MD (US); Steven M. Ruben, Olney, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 741 days.

(21) Appl. No.: 10/013,477

(22) Filed: Dec. 13, 2001

(65) Prior Publication Data

US 2003/0049732 A1 Mar. 13, 2003

Related U.S. Application Data

(63) Continuation of application No. 09/669,445, filed on Sep. 25, 2000, now abandoned, which is a continuation-in-part of application No. PCT/US00/06642, filed on Mar. 15, 2000.

(60) Provisional application No. 60/126,018, filed on Mar. 24, 1999, provisional application No. 60/139,638, filed on Jun. 17, 1999, provisional application No. 60/149,449, filed on Aug. 18, 1999.

(51) Int. Cl.
*C12P 21/06* (2006.01)
(52) U.S. Cl. ............... 435/69.1; 435/70.1; 435/320.1; 435/325; 435/252.3; 536/23.1; 536/23.4; 536/23.5
(58) Field of Classification Search ............... 536/23.1, 536/23.5, 23.4; 435/69.1, 252.3, 320.1, 325, 435/70.1
See application file for complete search history.

(56) References Cited

U.S. PATENT DOCUMENTS

| | | | |
|---|---|---|---|
| 6,569,662 B1 | 5/2003 | Tang et al. | |
| 2003/0049702 A1 | 3/2003 | Reed et al. | |
| 2003/0064072 A9 | 4/2003 | Rosen et al. | |
| 2003/0109690 A1 | 6/2003 | Ruben | |
| 2003/0165933 A1 | 9/2003 | Tang et al. | |

FOREIGN PATENT DOCUMENTS

| | | |
|---|---|---|
| EP | 1 201 754 | 5/2002 |
| WO | WO-01/04300 | 1/2001 |
| WO | WO-03/054195 | 7/2003 |

OTHER PUBLICATIONS

Miller (1995, FASEB J., vol. 9, pp. 190-199)*
Deonarain (1998, Expert Opin. Ther. Pat., vol. 8, pp. 53-69).*
Verma (Sep. 1997, Nature, vol. 389, pp. 239-242).*
Crystal (1995, Science, vol. 270, pp. 404-410).*
Alcivar et al., "DEDD and DEDD2 associate with caspase-8/10 and signal cell death," *Oncogene*, 22(2):291-297 (Jan. 16, 2003).
Barnhart et al., "The death effector domain protein family," *Oncogene*, 22(53):8634-8644 (Nov. 24, 2003).
GenBank Accession No. NP_579874, Alcivar et al., "death effector domain-containing DNA binding protein 2 [*Homo sapiens*]" (Oct. 27, 2004).
GenBank Accession No. NM_133328, Lee et al., "*Homo sapiens* death effector domain containing 2 (DEDD2), mRNA" (Oct. 27, 2004).
Geneseq Accession No. ADC79259, Suzu et al., "Human DEDD2 encoding cDNA SEQ ID No.:1" (Jan. 1, 2004).
Hill et al., "Recognition of ERK MAP kinase by PEA-15 reveals a common docking site within the death domain and death effector domain," *EMBO Journal*, 21(23):6494-6504 (2002).
Lee et al., "DEDD regulates degradation of intermediate filaments during apoptosis," *J. Cell Biol.*, 158(6):1051-1066 (Sep. 16, 2002).
Roth et al., "Identification and Characterization of DEDD2, a Death Effector Domain-containing Protein," *J. Biol. Chem.*, 277(9):7501-7508 (Mar. 1, 2002).
Stegh et al., "DEDD, a novel death effector domain-containing protein, targeted to the nucleolus," *EMBO Journal*, 17(20):5974-5986 (Oct. 15, 1998).
Supplementary Partial European Search Report, Application No. EP 00 913925, mailed Oct. 29, 2004.
Zhan et al., "Death effector domain-containing proteins DEDD and FLAME-3 form nuclear complexes with the TFIIIC102 subunit of human transcription factor IIIC," *Cell Death Differ.*, 9(4):439-447 (Apr. 2002).

* cited by examiner

Primary Examiner—Susan Ungar
Assistant Examiner—Minh-Tam Davis
(74) *Attorney, Agent, or Firm*—Human Genome Sciences, Inc.

(57) ABSTRACT

The present invention relates to novel human apoptosis related polypeptides and isolated nucleic acids containing the coding regions of the genes encoding such polypeptides. Also provided are vectors, host cells, antibodies, and recombinant methods for producing human apoptosis related polypeptides. The invention further relates to diagnostic and therapeutic methods useful for diagnosing and treating disorders related to these novel human apoptosis related polypeptides.

20 Claims, No Drawings

SEQUENCE LISTING

```
<160> NUMBER OF SEQ ID NOS: 27

<210> SEQ ID NO 1
<211> LENGTH: 733
<212> TYPE: DNA
<213> ORGANISM: Homo sapiens

<400> SEQUENCE: 1
gggatccgga gcccaaatct tctgacaaaa ctcacacatg cccaccgtgc ccagcacctg        60
aattcgaggg tgcaccgtca gtcttcctct tccccccaaa acccaaggac accctcatga       120
```

```
tctcccggac tcctgaggtc acatgcgtgg tggtggacgt aagccacgaa gaccctgagg      180
tcaagttcaa ctggtacgtg gacggcgtgg aggtgcataa tgccaagaca aagccgcggg      240
aggagcagta caacagcacg taccgtgtgg tcagcgtcct caccgtcctg caccaggact      300
ggctgaatgg caaggagtac aagtgcaagg tctccaacaa agccctccca acccccatcg      360
agaaaaccat ctccaaagcc aaagggcagc ccgagaacca caggtgtac accctgcccc       420 catcccggga tgagctgacc aagaaccagg tcagcctgac ctgcctggtc aaaggcttct      480
atccaagcga catcgccgtg gagtgggaga gcaatgggca gccggagaac aactacaaga      540
ccacgcctcc cgtgctggac tccgacggct ccttcttcct ctacagcaag ctcaccgtgg      600
acaagagcag gtggcagcag gggaacgtct tctcatgctc cgtgatgcat gaggctctgc      660
acaaccacta cacgcagaag agcctctccc tgtctccggg taaatgagtg cgacggccgc      720
gactctagag gat                                                        733
```

<210> SEQ ID NO 2
<211> LENGTH: 2045
<212> TYPE: DNA
<213> ORGANISM: Homo sapiens
<400> SEQUENCE: 2

```
cccgggtcga cccacgcgtc cggaaagatc caaaacaagt ggctgcggcc gtcgcccagg       60
agtcatcgga cgccagaatc tggccgggtt ctgagcttgt tccgcctccc tcccccggga      120
atggcgctat ccgggtcgac cccggccccg tgctggaggg aggatgagtg cctggactac      180
tacgggatgc tgtcgcttca ccgtatgttc gaggtggtgg gcgggcaact gaccgagtgc      240
gagctggagc tcctggcctt tctgctggat gaggctcctg cgccgccgg aggcttagcc       300 cgggcccgca gcggcctaga gctcctgctg gagctggagc gccgcgggca gtgcgacgag      360
agcaacctgc ggctgctggg gcaactcctg cgcgtgctgg cccgccacga cctgctgccg      420
cacctggcgc gcaagcggcg ccggccagtg tctccagaac gctatagcta tggcacctcc      480
agctcttcaa agaggacaga gggtagctgc cgtcgccgtc ggcagtcaag cagttctgca      540
aattctcagc agggtcagtg ggagacaggc tccccccaa ccaagcggca gcggcggagt       600
cggggccggc ccagtggtgg tgccagacgc cggcggagag gggccccagc cgcaccccag      660
cagcagtcag agcccgccag accttcctct gaaggcaaag tgacctgtga catccggctc      720
cgggttcgag cagagtactg cgagcatggg ccagccttgg agcagggcgt ggcatcccgg      780
cggccccagg cgctggcgcg gcagctggac gtgtttgggc aggccaccgc agtgctgcgc      840
tcaagggacc tgggctctgt ggtttgtgac atcaagttct cagagctctc ctatctggac      900
gccttctggg gcgactacct gagtggcgcc ctgctgcagg ccctgcgggg cgtgttcctg      960
actgaggccc tgcgagaggc tgtgggccgg gaggctgttc gcctgctggt cagtgtggat     1020
gaggctgact atgaggctgg ccggcgccgc ctgttgctga tggaggagga agggggggcgg    1080 cgcccgacag aggcctcctg atccaggact ggcaggattg atcccacctc caagtctccg     1140
ggccaccttc tcctgggagg acgaccatct ctaccctag aggactgtca ctctagcatc      1200
tttgaggact cgacaggac cgggacagca ggccccttga cagcccctcc cacaggatgt      1260
gggctctgag gcctaaacca tttccagctg agtttccttc ccagactcct cctacccca      1320 ggtgtgcccc cttagcctcc ggaggcgggg gctgggcctg tatctcagaa gggaggggca     1380
cagctacaca ctcaccaaag gccccctgc acattgtatc tctgatcttg ggctgtctgc      1440
```

```
actgtcacag gtgcacacac tcgctcatgc tcacactgcc cctgctgaga tcttccctgg    1500
gcctctgccc tggcctgctt cccagcacac acttctttgg cctaagggct tctctctcag    1560
gacctctaat ttgaccacaa ccaacctggg cttcagccac atcagtgggc actggagctg    1620
gggtgcacat ggggcctgct caccttgccc acacatctcc agccagccag ggccctgccc    1680
agcttcaatt tacagacctg actctcctca ccttcccccc tgctgtccag agctgaacat    1740
agacttgcac ttggatgtca cctggagtgt cacatgggag tgttatggca gcatcatacc    1800
aaggcctact gttgcacatg ggccaaaac cagtaaacag ccaccttctt ggaaagggaa     1860
tgcaaaggct ttgggggtga tggaaaagac ctttaacaaa tgataccaat taaactgccc    1920
tggaaagggc ataggtggga aaaaaaaaaa aaaaaaaaa aaaaaaaaaa aaaaaaaaa      1980 aaaaaaaaaa aaaaaaaaaa aaaaaaaaaa aaaaaaaaaa aaaaaaaaaa aaaaaaaaaa    2040
aaaaa                                                                2045

<210> SEQ ID NO 3
<211> LENGTH: 4415
<212> TYPE: DNA
<213> ORGANISM: Homo sapiens

<400> SEQUENCE: 3
ctctagctct cagcggctgc gaagtctgta aacctggtgg ccaagtgatt gtaagtcagg      60
agactttcct tcggtttctg cctttgatgg caatttcctt cggtttctgc ctttgatggc     120
aagaggtgga gattgtggcg gcgattacag agaacgtctg ggaagacaag ttgctgtttt     180
tatgggaatc gcaggcttgg aagagacaga agcaattcca gaaataaatt ggaaattgaa     240
gatttaaaca atgttgtttt aaaatattct aacttcaaag aatgatgcca gaaacttaaa     300 aagggggctgc gcagagtagc aggggccctg gagggcgcgg cctgaatcct gattgccctt    360
ctgctgagag gacacacgca gctgaagatg aatttgggaa aagtagccgc ttgctacttt     420
aactatggaa gagcagggcc acagtgagat ggaaataatc ccatcagagt ctcaccccca     480
cattcaatta ctgaaaagca atcgggaact tctggtcact cacatccgca atactcagtg     540
tctggtggac aacttgctga gaatgactca cttctcggcc gaagatgcgg agattgtgtg     600
tgcctgcccc acccagcctg acaaggtccg caaaattctg gacctggtac agagcaaggg     660
cgaggaggtg tccgagttct ccctctactt gctccagcaa ctcgcagatg cctacgtgga     720
cctcaggcct tggctgctgg atcggcttc ctccccttcc ctgctcactc agagcaaagt      780
cgtggtcaac actgacccag tgagcaggta tacccagcag ctgcgacacc atctgggccg     840
tgactccaag ttcgtgctgt gctatgccca gaggaggag ctgctgctgg aggagatcta      900 catgacacc atcatggagc tggttggctt cagcaatgag agcctgggca gcctgaacag      960
cctggcctgc ctcctggacc acaccaccgg catcctcaat gagcagggtg agaccatctt    1020
catcctgggt gatgctgggg tggcaagtc catgctgcta cagcggctgc agagcctctg    1080
ggccacgggc cggctagacg cagggtcaa attcttcttc cactttcgct gccgcatgtt     1140
cagctgcttc aaggaaagtg acaggctgtg tctgcaggac ctgctcttca agcactactg    1200
ctacccagag cgggaccccg aggaggtgtt tgccttcctg ctgcgcttcc ccacgtggc     1260 cctcttcacc ttcgatggcc tggacgagct gcactggac ttggacctga gccgcgtgcc     1320
tgacagctcc tgccctggg agcctgccca cccctggtc ttgctggcca acctgctcag     1380
tgggaagctg ctcaagggggg ctagcaagct gctcacagcc cgcacaggca tcgaggtccc   1440
gcgccagttc ctgcggaaga aggtgcttct ccggggcttc tccccagcc acctgcgcgc     1500
```

-continued

```
ctatgccagg aggatgttcc ccgagcgggc cctgcaggac cgcctgctga gccagctgga    1560
ggccaacccc aacctctgca gcctgtgctc tgtgcccctc ttctgctgga tcatcttccg    1620
gtgcttccag cacttccgtg ctgcctttga aggctcacca cagctgcccg actgcacgat    1680
gaccctgaca gatgtcttcc tcctggtcac tgaggtccat ctgaacagga tgcagcccag    1740
cagcctggtg cagcggaaca cacgcagccc agtggagacc ctccacgccg gccgggacac    1800
tctgtgctcg ctggggcagg tgcccaccg gggcatggag aagagcctct tgtcttcac     1860
ccaggaggag gtgcaggcct ccgggctgca ggagagagac atgcagctgg gcttcctgcg    1920
ggctttgccg gagctgggcc ccgggggtga ccagcagtcc tatgagtttt tccacctcac    1980
cctccaggcc ttctttacag ccttcttcct cgtgctggac gacagggtgg gcactcagga    2040
gctgctcagg ttcttccagg agtggatgcc ccctgcgggg gcagcgacca cgtcctgcta    2100
tcctcccttc ctcccgttcc agtgcctgca gggcagtggt ccggcgcggg aagacctctt    2160
caagaacaag gatcacttcc agttcaccaa cctcttcctg tgcgggctgt tgtccaaagc    2220
caaacagaaa ctcctgcggc atctggtgcc cgcggcagcc ctgaggagaa gcgcaaggc     2280
cctgtgggca cacctgtttt ccagcctgcg gggctacctg aagagcctgc cccgcgttca    2340
ggtcgaaagc ttcaaccagg tgcaggccat gcccacgttc atctggatgc tgcgctgcat    2400
ctacgagaca cagagccaga aggtggggca gctggcggcc aggggcatct gcgccaacta    2460
cctcaagctg acctactgca acgcctgctc ggccgactgc agcgccctct ccttcgtcct    2520
gcatcacttc cccaagcggc tggccctaga cctagacaac aacaatctca acgactacgg    2580
cgtgcgggag ctgcagccct gcttcagccg cctcactgtt ctcagactca gcgtaaacca    2640
gatcactgac ggtggggtaa aggtgctaag cgaagagctg accaaataca aaattgtgac    2700
ctatttgggt ttatacaaca accagatcac cgatgtcgga gccaggtacg tcaccaaaat    2760
cctggatgaa tgcaaaggcc tcacgcatct taaactggga aaaacaaaa taacaagtga     2820
aggagggaag tatctcgccc tggctgtgaa gaacagcaaa tcaatctctg aggttgggat    2880
gtggggcaat caagttgggg atgaaggagc aaaagccttc gcagaggctc tgcggaacca    2940
ccccagcttg accaccctga gtcttgcgtc aacggcatc tccacagaag gaggaaagag     3000
ccttgcgagg gccctgcagc agaacacgtc tctagaaata ctgtggctga cccaaaatga    3060
actcaacgat gaagtggcag agagtttggc agaaatgttg aaagtcaacc agacgttaaa    3120
gcatttatgg cttatccaga atcagatcac agctaagggg actgcccagc tggcagatgc    3180
gttacagagc aacactggca taacagagat ttgcctaaat ggaaacctga taaaaccaga    3240
ggaggccaaa gtctatgaag atgagaagcg gattatctgt ttctgagagg atgctttcct    3300
gttcatgggg tttttgccct ggagcctcag cagcaaatgc cactctgggc agtcttttgt    3360
gtcagtgtct taaaggggcc tgcgcaggcg ggactatcag gagtccactg cctccatgat    3420
gcaagccagc ttcctgtgca gaaggtctgg tcggcaaact ccctaagtac ccgctacaat    3480
tctgcagaaa aagaatgtgt cttgcgagct gttgtagtta cagtaaatac actgtgaaga    3540
gactttattg cctattataa ttatttttat ctgaagctag aggaataaag ctgtgagcaa    3600
acagaggagg ccagcctcac ctcattccaa cacctgccat agggaccaac gggagcgagt    3660
tggtcaccgc tcttttcatt gaagagttga ggatgtggca caagttggt gccaagcttc     3720
ttgaataaaa cgtgtttgat ggattagtat tatacctgaa atatttttt ccttctcagc     3780
actttcccat gtattgatac tggtcccact tcacagctgg agacaccgga gtatgtgcag    3840
```

```
tgtgggattt gactcctcca aggttttgtg gaaagttaat gtcaaggaaa ggatgcacca      3900
cgggctttta attttaatcc tggagtctca ctgtctgctg gcaaagatag agaatgccct      3960
cagctcttag ctggtctaag aatgacgatg ccttcaaaat gctgcttcca ctcagggctt      4020
ctcctctgct aggctaccct cctctagaag gctgagtacc atgggctaca gtgtctggcc      4080
ttgggaagaa gtgattctgt ccctccaaag aaatagggca tggcttgccc ctgtggccct      4140
ggcatccaaa tggctgcttt tgtctccctt acctcgtgaa gaggggaagt ctcttcctgc      4200
ctcccaagca gctgaagggt gactaaacgg gcgccaagac tcaggggatc ggctgggaac      4260
tgggccagca gagcatgttg gacacccccc accatggtgg gcttgtggtg gctgctccat      4320
gagggtgggg gtgatactac tagatcactt gtcctcttgc ccgctcattt gttaataaaa      4380
tactgaaaac aaaaaaaaaa aaaaaaaaaa aaaaa                                 4415

<210> SEQ ID NO 4
<211> LENGTH: 2066
<212> TYPE: DNA
<213> ORGANISM: Homo sapiens

<400> SEQUENCE: 4
gcggcggcaa aatggcggcg cctgaggagc gggatctaac ccaggagcag acagagaagc       60
tgctgcagtt tcaggatctc actggcatcg aatctatgga tcagtgtcgc catacccttgg     120 aacagcataa ctggaacata gaggctgctg tacaggacag attgaatgag caagagggcg      180
tacctagtgt tttcaaccca cctccatcac gaccccctgca ggttaataca gctgaccaca     240
ggatctacag ctatgttgtc tcaagacctc aaccaagggg gctgcttgga tggggttatt      300
acttgataat gcttccattc cggtttacct attacacgat acttgatata tttaggtttg      360
ctcttcgttt tatacggcct gaccctcgca gccgggtcac tgaccccgtt ggggacattg      420
tttcatttat gcactctttt gaagagaaat atgggaggc acaccctgtc ttctaccagg       480
gaacgtacag ccaggcactt aacgatgcca aaagggagct tcgctttctt ttggtttatc      540
ttcatggaga tgatcaccag gactctgatg agttttgtcg caacacactc tgtgcacctg      600
aagttatttc actaataaac actaggatgc tcttctgggc atgctctaca aacaaacctg      660
agggatacag ggtctcacag gctttacgag agaacaccta tccattcctg gccatgatta      720
tgctgaagga tcgaaggatg actgtggtgg gacggctaga aggcctcatt caacctgatg      780
acctcattaa ccaactgaca tttatcatgg atgctaacca gacttacctg gtgtcagaac      840
gcctagaaag ggaagaaaga aaccagaccc aagtgctgag acaacagcag gatgaggcct      900
acctggcctc tctcagagct gaccaggaga agaaagaaa gaaacgggag gagcgggagc      960
gtaagcggcg gaaggaggag gaggtgcaac agcaaaagtt ggcagaggag agacggcggc     1020
agaatttaca ggaggaaaag gaaaggaagt tggaatgcct gcccccctgaa ccttcccctg     1080 atgaccctga aagtgtcaag atcatcttca aattacctaa tgattctcga gtagagagac     1140
gattccactt ttcacagtct ctaacagtaa tccacgactt cttattctcc ttgaaggaaa     1200
gcccagaaaa gtttcagatt gaagccaatt ttcccaggcg agtgctgccc tgcatccctt     1260
cagaggagtg gcccaatccc cctacgctac aggaggccgg actcagccac acagaagttc     1320 ttttttgttca ggacctaact gacgaatgac attttttttct tcctgtcccc tcctacccca     1380
gtccctaaaa gaaatgggga aaaagaaaa caacagcaag tcagaaaaaa aaaacaagag     1440
agagaaattc atattattat tattattata atacaatatt ttttttaaaa gactgctgca     1500
tccttaggaa ggatcagaaa ccatgctgcc cgtaagagtc acaacctgtg tgtgcgcgca     1560
```

-continued

```
aggttagcaa caaacgtacc cgcttggcaa gcccacccTT cctgtggcct ctgtgcacgc    1620
accttccagt gaacagagac tcttcacctt cgacccatcc attgtcccag ctgggaaggg    1680
gacattccca ctagttctca ttcattcttg cttttatgaa aaataaaagt gaaaaacctc    1740
catcaaccag ctacttgcag catctcctga ggacttgctt ctcctgcctc tggggaagag    1800
agggaagaga aagcacagag cagagaagca gagatgttcc ttgaactgcc cacaagtttt    1860
caataacttt tatttctgtt ttgtaatgac caaaggaatg aggctgacat aggtatatat    1920 atatatttt ttcctttatt tgataaagag ccaattcttt aaacccatga gtttatgccc    1980
tgggctcctt agcccacaat agtgtaataa aagtgccccg ggctggtttg tgcttaaaaa    2040
aaaaaaaaaa aaaaaaaaaa aaaaaa                                          2066

<210> SEQ ID NO 5
<211> LENGTH: 1406
<212> TYPE: DNA
<213> ORGANISM: Homo sapiens

<400> SEQUENCE: 5
ggagcctcgt cgagtctcca tgcaggtggt gcgcatggct ggccgagagc tgcaggccct      60
cctgggagaa ccagaggctg cagtgagccc cctgctgtgc ctgtcacaga gcggtccccc     120
cagcttcctc caaccggtca ccgtgcagct gcctctgccc tctggcatca caggcctcag     180
tctggaccgc tcccgcctgc acctgttgta ctgggcccct cctgcagcca ctgggatga     240 catcacagct caggtggtcc tggagctcac ccacctgtac gcacgcttcc aggtactggc     300
tctggtacac caccaagaac tgtgtgggag gcctggctcg aaggcctgg gagcggctgc     360 ggctgcaccg tgtgaacctc atcgctctgc agcggcgccg ggaccctgag caggtcctgc     420
tgcagtgcct gccccgaaac aaggtggacg ccaccttcg gcggctgctg agcggtacc      480 gggggcccga gccctctgac acggtggaga tgttcgaggg cgaagagttc tttgcggcct     540
tcgagcgcgg catygacgtg gatgctgacc gccctgactg tgtggagggc agaatctgct     600
ttgtcttcta ctcgcacctg aagaatgtga aggaggtata cgtgaccacc actctggacc     660
gggaggctca ggctgtgcgg ggccaggtgt ccttctaccg tggcgcggtg cctgtgcggg     720
tgcccgagga ggctgaggct gcccggcaga ggaagggcgc agacgccctg tggatgccca     780
ctctgcccat caagctgccg agacttcgag gtccgaggg gccacggcgg ggggctggcc     840
tctccttggc acccttgaat ctgggagatg ccgagaccgg ctttctgacg cagagcarcc     900
tgctgartgt ggctgggcgt ctgggtctgg actggccagc cgtggccctg cacctgggggg    960 tgtcctaccg ggaggtgcag cgcatccggc acgagttccg ggatgatctg gatgagcaga   1020
tccgtcacat gctcttctcc tgggctgagc gccaggctgg gcagccaggg gctgtgggc    1080 tcctggtgca ggccctggag cagagtgacc ggcaggacgt ggctgaagag gtgcgcgcag   1140
tcttggagct cggccgccgc aagtaccagg acagcatccg acgcatgggc ttggccccca   1200 aggacccgc tctgcctggc tcctcggctc cacagccccc agagcctgcc caggcctagg   1260
ccccacagac ttttaggctg gcccagatat tccccagtgg atgggcagag ccccacctt   1320 caagtctctc cagtgtgtgg ggacgggtcc ctgtgagcaa caaaactgca ctgtttcttt   1380
caaaaaaaaa aaaaaaaaaa aactcc                                       1406

<210> SEQ ID NO 6
<211> LENGTH: 3172
<212> TYPE: DNA
```

```
<213> ORGANISM: Homo sapiens
<220> FEATURE:
<221> NAME/KEY: SITE
<222> LOCATION: (148)
<223> OTHER INFORMATION: n equals a,t,g, or c
<221> NAME/KEY: SITE
<222> LOCATION: (1013)
<223> OTHER INFORMATION: n equals a,t,g, or c

<400> SEQUENCE: 6
agcttcccgg gtgaggctgg gacccggcac cagggcagta ctgtggccgc tgcggcttca       60
tctgccgact gggtcaggtt gcggagactc caggccgctt ccagggmgag tactcctgaa      120
ttgtgaacat cacattcatc ccctgggncg atggagcttg tcactgagtg gaggcatcag      180
ggggttggag ccttgtgaac agggaacctg cccccccaaca cttggaagga cctgggtttc     240
agtgatgaga catgggtgtat gatgtaaccc gtttccaggg ggatgttgac gaagatctta    300
tctgccctat ttgcagtgga gtcttggagg agccagtaca ggcacctcat tgtgaacatg     360
cttctgcaa cgcctgcatc acccagtggt tctctcagca acagacatgt ccagtggacc      420
gtagtgttgt gacggtcgcc catctgcgcc cagtacctcg gatcatgcgg aacatgttgt     480
caaagctgca gattgcctgt gacaacgctg tgttcggctg tagtgccgtt gtccggcttg     540
acaacctcat gtctcacctc agcgactgtg agcacaaccc gaagcggcct gtgacctgtg    600
aacagggctg tggcctggag atgcccaaag atgagctgcc caaccataac tgcattaagc    660
acctgcgctc agtggtacag cagcagcaga cacgcatcgc agagctggag aagacgtcag    720
ctgaacacaa acaccagctg gcggagcaga agcgagacat ccagctgcta aaggcataca    780
tgcgtgcaat ccgcagtgtc aaccccaacc ttcagaacct ggaggagaca attgaataca    840
acgagatcct agagtgggtg aactcccttc agccagcaag agtgacccgc tggggagggda    900
tgatctcgac tcctgatgct gtgctccagg ctgtaatcaa gcgctccctg gtggagagtg    960
gctgtcctgc ttctattgtc aacgagctga ttgaaaatgc ccacgagcgt agntggcccc   1020
agggtctggc cacactagag actagacaga tgaaccgacg ctactatgag aactacgtgg   1080
ccaagcgcat ccctggcaag caggctgttg tcgtgatggc ctgtgagaac cagcacatgg   1140
gggatgacat ggtgcaagag ccaggccttg tcatgatatt tgcgcatggc gtggaagaga   1200
tataagagaa ctcgactggc tatcaggaag agatggaaat cagaaaatcc catcactcca   1260
gcagctggga cctgagtcct acccaccatt cttaatactg tggcttatac ctgagccaca   1320
catctccctg cccttctggc actgaagggc cttggggtag tttgctcagc cttttcaggtg  1380
ggaaacccag atttcctccc tttgccatat tccctaaaa tgtctataaa ttatcagtct    1440
gggtgggaaa gccccacct ccatccattt tcctgcttag ggtccctggt tccagttatt    1500
ttcagaaagc acaaagagat tcaatttccc tggaggatca ggacagagga aggaatctct   1560
aatcgtccct ctcctccaaa accagggaat cagagcagtc aggcctgttg actctaagca   1620
gcagacatcc tgaagaaatg gtaagggtgg agccaaatct ctagaaataa gtagtgaggc   1680
cgttaattgg ccatcactga tggcccttag ggaaagactg gacctctgtg ccaagcagta   1740
tccctgttca gcccacctta aaggtgtagg cacccactgg gtctaccagt atgcaggttg   1800
ggatactgaa aatttccaga tgagctcttc ttttcctacaa gttttcataa ttagggaatg   1860
ccagggttta gggtaggggt taatctgttg ggggttgatg tgtttagcaa gaagctactc   1920
ctagcttttg ctaaaatatg gttggcactg cctcttgtgg cacaggccat aattgttcca    1980
tagaccccct ctctagccctg tgactgtagt tagttacttt gataatttc ttttggccatt   2040
```

```
gtttgtttat atttcacaaa ctccacctac tgccccccccc cctcttttttt ttaagaatgg    2100 cctgatcatg gctatctcag ccacattgtt ggcaatttaa tttatttact tccttttttt     2160
tttttaagaa aggaaaaaag aaaaaaaaat caaacttgaa actttctctt tgakgttcct     2220 attgtgggggg ttctggatag ggtgggacag ggatggggggt gtgttttata ttttttcctt    2280
ttcagcacaa cctttggctt taatatagga agagccaagg gagtcctcgg ctgaacttac     2340
gatatctgcc ccaaacctct gtaacccccaa ctgaaatgag gagcttcctc tcttcctgtg     2400
aaggatatga cagtccagca tcgatgcctg tgccctctgg aaaaatttcc tcctagccct     2460
tccagggcct tatcataaaa ctctggatttt agagtattca ttttgaaggc aactcccccct    2520 tccccaagtt tccttggagc tgtatagctg ggttctaagc ttcaccatgc aaatcagaaa     2580
ttttatctct aagtacaggc tgtgccgtgt ctcacccaca ccccccctggg gacttcagtt     2640 ccatttcagg ttacctgggg tataccttga tccctagagt gactggcaga gtaagagaag     2700
gggagagata ataggtgtga ttattttaat atggaggtgg gagtgtggtt ggagatagaa     2760
aggctcctcc ccascatgta atggcttckc tcagaatttk attccaggct agcttgctsm     2820
aggtctgggt agttggatca tgcgtcactg gaattggggg gaagcttgag gaagtaggtc     2880
cagtctggaa atggctccga atttaaagct gatactagct ggtacgaatc ttcctccgtt     2940
ccgagtgcgt acaggcataa gctgtcgtcc caggggccgg gagcgtaagt ccgcctgtcg     3000
agcctcagga gcgggttgtg gtcagggtgt gggaaacagg tgtgcgtcct agaagaattg     3060
gggctcttgg gtatggcggg gtaaggagat tgccaagtga ccctcggtta agccctcctg     3120
gtggcgccgg gggtgggccc gaccttccta gggtcaaggc gctcccctttc gg           3172

<210> SEQ ID NO 7
<211> LENGTH: 2290
<212> TYPE: DNA
<213> ORGANISM: Homo sapiens

<400> SEQUENCE: 7
gcccacgcgt ccgcccacgc gtccggatct ccaggacaat gaggttctta ctgagaatga      60
gaaggagctg gtggagcagg aaaagacacg gcagagcaag aatgaggcct tgctgagcat     120
ggtggagaag aaaggggacc tggccctgga cgtgctcttc agaagcatta gtgaaaggga     180
cccttacctc gtgtcctatc ttagacagca gaatttgtaa aatgagtcag ttaggtagtc     240
tggaagagag aatccagcgt tctcattgga aatggataaa cagaaatgtg atcattgatt     300
tcagtgttca agacagaaga agactgggta acatctatca cacaggcttt caggacagac     360
ttgtaacctg gcatgtacct attgactgta tcctcatgca ttttcctcaa gaatgtctga     420
agaaggtagt aatattcctt ttaaattttt tccaaccatt gcttgatata tcactatttt     480
atccattgac atgattcttg aagacccagg ataaaggaca tccggatagg tgtgtttatg     540
aaggatgggg cctggaaagg caacttttcc tgattaatgt gaaaaataat tcctatggac     600
actccgtttg aagtatcacc ttctcataac taaaagcaga aaagctaaca aaagcttctc     660
agctgaggac actcaaggca tacatgatga cagtcttttt tttttttttgt atgttaggac     720 tttaacactt tatctatggc tactgttatt agaacaatgt aaatgtattt gctgaaagag     780
agcacaaaaa tgggagaaaa tgcaaacatg agcagaaaat attttcccac tggtgtgtag     840
cctgctacaa ggagttgttg ggttaaatgt tcatggtcaa ctccaaggaa tactgagatg     900
aaatgtggta aatcaactcc acagaaccac caaaaagaaa atgagggtaa ttcagcttat     960
tctgagacag acattcctgg caatgtacca tacaaaaaat aagccaactc tgacatttgg    1020
```

```
attctaccat agactctgtc attttgtagc catttcagct gtcttttgat taatgttttc    1080
gtggcacaca tatttccatc cttttatgtt taatctgttt aaaacaagtt cctagtagac    1140
accatctggt tgagtcagtt ttttttatgg tgtattttga acccattctg atagtctctt    1200
ttaactggaa gatttcaatt acttacgtta atgtaattat taatatgtta ggatttatcc    1260
tcagtcagcc agtttgttat gtcttttcta ttctactgtt atcacatttg taccacttaa    1320
agtggaatct aggcactttta tcaccatttta gatcctatta ccttttctca tctaggatat    1380
agttatcttc tacataatct ttctgtatct taaaacccat caataaatta ttatatattt    1440
tctactttta atcactcaga agatttaaaa aactcatgag aagagtaatc tgttatgttt    1500
ttccagatat ttaccatttc tgttgctctt ccttcattat tttccaaatt tcgttctgca    1560
aatttccact tcttctgata gacgtttttt agttctttta gagtggttct gataggtaca    1620
gattctctta ttttttgctt cctctgagga catcttttc tcaccttcat tctcagtgat    1680
gttttttgct tgtagtattt ttagttgaca ttgttttctg ttcagcagtt tccttttagc    1740 ttccgtatt cctgatgaga aatctgcagt cattcaaatt gttgtttccc tgtatgtagt    1800
gtgtcatttt tctgtcagat ttcaaggtat ttatctttag ttttttagcca tttcattatg    1860 ttggggatga gtttccttgt tttattccct ttggaatttg ctccaattca taaatttgca    1920
gttttatgtc ttttaccaaa cttagaggtt ttcagcctaa tttctaaaaa tacttttat    1980 tagcctgatt ttcatcttta taggaaatag tttaagtgat gacaagttcc aatagcttat    2040
atgcccagaa ggccttcaaa ataagaattt tgaaagaata cagaaaacaa acttttatat    2100
ccttctcatg tcttctactg taaaattcat atgctttgct actctaaacc tagtttgaaa    2160
tcaacagtct tgagaataga tgaaaatttt gatgaatagt ggaattcttt taaatggaaa    2220
cctcttacat gtgattttcc ttgccatcta gaaataaacc atagtattta tgttgaaaaa    2280
aaaaaaaaaa                                                          2290

<210> SEQ ID NO 8
<211> LENGTH: 1316
<212> TYPE: DNA
<213> ORGANISM: Homo sapiens
<220> FEATURE:
<221> NAME/KEY: SITE
<222> LOCATION: (7)
<223> OTHER INFORMATION: n equals a,t,g, or c

<400> SEQUENCE: 8
tcaattntca ggccagcgtg aggccatcac tgtgccgttc actgtgaaaa gaaaaccacc      60
ctggcgccca atacgcaaac cgcctctccc cgcgcgttgg ccgattcatt aatgcagctg     120
gcacgacagg tttcccgact ggaaagcggg cagtgagcgc aacgcaatta atgtgagtta     180
gctcactcat taggcacccc aggctttaca ctttatgctt ccggctcgta tgttgtgtgg     240
aattgtgagc ggataacaat ttcacacagg aaacagctat gaccatgatt acgccaagct     300
cgaaattaac cctcactaaa gggaaagctg gtacgcctgc aggtaccggt ccggaattcc     360
cgggtcgacc cacgcgtccg cccacgcgtc cgtgaaaatc cgaagtgccg cggaaagtgg     420
aggtgagggc cgcccgccct agaggtgccc gtccgagagg cagagctgac aaggaaggtt     480
tcgagcgttt tgctggcaaa gggatttctt acaacctcca ggcatgcgtc tttctgccct     540
gctggccttg gcatccaagg tcactctgcc cccccattac cgctatggga tgagcccccc     600
aggctctgtt gcagacaaga ggaagaaccc cccatggatc aggcggcgcc cagtggttgt     660
```

-continued

| | |
|---|---|
| ggaacccatc tctgatgaag actggtatct gttctgtggg gacacggtgg agatcctaga | 720 |
| aggcaaggat gccgggaagc agggcaaagt ggttcaagtt atccggcagc gaaactgggt | 780 |
| ggtcgtggga gggctgaaca cacattaccg ctacattggc aagaccatgg attaccgggg | 840 |
| aaccatgatc cctagtgaag ccccttgct ccaccgccag gtcaaacttg tggatcctat | 900 |
| ggacaggaaa cccactgaga tcgagtggag atttactgaa gcaggagagc gggtacgagt | 960 |
| ctccacacga tcagggagaa ttatccctaa acccgaattt cccagagctg atggcatcgt | 1020 |
| ccctgaaacg tggattgatg cccccaaaga cacatcagtg aagatgcttt agaaagaac | 1080 |
| ctatgtgccc tgtctaaaga cactgcagga ggaggtgatg gaggccatgg ggatcaagga | 1140 |
| gacccggaaa tacaagaagg tctattggta ttgagcctgg ggcagagcag ctcctcccca | 1200 |
| acttctgtcc cagccttgaa ggctgaggca cttcttttc agatgccaat aaagagcact | 1260 |
| ttatgagtca aaaaaaaaa aaaaaaaaa aaaaaaaa aaaaaaaaa aaaaaa | 1316 |

<210> SEQ ID NO 9
<211> LENGTH: 2150
<212> TYPE: DNA
<213> ORGANISM: Homo sapiens

<400> SEQUENCE: 9

| | |
|---|---|
| gcggacgcgt gggtcgaccc acgcgtccgg tttgacccgt cggtcgtgcg tgagaggaaa | 60 |
| gggaaggagg aggtcccgaa tagcggtcgc cgaaatgttc cggtgtggag gcctggcggc | 120 |
| gggtgctttg aagcagaagc tggtgcccct ggtgcggacc gtgtgcgtcc gaagcccgag | 180 |
| gcagaggaac cggctcccag gcaacttgtt ccagcgatgg catgttcctc tagaactcca | 240 |
| gatgacaaga caaatggcta gctctggtgc atcagggggc aaaatcgata attctgtgtt | 300 |
| agtccttatt gtgggcttat caacagtagg agctggtgcc tatgcctaca agactatgaa | 360 |
| agaggatgaa aaaagataca atgaaagaat tcagggtta gggctgacac agaacagaa | 420 |
| acagaaaaag gccgcgttat ctgcttcaga aggagaggaa gttcctcaag acaaggcgcc | 480 |
| aagtcatgtt cctttcctgc taattggtgg aggcacagct gcttttgctg cagccagatc | 540 |
| catccgggct cgggatcctg ggccagggt actgattgta tctgaagatc ctgagctgcc | 600 |
| gtacatgcga cctcctctttt caaaagaact gtggttttca gatgacccaa atgtcacaaa | 660 |
| gacactgcga ttcaaacagt ggaatggaaa agagagaagc atatatttcc agccaccttc | 720 |
| tttctatgtc tctgctcagg acctgcctca tattgagaat ggtggtgtgg ctgtcctcac | 780 |
| tgggaagaag gtagtacagc tggatgtgag agacaacatg gtgaaactta atgatggctc | 840 |
| tcaaataacc tatgaaaagt gcttgattgc aacaggaggt actccaagaa gtctgtctgc | 900 |
| cattgatagg gctggagcag aggtgaagag tagaacaacg cttttcagaa agattggaga | 960 |
| ctttagaagc ttggagaaga tttcacggga agtcaaatca attacgatta tcggtggggg | 1020 |
| cttccttggt agcgaactgg cctgtgctct tggcagaaag gctcgagcct tgggcacaga | 1080 |
| agtgattcaa ctcttcccg agaaaggaaa tatgggaaag atcctccccg aatacctcag | 1140 |
| caactggacc atgaaaaag tcagacgaga gggggttaag gtgatgccca atgctattgt | 1200 |
| gcaatccgtt ggagtcagca gtggcaagtt acttatcaag ctgaaagacg gcaggaaggt | 1260 |
| agaaactgac cacatagtgg cagctgtggg cctggagccc aatgttgagt ggccaagac | 1320 |
| tggtggcctg gaaatagact cagattttgg tggcttccgg gtaaatgcag agctacaagc | 1380 |
| acgctctaac atctgggtgg caggagatgc tgcatgcttc tacgatataa agttgggaag | 1440 |
| gaggcgggta gagcaccatg atcacgctgt tgtgagtgga agattggctg agaaaatat | 1500 |

```
gactggagct gctaagccgt actggcatca gtcaatgttc tggagtgatt tgggccccga   1560
tgttggctat gaagctattg gtcttgtgga cagtagtttg cccacagttg gtgttttgc   1620 aaaagcaact gcacaagaca accccaaatc tgccacagag cagtcaggaa ctggtatccg   1680
atcagagagt gagacagagt ccgaggcctc agaaattact attcctccca gcaccccggc   1740
agttccacag gctcccgtcc aggggaggaa ctacggcaaa gtgtcatct tctacctcag   1800 ggacaaagtg gtcgtgggga ttgtgctatg aacatctttt aaccgaatgc caatagcaag   1860
gaagatcatt aaggacggtg agcagcatga agatctcaat gaagtagcca aactattcaa   1920
cattcatgaa gactgaagcc ccacagtgga attggcaaac ccactgcagc ccctgagagg   1980
aggtcgaatg ggtaaaggag cattttttta ttcagcagac tttctctgtg tatgagtgtg   2040
aatgatcaag tcctttgtga atattttcaa ctatgtaggt aaattcttaa tgttcacata   2100
gtgaaataaa ttctgattct tctaaaaaaa aaaaaaaaa aaaaaaaaa   2150
```

<210> SEQ ID NO 10
<211> LENGTH: 3789
<212> TYPE: DNA
<213> ORGANISM: Homo sapiens
<220> FEATURE:
<221> NAME/KEY: SITE
<222> LOCATION: (3677)
<223> OTHER INFORMATION: n equals a,t,g, or c

<400> SEQUENCE: 10

```
tcgacccacg cgtccgatcc catcagagtc tcaccccac attcaattac tgaaaagcaa     60
tcgggaactt ctggtcactc acatccgcaa tactcagtgt ctggtggaca acttgctgaa    120
gaatgactac ttctcggccg aagatgcgga gattgtgtgt gcctgcccca cccagcctga    180
caaggtccgc aaaattctgg acctggtaca gagcaagggc gaggaggtgt ccgagttctt    240
cctctacttg ctccagcaac tcgcagatgc ctacgtggac ctcaggcctt ggctgctgga    300
gatcggcttc tcccttccc tgctcactca gagcaaagtc gtggtcaaca ctgacccagt    360
gagcaggtat acccagcagc tgcgacacca tctgggccgt gactccaagt tcgtgctgtg    420
ctatgcccag aaggaggagc tgctgctgga ggagatctac atggacacca tcatggagct    480
ggttggcttc agcaatgaga gcctgggcag cctgaacagc ctggcctgcc tcctggacca    540
caccaccggc atcctcaatg agcagggacc tgctcttcaa gcactactgc tacccagagc    600
gggaccccga ggaggtgttt gccttcctgc tgcgcttccc ccacgtggcc ctcttcacct    660
tcgatggcct ggacgagctg cactcggact tggacctgag ccgcgtgcct gacagctcct    720
gcccctggga gcctgcccac cccctggtct tgctggccaa cctgctcagt gggaagctgc    780
tcaagggggc tagcaagctg ctcacagccc gcacaggcat cgaggtcccg cgccagttcc    840
tgcggaagaa ggtgcttctc cggggcttct ccccagcca cctgcgcgcc tatgccagga    900
ggatgttccc cgagcgggcc ctgcaggacc gcctgctgag ccagctggag gccaaccca    960 acctctgcag cctgtgctct gtgccccctct tctgctggat catcttccgg tgcttccagc   1020
acttccgtgc tgcctttgaa ggctcaccac agctgcccga ctgcacgatg accctgacag   1080
atgtcttcct cctggtcact gaggtccatc tgaacaggat gcagcccagc agcctggtgc   1140
agcggaacac acgcagccca gtggagaccc tccacgccgg ccgggacact ctgtgctcgc   1200
tggggcaggt ggcccaccgg ggcatggaga agagcctctt tgtcttcacc caggaggagg   1260
tgcakgcctc cgggctgcag gagagagaca tgcagctggg cttyctgcgg gctttgccgg   1320
```

```
arctgggccc cggrggtgac cagcagtyct atgagttttt ccacctcacc ctccaggcct    1380
tctttacagc cttcttcctc gtgctggacg acagggtggg cactcaggag ctgctcaggt    1440
tcttccagga gtggatgccc cctgcggggg cagcgaccac gtcctgctat cctcccttcc    1500
tcccgttcca gtgcctgcag ggcagtggtc cggcgcggga agacctcttc aagaacaagg    1560
atcacttcca gttcaccaac ctcttcctgt gcgggctgtt gtccaaagcc aaacagaaac    1620
tcctgcggca tctggtgccc gcggcagccc tgaggagaaa gcgcaaggcc ctgtgggcac    1680
acctgttttc cagcctgcgg ggctacctga agagcctgcc ccgcgttcag gtcgaaagct    1740
tcaaccaggt gcaggccatg cccacgttca tctggatgct gcgctgcatc tacgagacac    1800
agagccagaa ggtggggcag ctggcggcca gggcatctg cgccaactac ctcaagctga    1860
cctactgcaa cgcctgctcg gccgactgca gcgccctctc cttcgtcctg catcacttcc    1920
ccaagcggct ggccctagac ctagacaaca acaatctcaa cgactacggc gtgcgggagc    1980
tgcagccctg cttcagccgc ctcactgttc tcagactcag cgtaaaccag atcactgacg    2040
gtgggtaaa ggtgctaagc gaagagctga ccaaatacaa aattgtgacc tatttgggtt    2100
tatacaacaa ccagatcacc gatgtcggag ccaggtacgt caccaaaatc ctggatgaat    2160
gcaaaggcct cacgcatctt aaactgggaa aaaacaaaat aacaagtgaa ggagggaagt    2220
atctcgccct ggctgtgaag aacagcaaat caatctctga ggttgggatg tgggcaatc    2280
aagttgggga tgaaggagca aaagccttcg cagaggctct gcggaaccac cccagcttga    2340
ccaccctgag tcttgcgtcc aacggcatct ccacagaagg aggaaagagc cttgcgaggg    2400
ccctgcagca gaacacgtct ctagaaatac tgtggctgac ccaaaatgaa ctcaamgatg    2460
aaktggcaga gagtttggca gaaatgttga aagtcaacca gacgttaaag catttatggc    2520
ttatccagaa tcagatcaca gctaagggga ctgcccagct ggcagatgcg ttacagagca    2580
acactggcat aacagagatt tgcctaaatg gaaacctgat aaaaccagag gaggccaaag    2640
tctatgaaga tgagaagcgg attatctgtt tctgagagga tgctttcctg ttcatggggt    2700
tttgccctg gagcctcagc agcaaatgcc actctgggca gtcttttgtg tcagtgtctt    2760
aaagggcct gcgcaggcgg gactatcagg agtccactgc ctccatgatg caagccagct    2820
tcctgtgcag aaggtctggt cggcaaactc cctaagtacc cgctacaatt ctgcagraaa    2880
agaatgtgtc ttgcgagctg ttgtagttac agtaaataca ctgtgaagag actttattgc    2940
ctattataat tattttttatc tgaagctaga ggaataaagc tgtgagcaaa cagaggaggc    3000
cagcctcacc tcattccaac acctgccata gggaccaacg ggagcgagtt ggtcaccgct    3060
cttttcattg aagagttgag gatgtggcac aaagttggtg ccaagcttct tgaataaaac    3120
gtgtttgatg gattagtatt atacctgaaa tattttcttc cttctcagca ctttcccatg    3180
tattgatact ggtcccactt cacagctgga gacaccggag tatgtgcagt gtgggatttg    3240
actcctccaa ggttttgtgg aaagttaatg tcaaggaaag gatgcaccac gggcttttaa    3300
ttttaatcct ggagtctcac tgtctgctgg caaagataga gaatgccctc agctcttagc    3360
tggtctaaga atgacgatgc cttcaaaatg ctgcttccac tcagggcttc tcctctgcta    3420
ggctacctc ctctagaagg ctgagtacca tgggctacag tgtctggcct tgggaagaag    3480
tgattctgtc cctccaaaga aatagggcat ggcttgcccc tgtggccctg catccaaat    3540
ggctgctttt gtctccctta cctcgtgaag agggaagtc tcttcctgcc tcccaagcag    3600
ctgaagggtg actaaacggg cgccaagact caggggatcg gctgggaact gggccagcag    3660
agcatgttgg acacccncca ccatggtggg cttgtggtgg ctgctccatg agggtggggg    3720
```

```
tgatactact agatcacttg tcctcttgcc agctcatttg ttaataaaat actgaaaaca      3780 cwmaaaaaa                                                              3789
```

<210> SEQ ID NO 11
<211> LENGTH: 304
<212> TYPE: PRT
<213> ORGANISM: Homo sapiens

<400> SEQUENCE: 11

```
Met Leu Ser Leu His Arg Met Phe Glu Val Val Gly Gly Gln Leu Thr
 1               5                  10                  15

Glu Cys Glu Leu Glu Leu Leu Ala Phe Leu Leu Asp Glu Ala Pro Gly
             20                  25                  30

Ala Ala Gly Gly Leu Ala Arg Ala Arg Ser Gly Leu Glu Leu Leu Leu
         35                  40                  45

Glu Leu Glu Arg Arg Gly Gln Cys Asp Glu Ser Asn Leu Arg Leu Leu
     50                  55                  60

Gly Gln Leu Leu Arg Val Leu Ala Arg His Asp Leu Leu Pro His Leu
 65                  70                  75                  80

Ala Arg Lys Arg Arg Pro Val Ser Pro Glu Arg Tyr Ser Tyr Gly
                 85                  90                  95

Thr Ser Ser Ser Lys Arg Thr Glu Gly Ser Cys Arg Arg Arg
            100                 105                 110

Gln Ser Ser Ser Ala Asn Ser Gln Gln Gly Gln Trp Glu Thr Gly
        115                 120                 125

Ser Pro Pro Thr Lys Arg Gln Arg Ser Arg Gly Arg Pro Ser Gly
    130                 135                 140

Gly Ala Arg Arg Arg Arg Gly Ala Pro Ala Pro Gln Gln Gln
145                 150                 155                 160

Ser Glu Pro Ala Arg Pro Ser Glu Gly Lys Val Thr Cys Asp Ile
                165                 170                 175

Arg Leu Arg Val Arg Ala Glu Tyr Cys Glu His Gly Pro Ala Leu Glu
            180                 185                 190

Gln Gly Val Ala Ser Arg Arg Pro Gln Ala Leu Ala Arg Gln Leu Asp
        195                 200                 205

Val Phe Gly Gln Ala Thr Ala Val Leu Arg Ser Arg Asp Leu Gly Ser
    210                 215                 220

Val Val Cys Asp Ile Lys Phe Ser Glu Leu Ser Tyr Leu Asp Ala Phe
225                 230                 235                 240

Trp Gly Asp Tyr Leu Ser Gly Ala Leu Leu Gln Ala Leu Arg Gly Val
                245                 250                 255

Phe Leu Thr Glu Ala Leu Arg Glu Ala Val Gly Arg Glu Ala Val Arg
            260                 265                 270

Leu Leu Val Ser Val Asp Glu Ala Asp Tyr Glu Ala Gly Arg Arg Arg
        275                 280                 285

Leu Leu Leu Met Glu Glu Glu Gly Gly Arg Arg Pro Thr Glu Ala Ser
    290                 295                 300
```

<210> SEQ ID NO 12
<211> LENGTH: 953
<212> TYPE: PRT
<213> ORGANISM: Homo sapiens

<400> SEQUENCE: 12

Met Glu Glu Gln Gly His Ser Glu Met Glu Ile Ile Pro Ser Glu Ser

-continued

```
  1               5              10              15
His Pro His Ile Gln Leu Leu Lys Ser Asn Arg Glu Leu Leu Val Thr
             20              25              30
His Ile Arg Asn Thr Gln Cys Leu Val Asp Asn Leu Leu Lys Asn Asp
             35              40              45
Tyr Phe Ser Ala Glu Asp Ala Glu Ile Val Cys Ala Cys Pro Thr Gln
             50              55              60
Pro Asp Lys Val Arg Lys Ile Leu Asp Leu Val Gln Ser Lys Gly Glu
 65              70              75              80
Glu Val Ser Glu Phe Phe Leu Tyr Leu Gln Gln Leu Ala Asp Ala
             85              90              95
Tyr Val Asp Leu Arg Pro Trp Leu Leu Glu Ile Gly Phe Ser Pro Ser
            100             105             110
Leu Leu Thr Gln Ser Lys Val Val Asn Thr Asp Pro Val Ser Arg
            115             120             125
Tyr Thr Gln Gln Leu Arg His His Leu Gly Arg Asp Ser Lys Phe Val
            130             135             140
Leu Cys Tyr Ala Gln Lys Glu Glu Leu Leu Glu Glu Ile Tyr Met
145             150             155             160
Asp Thr Ile Met Glu Leu Val Gly Phe Ser Asn Glu Ser Leu Gly Ser
                165             170             175
Leu Asn Ser Leu Ala Cys Leu Leu Asp His Thr Thr Gly Ile Leu Asn
            180             185             190
Glu Gln Gly Glu Thr Ile Phe Ile Leu Gly Asp Ala Gly Val Gly Lys
            195             200             205
Ser Met Leu Leu Gln Arg Leu Gln Ser Leu Trp Ala Thr Gly Arg Leu
            210             215             220
Asp Ala Gly Val Lys Phe Phe His Phe Arg Cys Arg Met Phe Ser
225             230             235             240
Cys Phe Lys Glu Ser Asp Arg Leu Cys Leu Gln Asp Leu Leu Phe Lys
                245             250             255
His Tyr Cys Tyr Pro Glu Arg Asp Pro Glu Glu Val Phe Ala Phe Leu
            260             265             270
Leu Arg Phe Pro His Val Ala Leu Phe Thr Phe Asp Gly Leu Asp Glu
            275             280             285
Leu His Ser Asp Leu Asp Leu Ser Arg Val Pro Asp Ser Ser Cys Pro
            290             295             300
Trp Glu Pro Ala His Pro Leu Val Leu Leu Ala Asn Leu Leu Ser Gly
305             310             315             320
Lys Leu Leu Lys Gly Ala Ser Lys Leu Leu Thr Ala Arg Thr Gly Ile
                325             330             335
Glu Val Pro Arg Gln Phe Leu Arg Lys Val Leu Leu Arg Gly Phe
            340             345             350
Ser Pro Ser His Leu Arg Ala Tyr Ala Arg Arg Met Phe Pro Glu Arg
            355             360             365
Ala Leu Gln Asp Arg Leu Leu Ser Gln Leu Glu Ala Asn Pro Asn Leu
            370             375             380
Cys Ser Leu Cys Ser Val Pro Leu Phe Cys Trp Ile Ile Phe Arg Cys
385             390             395             400
Phe Gln His Phe Arg Ala Ala Phe Glu Gly Ser Pro Gln Leu Pro Asp
                405             410             415
Cys Thr Met Thr Leu Thr Asp Val Phe Leu Leu Val Thr Glu Val His
            420             425             430
```

-continued

```
Leu Asn Arg Met Gln Pro Ser Ser Leu Val Gln Arg Asn Thr Arg Ser
        435                 440                 445

Pro Val Glu Thr Leu His Ala Gly Arg Asp Thr Leu Cys Ser Leu Gly
    450                 455                 460

Gln Val Ala His Arg Gly Met Glu Lys Ser Leu Phe Val Phe Thr Gln
465                 470                 475                 480

Glu Glu Val Gln Ala Ser Gly Leu Gln Glu Arg Asp Met Gln Leu Gly
                485                 490                 495

Phe Leu Arg Ala Leu Pro Glu Leu Gly Pro Gly Gly Asp Gln Gln Ser
            500                 505                 510

Tyr Glu Phe Phe His Leu Thr Leu Gln Ala Phe Phe Thr Ala Phe Phe
        515                 520                 525

Leu Val Leu Asp Asp Arg Val Gly Thr Gln Glu Leu Leu Arg Phe Phe
        530                 535                 540

Gln Glu Trp Met Pro Pro Ala Gly Ala Ala Thr Thr Ser Cys Tyr Pro
545                 550                 555                 560

Pro Phe Leu Pro Phe Gln Cys Leu Gln Gly Ser Gly Pro Ala Arg Glu
                565                 570                 575

Asp Leu Phe Lys Asn Lys Asp His Phe Gln Phe Thr Asn Leu Phe Leu
            580                 585                 590

Cys Gly Leu Leu Ser Lys Ala Lys Gln Lys Leu Leu Arg His Leu Val
        595                 600                 605

Pro Ala Ala Ala Leu Arg Arg Lys Arg Lys Ala Leu Trp Ala His Leu
    610                 615                 620

Phe Ser Ser Leu Arg Gly Tyr Leu Lys Ser Leu Pro Arg Val Gln Val
625                 630                 635                 640

Glu Ser Phe Asn Gln Val Gln Ala Met Pro Thr Phe Ile Trp Met Leu
                645                 650                 655

Arg Cys Ile Tyr Glu Thr Gln Ser Gln Lys Val Gly Gln Leu Ala Ala
            660                 665                 670

Arg Gly Ile Cys Ala Asn Tyr Leu Lys Leu Thr Tyr Cys Asn Ala Cys
        675                 680                 685

Ser Ala Asp Cys Ser Ala Leu Ser Phe Val Leu His His Phe Pro Lys
    690                 695                 700

Arg Leu Ala Leu Asp Leu Asp Asn Asn Leu Asn Asp Tyr Gly Val
705                 710                 715                 720

Arg Glu Leu Gln Pro Cys Phe Ser Arg Leu Thr Val Leu Arg Leu Ser
                725                 730                 735

Val Asn Gln Ile Thr Asp Gly Gly Val Lys Val Leu Ser Glu Glu Leu
            740                 745                 750

Thr Lys Tyr Lys Ile Val Thr Tyr Leu Gly Leu Tyr Asn Asn Gln Ile
        755                 760                 765

Thr Asp Val Gly Ala Arg Tyr Val Thr Lys Ile Leu Asp Glu Cys Lys
    770                 775                 780

Gly Leu Thr His Leu Lys Leu Gly Lys Asn Lys Ile Thr Ser Glu Gly
785                 790                 795                 800

Gly Lys Tyr Leu Ala Leu Ala Val Lys Asn Ser Lys Ser Ile Ser Glu
                805                 810                 815

Val Gly Met Trp Gly Asn Gln Val Gly Asp Glu Gly Ala Lys Ala Phe
            820                 825                 830

Ala Glu Ala Leu Arg Asn His Pro Ser Leu Thr Thr Leu Ser Leu Ala
        835                 840                 845
```

```
Ser Asn Gly Ile Ser Thr Glu Gly Gly Lys Ser Leu Ala Arg Ala Leu
    850                 855                 860

Gln Gln Asn Thr Ser Leu Glu Ile Leu Trp Leu Thr Gln Asn Glu Leu
865                 870                 875                 880

Asn Asp Glu Val Ala Glu Ser Leu Ala Glu Met Leu Lys Val Asn Gln
                885                 890                 895

Thr Leu Lys His Leu Trp Leu Ile Gln Asn Gln Ile Thr Ala Lys Gly
                900                 905                 910

Thr Ala Gln Leu Ala Asp Ala Leu Gln Ser Asn Thr Gly Ile Thr Glu
                915                 920                 925

Ile Cys Leu Asn Gly Asn Leu Ile Lys Pro Glu Glu Ala Lys Val Tyr
930                 935                 940

Glu Asp Glu Lys Arg Ile Ile Cys Phe
945                 950

<210> SEQ ID NO 13
<211> LENGTH: 445
<212> TYPE: PRT
<213> ORGANISM: Homo sapiens

<400> SEQUENCE: 13

Met Ala Ala Pro Glu Glu Arg Asp Leu Thr Gln Glu Gln Thr Glu Lys
1               5                   10                  15

Leu Leu Gln Phe Gln Asp Leu Thr Gly Ile Glu Ser Met Asp Gln Cys
                20                  25                  30

Arg His Thr Leu Glu Gln His Asn Trp Asn Ile Glu Ala Ala Val Gln
            35                  40                  45

Asp Arg Leu Asn Glu Gln Glu Gly Val Pro Ser Val Phe Asn Pro Pro
    50                  55                  60

Pro Ser Arg Pro Leu Gln Val Asn Thr Ala Asp His Arg Ile Tyr Ser
65                  70                  75                  80

Tyr Val Val Ser Arg Pro Gln Pro Arg Gly Leu Leu Gly Trp Gly Tyr
                85                  90                  95

Tyr Leu Ile Met Leu Pro Phe Arg Phe Thr Tyr Tyr Thr Ile Leu Asp
                100                 105                 110

Ile Phe Arg Phe Ala Leu Arg Phe Ile Arg Pro Asp Pro Arg Ser Arg
            115                 120                 125

Val Thr Asp Pro Val Gly Asp Ile Val Ser Phe Met His Ser Phe Glu
130                 135                 140

Glu Lys Tyr Gly Arg Ala His Pro Val Tyr Gln Gly Thr Tyr Ser
145                 150                 155                 160

Gln Ala Leu Asn Asp Ala Lys Arg Glu Leu Arg Phe Leu Val Tyr
                165                 170                 175

Leu His Gly Asp Asp His Gln Asp Ser Asp Glu Phe Cys Arg Asn Thr
                180                 185                 190

Leu Cys Ala Pro Glu Val Ile Ser Leu Ile Asn Thr Arg Met Leu Phe
            195                 200                 205

Trp Ala Cys Ser Thr Asn Lys Pro Glu Gly Tyr Arg Val Ser Gln Ala
210                 215                 220

Leu Arg Glu Asn Thr Tyr Pro Phe Leu Ala Met Ile Met Leu Lys Asp
225                 230                 235                 240

Arg Arg Met Thr Val Val Gly Arg Leu Glu Gly Leu Ile Gln Pro Asp
                245                 250                 255

Asp Leu Ile Asn Gln Leu Thr Phe Ile Met Asp Ala Asn Gln Thr Tyr
                260                 265                 270
```

-continued

```
Leu Val Ser Glu Arg Leu Glu Arg Glu Glu Arg Asn Gln Thr Gln Val
            275                 280                 285

Leu Arg Gln Gln Gln Asp Glu Ala Tyr Leu Ala Ser Leu Arg Ala Asp
        290                 295                 300

Gln Glu Lys Glu Arg Lys Lys Arg Glu Glu Arg Lys Arg Arg
305             310                 315                 320

Lys Glu Glu Glu Val Gln Gln Lys Leu Ala Glu Arg Arg Arg
                325                 330                 335

Gln Asn Leu Gln Glu Glu Lys Glu Arg Lys Leu Glu Cys Leu Pro Pro
            340                 345                 350

Glu Pro Ser Pro Asp Asp Pro Glu Ser Val Lys Ile Ile Phe Lys Leu
        355                 360                 365

Pro Asn Asp Ser Arg Val Glu Arg Arg Phe His Phe Ser Gln Ser Leu
        370                 375                 380

Thr Val Ile His Asp Phe Leu Phe Ser Leu Lys Glu Ser Pro Glu Lys
385                 390                 395                 400

Phe Gln Ile Glu Ala Asn Phe Pro Arg Arg Val Leu Pro Cys Ile Pro
            405                 410                 415

Ser Glu Glu Trp Pro Asn Pro Pro Thr Leu Gln Glu Ala Gly Leu Ser
            420                 425                 430

His Thr Glu Val Leu Phe Val Gln Asp Leu Thr Asp Glu
            435                 440                 445

<210> SEQ ID NO 14
<211> LENGTH: 340
<212> TYPE: PRT
<213> ORGANISM: Homo sapiens
<220> FEATURE:
<221> NAME/KEY: SITE
<222> LOCATION: (221)
<223> OTHER INFORMATION: Xaa equals any of the naturally occurring
      L-amino acids
<221> NAME/KEY: SITE
<222> LOCATION: (224)
<223> OTHER INFORMATION: Xaa equals any of the naturally occurring
      L-amino acids

<400> SEQUENCE: 14

Met Thr Ser Gln Leu Arg Trp Ser Trp Ser Ser Pro Thr Cys Thr His
1               5                  10                  15

Ala Ser Arg Tyr Trp Leu Trp Tyr Thr Thr Lys Asn Cys Val Gly Gly
            20                  25                  30

Leu Ala Arg Lys Ala Trp Glu Arg Leu Arg Leu His Arg Val Asn Leu
        35                  40                  45

Ile Ala Leu Gln Arg Arg Arg Asp Pro Glu Gln Val Leu Leu Gln Cys
    50                  55                  60

Leu Pro Arg Asn Lys Val Asp Ala Thr Leu Arg Arg Leu Leu Glu Arg
65                  70                  75                  80

Tyr Arg Gly Pro Glu Pro Ser Asp Thr Val Glu Met Phe Glu Gly Glu
                85                  90                  95

Glu Phe Phe Ala Ala Phe Glu Arg Gly Ile Asp Val Asp Ala Asp Arg
            100                 105                 110

Pro Asp Cys Val Glu Gly Arg Ile Cys Phe Val Phe Tyr Ser His Leu
        115                 120                 125

Lys Asn Val Lys Glu Val Tyr Val Thr Thr Thr Leu Asp Arg Glu Ala
    130                 135                 140

Gln Ala Val Arg Gly Gln Val Ser Phe Tyr Arg Gly Ala Val Pro Val
```

-continued

```
            145                 150                 155                 160
        Arg Val Pro Glu Glu Ala Glu Ala Ala Arg Gln Arg Lys Gly Ala Asp
                        165                 170                 175
        Ala Leu Trp Met Ala Thr Leu Pro Ile Lys Leu Pro Arg Leu Arg Gly
                        180                 185                 190
        Ser Glu Gly Pro Arg Arg Gly Ala Gly Leu Ser Leu Ala Pro Leu Asn
                        195                 200                 205
        Leu Gly Asp Ala Glu Thr Gly Phe Leu Thr Gln Ser Xaa Leu Leu Xaa
                    210                 215                 220
        Val Ala Gly Arg Leu Gly Leu Asp Trp Pro Ala Val Ala Leu His Leu
        225                 230                 235                 240
        Gly Val Ser Tyr Arg Glu Val Gln Arg Ile Arg His Glu Phe Arg Asp
                        245                 250                 255
        Asp Leu Asp Glu Gln Ile Arg His Met Leu Phe Ser Trp Ala Glu Arg
                        260                 265                 270
        Gln Ala Gly Gln Pro Gly Ala Gly Leu Leu Val Gln Ala Leu Glu
                        275                 280                 285
        Gln Ser Asp Arg Gln Asp Val Ala Glu Val Arg Ala Val Leu Glu
                    290                 295                 300
        Leu Gly Arg Arg Lys Tyr Gln Asp Ser Ile Arg Arg Met Gly Leu Ala
        305                 310                 315                 320
        Pro Lys Asp Pro Ala Leu Pro Gly Ser Ser Ala Pro Gln Pro Glu
                        325                 330                 335
        Pro Ala Gln Ala
                    340

<210> SEQ ID NO 15
<211> LENGTH: 317
<212> TYPE: PRT
<213> ORGANISM: Homo sapiens
<220> FEATURE:
<221> NAME/KEY: SITE
<222> LOCATION: (254)
<223> OTHER INFORMATION: Xaa equals any of the naturally occurring
      L-amino acids

<400> SEQUENCE: 15

Met Gly Tyr Asp Val Thr Arg Phe Gln Gly Asp Val Asp Glu Asp Leu
        1               5                   10                  15
        Ile Cys Pro Ile Cys Ser Gly Val Leu Glu Glu Pro Val Gln Ala Pro
                        20                  25                  30
        His Cys Glu His Ala Phe Cys Asn Ala Cys Ile Thr Gln Trp Phe Ser
                        35                  40                  45
        Gln Gln Gln Thr Cys Pro Val Asp Arg Ser Val Thr Val Ala His
                    50                  55                  60
        Leu Arg Pro Val Pro Arg Ile Met Arg Asn Met Leu Ser Lys Leu Gln
        65                  70                  75                  80
        Ile Ala Cys Asp Asn Ala Val Phe Gly Cys Ser Ala Val Val Arg Leu
                        85                  90                  95
        Asp Asn Leu Met Ser His Leu Ser Asp Cys Glu His Asn Pro Lys Arg
                        100                 105                 110
        Pro Val Thr Cys Glu Gln Gly Cys Gly Leu Glu Met Pro Lys Asp Glu
                    115                 120                 125
        Leu Pro Asn His Asn Cys Ile Lys His Leu Arg Ser Val Val Gln Gln
                    130                 135                 140
        Gln Gln Thr Arg Ile Ala Glu Leu Glu Lys Thr Ser Ala Glu His Lys
```

-continued

```
                145                 150                 155                 160
His Gln Leu Ala Glu Gln Lys Arg Asp Ile Gln Leu Lys Ala Tyr
                    165                 170                 175
Met Arg Ala Ile Arg Ser Val Asn Pro Asn Leu Gln Asn Leu Glu Glu
                180                 185                 190
Thr Ile Glu Tyr Asn Glu Ile Leu Glu Trp Val Asn Ser Leu Gln Pro
            195                 200                 205
Ala Arg Val Thr Arg Trp Gly Gly Met Ile Ser Thr Pro Asp Ala Val
        210                 215                 220
Leu Gln Ala Val Ile Lys Arg Ser Leu Val Glu Ser Gly Cys Pro Ala
225                 230                 235                 240
Ser Ile Val Asn Glu Leu Ile Glu Asn Ala His Glu Arg Xaa Trp Pro
                    245                 250                 255
Gln Gly Leu Ala Thr Leu Glu Thr Arg Gln Met Asn Arg Arg Tyr Tyr
                260                 265                 270
Glu Asn Tyr Val Ala Lys Arg Ile Pro Gly Lys Gln Ala Val Val Val
            275                 280                 285
Met Ala Cys Glu Asn Gln His Met Gly Asp Asp Met Val Gln Glu Pro
        290                 295                 300
Gly Leu Val Met Ile Phe Ala His Gly Val Glu Glu Ile
305                 310                 315

<210> SEQ ID NO 16
<211> LENGTH: 90
<212> TYPE: PRT
<213> ORGANISM: Homo sapiens

<400> SEQUENCE: 16

Met Ser Gln Leu Gly Ser Leu Glu Glu Arg Ile Gln Arg Ser His Trp
  1               5                  10                  15
Lys Trp Ile Asn Arg Asn Val Ile Ile Asp Phe Ser Val Gln Asp Arg
                 20                  25                  30
Arg Arg Leu Gly Asn Ile Tyr His Thr Gly Phe Gln Asp Arg Leu Val
             35                  40                  45
Thr Trp His Val Pro Ile Asp Cys Ile Leu Met His Phe Pro Gln Glu
         50                  55                  60
Cys Leu Lys Lys Val Val Ile Phe Leu Leu Asn Phe Phe Gln Pro Leu
 65                  70                  75                  80
Leu Asp Ile Ser Leu Phe Tyr Pro Leu Thr
                 85                  90

<210> SEQ ID NO 17
<211> LENGTH: 216
<212> TYPE: PRT
<213> ORGANISM: Homo sapiens

<400> SEQUENCE: 17

Met Arg Leu Ser Ala Leu Leu Ala Leu Ala Ser Lys Val Thr Leu Pro
  1               5                  10                  15
Pro His Tyr Arg Tyr Gly Met Ser Pro Pro Gly Ser Val Ala Asp Lys
                 20                  25                  30
Arg Lys Asn Pro Pro Trp Ile Arg Arg Pro Val Val Val Glu Pro
             35                  40                  45
Ile Ser Asp Glu Asp Trp Tyr Leu Phe Cys Gly Asp Thr Val Glu Ile
         50                  55                  60
Leu Glu Gly Lys Asp Ala Gly Lys Gln Gly Lys Val Val Gln Val Ile
```

```
                65                  70                  75                  80
Arg Gln Arg Asn Trp Val Val Gly Gly Leu Asn Thr His Tyr Arg
                    85                  90                  95
Tyr Ile Gly Lys Thr Met Asp Tyr Arg Gly Thr Met Ile Pro Ser Glu
                100                 105                 110
Ala Pro Leu Leu His Arg Gln Val Lys Leu Val Asp Pro Met Asp Arg
                115                 120                 125
Lys Pro Thr Glu Ile Glu Trp Arg Phe Thr Glu Ala Gly Glu Arg Val
    130                 135                 140
Arg Val Ser Thr Arg Ser Gly Arg Ile Ile Pro Lys Pro Glu Phe Pro
145                 150                 155                 160
Arg Ala Asp Gly Ile Val Pro Glu Thr Trp Ile Asp Gly Pro Lys Asp
                165                 170                 175
Thr Ser Val Glu Asp Ala Leu Glu Arg Thr Tyr Val Pro Cys Leu Lys
                180                 185                 190
Thr Leu Gln Glu Glu Val Met Glu Ala Met Gly Ile Lys Glu Thr Arg
                195                 200                 205
Lys Tyr Lys Lys Val Tyr Trp Tyr
    210                 215

<210> SEQ ID NO 18
<211> LENGTH: 613
<212> TYPE: PRT
<213> ORGANISM: Homo sapiens

<400> SEQUENCE: 18

Met Phe Arg Cys Gly Gly Leu Ala Ala Gly Ala Leu Lys Gln Lys Leu
1               5                   10                  15
Val Pro Leu Val Arg Thr Val Cys Val Arg Ser Pro Arg Gln Arg Asn
                20                  25                  30
Arg Leu Pro Gly Asn Leu Phe Gln Arg Trp His Val Pro Leu Glu Leu
            35                  40                  45
Gln Met Thr Arg Gln Met Ala Ser Ser Gly Ala Ser Gly Gly Lys Ile
        50                  55                  60
Asp Asn Ser Val Leu Val Leu Ile Val Gly Leu Ser Thr Val Gly Ala
65                  70                  75                  80
Gly Ala Tyr Ala Tyr Lys Thr Met Lys Glu Asp Glu Lys Arg Tyr Asn
                85                  90                  95
Glu Arg Ile Ser Gly Leu Gly Leu Thr Pro Glu Gln Lys Gln Lys Lys
                100                 105                 110
Ala Ala Leu Ser Ala Ser Glu Gly Glu Glu Val Pro Gln Asp Lys Ala
                115                 120                 125
Pro Ser His Val Pro Phe Leu Leu Ile Gly Gly Thr Ala Ala Phe
    130                 135                 140
Ala Ala Ala Arg Ser Ile Arg Ala Arg Asp Pro Gly Ala Arg Val Leu
145                 150                 155                 160
Ile Val Ser Glu Asp Pro Glu Leu Pro Tyr Met Arg Pro Pro Leu Ser
                165                 170                 175
Lys Glu Leu Trp Phe Ser Asp Asp Pro Asn Val Thr Lys Thr Leu Arg
                180                 185                 190
Phe Lys Gln Trp Asn Gly Lys Glu Arg Ser Ile Tyr Phe Gln Pro Pro
            195                 200                 205
Ser Phe Tyr Val Ser Ala Gln Asp Leu Pro His Ile Glu Asn Gly Gly
    210                 215                 220
```

-continued

```
Val Ala Val Leu Thr Gly Lys Lys Val Val Gln Leu Asp Val Arg Asp
225                 230                 235                 240

Asn Met Val Lys Leu Asn Asp Gly Ser Gln Ile Thr Tyr Glu Lys Cys
            245                 250                 255

Leu Ile Ala Thr Gly Gly Thr Pro Arg Ser Leu Ser Ala Ile Asp Arg
        260                 265                 270

Ala Gly Ala Glu Val Lys Ser Arg Thr Thr Leu Phe Arg Lys Ile Gly
    275                 280                 285

Asp Phe Arg Ser Leu Glu Lys Ile Ser Arg Glu Val Lys Ser Ile Thr
290                 295                 300

Ile Ile Gly Gly Gly Phe Leu Gly Ser Glu Leu Ala Cys Ala Leu Gly
305                 310                 315                 320

Arg Lys Ala Arg Ala Leu Gly Thr Glu Val Ile Gln Leu Phe Pro Glu
                325                 330                 335

Lys Gly Asn Met Gly Lys Ile Leu Pro Glu Tyr Leu Ser Asn Trp Thr
            340                 345                 350

Met Glu Lys Val Arg Arg Glu Gly Val Lys Val Met Pro Asn Ala Ile
        355                 360                 365

Val Gln Ser Val Gly Val Ser Ser Gly Lys Leu Leu Ile Lys Leu Lys
    370                 375                 380

Asp Gly Arg Lys Val Glu Thr Asp His Ile Val Ala Ala Val Gly Leu
385                 390                 395                 400

Glu Pro Asn Val Glu Leu Ala Lys Thr Gly Gly Leu Glu Ile Asp Ser
                405                 410                 415

Asp Phe Gly Gly Phe Arg Val Asn Ala Glu Leu Gln Ala Arg Ser Asn
            420                 425                 430

Ile Trp Val Ala Gly Asp Ala Ala Cys Phe Tyr Asp Ile Lys Leu Gly
        435                 440                 445

Arg Arg Arg Val Glu His His Asp His Ala Val Val Ser Gly Arg Leu
    450                 455                 460

Ala Gly Glu Asn Met Thr Gly Ala Ala Lys Pro Tyr Trp His Gln Ser
465                 470                 475                 480

Met Phe Trp Ser Asp Leu Gly Pro Asp Val Gly Tyr Glu Ala Ile Gly
                485                 490                 495

Leu Val Asp Ser Ser Leu Pro Thr Val Gly Val Phe Ala Lys Ala Thr
            500                 505                 510

Ala Gln Asp Asn Pro Lys Ser Ala Thr Glu Gln Ser Gly Thr Gly Ile
        515                 520                 525

Arg Ser Glu Ser Glu Thr Glu Ser Glu Ala Ser Glu Ile Thr Ile Pro
    530                 535                 540

Pro Ser Thr Pro Ala Val Pro Gln Ala Pro Val Gln Gly Glu Asp Tyr
545                 550                 555                 560

Gly Lys Gly Val Ile Phe Tyr Leu Arg Asp Lys Val Val Val Gly Ile
                565                 570                 575

Val Leu Trp Asn Ile Phe Asn Arg Met Pro Ile Ala Arg Lys Ile Ile
            580                 585                 590

Lys Asp Gly Glu Gln His Glu Asp Leu Asn Glu Val Ala Lys Leu Phe
        595                 600                 605

Asn Ile His Glu Asp
        610

<210> SEQ ID NO 19
<211> LENGTH: 705
<212> TYPE: PRT
```

-continued

```
<213> ORGANISM: Homo sapiens
<220> FEATURE:
<221> NAME/KEY: SITE
<222> LOCATION: (236)
<223> OTHER INFORMATION: Xaa equals any of the naturally occurring
      L-amino acids
<221> NAME/KEY: SITE
<222> LOCATION: (264)
<223> OTHER INFORMATION: Xaa equals any of the naturally occurring
      L-amino acids
<221> NAME/KEY: SITE
<222> LOCATION: (633)
<223> OTHER INFORMATION: Xaa equals any of the naturally occurring
      L-amino acids
<221> NAME/KEY: SITE
<222> LOCATION: (636)
<223> OTHER INFORMATION: Xaa equals any of the naturally occurring
      L-amino acids

<400> SEQUENCE: 19
```

Met Ser Arg Asp Leu Leu Phe Lys His Tyr Cys Tyr Pro Glu Arg Asp
 1               5                  10                  15

Pro Glu Glu Val Phe Ala Phe Leu Leu Arg Phe Pro His Val Ala Leu
            20                  25                  30

Phe Thr Phe Asp Gly Leu Asp Glu Leu His Ser Asp Leu Asp Leu Ser
        35                  40                  45

Arg Val Pro Asp Ser Ser Cys Pro Trp Glu Pro Ala His Pro Leu Val
    50                  55                  60

Leu Leu Ala Asn Leu Leu Ser Gly Lys Leu Leu Lys Gly Ala Ser Lys
65                  70                  75                  80

Leu Leu Thr Ala Arg Thr Gly Ile Glu Val Pro Arg Gln Phe Leu Arg
                85                  90                  95

Lys Lys Val Leu Leu Arg Gly Phe Ser Pro Ser His Leu Arg Ala Tyr
            100                 105                 110

Ala Arg Arg Met Phe Pro Glu Arg Ala Leu Gln Asp Arg Leu Leu Ser
        115                 120                 125

Gln Leu Glu Ala Asn Pro Asn Leu Cys Ser Leu Cys Ser Val Pro Leu
    130                 135                 140

Phe Cys Trp Ile Ile Phe Arg Cys Phe Gln His Phe Arg Ala Ala Phe
145                 150                 155                 160

Glu Gly Ser Pro Gln Leu Pro Asp Cys Thr Met Thr Leu Thr Asp Val
                165                 170                 175

Phe Leu Leu Val Thr Glu Val His Leu Asn Arg Met Gln Pro Ser Ser
            180                 185                 190

Leu Val Gln Arg Asn Thr Arg Ser Pro Val Glu Thr Leu His Ala Gly
        195                 200                 205

Arg Asp Thr Leu Cys Ser Leu Gly Gln Val Ala His Arg Gly Met Glu
    210                 215                 220

Lys Ser Leu Phe Val Phe Thr Gln Glu Val Xaa Ala Ser Gly Leu
225                 230                 235                 240

Gln Glu Arg Asp Met Gln Leu Gly Phe Leu Arg Ala Leu Pro Glu Leu
                245                 250                 255

Gly Pro Gly Gly Asp Gln Xaa Tyr Glu Phe Phe His Leu Thr Leu
            260                 265                 270

Gln Ala Phe Phe Thr Ala Phe Leu Val Leu Asp Asp Arg Val Gly
        275                 280                 285

Thr Gln Glu Leu Leu Arg Phe Phe Gln Glu Trp Met Pro Pro Ala Gly
    290                 295                 300

Ala Ala Thr Thr Ser Cys Tyr Pro Pro Phe Leu Pro Phe Gln Cys Leu

```
                305                 310                 315                 320
Gln Gly Ser Gly Pro Ala Arg Glu Asp Leu Phe Lys Asn Lys Asp His
                325                 330                 335
Phe Gln Phe Thr Asn Leu Phe Leu Cys Gly Leu Leu Ser Lys Ala Lys
                340                 345                 350
Gln Lys Leu Leu Arg His Leu Val Pro Ala Ala Leu Arg Arg Lys
                355                 360                 365
Arg Lys Ala Leu Trp Ala His Leu Phe Ser Ser Leu Arg Gly Tyr Leu
        370                 375                 380
Lys Ser Leu Pro Arg Val Gln Val Glu Ser Phe Asn Gln Val Gln Ala
385                 390                 395                 400
Met Pro Thr Phe Ile Trp Met Leu Arg Cys Ile Tyr Glu Thr Gln Ser
                405                 410                 415
Gln Lys Val Gly Gln Leu Ala Ala Arg Gly Ile Cys Ala Asn Tyr Leu
                420                 425                 430
Lys Leu Thr Tyr Cys Asn Ala Cys Ser Ala Asp Cys Ser Ala Leu Ser
                435                 440                 445
Phe Val Leu His His Phe Pro Lys Arg Leu Ala Leu Asp Leu Asp Asn
        450                 455                 460
Asn Asn Leu Asn Asp Tyr Gly Val Arg Glu Leu Gln Pro Cys Phe Ser
465                 470                 475                 480
Arg Leu Thr Val Leu Arg Leu Ser Val Asn Gln Ile Thr Asp Gly Gly
                485                 490                 495
Val Lys Val Leu Ser Glu Glu Leu Thr Lys Tyr Lys Ile Val Thr Tyr
                500                 505                 510
Leu Gly Leu Tyr Asn Asn Gln Ile Thr Asp Val Gly Ala Arg Tyr Val
        515                 520                 525
Thr Lys Ile Leu Asp Glu Cys Lys Gly Leu Thr His Leu Lys Leu Gly
        530                 535                 540
Lys Asn Lys Ile Thr Ser Glu Gly Gly Lys Tyr Leu Ala Leu Ala Val
545                 550                 555                 560
Lys Asn Ser Lys Ser Ile Ser Glu Val Gly Met Trp Gly Asn Gln Val
                565                 570                 575
Gly Asp Glu Gly Ala Lys Ala Phe Ala Glu Ala Leu Arg Asn His Pro
        580                 585                 590
Ser Leu Thr Thr Leu Ser Leu Ala Ser Asn Gly Ile Ser Thr Glu Gly
        595                 600                 605
Gly Lys Ser Leu Ala Arg Ala Leu Gln Gln Asn Thr Ser Leu Glu Ile
        610                 615                 620
Leu Trp Leu Thr Gln Asn Glu Leu Xaa Asp Glu Xaa Ala Glu Ser Leu
625                 630                 635                 640
Ala Glu Met Leu Lys Val Asn Gln Thr Leu Lys His Leu Trp Leu Ile
                645                 650                 655
Gln Asn Gln Ile Thr Ala Lys Gly Thr Ala Gln Leu Ala Asp Ala Leu
                660                 665                 670
Gln Ser Asn Thr Gly Ile Thr Glu Ile Cys Leu Asn Gly Asn Leu Ile
                675                 680                 685
Lys Pro Glu Glu Ala Lys Val Tyr Glu Asp Glu Lys Arg Ile Ile Cys
        690                 695                 700
Phe
705

<210> SEQ ID NO 20
```

-continued

```
<211> LENGTH: 40
<212> TYPE: PRT
<213> ORGANISM: Homo sapiens

<400> SEQUENCE: 20

Pro Gly Ser Thr His Ala Ser Gly Lys Ile Gln Asn Lys Trp Leu Arg
1               5                   10                  15

Pro Ser Pro Arg Ser His Arg Thr Pro Glu Ser Gly Arg Val Leu Ser
            20                  25                  30

Leu Phe Arg Leu Pro Pro Gly
        35              40

<210> SEQ ID NO 21
<211> LENGTH: 14
<212> TYPE: PRT
<213> ORGANISM: Homo sapiens

<400> SEQUENCE: 21

Thr Ala Trp Pro Ala Ser Trp Thr Thr Pro Pro Ala Ser Ser
1               5                   10

<210> SEQ ID NO 22
<211> LENGTH: 705
<212> TYPE: PRT
<213> ORGANISM: Homo sapiens
<220> FEATURE:
<221> NAME/KEY: SITE
<222> LOCATION: (236)
<223> OTHER INFORMATION: Xaa equals any of the naturally occurring
      L-amino acids
<221> NAME/KEY: SITE
<222> LOCATION: (264)
<223> OTHER INFORMATION: Xaa equals any of the naturally occurring
      L-amino acids
<221> NAME/KEY: SITE
<222> LOCATION: (633)
<223> OTHER INFORMATION: Xaa equals any of the naturally occurring
      L-amino acids
<221> NAME/KEY: SITE
<222> LOCATION: (636)
<223> OTHER INFORMATION: Xaa equals any of the naturally occurring
      L-amino acids

<400> SEQUENCE: 22

Met Ser Arg Asp Leu Leu Phe Lys His Tyr Cys Tyr Pro Glu Arg Asp
1               5                   10                  15

Pro Glu Glu Val Phe Ala Phe Leu Leu Arg Phe Pro His Val Ala Leu
            20                  25                  30

Phe Thr Phe Asp Gly Leu Asp Glu Leu His Ser Asp Leu Asp Leu Ser
        35                  40                  45

Arg Val Pro Asp Ser Ser Cys Pro Trp Glu Pro Ala His Pro Leu Val
    50                  55                  60

Leu Leu Ala Asn Leu Leu Ser Gly Lys Leu Leu Lys Gly Ala Ser Lys
65                  70                  75                  80

Leu Leu Thr Ala Arg Thr Gly Ile Glu Val Pro Arg Gln Phe Leu Arg
                85                  90                  95

Lys Lys Val Leu Leu Arg Gly Phe Ser Pro Ser His Leu Arg Ala Tyr
            100                 105                 110

Ala Arg Arg Met Phe Pro Glu Arg Ala Leu Gln Asp Arg Leu Leu Ser
        115                 120                 125

Gln Leu Glu Ala Asn Pro Asn Leu Cys Ser Leu Cys Ser Val Pro Leu
    130                 135                 140

Phe Cys Trp Ile Ile Phe Arg Cys Phe Gln His Phe Arg Ala Ala Phe
```

-continued

```
            145                 150                 155                 160
        Glu Gly Ser Pro Gln Leu Pro Asp Cys Thr Met Thr Leu Thr Asp Val
                        165                 170                 175
        Phe Leu Leu Val Thr Glu Val His Leu Asn Arg Met Gln Pro Ser Ser
                        180                 185                 190
        Leu Val Gln Arg Asn Thr Arg Ser Pro Val Glu Thr Leu His Ala Gly
                        195                 200                 205
        Arg Asp Thr Leu Cys Ser Leu Gly Gln Val Ala His Arg Gly Met Glu
                        210                 215                 220
        Lys Ser Leu Phe Val Phe Thr Gln Glu Val Xaa Ala Ser Gly Leu
        225                 230                 235                 240
        Gln Glu Arg Asp Met Gln Leu Gly Phe Leu Arg Ala Leu Pro Glu Leu
                        245                 250                 255
        Gly Pro Gly Gly Asp Gln Gln Xaa Tyr Glu Phe Phe His Leu Thr Leu
                        260                 265                 270
        Gln Ala Phe Phe Thr Ala Phe Leu Val Leu Asp Asp Arg Val Gly
                        275                 280                 285
        Thr Gln Glu Leu Leu Arg Phe Phe Gln Glu Trp Met Pro Pro Ala Gly
                        290                 295                 300
        Ala Ala Thr Thr Ser Cys Tyr Pro Pro Phe Leu Pro Phe Gln Cys Leu
        305                 310                 315                 320
        Gln Gly Ser Gly Pro Ala Arg Glu Asp Leu Phe Lys Asn Lys Asp His
                        325                 330                 335
        Phe Gln Phe Thr Asn Leu Phe Leu Cys Gly Leu Leu Ser Lys Ala Lys
                        340                 345                 350
        Gln Lys Leu Leu Arg His Leu Val Pro Ala Ala Ala Leu Arg Arg Lys
                        355                 360                 365
        Arg Lys Ala Leu Trp Ala His Leu Phe Ser Ser Leu Arg Gly Tyr Leu
                        370                 375                 380
        Lys Ser Leu Pro Arg Val Gln Val Glu Ser Phe Asn Gln Val Gln Ala
        385                 390                 395                 400
        Met Pro Thr Phe Ile Trp Met Leu Arg Cys Ile Tyr Glu Thr Gln Ser
                        405                 410                 415
        Gln Lys Val Gly Gln Leu Ala Ala Arg Gly Ile Cys Ala Asn Tyr Leu
                        420                 425                 430
        Lys Leu Thr Tyr Cys Asn Ala Cys Ser Ala Asp Cys Ser Ala Leu Ser
                        435                 440                 445
        Phe Val Leu His His Phe Pro Lys Arg Leu Ala Leu Asp Leu Asp Asn
        450                 455                 460
        Asn Asn Leu Asn Asp Tyr Gly Val Arg Glu Leu Gln Pro Cys Phe Ser
        465                 470                 475                 480
        Arg Leu Thr Val Leu Arg Leu Ser Val Asn Gln Ile Thr Asp Gly Gly
                        485                 490                 495
        Val Lys Val Leu Ser Glu Glu Leu Thr Lys Tyr Lys Ile Val Thr Tyr
                        500                 505                 510
        Leu Gly Leu Tyr Asn Asn Gln Ile Thr Asp Val Gly Ala Arg Tyr Val
                        515                 520                 525
        Thr Lys Ile Leu Asp Glu Cys Lys Gly Leu Thr His Leu Lys Leu Gly
                        530                 535                 540
        Lys Asn Lys Ile Thr Ser Glu Gly Gly Lys Tyr Leu Ala Leu Ala Val
        545                 550                 555                 560
        Lys Asn Ser Lys Ser Ile Ser Glu Val Gly Met Trp Gly Asn Gln Val
                        565                 570                 575
```

```
Gly Asp Glu Gly Ala Lys Ala Phe Ala Glu Ala Leu Arg Asn His Pro
            580                 585                 590

Ser Leu Thr Thr Leu Ser Leu Ala Ser Asn Gly Ile Ser Thr Glu Gly
        595                 600                 605

Gly Lys Ser Leu Ala Arg Ala Leu Gln Gln Asn Thr Ser Leu Glu Ile
    610                 615                 620

Leu Trp Leu Thr Gln Asn Glu Leu Xaa Asp Glu Xaa Ala Glu Ser Leu
625                 630                 635                 640

Ala Glu Met Leu Lys Val Asn Gln Thr Leu Lys His Leu Trp Leu Ile
                645                 650                 655

Gln Asn Gln Ile Thr Ala Lys Gly Thr Ala Gln Leu Ala Asp Ala Leu
            660                 665                 670

Gln Ser Asn Thr Gly Ile Thr Glu Ile Cys Leu Asn Gly Asn Leu Ile
        675                 680                 685

Lys Pro Glu Glu Ala Lys Val Tyr Glu Asp Lys Arg Ile Ile Cys
    690                 695                 700

Phe
705

<210> SEQ ID NO 23
<211> LENGTH: 50
<212> TYPE: PRT
<213> ORGANISM: Homo sapiens

<400> SEQUENCE: 23

Ala Pro Cys Cys Ala Cys His Arg Ala Val Pro Ala Ser Ser Asn
1               5                   10                  15

Arg Ser Pro Cys Ser Cys Leu Cys Pro Leu Ala Ser Gln Ala Ser Val
            20                  25                  30

Trp Thr Ala Pro Ala Cys Thr Cys Cys Thr Gly Pro Leu Leu Gln Pro
        35                  40                  45

Pro Gly
    50

<210> SEQ ID NO 24
<211> LENGTH: 34
<212> TYPE: PRT
<213> ORGANISM: Homo sapiens

<400> SEQUENCE: 24

Ala Trp Trp Arg Arg Lys Gly Thr Trp Pro Thr Cys Ser Ser Glu
1               5                   10                  15

Ala Leu Val Lys Gly Thr Leu Thr Ser Cys Pro Ile Leu Asp Ser Ile
            20                  25                  30

Cys Lys

<210> SEQ ID NO 25
<211> LENGTH: 18
<212> TYPE: PRT
<213> ORGANISM: Homo sapiens

<400> SEQUENCE: 25

Gln Gly Arg Phe Arg Ala Phe Cys Trp Gln Arg Asp Phe Leu Gln Pro
1               5                   10                  15

Pro Gly

<210> SEQ ID NO 26
```

<211> LENGTH: 613
<212> TYPE: PRT
<213> ORGANISM: Homo sapiens

<400> SEQUENCE: 26

```
Met Phe Arg Cys Gly Gly Leu Ala Ala Gly Ala Leu Lys Gln Lys Leu
 1               5                  10                  15

Val Pro Leu Val Arg Thr Val Cys Val Arg Ser Pro Arg Gln Arg Asn
             20                  25                  30

Arg Leu Pro Gly Asn Leu Phe Gln Arg Trp His Val Pro Leu Glu Leu
         35                  40                  45

Gln Met Thr Arg Gln Met Ala Ser Ser Gly Ala Ser Gly Gly Lys Ile
 50                  55                  60

Asp Asn Ser Val Leu Val Leu Ile Val Gly Leu Ser Thr Val Gly Ala
 65                  70                  75                  80

Gly Ala Tyr Ala Tyr Lys Thr Met Lys Glu Asp Glu Lys Arg Tyr Asn
                 85                  90                  95

Glu Arg Ile Ser Gly Leu Gly Leu Thr Pro Glu Gln Lys Gln Lys Lys
                100                 105                 110

Ala Ala Leu Ser Ala Ser Glu Gly Glu Glu Val Pro Gln Asp Lys Ala
            115                 120                 125

Pro Ser His Val Pro Phe Leu Leu Ile Gly Gly Thr Ala Ala Phe
130                 135                 140

Ala Ala Ala Arg Ser Ile Arg Ala Arg Asp Pro Gly Ala Arg Val Leu
145                 150                 155                 160

Ile Val Ser Glu Asp Pro Glu Leu Pro Tyr Met Arg Pro Pro Leu Ser
                165                 170                 175

Lys Glu Leu Trp Phe Ser Asp Asp Pro Asn Val Thr Lys Thr Leu Arg
            180                 185                 190

Phe Lys Gln Trp Asn Gly Lys Glu Arg Ser Ile Tyr Phe Gln Pro Pro
        195                 200                 205

Ser Phe Tyr Val Ser Ala Gln Asp Leu Pro His Ile Glu Asn Gly Gly
    210                 215                 220

Val Ala Val Leu Thr Gly Lys Lys Val Gln Leu Asp Val Arg Asp
225                 230                 235                 240

Asn Met Val Lys Leu Asn Asp Gly Ser Gln Ile Thr Tyr Glu Lys Cys
                245                 250                 255

Leu Ile Ala Thr Gly Gly Thr Pro Arg Ser Leu Ser Ala Ile Asp Arg
            260                 265                 270

Ala Gly Ala Glu Val Lys Ser Arg Thr Thr Leu Phe Arg Lys Ile Gly
        275                 280                 285

Asp Phe Arg Ser Leu Glu Lys Ile Ser Arg Glu Val Lys Ser Ile Thr
    290                 295                 300

Ile Ile Gly Gly Gly Phe Leu Gly Ser Glu Leu Ala Cys Ala Leu Gly
305                 310                 315                 320

Arg Lys Ala Arg Ala Leu Gly Thr Glu Val Ile Gln Leu Phe Pro Glu
                325                 330                 335

Lys Gly Asn Met Gly Lys Ile Leu Pro Glu Tyr Leu Ser Asn Trp Thr
            340                 345                 350

Met Glu Lys Val Arg Arg Glu Gly Val Lys Val Met Pro Asn Ala Ile
        355                 360                 365

Val Gln Ser Val Gly Val Ser Ser Gly Lys Leu Leu Ile Lys Leu Lys
    370                 375                 380

Asp Gly Arg Lys Val Glu Thr Asp His Ile Val Ala Ala Val Gly Leu
```

```
385                 390                 395                 400
Glu Pro Asn Val Glu Leu Ala Lys Thr Gly Gly Leu Glu Ile Asp Ser
                405                 410                 415

Asp Phe Gly Gly Phe Arg Val Asn Ala Glu Leu Gln Ala Arg Ser Asn
            420                 425                 430

Ile Trp Val Ala Gly Asp Ala Ala Cys Phe Tyr Asp Ile Lys Leu Gly
        435                 440                 445

Arg Arg Arg Val Glu His His Asp His Ala Val Val Ser Gly Arg Leu
    450                 455                 460

Ala Gly Glu Asn Met Thr Gly Ala Ala Lys Pro Tyr Trp His Gln Ser
465                 470                 475                 480

Met Phe Trp Ser Asp Leu Gly Pro Asp Val Gly Tyr Glu Ala Ile Gly
            485                 490                 495

Leu Val Asp Ser Ser Leu Pro Thr Val Gly Val Phe Ala Lys Ala Thr
                500                 505                 510

Ala Gln Asp Asn Pro Lys Ser Ala Thr Glu Gln Ser Gly Thr Gly Ile
            515                 520                 525

Arg Ser Glu Ser Glu Thr Glu Ser Glu Ala Ser Glu Ile Thr Ile Pro
    530                 535                 540

Pro Ser Thr Pro Ala Val Pro Gln Ala Pro Val Gln Gly Glu Asp Tyr
545                 550                 555                 560

Gly Lys Gly Val Ile Phe Tyr Leu Arg Asp Lys Val Val Val Gly Ile
            565                 570                 575

Val Leu Trp Asn Ile Phe Asn Arg Met Pro Ile Ala Arg Lys Ile Ile
            580                 585                 590

Lys Asp Gly Glu Gln His Glu Asp Leu Asn Glu Val Ala Lys Leu Phe
            595                 600                 605

Asn Ile His Glu Asp
    610

<210> SEQ ID NO 27
<211> LENGTH: 31
<212> TYPE: PRT
<213> ORGANISM: Homo sapiens

<400> SEQUENCE: 27

Arg Thr Arg Gly Ser Thr His Ala Ser Gly Leu Thr Arg Arg Ser Cys
 1               5                  10                  15

Val Arg Gly Lys Gly Arg Arg Ser Arg Ile Ala Val Ala Glu
            20                  25                  30
```

APOPTOSIS RELATED POLYNUCLEOTIDES, POLYPEPTIDES, AND ANTIBODIES

This application is a continuation of application Ser. No. 09/669,445, filed Sep. 25, 2000, now abandoned, which is a continuation-in-part of, and claims benefit under 35 U.S.C. 120 of copending PCT International Application Serial No. PCT/US00/06642, filed Mar. 15, 2000, which is hereby incorporated by reference, which claims benefit under 35 U.S.C. 119(e) based on U.S. Provisional Applications Nos. 60/126,018, filed Mar. 24, 1999, now abandoned, 60/139,638, filed Jun. 17, 1999, now abandoned, and 60/149,449, filed Aug. 18, 1999, now abandoned, which are hereby incorporated by reference in their entireties.

FIELD OF THE INVENTION

The present invention relates to novel apoptosis related proteins. More specifically, isolated nucleic acid molecules are provided encoding novel apoptosis related polypeptides. Novel apoptosis related polypeptides and antibodies that bind to these polypeptides are provided. Also provided are vectors, host cells, and recombinant and synthetic methods for producing human apoptosis related polynucleotides and/or polypeptides. The invention further relates to diagnostic and therapeutic methods useful for diagnosing, treating, preventing and/or prognosing disorders related to these novel apoptosis related polypeptides. The invention further relates to screening methods for identifying agonists and antagonists of polynucleotides and polypeptides of the invention. The present invention further relates to methods and/or compositions for inhibiting the production and function of the polypeptides of the present invention.

BACKGROUND OF THE INVENTION

Apoptosis or programmed cell death is the innate mechanism by which the organism eliminates unwanted cells. In contrast to necrosis, apoptosis is the most common physiological form of cell death and occurs during embryonic development, tissue remodeling, immune regulation and tumor regression. Cells undergoing apoptosis show a sequence of cardinal morphological features including membrane blebbing, cellular shrinkage and condensation of chromatin. Biochemically, these alterations are associated with the translocation of phosphatidylserine to the outer leaflet of the plasma membrane and the activation of an endonuclease which cleaves genomic DNA into multiples of internucleosomal fragments. In contrast, necrosis is classically induced following traumatic injury or exposure to high concentrations of noxious agents. Irreversible damage of the plasma membrane, mitochondrial dysfunction and cell lysis are characteristic for necrotic cell death.

Higher organisms have developed several mechanisms to rapidly and selectively eliminate cells by apoptosis. A fine-tuned mechanism to regulate life and death of a cell is the interaction of surface receptors with their cognate ligands. Several receptors are able to transmit cytotoxic signals into the cytoplasm, but in most cases they have a wide range of other functions unrelated to cell death, such as induction of cell activation, differentiation and proliferation. Whether the signals induced by a given receptor lead to cell activation or death is highly cell-type specific and tightly regulated during differentiation. For example, TNF receptors can exert co-stimulatory signals for proliferation of naive lymphocytes as well as inducing death signals required for deletion of activated lymphocytes.

Many receptors with important functions in differentiation, survival and cell death belong to an emerging family of structurally related molecules, called the TNF receptor superfamily. For some members of the family an apoptosis-inducing activity has been reported. However, most of them also have other functions such as induction of proliferation, differentiation, immune regulation and gene expression. Receptors with pleiotropic functions include TNF-R1, TNF-R2, NGF-R, CD27, CD30, CD40, OX-40, NGF-R, TRAMP (DR3/ws1-1/APO-3/LARD), HVEM (ATAR/TR2), GITR and RANK Anderson, D. M., et al., Nature 390, 175–179 (1997); Bodmer, J. L. et al., Immunity 6, 79–88 (1997); Nocentini, G. et al., Proc. Natl. Acad. Sci. 94, 6216–6221 (1997)). These receptors are type I membrane proteins which are structurally similar. Each possesses in its extracellular domain two-six imperfect repeats of about 40 amino acids, with each of approximately six Cys residues. Their cytoplasmic domains generally lack considerable sequence similarity.

APO-1/Fas, now called CD95, was the first member of the TNF receptor superfamily described in terms of its function in apoptosis (Itoh, N. et al., Cell 66, 233–243 (1991); Oehm, A. et al., J. Biol. Chem. 267, 10709–10715 (1992)). Sequence comparison of the intracellular domain of CD95 with TNF-R1 revealed that both receptors contained a similar stretch of about 80 amino acids. This region has been designated the death domain (DD) since it enables transmission of a cytotoxic signal by both molecules (Tartaglia, L. A. et al., Cell 74, 845–853 (1993); Itoh, N. et al., J. Biol. Chem. 268, 10932–10937 (1993)). Recent similarity searches in EST databases led to the cloning of a number of novel membrane receptors that contain such a death domain and are therefore referred to as the death receptors (DRs). TRAMP (DR3/ws1-1/APO-3/LARD), is both structurally and functionally similar to TNF-R1 and is abundantly expressed in T-lymphocytes (Bodmer, J. L. et al., Immunity 6, 79–88 (1997)). TRAIL-R1 (DR4, APO-2) and TRAIL-R2(DR5) have been found as receptors binding to a novel cytokine, called TRAIL for TNF-related apoptosis-inducing ligand. The two TRAIL receptors are functionally similar to CD95 as their main function seems to be to induce apoptosis (Pan, G. et al, Science 276, 111–113 (1997)). The TRAIL system, in addition, consists of two neutralizing decoy receptors, called DcR1 (TRAIL-R3, TRID, LIT) and DcR2 (TRAIL-R4) (Pan, G. et al., Science 277, 815–818 (1997); Degli-Esposti, M. A. et al., J. Exp. Med. 186, 1165–1170 (1997)). The sequence of DcR1 encodes a protein that contains the external TRAIL-binding region as well as a stretch of amino acids that anchors the receptor to the membrane. But, unlike the other receptors, DcR1 lacks an intracellular tail needed to spark the death pathway. DcR2 is also able to find TRAIL but contains a truncated death domain. Thus, both decoy receptors will prevent TRAIL from engaging functional TRAIL receptors and thereby render cells resistant to apoptosis. Collectively, this underlines that the death domain is required to induce apoptosis triggered by the different surface receptors.

For most members of the TNF-R superfamily their cognate ligands have been identified. Four of them, CD95L, TNFα, lymphotoxin-α (LTα, TNFβ) and TRAIL bind to death receptors. It was not surprising to find that, in addition to the receptors, also the ligands display structural similarities, which are reflected by similar mechanisms of receptor recognition and triggering. The ligands recognize their receptors through a shared structure composed of anti-parallel β-sheets, arranged in a jelly roll structure. As supported by structural and biochemical data, it is believed that all active ligands consist of three identical subunits and activate their receptors by oligomerization (Eck, M. J. et al., *J. Biol.. Chem.* 267, 2119–2122 (1992); Jones. E. Y., *Immunol. Ser.* 56, 93–127 (1992); Banner, D. W. et al., *Cell* 73, 431–445 (1993); Dhein, J. et al., *J. Immunol.* 149, 3166–3173 (1992)). Another common feature of the ligands is that almost all of them are type II transmembrane proteins. The only exception is LTα which, although formed as a soluble protein, binds to membrane-bound LTβ and thereby also acts as a cell-bound form. Lymphotoxins can be found as homotrimers (LTα$_3$) or heterotrimers (LTα$_1$/β$_2$ or LTα$_2$/β$_1$). The LTα homotrimer binds the TNF receptors, whereas the heterotrimers bind to the LTβ receptor which does not contain a death domain. Although TNF-related ligands are synthesized as membrane-bound molecules, most of them also exist as soluble forms. The secreted forms are generated by rather specific metalloproteases. For TNF, a zinc-dependent metalloprotease, called TACE (TNFα-converting enzyme) was recently cloned and shown to specifically cleave TNF (Black, R. A. et al., *Nature* 385, 729–733 (1997); Moss, M. L. et al., *Nature* 385, 733–736 (1997)).

Death Receptor-Associating Proteins

A major progress in the understanding of death receptor signaling was the definition of the so-called death domain (DD), an intracellular region of about 80 amino acids that is essential for triggering cell death. Delineation of the DD was not only a major aid for the identification of new adaptor molecules when used as a bait in interactive cloning approaches. The DD exerts its effects via interactive properties, as it can self-associate and bind to the DD of other proteins. These associations between DDs occur as a consequence of receptor-ligand binding and seem to involve electrostatic interactions. As assessed by NMR spectroscopy, the DD of CD95 comprises a series of antiparallel amphipathic α-helices with many exposed charged residues (Huang, B. et al., *Nature* 384, 638–641 (1996)), although it should be noted that this structure was determined at acidic pH. The tendency of the DD to self-associate apparently strengthens the interactions of the receptors imposed by ligand binding. Following self-association, the DD of the receptors recruits other DD-containing proteins which then serve as adapters in the signaling cascades.

The first DD-containing adaptor proteins identified were FADD (MORT1) (Chinnaiyan et al., *Cell*, 81:505–512 (1995); Boldin et al., *J. Biol. Chem.*, 270:7795–7798 (1995)), RIP (Stanger et al., *Cell*, 81:513–523 (1995)) and TRADD (Hsu et al., *Cell*, 81:495–504 (1995)). TRADD is most effectively bound following ligation of TNF-R1 where it then probably serves to recruit the DD proteins FADD and RIP as well as the RING domain adaptor protein TRAF2, FADD, in contrast, is preferentially recruited to CD95. Thus, the DD of FADD can bind to the DD of TRADD and the DD of RIP to the DDs of both TRADD and FADD. These mutual interactions may account for a potential crosstalk of the different receptor signaling pathways.

Overexpression of most DD proteins causes cell death, indicating that these molecules are involved in apoptosis signaling. In the case of FADD, transient expression of the N-terminal region was sufficient to cause apoptosis. (Chinnaiyan et al., *Cell*, 81:505–512 (1995)). This part of FADD was therefore termed the death effector domain (DED). In contrast, overexpression of the C-terminal DD-containing part, lacking the DED (FADD-DN), protected cells from CD95-mediated apoptosis and functioned as a dominant-negative mutant. This suggested that the N-terminus of FADD is coupled to the cytotoxic machinery. Both TRADD and RIP induce apoptosis but can also activate NF-κB, which is a typical feature of TNF-induced signaling. (Hsu et al., *Cell*, 81:495–504 (1995)). Similar to FADD, the C-terminus of TRADD contains a DD enabling self-association and association with the DD of other signaling molecules including TNF-R1 and FADD. TRADD, however, lacks the typical DED present in FADD.

While most of the information regarding death pathways has been obtained from yeast two-hybrid assays or supraphysiological overexpression in mammalian cells, for CD95 the signaling complexes have also been identified in vivo using classical biochemical methods. (Kischkel et al., *EMBO J.*, 14:5579–5588 (1995)). Treatment of cells with agonistic anti-APO-1 antibodies and subsequent co-immunoprecipitation of CD95 resulted in the identification of four cytotoxicity-dependent APO-1-associated proteins (CAP1–4) on two-dimensional gels, within seconds after receptor triggering. Together with the receptor, these proteins formed the death-inducing signaling complex (DISC). Two spots were identified as two different serine-phosphorylated species of FADD, and it was demonstrated that FADD bound to CD95 in a stimulation-dependent fashion.

Sequencing of the other immunoprecipitated proteins resulted in the identification of a downstream molecule which contained two DEDs at its N-terminus that associate with the DED of FADD. (Muzio et al., *Cell*, 85:817–827 (1996)). At its C-terminus it had the typical domain structure of a protease like interleukin-1β converting enzyme (ICE) and was therefore termed FLICE (FADD-like ICE). FLICE was also cloned by two other groups and named MACH and Mch5. (Srinivasula et al., *Proc. Natl. Acad. Sci. USA*, 93:14486–14491 (1996); Alnemri et al., *Cell*, 87:171 (1996)). It belongs to cysteine proteases of the caspase family and is therefore now referred to as caspase-8 (Alnemri. et al., *Cell*, 87:171 (1996)).

Caspases have been found in organisms ranging from *C. elegans* to humans. Caspases were implicated in apoptosis with the discovery that CED-3, the product of a gene required for cell death in the nematode *Caenorhabditis elegans*, is related to mammalian interleukin-1[beta]-converting enzyme (ICE or caspase-1). (J. Yuan et al., *Cell*, 75:641 (1993); Thornberry et al., *Nature*, 356:768 (1992)). Although caspase-1 has no obvious role in cell death, it has become the first identified member of a large family of proteases whose members have distinct roles in inflammation and apoptosis. In apoptosis, caspases function in both cell disassembly (effectors) and in initiating this disassembly in response to proapoptotic signals (initiators).

Caspases share similarities in amino acid sequence, structure, and substrate specificity. (Nicholson et al., *Trends Biochem. Sci.*, 22:299 (1997)). They are all expressed as proenzymes (30 to 50 kD) that contain three domains: an NH2-terminal domain, a large subunit (~20 kD), and a small subunit (~10 kD). Activation involves proteolytic processing between domains, followed by association of the large and small subunits to form a heterodimer. Crystal structures of two active caspases (caspase-1 and caspase-3) have been determined: in both cases, two heterodimers associate to form a tetramer, with two catalytic sites that appear to function independently. (Walker et al., *Cell*, 78:343 (1994); Wilson et al., *Nature*, 370:270 (1994); Rotonda et al., *Nature Struct. Biol.*, 3:619 (1996)). Within each catalytic domain, the large and small subunits are intimately associated, with both contributing residues necessary for substrate binding and catalysis.

Two features of the proenzyme structure are central to the mechanism of activation of these enzymes. First, the NH2- terminal domain, which is highly variable in sequence and length, is involved in regulation of activation. Second, all domains are derived from the proenzyme by cleavage at caspase consensus sites, implying that these enzymes can be activated either autocatalytically or in a cascade by enzymes with similar specificity.

Caspases are among the most specific of proteases, with an unusual and absolute requirement for cleavage after aspartic acid (The only other eukaryotic protease known to have a similar specificity is the serine protease granzyme B, a mediator of granule-dependent cytotoxic T lymphocyte-mediated apoptosis). Recognition of at least four amino acids NH2-terminal to the cleavage site is also a necessary requirement for efficient catalysis. The preferred tetrapeptide recognition motif differs significantly among caspases and explains the diversity of their biological functions. (Thornberry et al., *J. Biol. Chem.*, 272:17907 (1997)). Their specificity is even more stringent: not all proteins that contain the optimal tetrapeptide sequence are cleaved, implying that tertiary structural elements may influence substrate recognition. Cleavage of proteins by caspases is not only specific, but also highly efficient ($k_{cat}/K_m > 10^6$ $M^{-1} s^{-1}$). The strict specificity of caspases is consistent with the observation that apoptosis is not accompanied by indiscriminate protein digestion; rather, a select set of proteins is cleaved in a coordinated manner, usually at a single site, resulting in a loss or change in function.

As stated, apoptotic events include DNA fragmentation, chromatin condensation, membrane blebbing, cell shrinkage, and disassembly into membrane-enclosed vesicles (apoptotic bodies). In vivo, this process culminates with the engulfment of apoptotic bodies by other cells, preventing complications that would result from a release of intracellular contents. These changes occur in a predictable, reproducible sequence and can be completed within 30 to 60 min. Current research suggests that a subset of caspases (effectors) is responsible for the cellular changes that occur during apoptosis and provide insights into the mechanisms that they employ.

One role of caspases is to inactivate proteins that protect living cells from apoptosis. A clear example is the cleavage of ICAD/DFF45 (Enari et al., *Nature*, 391:43 (1998); Liu et al., *Cell*, 89:175 (1997)), an inhibitor of the nuclease responsible for DNA fragmentation, CAD (caspase-activated deoxyribonuclease). In nonapoptotic cells, CAD is present as an inactive complex with ICAD. During apoptosis, ICAD is inactivated by caspases, leaving CAD free to function as a nuclease. This system is not as simple as it appears: CAD synthesized in the absence of ICAD is not active, implying that the CAD-ICAD complex is formed co-translationally, and that ICAD is required for both the activity and inhibition of this nuclease.

Other negative regulators of apoptosis cleaved by caspases are Bcl-2 proteins. (Xue et al., *Nature*, 390:305 (1997); Cheng et al., *Science*, 278:1966 (1997); Cory ibid. 281:1322 (1998)). It appears that cleavage not only inactivates these proteins, but also produces a fragment that promotes apoptosis. That such positive feedbacks are involved in the control of apoptosis is not surprising, given their importance in the regulation of other proteolytic systems.

Caspases contribute to apoptosis through direct disassembly of cell structures, as illustrated by the destruction of nuclear lamina (Takahashi et al., *Proc. Natl. Acad. Sci. U.S.A.*, 93:8395 (1996); Orth et al., *J. Biol. Chem.*, 271: 16443 (1996)), a rigid structure that underlies the nuclear membrane and is involved in chromatin organization. Lamina is formed by head-to-tail polymers of intermediate filament proteins called lamins. During apoptosis, lamins are cleaved at a single site by caspases, causing lamina to collapse and contributing to chromatin condensation.

Caspases also reorganize cell structures indirectly by cleaving several proteins involved in cytoskeleton regulation, including gelsolin (S. Kothakota et al., *Science*, 278: 294 (1997)), focal adhesion kinase (FAK) (Wen et al., *J. Biol. Chem.* 272:26056 (1997)), and p21-activated kinase 2 (PAK2). Cleavage of these proteins results in deregulation of their activity. For example, in the case of gelsolin (a protein that severs actin filaments in a regulated manner), caspase cleavage generates a fragment that is instead constitutively active.

Dissociation of regulatory and effector domains is a hallmark of caspase function. For example, they inactivate or deregulate proteins involved in DNA repair (such as DNA-PKcs), mRNA splicing (such as U1-70K), and DNA replication (such as replication factor C). Although the relationship of these cleavages to cell death is not clearly understood, it is likely that the disabling of critical homeostatic and repair functions facilitates cellular disassembly.

The observations that caspase precursors are constitutively expressed in living cells (even in neurons that can live for a lifetime) but that apoptosis can be induced quickly indicates that caspase regulation is sophisticated and effective. Complex proteolytic systems often involve a combination of regulatory proteases, cofactors, feedbacks, and thresholds that converge to control the activity of an effector protease, that in turn carries out the function of the whole process. (Beltrami et al., *Proc. Natl. Acad. Sci. U.S.A.*, 92:8744 (1995)). This intricate regulation accounts for a spectacular feature of these systems: they keep the effector protease inactive but are able to rapidly activate large amounts of it in response to minute quantities of an appropriate inducer. Given the function of caspases as mediators of cell death, the complexity of their regulation is likely to rival that of the coagulation and complement systems.

Activation of effector caspases. A large body of genetic and biochemical evidence supports a cascade model for effector caspase activation: a proapoptotic signal culminates in activation of an initiator caspase which, in turn, activates effector caspases, resulting in cellular disassembly. Different initiator caspases mediate distinct sets of signals. For example, caspase-8 is associated with apoptosis involving death receptors. (Ashkenazi et al., *Science*, 281:1305 (1998)). In contrast, caspase-9 is involved in death induced by cytotoxic agents. (Hakem et al., *Cell*, in press; Kuida et al., ibid., in press). This model explains how distinct apoptotic signals induce the same biochemical and morphological changes.

Activation of initiator caspases. The available evidence indicates that activation of initiator caspases requires binding to specific cofactors, a mechanism commonly observed with proteases. This binding is triggered by a proapoptotic signal and mediated through one of at least two distinct structural motifs that reside in both the caspase prodomain and its corresponding cofactor. Activation of procaspase-8 requires association with its cofactor FADD (Fas-associated protein with death domain) through the DED (death effector domain) Boldin et al. ibid., 85:803 (1996); Muzio et al., ibid., p. 817), while procaspase-9 activation involves a complex with the cofactor APAF-1 through the CARD (caspase recruitment domain) (Li et al., ibid., 91:479 (1997)). Activation of caspase-9 also requires cytochrome c and deoxyadenosine triphosphate, indicating that caspase activation may require multiple cofactors.

Thus there exists a clear need for identifying and exploiting novel apoptosis related proteins. Although structurally related, such proteins may possess diverse and multifaceted functions in a variety of cell and tissue types. The inventive purified apoptosis related polypeptides are research tools useful for the identification, characterization and purification of additional proteins involved in apoptosis. Furthermore, the identification of new apoptosis related polypeptides permits the development of a range of derivatives, agonists and antagonists at the nucleic acid and protein levels which in turn have applications in the treatment and diagnosis of a range of conditions such as cancer, inflammation, neurological disorders and aberrant cell growth, amongst many other conditions.

SUMMARY OF THE INVENTION

The present invention includes isolated nucleic acid molecules comprising, or alternatively, consisting of a polynucleotide sequence disclosed in the sequence listing and/or contained in a human cDNA plasmid described in Table 1 and deposited with the American Type Culture Collection (ATCC). Fragments, variants, and derivatives of these nucleic acid molecules are also encompassed by the invention. The present invention also includes isolated nucleic acid molecules comprising, or alternatively, consisting of, a polynucleotide encoding apoptosis related polypeptides. The present invention further includes apoptosis related polypeptides encoded by these polynucleotides. Further provided for are amino acid sequences comprising, or alternatively, consisting of, apoptosis related polypeptides as disclosed in the sequence listing and/or encoded by the human cDNA plasmids described in Table 1 and deposited with the ATCC. Antibodies that bind these polypeptides are also encompassed by the invention. Polypeptide fragments, variants, and derivatives of these amino acid sequences are also encompassed by the invention, as are polynucleotides encoding these polypeptides and antibodies that bind these polypeptides.

DETAILED DESCRIPTION

Tables

Table 1 summarizes ATCC Deposits, Deposit dates, and ATCC designation numbers of deposits made with the ATCC in connection with the present application. Table 1 further summarizes the information pertaining to each "Gene No." described below, including cDNA clone identifier, the type of vector contained in the cDNA clone identifier, the nucleotide sequence identifier number, nucleotides contained in the disclosed sequence, the location of the 5' nucleotide of the start codon of the disclosed sequence, the amino acid sequence identifier number, and the last amino acid of the ORF encoded by the disclosed sequence.

Table 2 indicates public ESTs, of which at least one, two, three, four, five, ten, or more of any one or more of these public EST sequences are optionally excluded from certain embodiments of the invention.

Table 3 summarizes the expression profile of polynucleotides corresponding to the clones disclosed in Table 1. The first column provides a unique clone identifier, "Clone ID NO:Z", for a cDNA clone related to each contig sequence disclosed in Table 1. Column 2, "Library Code" shows the expression profile of tissue and/or cell line libraries which express the polynucleotides of the invention. Each Library Code in column 2 represents a tissue/cell source identifier code corresponding to the Library Code and Library description provided in Table 5. Expression of these polynucleotides was not observed in the other tissues and/or cell libraries tested. One of skill in the art could routinely use this information to identify tissues which show a predominant expression pattern of the corresponding polynucleotide of the invention or to identify polynucleotides which show predominant and/or specific tissue expression.

Table 4, column 1, provides a nucleotide sequence identifier, "SEQ ID NO:X," that matches a nucleotide SEQ ID NO:X disclosed in Table 1, column 5, Table 4, column 2, provides the chromosomal location, "Cytologic Band or Chromosome," of polynucleotides corresponding to SEQ ID NO:X. Chromosomal location was determined by finding exact matches to EST and cDNA sequences contained in the NCBI (National Center for Biotechnology Information) UniGene database. Given a presumptive chromosomal location, disease locus association was determined by comparison with the Morbid Map, derived from Online Mendelian Inheritance in Man (Online Mendelian Inheritance in Man, OMIM™. McKusick-Nathans Institute for Genetic Medicine, Johns Hopkins University (Baltimore, Md.) and National Center for Biotechnology Information, National Library of Medicine (Bethesda, Md.) 2000. World Wide Web URL: http://www.ncbi.nlm.nih.gov/omim/). If the putative chromosomal location of the Query overlapped with the chromosomal location of a Morbid Map entry, the OMIM reference identification number of the morbid map entry is provided in Table 4, column 3, labelled "OMIM ID." A key to the OMIM reference identification numbers is provided in Table 6.

Table 5, column 1, provides the Library Code disclosed in Table 3, column 2. Column 2 provides a description of the tissue or cell source from which the corresponding library was derived.

Table 6 provides a key to the OMIM reference identification numbers disclosed in Table 4, column 3. OMIM reference identification numbers (Column 1) were derived from Online Mendelian Inheritance in Man (Online Mendelian Inheritance in Man, OMIM. McKusick-Nathans Institute for Genetic Medicine, Johns Hopkins University (Baltimore, Md.) and National Center for Biotechnology Information, National Library of Medicine, (Bethesda, Md.) 2000. World Wide Web URL: http://www.ncbi.nlm.nih.giv/omim/). Column 2 provides diseases associated with the cytologic band disclosed in Table 4, column 2, as determined from the Morbid Map database.

Definitions

The following definitions are provided to facilitate understanding of certain terms used throughout this specification.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

As used herein, a "polynucleotide" refers to a molecule having a nucleic acid sequence contained in SEQ ID NO:X (as described in column 5 of Table 1), or cDNA plasmid:Z (as described in column 3 of Table 1 and contained within a pool of plasmids deposited with the ATCC). For example, the polynucleotide can contain the nucleotide sequence of the full length cDNA sequence, including the 5' and 3' untranslated sequences, the coding region, with or without a natural or artificial signal sequence, the protein coding region, as well as fragments, epitopes, domains, and variants of the nucleic acid sequence. Moreover, as used herein, a "polypeptide" refers to a molecule having an amino acid sequence encoded by a polynucleotide of the invention as broadly defined (obviously excluding poly-Phenylalanine or poly-Lysine peptide sequences which result from translation of a polyA tail of a sequence corresponding to a cDNA).

In the present invention, a representative plasmid containing the sequence of SEQ ID NO:X was deposited with the American Type Culture Collection ("ATCC") and/or described in Table 1. As shown in Table 1, each plasmid is identified by a cDNA Clone ID (Identifier) and the ATCC Deposit Number (ATCC Deposit No:Z). Plasmids that were pooled and deposited as a single deposit have the same ATCC Deposit Number. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure.

A "polynucleotide" of the present invention also includes those polynucleotides capable of hybridizing, under stringent hybridization conditions, to sequences contained in SEQ ID NO:X, or the complement thereof (e.g., the complement of any one, two, three, four, or more of the polynucleotide fragments described herein) and/or sequences contained in cDNA plasmid:Z (e.g., the complement of any one, two, three, four, or more of the polynucleotide fragments described herein). "Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65 degree C.

Also included within "polynucleotides" of the present invention are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6×SSPE (20× SSPE=3M NaCl; 0.2M NaH$_2$PO$_4$; 0.02M EDTA, pH 7.4), 0.5% SDS, 30% formamide, 100 ug/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using oligo dT as a primer).

The polynucleotides of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kg, or 1 kb, in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

"SEQ ID NO:X" refers to a polynucleotide sequence described in column 5 of Table 1, while "SEQ ID NO:Y" refers to a polypeptide sequence described in column 10 of Table 1. SEQ ID NO:X is identified by an integer specified in column 6 of Table 1. The polypeptide sequence SEQ ID NO:Y is a translated open reading frame (ORF) encoded by polynucleotide SEQ ID NO:X. The polynucleotide sequences are shown in the sequence listing immediately followed by all of the polypeptide sequences. Thus, a polypeptide sequence corresponding to polynucleotide sequence SEQ ID NO:2 is the first polypeptide sequence shown in the sequence listing. The second polypeptide sequence corresponds to the polynucleotide sequence shown as SEQ ID NO:3, and so on.

The polypeptides of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfonation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992)).

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the secreted protein, including the mature form, or may be a part of a larger protein, such as a fusion protein (see below). It is often advantageous to include an additional amino acid sequence which contains secretory or leader sequences, pro-sequences, sequences which aid in purification, such as multiple hisitidine residues, or an additional sequence for stability during recombinant production.

The polypeptides of the present invention are preferably provided in an isolated form, and preferably are substantially purified. A recombinantly produced version of a polypeptide, including the secreted polypeptide, can be substantially purified using techniques described herein or otherwise known in the art, such as, for example, by the one-step method described in Smith and Johnson, Gene 67:31–40 (1988). Polypeptides of the invention also can be purified from natural, synthetic or recombinant sources using techniques described herein or otherwise known in the art, such as, for example, antibodies of the invention raised against the polypeptides of the present invention in methods which are well known in the art.

By a polypeptide demonstrating a "functional activity" is meant, a polypeptide capable of displaying one or more known functional activities associated with a full-length (complete) protein of the invention. Such functional activities include, but are not limited to, biological activity, antigenicity [ability to bind (or compete with a polypeptide for binding) to an anti-polypeptide antibody], immunogenicity (ability to generate antibody which binds to a specific polypeptide of the invention), ability to form multimers with polypeptides of the invention, and ability to bind to a receptor or ligand for a polypeptide.

"A polypeptide having functional activity" refers to polypeptides exhibiting activity similar, but not necessarily identical to, an activity of a polypeptide of the present invention, including mature forms, as measured in a particular assay, such as, for example, a biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention).

The functional activity of the polypeptides, and fragments, variants derivatives, and analogs thereof, can be assayed by various methods.

For example, in one embodiment where one is assaying for the ability to bind or compete with full-length polypeptide of the present invention for binding to an antibody to the full length polypeptide, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a ligand is identified, or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., Microbiol. Rev. 59:94–123 (1995). In another embodiment, physiological correlates polypeptide of the present invention binding to its substrates (signal transduction) can be assayed.

In addition, assays described herein (see Examples) and otherwise known in the art may routinely be applied to measure the ability of polypeptides of the present invention and fragments, variants derivatives and analogs thereof to elicit polypeptide related biological activity (either in vitro or in vivo). Other methods will be known to the skilled artisan and are within the scope of the invention.

POLYNUCLEOTIDES AND POLYPEPTIDES OF THE INVENTION

FEATURES OF PROTEIN ENCODED BY GENE NO: 1

Translation products corresponding to this gene share sequence homology with the human death effector domain-containing molecule, DEDD (See Genbank Accession CAA09445), which is thought to play a role in inhibiting transcription within cells. Several proteins contain a domain called a death effector domain (DED). These DED domains interact with other proteins in the apoptotic pathway to either inhibit or promote apoptosis. The pivotal protein in this pathway, FADD, contains both a Death-domain (DD) and a DED. Although the death domain is required for it to associate with Fas and to initiate apoptosis, it is not sufficient for apoptosis. In fact, the expression of only the death domain inhibits apoptosis. The DED is the critical part of the molecule, recruiting downstream proteins that actually effect apoptosis. Overexpression of this domain alone is sufficient for apoptosis. The DED of FADD recruits, through their own death effector domains, caspase-8 and caspase-10, which are the most proximal and critical caspases in the death signaling pathway. Overexpression of the death domain alone inhibits apoptosis since it occupies Fas but does not allow association of the caspases, and possibly other critical molecules. Several death effector-containing proteins have been discovered that function completely opposite FADD to inhibit apoptosis. The DED of equine herpesvirus protein E8 interacts with the caspase-8 prodomain whereas that in molluscum contagiosum virus protein MC159 interacts with FADD. Both of these interactions block both FAS- and TNFR1-induced apoptosis. Binding of MC159 with FADD presumably prevents FADD from recruiting the caspase-8 and/or -10. E8 may inhibit caspase-8 directly by binding to it.

In specific embodiments, polypeptides of the invention comprise, or alternatively consist of, the following amino acid sequence: PGSTHASGKIQNKWLRPSPRSHRTPES-GRVLSLFRLPPPG (SEQ ID NO: 20). Polynucleotides encoding these polypeptides are also encompassed by the invention, as are antibodies that bind one or more of these polypeptides. Moreover, fragments and variants of these polypeptides (e.g. fragments are described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Preferred polypeptides of the present invention comprise, or alternatively consist of, one, two, three, four, five, or all five of the immunogenic epitopes shown in SEQ ID NO: 20 as residues: Glu-51 to Asn-60, Arg-82 to Gly-152, Ala-156 to Gly-170, Arg-181 to Glu-186, and Glu-294 to Ser-304. Polynucleotides encoding these polypeptides are also encompassed by the invention, as are antibodies that bind one or more of these polypeptides. Moreover, fragments and variants of these polypeptides (e.g. fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

It has been discovered that this gene is expressed primarily in larynx tissue, and cancerous tissue thereof, as well as in macrophage. Diseases associated with increased cell survival, or the inhibition of apoptosis, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposiís sarcoma and ovarian cancer); autoimmune disorders (such as, multiple sclerosis, Sjogrenís syndrome, Hashimotoís thyroiditis, biliary cirrhosis, Behcetís disease, Crohnís disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, TNFR polynucleotides, polypeptides, and/or antagonists of the invention are used to inhibit growth, progression, and/or metasis fo cancers, in particular those listed above. Additional diseases or conditions associated with increased cell survival include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. Diseases associated with increased apoptosis include AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogrenís syndrome, Hashimotoís thyroiditis, biliary cirrhosis, Behcetís disease, Crohnís disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Therefore, polynucleotides and polypeptides of the invention, including antibodies, are useful as reagents for differential identification of the tissue(s) or cell type(s) present in a biological sample and for diagnosis of the following diseases and conditions: diseases involving aberrant apoptosis, cancers, immune system disorders, or pulmonary disorders. Similarly, polypeptides and antibodies directed to those polypeptides are useful to provide immunological probes for differential identification of the tissue(s) or cell type(s). For a number of disorders of the above tissues or cells, particularly of the immune and pulmonary systems, expression of this gene at significantly higher or lower levels may be detected in certain tissues (e.g., immune, pulmonary, cancerous and wounded tissues) or bodily fluids (e.g., lymph, serum, plasma, urine, synovial fluid or spinal fluid) taken from an individual having such a disorder, relative to the standard gene expression level, i.e., the expression level in healthy tissue from an individual not having the disorder.

The tissue distribution and homology to DEDD suggests that the protein product of this clone is useful for the diagnosis and/or treatment of diseases involving aberrant apoptosis. Furthermore, the homology of the translation product of this gene to DEDD implicates this gene as being involved in the apoptotic pathway. Therefore, this gene may be important in controlling cell death, and thus, could be extremely important in controlling tumor proliferation.

Furthermore, the tissue distribution in larynx carcinoma tissue supports the notion that this gene may somehow be involved in aberrant cell proliferation, or aberrant apoptosis. Similarly, expression of this gene product in macrophage also strongly suggests a role for this protein in immune function and immune surveillance. Protein, as well as, antibodies directed against the protein may show utility as a tumor marker and/or immunotherapy targets for the above listed tissues.

The ability of polynucleotides and polypeptides of the invention to increase or decrease apoptosis can routinely be determined using techniques known in the art. For example, biological activity can routinely be measured using cell death assays performed essentially as previously described (Chinnaiyan et al., Cell 81:505–512 (1995); Boldin et al., J. Biol. Chem. 270:7795–8(1995); Kischkel et al., EMBO 14:5579–5588 (1995); Chinnaiyan et al., J. Biol. Chem. 271:4961–4965 (1996)).

FEATURES OF PROTEIN ENCODED BY GENE NO: 2

For the purposes of the present application, this gene and translation products corresponding to this gene may be referred to as Nod1. Nod1 polypeptides are thought to function as enhancers of Caspase-9 activity and NF-kB activation (Examples 17 and 18). Translation products corresponding to this gene share sequence homology with inhibitor of apoptosis protein 2, which is a member of the human family of inhibitor of apoptosis genes, which are thought to function as apoptotic suppressors (See Genbank Accession AAC50372, and Nature Jan. 25, 1996; 379(6563):349–53).

In specific embodiments, polypeptides of the invention comprise, or alternatively consist of, the following amino acid sequence: TAWPASWTTPPASS (SEQ ID NO: 21). Polynucleotides encoding these polypeptides are also encompassed by the invention, as are antibodies that bind one or more of these polypeptides. Moreover, fragments and variants of these polypeptides (e.g. fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

In further specific embodiments of the invention, polypeptides of the invention comprise, or alternatively consist of, the following amino acid sequence:

```
MSRDLLFKHYCYPERDPEEVFAFLLRFPHVALFTFDGLDELHSDLDLSRV

PDSSCPWEPAHPLVLLANLLSGKLLKGASKLLTARTGIEVPRQFLRKKVL

LRGFSPSHLRAYARRMFPERALQDRLLSQLEANPNLCSLCSVPLFCWIIF

RCFQHFRAAFEGSPQLPDCTMTLTDVFLLVTEVHLNRMQPSSLVQRNTRS

PVETLHAGRDTLCSLGQVAEHRGMEKSLFVFTQEEVXASGLQERDMQLGF

LRALPELGPGGDQQXYEFFHLTLQAFFTAFFLVLDDRVGTQELLRFFQEW

MPPAGAATTSCYPPFLPFQCLQGSGPAREDLFKNKDHFQFTNLFLCGLLS

KAKQKLLRHLVPAAALRRKRKALWAHLFSSLRGYLKSLPRVQVESFNQVQ

AMPTFTWMLRCIYETQSQKVGQLAARGICANYLKLTYCNACSADCSALSF

VLHHFPKRLALDLDNNNLNDYGVRELQPCFSRLTVLRLSVNQITDGGVKV

LSEELTKYKIVTYLGLYNNQITDVGARYVTKILDECKGLTHLKLGKNKIT

SEGGKYLALAVKNSKSISEVGMWGNQVGDEGAKAFAEALRNHPSLTTLSL

ASNGISTEGGKSLARALQQNTSLEILWLTQNELXDEXAESLAEMLKVNQT

LKHLWLIQNQITAKGTAQLADALQSNTGITEICLNGNLIKPEEAKVYEDE

KRIICF (SEQ ID NO:22).
```

Polynucleotides encoding these polypeptides are also encompassed by the invention, as are antibodies that bind one or more of these polypeptides. Moreover, fragments and variants of these polypeptides (e.g. fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Preferred polypeptides of the present invention comprise, or alternatively consist of, one, two, three, four, five, six, seven, eight, nine, ten, eleven, twelve, thirteen, fourteen, or all fourteen of the immunogenic epitopes shown in SEQ ID NO: 21 as residues: Met-1 to Ser-7, Pro-62 to Val-68, Ser-77 to Val-82, Pro-125 to Gln-132, Pro-261 to Glu-266, Pro-299 to Trp-305, Val-442 to Pro-449, His-454 to Thr-459, Pro-506 to Tyr-513, Asp-577 to Asp-583, Tyr-660 to Lys-666, Leu-710 to Tyr-718, Gly-792 to Lys-802, and Thr-876 to Asn-881. Polynucleotides encoding these polypeptides are also encompassed by the invention, as are antibodies that bind one or more of these polypeptides. Moreover, fragments and variants of these polypeptides (e.g. fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

It has been discovered that this gene is expressed primarily in a wide variety of cancerous and tumor tissues, such as colon cancer tissue, thyroid tumor tissue, pancreatic tumor tissue, testes tumor tissue, and endometrial tumor tissue. Diseases associated with increased cell survival, or the inhibition of apoptosis, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposiís sarcoma and ovarian cancer); autoimmune disorders (such as, multiple sclerosis, Sjogrenís syndrome, Hashimotoís thyroiditis, biliary cirrhosis, Behcetís disease, Crohnís disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, TNFR polynucleotides, polypeptides, and/or antagonists of the invention are used to inhibit growth, progression, and/or metasis fo cancers, in particular those listed above. Additional diseases or conditions associated with increased cell survival include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. Diseases associated with increased apoptosis include AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogrenís syndrome, Hashimotoís thyroiditis, biliary cirrhosis, Behcetís disease, Crohnís disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Therefore, polynucleotides and polypeptides of the invention, including antibodies, are useful as reagents for differential identification of the tissue(s) or cell type(s) present in a biological sample and for diagnosis of the following diseases and conditions: disorders involving aberrant apoptosis and cancer. Similarly, polypeptides and antibodies directed to those polypeptides are useful to provide immunological probes for differential identification of the tissue(s) or cell type(s). For a number of disorders of the above tissues or cells, particularly of tumor tissues, expression of this gene at significantly higher or lower levels may be detected in certain tissues (e.g., reproductive, endocrine, gastrointestinal, cancerous and wounded tissues) or bodily fluids (e.g., lymph, serum, plasma, urine, synovial fluid or spinal fluid) taken from an individual having such a disorder, relative to the standard gene expression level, i.e., the expression level in healthy tissue from an individual not having the disorder.

Translation products corresponding to this gene may be involved in pro-apoptotic activities such as the activation of Caspases, such as Caspase-9 (Examples 17 and 18). Accordingly, Nod1 polynucleotides and polypeptides, or agonists and/or antagonists of Nod1 polynucleotides and polypeptides, may be useful for the promotion and/or inhibition, respectively, of apoptotic activities mediated by Nod1 polynucleotides and polypeptides, particularly polypeptide fragments such as CARD domains.

In addition, the tissue distribution in a wide variety of tumor tissues, and the homology to inhibitor of apoptosis protein 2 (a member of the inhibitor of apoptosis family of genes), suggests that the protein product of this clone is useful for the detection and/or treatment of disorders involving aberrant apoptosis, such as cancer. Furthermore, the homology of the translation product of this gene to inhibitor of apoptosis protein 2 potentially implicates this gene in the regulation of the apoptotic pathway, and therefore, this gene and its translation product are potentially useful in controlling aberrant cell growth and/or apoptosis, as one might find in cancerous tissues and/or malignant cells. Protein, as well as, antibodies directed against the protein may show utility as a tumor marker and/or immunotherapy targets for the above listed tissues.

Alternatively, in a further aspect, the present invention is directed to a method for inhibiting apoptosis induced by a TNF-family ligand, which involves administering to a cell which expresses the homolog of the inhibitor of apoptosis protein 2 polypeptide of the present invention, an analog or an agonist capable of increasing apoptotic suppression signaling mediated by the homolog of the inhibitor of apoptosis protein 2 polypeptide of the present invention. Preferably, apoptotic signaling is decreased to treat a disease wherein increased apoptosis, NFkB expression and/or JNK expression is exhibited.

The ability of polynucleotides and polypeptides of the invention to increase or decrease apoptosis can routinely be determined using techniques known in the art. For example, biological activity can routinely be measured using cell death assays performed essentially as previously described (Chinnaiyan et al., Cell 81:505–512 (1995); Boldin et al., J. Biol. Chem. 270:7795–8(1995); Kischkel et al., EMBO 14:5579–5588 (1995); Chinnaiyan et al., J. Biol. Chem. 271:4961–4965 (1996)).

FEATURES OF PROTEIN ENCODED BY GENE NO: 3

Translation products corresponding to this gene share sequence homology with murine Fas-associated factor 1 (FAF1), which is a protein which specifically interacts with the cytoplasmic domain of wild-type Fas in mice. Thus, it is thought that FAF1 may potentiate Fas-induced cell killing, and therefore be a candidate signal transducing molecule in the regulation of apoptosis (See Genbank Accession AAA92091, as well as Proc Natl Acad Sci U S A Dec. 5, 1995; 92(25):11894–8). Additionally, the translation product of this gene shares sequence homology with the Drosophila Fly Fas-associated factor (FFAF), which is a homolog of the murine FAF1 (See Genbank Accession BAA33466).

Preferred polypeptides of the present invention comprise, or alternatively consist of, one, two, three, four, five, six, seven, eight, nine, ten, eleven, twelve, thirteen, fourteen, or all fourteen of the immunogenic epitopes shown in SEQ ID NO: 22 as residues: Ala-3 to Lys-16, Arg-50 to Gly-56, Arg-85 to Gly-90, Pro-123 to Val-129, Glu-144 to Arg-149, Asn-164 to Glu-169, His-178 to Cys-189, Ser-212 to Tyr-219, Arg-277 to Glu-295, Ala-303 to Lys-346, Pro-352 to Glu-360, Pro-369 to His-379, Lys-395 to Lys-400, Pro-416 to Leu-426. Polynucleotides encoding these polypeptides are also encompassed by the invention, as are antibodies that bind one or more of these polypeptides. Moreover, fragments and variants of these polypeptides (e.g. fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

It has been discovered that this gene is expressed primarily in immune cells such as monocytes, primary dendritic cells, fetal liver/spleen tissue, and bone marrow, and to a lesser extent in vascular tissues such as heart tissue. Diseases associated with increased cell survival, or the inhibition of apoptosis, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposiís sarcoma and ovarian cancer); autoimmune disorders (such as, multiple sclerosis, Sjogreńís syndrome, Hashimotoís thyroiditis, biliary cirrhosis, Behcetís disease, Crohnís disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, TNFR polynucleotides, polypeptides, and/or antagonists of the invention are used to inhibit growth, progression, and/or metasis fo cancers, in particular those listed above. Additional diseases or conditions associated with increased cell survival include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. Diseases associated with increased apoptosis include AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogreńís syndrome, Hashimotoís thyroiditis, biliary cirrhosis, Behcetís disease, Crohnís disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Therefore, polynucleotides and polypeptides of the invention, including antibodies, are useful as reagents for differential identification of the tissue(s) or cell type(s) present in a biological sample and for diagnosis of the following diseases and conditions: immune system disorders, and aberrant apoptosis. Similarly, polypeptides and antibodies directed to those polypeptides are useful to provide immunological probes for differential identification of the tissue(s) or cell type(s). For a number of disorders of the above tissues or cells, particularly of the immune system, expression of this gene at significantly higher or lower levels may be detected in certain tissues (e.g., immune, vascular, cancerous and wounded tissues) or bodily fluids (e.g., lymph, serum, plasma, urine, synovial fluid or spinal fluid) taken from an individual having such a disorder, relative to the standard gene expression level, i.e., the expression level in healthy tissue from an individual not having the disorder.

The tissue distribution in immune tissues, and the homology to the murine FAF1, as well as the Drosophila FFAF, suggests that the protein product of this clone is useful for the detection and/or treatment of disorders involving aberrant apoptosis. The homology of the translation product of this gene to both FAF1 and FFAF strongly suggests that this gene is involved in the regulation of the apoptotic pathway, most likely as a protein that directly interacts with Fas, and thereby mediates Fas-associated apoptosis and cell death. Therefore, this gene would be useful for the detection and/or treatment of disorders involving aberrant cell growth and or apoptosis, such as one might find in cancerous tissues and/or malignant cells. Protein, as well as, antibodies directed against the protein may show utility as a tumor marker and/or immunotherapy targets for the above listed tissues.

Thus, in one aspect, the present invention is directed to a method for enhancing apoptosis induced by a TNF-family ligand, which involves administering to a cell which expresses the polypeptide of the FAF1 homolog of the present invention, or an agonist capable of increasing signaling mediated by the polypeptide of the FAF1 homolog of the present invention. Preferably, apoptotic signalling mediated by the polypeptide of the FAF1 homolog of the present invention is increased to treat a disease wherein decreased apoptosis or decreased cytokine and adhesion molecule expression is exhibited. Agonists include, but are not limited to, soluble forms of the polypeptide of the FAF1 homolog of the present invention and antibodies (preferably monoclonal) directed against the polypeptide of the FAF1 homolog of the present invention.

The ability of polynucleotides and polypeptides of the invention to increase or decrease apoptosis can routinely be determined using techniques known in the art. For example, biological activity can routinely be measured using cell death assays performed essentially as previously described (Chinnaiyan et al., Cell 81:505–512 (1995); Boldin et al., J. Biol. Chem. 270:7795–8(1995); Kischkel et al., EMBO 14:5579–5588 (1995); Chinnaiyan et al., J. Biol. Chem. 271:4961–4965 (1996)).

FEATURES OF PROTEIN ENCODED BY GENE NO: 4

Translation products corresponding to this gene share sequence homology with human receptor interacting protein (RIP). When RIP is transiently overexpressed, transfected cells undergo the morphological changes characteristic of apoptosis. Thus, RIP is thought to be a novel form of an apoptosis-inducing protein (See Genbank Accession AAC50137, as well as Cell May 19, 1995; 81(4):513–23). In addition to RIP, as well as FADD and TRADD, there are other non-receptor proteins that contain death domains and participate in transducing signals. Some serve as adaptor molecules to bring various components to the signaling complex. RAIDD, for example, which causes apoptosis when overexpressed, binds to the homologous domain of RIP through the death domain and to caspase-2 through another part of the molecule. The binding results suggested that RAIDD functions as an adaptor to recruit caspase-2 to the TNFR1 signaling complex. RAIDD, however, may not be essential for apoptosis, since various putative dominant mutants of RAIDD failed to block TNFR1-induced apoptosis. MADD associates with the death domain of TNFR1 and activates mitogen-activated kinase, another signal transduced through the TNFR1. An interesting example of a death domain in an adaptor protein is Siva, which forms a complex with CD27, a non-death domain-containing receptor, and induces apoptosis. Death domain-containing intracellular proteins have also been found in other organisms, for example, reaper, which is in Drosophila.

In specific embodiments, polypeptides of the invention comprise, or alternatively consist of, the following amino acid sequence: APCCACHRAVPPASSNRSPCSCLCPLASQASVWTAPACTCCTGPLLQPPG (SEQ ID NO: 23). Polynucleotides encoding these polypeptides are also encompassed by the invention, as are antibodies that bind one or more of these polypeptides. Moreover, fragments and variants of these polypeptides (e.g. fragments are described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Preferred polypeptides of the present invention comprise, or alternatively consist of, one, two, three, four, or all four of the immunogenic epitopes shown in SEQ ID NO: 23 as residues: Arg-53 to Glu-58, Glu-79 to Asp-88, Asp-109 to Val-116, and Leu-190 to Ala-200. Polynucleotides encoding these polypeptides are also encompassed by the invention, as are antibodies that bind one or more of these polypeptides. Moreover, fragments and variants of these polypeptides (e.g. fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

It has been discovered that this gene is expressed primarily in immune system cells and tissues such as monocytes and fetal liver/spleen tissue, and to a lesser extent in Wilm's tumor and breast cancer tissues. Diseases associated with increased cell survival, or the inhibition of apoptosis, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposiís sarcoma and ovarian cancer); autoimmune disorders (such as, multiple sclerosis, Sjogrenís syndrome, Hashimotoís thyroiditis, biliary cirrhosis, Behcetís disease, Crohnís disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, TNFR polynucleotides, polypeptides, and/or antagonists of the invention are used to inhibit growth, progression, and/or metasis fo cancers, in particular those listed above. Additional diseases or conditions associated with increased cell survival include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. Diseases associated with increased apoptosis include AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogrenís syndrome, Hashimotoís thyroiditis, biliary cirrhosis, Behcetís disease, Crohnís disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Therefore, polynucleotides and polypeptides of the invention, including antibodies, are useful as reagents for differential identification of the tissue(s) or cell type(s) present in a biological sample and for diagnosis of the following diseases and conditions: disorders involving aberrant apoptosis, and immune system disorders. Similarly, polypeptides and antibodies directed to those polypeptides are useful to provide immunological probes for differential identification of the tissue(s) or cell type(s). For a number of disorders of the above tissues or cells, particularly of the immune system, expression of this gene at significantly higher or lower levels may be detected in certain tissues (e.g., immune, cancerous and wounded tissues) or bodily fluids (e.g., lymph, serum, plasma, urine, synovial fluid or spinal fluid) taken from an individual having such a disorder, relative to the standard gene expression level, i.e., the expression level in healthy tissue from an individual not having the disorder.

The tissue distribution in immune system tissues and cells, and homology to human RIP, suggests that the protein product of this clone is useful for the diagnosis and/or treatment of disorders involving aberrant apoptosis. Furthermore, the homology of the translation product of this gene to RIP strongly suggests that the translation product of this gene may be involved in the regulation of the apoptotic pathway, in particular in the promotion of apoptosis. Thus, the gene, and its corresponding translation product, are useful for the diagnosis and/or treatment of disorders involving aberrant apoptosis, such as one might find in cancerous tissues and/or malignant cells. Protein, as well as, antibodies directed against the protein may show utility as a tumor marker and/or immunotherapy targets for the above listed tissues.

Thus, in one aspect, the present invention is directed to a method for enhancing apoptosis induced by a TNF-family ligand, which involves administering to a cell which expresses the polypeptide of the RIP homolog of the present invention, or an agonist capable of increasing signaling mediated by the polypeptide of the RIP homolog of the present invention. Preferably, apoptotic signaling mediated by the polypeptide of the RIP homolog of the present invention is increased to treat a disease wherein decreased apoptosis or decreased cytokine and adhesion molecule expression is exhibited. Agonists include, but are not limited to, soluble forms of the polypeptide of the RIP homolog of the present invention and antibodies (preferably monoclonal) directed against the polypeptide of the RIP homolog of the present invention.

The ability of polynucleotides and polypeptides of the invention to increase or decrease apoptosis can routinely be determined using techniques known in the art. For example, biological activity can routinely be measured using cell death assays performed essentially as previously described (Chinnaiyan et al., Cell 81:505–512 (1995); Boldin et al., J. Biol. Chem. 270:7795–8(1995); Kischkel et al., EMBO 14:5579–5588 (1995); Chinnaiyan et al., J. Biol. Chem. 271:4961–4965 (1996)).

FEATURES OF PROTEIN ENCODED BY GENE NO: 5

Translation products corresponding to this gene share sequence homology with human cystein rich domain associated to RING and TRAF protein (See Genbank Accession CAA56491), which is thought to be involved in the regulation of the apoptotic pathway. A group of proteins, whose first member was isolated based on its association with TNFR2, also function as adaptors for transducing signals. They are defined by the presence of a C-terminal domain, designated TRAF, of about 230 amino acids. This region has been further divided into TRAF-N and TRAF-C subdomains. Several of the 6 TRAFs identified thus far interact with many receptors belonging to the TNFR superfamily, but there is only limited direct association of any of the TRAFs with death domain-containing receptors. TRAF2 is recruited to the TNFR1 signaling complex through TRADD. Similarly, there is only a weak association of TRAF2 with DR3, but the association is enhanced when TRADD is overexpressed. TRAF1 and TRAF2 are involved in CD30-mediated cell death of T cell hybridomas, and overexpression of TRAF1 in transgenic mice inhibits antigen-induced apoptosis of CD8+ lymphocytes.

Preferred polypeptides of the present invention comprise, or alternatively consist of, one, two, three, four, five, six, or all six of the immunogenic epitopes shown in SEQ ID NO: 24 as residues: Phe-47 to Thr-52, Ser-104 to Thr-115, Pro-125 to Asn-131, Gln-143 to Arg-148, Glu-153 to Glu-158, and Pro-185 to Leu-190. Polynucleotides encoding these polypeptides are also encompassed by the invention, as are antibodies that bind one or more of these polypeptides. Moreover, fragments and variants of these polypeptides (e.g. fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

It has been discovered that this gene is expressed primarily in neural tissues such as infant brain, and to a lesser extent in musculo-skeletal tissues such as muscle tissue and synovial hypoxia tissues.

Therefore, polynucleotides and polypeptides of the invention, including antibodies, are useful as reagents for differential identification of the tissue(s) or cell type(s) present in a biological sample and for diagnosis of the following diseases and conditions: disorders associated with aberrant apoptosis, neural disorders, and musculo-skeletal disorders. Similarly, polypeptides and antibodies directed to those polypeptides are useful to provide immunological probes for differential identification of the tissue(s) or cell type(s). For a number of disorders of the above tissues or cells, particularly of the neural and musculo-skeletal systems, expression of this gene at significantly higher or lower levels may be detected in certain tissues (e.g., neural, musculo-skeletal, cancerous and wounded tissues) or bodily fluids (e.g., lymph, serum, plasma, urine, synovial fluid or spinal fluid) taken from an individual having such a disorder, relative to the standard gene expression level, i.e., the expression level in healthy tissue from an individual not having the disorder.

The homology of the translation product of this clone to human cystein rich domain associated to RING and TRAF protein, suggests that the protein product of this clone is useful for the diagnosis and/or treatment of disorders involving aberrant apoptosis. Furthermore, the homology of the translation product of this clone, it is possible that this gene is involved in the apoptotic pathway, and thus, could be useful in controlling aberrant cell growth or apoptosis, as one might find in cancerous tissues and/or malignant cells.

Alternatively, given the tissue distribution in neural tissues such as infant brain, the protein product of this clone may be useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders.

Likewise, the tissue distribution in muscle tissue and indicates that the protein product of this gene is useful for the diagnosis and treatment of conditions and pathologies of the cardiovascular system, such as heart disease, restenosis, atherosclerosis, stoke, angina, thrombosis, and would healing. In addition, the expression of this gene product in synovium suggests a role in the detection and treatment of disorders and conditions affecting the skeletal system, in particular osteoporosis as well as disorders afflicting connective tissues (e.g. arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (ie. spondyloepiphyseal dysplasia congenita, familiar arthritis, Atelosteogenesis type II, metaphyseal chondrodysplasia type Schmid). Protein, as well as, antibodies directed against the protein may show utility as a tumor marker and/or immunotherapy targets for the above listed tissues.

The ability of polynucleotides and polypeptides of the invention to increase or decrease apoptosis can routinely be determined using techniques known in the art. For example, biological activity can routinely be measured using cell death assays performed essentially as previously described (Chinnaiyan et al., Cell 81:505–512 (1995); Boldin et al., J. Biol. Chem. 270:7795–8(1995); Kischkel et al., EMBO 14:5579–5588 (1995); Chinnaiyan et al., J. Biol. Chem. 271:4961–4965 (1996)).

FEATURES OF PROTEIN ENCODED BY GENE NO: 6

Translation products corresponding to this gene share sequence homology with human eosinophil peroxidase, which is thought to be important in immune system function and surveillance (See Genbank Accession AAA58458), as well as with hSNF2b (See Genbank Accession BAA05143), which is thought to function as a transcriptional activator.

In specific embodiments, polypeptides of the invention comprise, or alternatively consist of, the following amino acid sequence: AWWRRKGTWPWTCS-SEALVKGTLTSCPILDSICK (SEQ ID NO: 24). Polynucleotides encoding these polypeptides are also encompassed by the invention, as are antibodies that bind one or more of these polypeptides. Moreover, fragments and variants of these polypeptides (e.g. fragments are described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Preferred polypeptides of the present invention comprise, or alternatively consist of, one, two, or both of the immunogenic epitopes shown in SEQ ID NO: 25 as residues: Leu-7 to Trp-18 and Gln-30 to Asn-37. Polynucleotides encoding these polypeptides are also encompassed by the invention, as are antibodies that bind one or more of these polypeptides. Moreover, fragments and variants of these polypeptides (e.g. fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

It has been discovered that this gene is expressed primarily in dendritic cells, and to a lesser extent in ovarian tumor tissue.

Therefore, polynucleotides and polypeptides of the invention, including antibodies, are useful as reagents for differential identification of the tissue(s) or cell type(s) present in a biological sample and for diagnosis of the following diseases and conditions: immune system disorders, and aberrant apoptosis. Similarly, polypeptides and antibodies directed to those polypeptides are useful to provide immunological probes for differential identification of the tissue(s) or cell type(s). For a number of disorders of the above tissues or cells, particularly of the immune system, expression of this gene at significantly higher or lower levels may be detected in certain tissues (e.g., immune, cancerous and wounded tissues) or bodily fluids (e.g., lymph, serum, plasma, urine, synovial fluid or spinal fluid) taken from an individual having such a disorder, relative to the standard gene expression level, i.e., the expression level in healthy tissue from an individual not having the disorder.

The tissue distribution in primary dendritic cells, and the homology to eosinophil peroxidase, suggests that the protein product of this clone is useful for the detection and/or treatment of immune system disorders associated with cells involved in immune system function and immune surveillance.

Alternatively, the tissue distribution in ovarian tumor tissue suggests that the translation product of this gene may be involved in apoptosis. Expression within cellular sources marked by proliferating cells suggests that this protein may play a role in the regulation of cellular division, and may show utility in the diagnosis and treatment of cancer and other proliferative disorders. Thus, this protein may also be involved in apoptosis and could be useful in cancer therapy. Protein, as well as, antibodies directed against the protein may show utility as a tumor marker and/or immunotherapy targets for the above listed tissues.

The ability of polynucleotides and polypeptides of the invention to increase or decrease apoptosis can routinely be determined using techniques known in the art. For example, biological activity can routinely be measured using cell death assays performed essentially as previously described (Chinnaiyan et al., Cell 81:505–512 (1995); Boldin et al., J. Biol. Chem. 270:7795–8(1995); Kischkel et al., EMBO 14:5579–5588 (1995); Chinnaiyan et al., J. Biol. Chem. 271:4961–4965 (1996)).

FEATURES OF PROTEIN ENCODED BY GENE NO: 7

Translation products corresponding to this gene share sequence homology with a *C. elegans* protein of unknown function (See Genbank Accession AAB37815).

In specific embodiments, polypeptides of the present invention comprise, or alternatively consist of, the following amino acid sequence: QGRFRAFCWQRDFLQPPG (SEQ ID NO: 25). Polynucleotides encoding these polypeptides are also encompassed by the invention, as are antibodies that bind one or more of these polypeptides. Moreover, fragments and variants of these polypeptides (e.g. fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Preferred polypeptides of the present invention comprise, or alternatively consist of, one, two, three, four, five, six, seven, eight, or all eight of the immunogenic epitopes shown in SEQ ID NO: 26 as residues: Pro-17 to Met-23, Ala-30 to Trp-38, Ile-49 to Trp-54, Lys-68 to Gly-74, Thr-93 to Gly-99, Met-126 to Glu-132, Gly-173 to Ser-178, and Lys-205 to Tyr-214. Polynucleotides encoding these polypeptides are also encompassed by the invention, as are antibodies that bind one or more of these polypeptides. Moreover, fragments and variants of these polypeptides (e.g. fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

It has been discovered that this gene is expressed primarily in primary dendritic cells, and to a lesser extent in ovarian tumor tissue.

Therefore, polynucleotides and polypeptides of the invention, including antibodies, are useful as reagents for differential identification of the tissue(s) or cell type(s) present in a biological sample and for diagnosis of the following diseases and conditions: immune system disorders and cancers. Similarly, polypeptides and antibodies directed to those polypeptides are useful to provide immunological probes for differential identification of the tissue(s) or cell type(s). For a number of disorders of the above tissues or cells, particularly of the immune and reproductive systems, expression of this gene at significantly higher or lower levels may be detected in certain tissues (e.g., immune, reproductive, cancerous and wounded tissues) or bodily fluids (e.g., lymph, serum, plasma, urine, synovial fluid or spinal fluid) taken from an individual having such a disorder, relative to the standard gene expression level, i.e., the expression level in healthy tissue from an individual not having the disorder.

The tissue distribution in primary dendritic cells suggests that the protein product of this clone is useful for the detection and/or treatment of disorders involving the immune system. This gene product may be involved in the regulation of cytokine production, antigen presentation, or other processes that may also suggest a usefulness in the treatment of cancer (e.g. by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types.

Alternatively, the tissue distribution in ovarian cancer tissue suggests that the translation product of this gene is useful for the detection and/or treatment of ovarian cancer, as well as cancers of other tissues where expression has been observed. Furthermore, it is possible that this gene is involved in the apoptotic pathway, and thus, could be useful in controlling aberrant cell growth or apoptosis, as one might find in cancerous tissues and/or malignant cells. Protein, as well as, antibodies directed against the protein may show utility as a tumor marker and/or immunotherapy targets for the above listed tissues.

Polynucleotides and polypeptides corresponding to this gene are thought to be involved in apoptosis. The ability of polynucleotides and polypeptides of the invention to increase or decrease apoptosis can routinely be determined using techniques known in the art. For example, biological activity can routinely be measured using cell death assays performed essentially as previously described (Chinnaiyan et al., Cell 81:505–512 (1995); Boldin et al., J. Biol. Chem. 270:7795–8(1995); Kischkel et al., EMBO 14:5579–5588 (1995); Chinnaiyan et al., J. Biol. Chem. 271:4961–4965 (1996)).

FEATURES OF PROTEIN ENCODED BY GENE NO: 8

Preferred polypeptides of the invention comprise, or alternatively consist of, an amino acid sequence selected from the group consisting of:

MFRCGGLAAGALKQKLVPLVRTVCVRSPRQRNRLPGNLFQRWHVPLELQM

TRQMASSGASGGKIDNSVLVLIVGLSTVGAGAYAYKTMKEDEKRYNERIS

GLGLTPEQKQKKAALSASEGEEVPQDKAPSHVPFLLIGGGTAAFAAARSI

RARDPGARVLIVSEDPELPYMRPPLSKELWFSDDPNVTKTLRFKQWNGKE

RSIYFQPPSFYVSAQDLPHIENGGVAVLTGKKVVQLDVRDNMVKLNDGSQ

ITYEKCLIATGGTPRSLSAIDRAGAEVKSRTTLFRKIGDFRSLEKISREV

KSITIIGGGFLGSELACALGRKARALGTEVIQLFPEKGNMGKILPEYLSN

WTMEKVRREGVKVMPNAIVQSVGVSSGKLLIKLKDGRKVETDHIVAAVGL

EPNVELAKTGGLEIDSDFGGFRVNAELQARSNIWVAGDAACFYDIKLGRR

RVEHHDHAVVSGRLAGENMTGAAKPYWHQSMFWSDLGPDVGYEAIGLVDS

SLPTVGVFAKATAQDNPKSATEQSGTGIRSESETESEASEITIPPSTPAV

PQAPVQGEDYGKGVIFYLRDKVVVGIVLWNIFNRMPIARKIIKDGEQHED

LNEVAKLFNTHED (SEQ ID NO:26), and

RTRGSTHASGLTRRSCVRGKGRRRSRIAVAE (SEQ ID NO:27).

Polynucleotides encoding these polypeptides are also encompassed by the invention, as are antibodies that bind one or more of these polypeptides. Moreover, fragments and variants of these polypeptides (e.g. fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

Preferred polypeptides of the present invention comprise, or alternatively consist of, one, two, three, four, five, six, seven, eight, nine, ten, eleven, twelve, or all twelve of the immunogenic epitopes shown in SEQ ID NO: 27 as residues: Ser-27 to Pro-35, Thr-87 to Ile-99, Pro-106 to Lys-112, Glu-119 to Ser-130, Ser-182 to Val-187, Lys-194 to Tyr-204, Lys-295 to Val-300, Lys-384 to Glu-390, Thr-512 to Thr-526, Ser-530 to Glu-537, Gln-556 to Lys-562, Lys-593 to Leu-601. Polynucleotides encoding these polypeptides are also encompassed by the invention, as are antibodies that bind one or more of these polypeptides. Moreover, fragments and variants of these polypeptides (e.g. fragments as described herein, polypeptides at least 80%, 85%, 90%, 95%, 96%, 97%, 98%, or 99% identical to these polypeptides and polypeptides encoded by the polynucleotide which hybridizes, under stringent conditions, to the polynucleotide encoding these polypeptides, or the complement thereof) are encompassed by the invention. Antibodies that bind these fragments and variants of the invention are also encompassed by the invention. Polynucleotides encoding these fragments and variants are also encompassed by the invention.

It has been discovered that this gene is expressed primarily in the following tissues/cDNA libraries: primary dendritic cells, lib 1; and to a lesser extent in soares ovary tumor; human testes; soares parathyroid tumor; human adult small intestine, re-excision; human adult small intestine; human heart cDNA; T-cell helper II; and soares fetal liver spleen.

Therefore, polynucleotides and polypeptides of the invention, including antibodies, are useful as reagents for differential identification of the tissue(s) or cell type(s) present in a biological sample and for diagnosis of the following diseases and conditions: immune and hematopoietic diseases and/or disorders, particularly infectious and proliferative diseases. Similarly, polypeptides and antibodies directed to those polypeptides are useful to provide immunological probes for differential identification of the tissue(s) or cell type(s). For a number of disorders of the above tissues or cells, particularly of the immune system, expression of this gene at significantly higher or lower levels may be detected in certain tissues (e.g., immune, hematopoietic, and cancerous and wounded tissues) or bodily fluids (e.g., lymph, serum, plasma, urine, synovial fluid or spinal fluid) taken from an individual having such a disorder, relative to the standard gene expression level, i.e., the expression level in healthy tissue from an individual not having the disorder.

The tissue distribution in dendritic cells suggests the protein product of this clone is useful for the diagnosis and treatment of a variety of immune system disorders. Representative uses are described in the "Immune Activity" and "Infectious Disease" sections below. Briefly, the expression of this gene product indicates a role in regulating the proliferation; survival; differentiation; and/or activation of hematopoietic cell lineages, including blood stem cells. This gene product is involved in the regulation of cytokine production, antigen presentation, or other processes suggesting a usefulness in the treatment of cancer (e.g. by boosting immune responses). Since the gene is expressed in cells of lymphoid origin, the natural gene product is involved in immune function. Therefore it is also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types.

Moreover, the expression within cellular sources marked by proliferating cells indicates this protein may play a role in the regulation of cellular division, and may show utility in the diagnosis, treatment, and/or prevention of developmental diseases and disorders, cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation.

Polynucleotides and polypeptides corresponding to this gene are thought to function in apoptosis. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention are useful in treating, detecting, and/or preventing said disorders and conditions, in addition to other types of degenerative conditions. Thus translation products corresponding to this gene may modulate apoptosis or tissue differentiation and would be useful in the detection, treatment, and/or prevention of degenerative or proliferative conditions and diseases. The protein is useful in modulating the immune response to aberrant polypeptides, as may exist in proliferating and cancerous cells and tissues. The protein can also be used to gain new insight into the regulation of cellular growth and proliferation.

Polypeptides of the present invention have been shown to include a flavin moiety, and share sequence homology to bacterial oxidoreductases. Such flavin moieties are subject to regulation either by the reduction/oxidation potential of the intracellular environment or through the application of specific suicide inhibitors such as N,N-dimethylpropargylamine, for example (See Enzyme Structure and Mechanism; Fersht, Alan, W.H. Freeman and Company, pp.260–261, (1985), which is hereby incorporated herein by reference). Based upon the potential for such regulation, antagonists for the present invention are contemplated and would be useful in inhibiting the specific apoptotic pathways subject to regulation by polypeptides of the present invention. Such inhibition would be useful, though not limited to, inhibiting stress-, disease-, and/or infection-induced apoptotic responses, for example. Polypeptides of the present invention may have other uses, aside from serving as a downstream effector for apoptosis, which are described above, and elseware herein.

Apoptosis, or programmed cell death, is a physiologic process essential to the normal development and homeostasis of multicellular organisms (H. Steller, Science 267, 1445–1449 (1995)). Derangements of apoptosis contribute to the pathogenesis of several human diseases including cancer, neurodegenerative disorders, and acquired immune deficiency syndrome (C. B. Thompson, Science 267, 1456–1462 (1995)). Recently, much attention has focused on the signal transduction and biological function of two cell surface death receptors, Fas/APO-1 and TNFR-1 (J. L. Cleveland, et al., Cell 81, 479–482 (1995); A. Fraser, et al., Cell 85, 781–784 (1996); S. Nagata, et al., Science 267, 1449–56 (1995)). Both are members of the TNF receptor family which also include TNFR-2, low affinity NGFR, CD40, and CD30, among others (C. A. Smith, et al., Science 248, 1019–23 (1990); M. Tewari, et al., in Modular Texts in Molecular and Cell Biology M. Purton, Heldin, Carl, Ed. (Chapman and Hall, London, 1995). While family members are defined by the presenceof cysteine-rich repeats in their extracellular domains, Fas/APO-1 and TNFR-1 also share a region of intracellular homology, appropriately designated the "death domain", which is distantly related to the Drosophila suicide gene, reaper (P. Golstein, et al., Cell 81, 185–6 (1995); K. White et al., Science 264, 677–83 (1994)). This shared death domain suggests that both receptors interact with a related set of signal transducing molecules that, until recently, remained unidentified. Activation of Fas/APO-1 recruits the death domain-containing adapter molecule FADD/MORT1 (A. M. Chinnaiyan, et al., Cell 81, 505–12 (1995); M. P. Boldin, et al., J. Biol Chem 270, 7795–8 (1995); F. C. Kischkel, et al., EMBO 14, 5579–5588 (1995)), which in turn binds and presumably activates FLICE/MACH1, a member of the ICE/CED-3 family of pro-apoptotic proteases (M. Muzio et al., Cell 85, 817–827 (1996); M. P. Boldin, et al., Cell 85, 803–815 (1996)). While the central role of Fas/APO-1 is to trigger cell death, TNFR-1 can signal an array of diverse biological activities—many of which stem from its ability to activate NF-kB (L. A. Tartaglia, et al., Immunol Today 13, 151–3 (1992)). Accordingly, TNFR-1 recruits the multivalent adapter molecule TRADD, which like FADD, also contains a death domain (H. Hsu, et al., Cell 81, 495–504 (1995); H. Hsu, et al., Cell 84, 299–308 (1996)). Through its associations with a number of signaling molecules including FADD, TRAF2, and RIP, TRADD can signal both apoptosis and NF-kB activation (H. Hsu, et al., Cell 84, 299–308 (1996); H. Hsu, et al., Immunity 4, 387–396 (1996)). Recently a new apoptosis inducing ligand was discovered. Wiley, S. R. et al., refer to the new molecule as TNF-related apoptosis-inducing ligand or (TRAIL) (Immunity 3:673–682 (1995)). Pitti, R. M. et al., refer to the new molecule as Apo-2 ligand or (iApo-2Lî). This molecule was also disclosed in copending U.S. Provisional Patent Application Ser. No. 60/013,405. For convenience, it will be referred to herein as TRAIL. Unlike FAS ligand whose transcripts appear to be largely restricted to stimulated T-cells, significant levels of TRAIL are seen in many tissues, and it is constitutively transcribed by some cell lines. It has been shown that TRAIL acts independently from FAS ligand (Wiley, S. R., et al. (1995)), supra). Studies by Marsters, S. A. et al., have indicated that TRAIL activates apoptosis rapidly, within a time frame that is similar to death signalling by FAS/Apo-1L but much faster than TNF-induced apoptosis (Current Biology, 6:750–752 (1996)). All work to date suggest that the receptor for TRAIL is not one of the many known TNF-receptors.

Based upon the localization of the protein of the present invention in mitochondria and its apoptosis-dependent translocation to the nucleus, it is clear that this protein is useful in treating and/or preventing a number of diseases and/or disorders, particularly proliferative conditions and would again be useful in modulating the immune response to transformed cells and aberrant phenotypes. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The potential for the polynucleotides and/or polypeptides of the present invention to elicit an apoptotic response can be assayed through a number of means, particular through the application of cell death assays. Briefly, cell death assays are performed essentially as previously described (A. M. Chinnaiyan, et al., Cell 81, 505–12 (1995); M. P. Boldin, et al., J Biol Chem 270, 7795–8 (1995); F. C. Kischkel, et al., EMBO 14, 5579–5588 (1995); A. M. Chinnaiyan, et al., J Biol Chem 271, 4961–4965 (1996)).

Briefly, MCF-7 human breast carcinoma clonal cell lines stably transfected with either vector alone or a CrmA expression construct (M. Tewari, et al., J Biol Chem 270, 3255–60 (1995)), are transiently transfected with pCMV-AIF-galatosidase (or pCMV-AIF-galactosidase an inactive form of AIF) in the presence of a ten-fold excess of pcDNA3 expression constructs encoding the indicated proteins using lipofectamine (GIBCO-BRL). 293 cells are likewise transfected using the CaPO4 method. The ICE family inhibitor z-VAD-fmk (Enzyme Systems Products, Dublin, Calif.) is added to the cells at a concentration of 10 µM, 5 hrs after transfection. 32 hours following transfection, cells are fixed and stained with X-Gal as previously described (A. M. Chinnaiyan, et al., Cell 81, 505–12 (1995); M. P. Boldin, et al., J Biol Chem 270, 7795–8 (1995); F. C. Kischkel, et al., EMBO 14, 5579–5588 (1995)).

The cDNA Clone ID was deposited on the date and given the corresponding deposit number listed in "ATCC Deposit No:Z and Date." Some of the deposits contain multiple different clones corresponding to the same gene. "Vector" refers to the type of vector contained in the cDNA Clone ID.

"Total NT Seq." refers to the total number of nucleotides in the contig identified by "Gene No:" The deposited plasmid contains all of these sequences, reflected by the nucleotide position indicated as "5' NT of Clone Seq." and the "3' NT of Clone Seq." of SEQ ID NO:X. The nucleotide position of SEQ ID NO:X of the putative methionine start codon (if present) is identified as "5' NT of Start Codon." Similarly, the nucleotide position of SEQ ID NO:X of the predicted signal sequence (if present) is identified as "5' NT of First AA of Signal Pep."

The translated amino acid sequence, beginning with the first translated codon of the polynucleotide sequence, is identified as "AA SEQ ID NO:Y," although other reading frames can also be easily translated using known molecular biology techniques. The polypeptides produced by these alternative open reading frames are specifically contemplated by the present invention.

SEQ ID NO:X (where X may be any of the polynucleotide sequences disclosed in the sequence listing) and the translated SEQ ID NO:Y (where Y may be any of the polypeptide sequences disclosed in the sequence listing) are sufficiently accurate and otherwise suitable for a variety of uses well known in the art and described further below. For instance, SEQ ID NO:X has uses including, but not limited to, in designing nucleic acid hybridization probes that will detect nucleic acid sequences contained in SEQ ID NO:X or the

TABLE 1

| Gene No. | CDNA Clone ID | ATCC Deposit No: Z and Date | Vector | NT SEQ ID NO: X | Total NT Seq. | 5' NT of Clone Seq. | 3' NT of Clone Seq. | 5' NT of Start Codon | AA SEQ ID NO: Y | Last AA of ORF |
|---|---|---|---|---|---|---|---|---|---|---|
| 1 | HLDOK36 | PTA161 Jun. 1, 1999 | pCMVSport 3.0 | 2 | 2045 | 1 | 2045 | 187 | 11 | 304 |
| 2 | HDPBW68 | PTA161 Jun. 1, 1999 | pCMVSport 3.0 | 3 | 4415 | 1 | 4415 | 425 | 12 | 953 |
| 2 | HDPBW68 | PTA161 Jun. 1, 1999 | pCMVSport 3.0 | 10 | 3789 | 1 | 3789 | 558 | 19 | 705 |
| 3 | HHEFO24 | PTA161 Jun. 1, 1999 | pCMVSport 3.0 | 4 | 2066 | 1 | 2066 | 12 | 13 | 445 |
| 4 | HEGAL46 | PTA161 Jun. 1, 1999 | Uni-ZAP XR | 5 | 1406 | 1 | 1406 | 237 | 14 | 340 |
| 5 | HFOYC02 | PTA161 Jun. 1, 1999 | pSport1 | 6 | 3172 | 372 | 2212 | 252 | 15 | 317 |
| 6 | HDABV82 | PTA161 Jun. 1, 1999 | pSport1 | 7 | 2290 | 1 | 2290 | 222 | 16 | 90 |
| 7 | HSVAF16 | PTA161 Jun. 1, 1999 | Uni-ZAP XR | 8 | 1316 | 101 | 1316 | 524 | 17 | 216 |
| 8 | HSIFO61 | PTA181 Jun. 7, 1999 | Uni-ZAP XR | 9 | 2150 | 647 | 2076 | 95 | 18 | 613 |

Table 1 summarizes the information corresponding to each "Gene No:" described above. The nucleotide sequence identified as "NT SEQ ID NO:X" was assembled from partially homologous ("overlapping") sequences obtained from the "cDNA clone ID" identified in Table 1 and, in some cases, from additional related DNA clones. The overlapping sequences were assembled into a single contiguous sequence of high redundancy (usually three to five overlapping sequences at each nucleotide position), resulting in a final sequence identified as SEQ ID NO:X.

cDNA contained in a deposited plasmid. These probes will also hybridize to nucleic acid molecules in biological samples, thereby enabling a variety of forensic and diagnostic methods of the invention. Similarly, polypeptides identified from SEQ ID NO:Y have uses that include, but are not limited to generating antibodies, which bind specifically to the secreted proteins encoded by the cDNA clones identified in Table 1.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:X, and the predicted translated amino acid sequence identified as SEQ ID NO:Y, but also a sample of plasmid DNA containing a human cDNA of the invention deposited with the ATCC, as set forth in Table 1. The nucleotide sequence of each deposited plasmid can readily be determined by sequencing the deposited plasmid in accordance with known methods.

The predicted amino acid sequence can then be verified from such deposits. Moreover, the amino acid sequence of the protein encoded by a particular plasmid can also be directly determined by peptide sequencing or by expressing the protein in a suitable host cell containing the deposited human cDNA, collecting the protein, and determining its sequence.

Also provided in Table 1 is the name of the vector which contains the cDNA plasmid. Each vector is routinely used in the art. The following additional information is provided for convenience.

Vectors Lambda Zap (U.S. Pat. Nos. 5,128,256 and 5,286,636), Uni-Zap XR (U.S. Pat. Nos. 5,128,256 and 5,286,636), Zap Express (U.S. Pat. Nos. 5,128,256 and 5,286,636), pBluescript (pBS) (Short, J. M. et al., *Nucleic Acids Res.* 16:7583–7600 (1988); Alting-Mees, M. A. and Short, J. M., *Nucleic Acids Res.* 17:9494 (1989)) and pBK (Alting-Mees, M. A. et al., *Strategies* 5:58–61 (1992)) are commercially available from Stratagene Cloning Systems, Inc., 11011 N. Torrey Pines Road, La Jolla, Calif., 92037. pBS contains an ampicillin resistance gene and pBK contains a neomycin resistance gene. Phagemid pBS may be excised from the Lambda Zap and Uni-Zap XR vectors, and phagemid pBK may be excised from the Zap Express vector. Both phagemids may be transformed into *E. coli* strain XL-1 Blue, also available from Stratagene.

Vectors pSport1, pCMVSport 1.0, pCMVSport 2.0 and pCMVSport 3.0, were obtained from Life Technologies, Inc., P. O. Box 6009, Gaithersburg, Md. 20897. All Sport vectors contain an ampicillin resistance gene and may be transformed into *E. coli* strain DH10B, also available from Life Technologies. See, for instance, Gruber, C. E., et al., *Focus* 15:59 (1993). Vector lafmid BA (Bento Soares, Columbia University, New York, N.Y.) contains an ampicillin resistance gene and can be transformed into *E. coli* strain XL-1 Blue. Vector pCR®2.1, which is available from Invitrogen, 1600 Faraday Avenue, Carlsbad, Calif. 92008, contains an ampicillin resistance gene and may be transformed into *E. coli* strain DH10B, available from Life Technologies. See, for instance, Clark, J. M., *Nuc. Acids Res.* 16:9677–9686 (1988) and Mead, D. et al., *Bio/Technology* 9: (1991).

The present invention also relates to the genes corresponding to SEQ ID NO:X, SEQ ID NO:Y, and/or a deposited cDNA (cDNA plasmid:Z). The corresponding gene can be isolated in accordance with known methods using the sequence information disclosed herein. Such methods include, but are not limited to, preparing probes or primers from the disclosed sequence and identifying or amplifying the corresponding gene from appropriate sources of genomic material.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to SEQ ID NO:X, SEQ ID NO:Y, and/or cDNA plasmid:Z, using information from the sequences disclosed herein or the clones deposited with the ATCC. For example, allelic variants and/or species homologs may be isolated and identified by making suitable probes or primers from the sequences provided herein and screening a suitable nucleic acid source for allelic variants and/or the desired homologue.

The present invention provides a polynucleotide comprising, or alternatively consisting of, the nucleic acid sequdnce of SEQ ID NO:X and/or cDNA plasmid:Z. The present invention also provides a polypeptide comprising, or alternatively, consisting of, the polypeptide sequence of SEQ ID NO:Y, a polypeptide encoded by SEQ ID NO:X, and/or a polypeptide encoded by the cDNA in cDNA plasmid:Z. Polynucleotides encoding a polypeptide comprising, or alternatively consisting of the polypeptide sequence of SEQ ID NO:Y, a polypeptide encoded by SEQ ID NO:X and/or a polypeptide encoded by the cDNA in cDNA plasmid:Z, are also encompassed by the invention. The present invention further encompasses a polynucleotide comprising, or alternatively consisting of the complement of the nucleic acid sequence of SEQ ID NO:X, and/or the complement of the coding strand of the cDNA in cDNA plasmid:Z.

Many polynucleotide sequences, such as EST sequences, are publicly available and accessible through sequence databases and may have been publicly available prior to conception of the present invention. Preferably, such related polynucleotides are specifically excluded from the scope of the present invention. To list every related sequence would unduly burden the disclosure of this application. Accordingly, preferably excluded from SEQ ID NO:X are one or more polynucleotides comprising a nucleotide sequence described by the general formula of a–b, where a is any integer between 1 and the final nucleotide minus 15 of SEQ ID NO:X, b is an integer of 15 to the final nucleotide of SEQ ID NO:X, where both a and b correspond to the positions of nucleotide residues shown in SEQ ID NO:X, and where b is greater than or equal to a+14.

RACE Protocol For Recovery of Full-Length Genes

Partial cDNA clones can be made full-length by utilizing the rapid amplification of cDNA ends (RACE) procedure described in Frohman, M. A., et al., Proc. Nat'l. Acad. Sci. USA, 85:8998–9002 (1988). A cDNA clone missing either the 5' or 3' end can be reconstructed to include the absent base pairs extending to the translational start or stop codon, respectively. In some cases, cDNAs are missing the start of translation, therefor. The following briefly describes a modification of this original 5' RACE procedure. Poly A+ or total RNA is reverse transcribed with Superscript II (Gibco/BRL) and an antisense or complementary primer specific to the cDNA sequence. The primer is removed from the reaction with a Microcon Concentrator (Amicon). The first-strand cDNA is then tailed with dATP and terminal deoxynucleotide transferase (Gibco/BRL). Thus, an anchor sequence is produced which is needed for PCR amplification. The second strand is synthesized from the dA-tail in PCR buffer, Taq DNA polymerase (Perkin-Elmer Cetus), an oligo-dT primer containing three adjacent restriction sites (XhoI, SalI and ClaI) at the 5' end and a primer containing just these restriction sites. This double-stranded cDNA is PCR amplified for 40 cycles with the same primers as well as a nested cDNA-specific antisense primer. The PCR products are size-separated on an ethidium bromide-agarose gel and the region of gel containing cDNA products the predicted size of missing protein-coding DNA is removed. cDNA is purified from the agarose with the Magic PCR Prep kit (Promega), restriction digested with XhoI or SalI, and ligated to a plasmid such as pBluescript SKII (Stratagene) at XhoI and EcoRV sites. This DNA is transformed into bacteria and the plasmid clones sequenced to identify the correct protein-coding inserts. Correct 5' ends are confirmed by comparing this sequence with the putatively identified homologue and overlap with the partial cDNA clone. Similar methods known in the art and/or commercial are used to amplify and recover 3' ends.

Several qualify-controlled kits are commercially available for purchase. Similar reagents and methods to those above are supplied in kit form from Gibco/BRL for both 5' and 3' RACE for recovery of full length genes. A second kit is available from Clontech which is a modification of a related technique, SLIC (single-stranded ligation to single-stranded cDNA), developed by Dumas et al., Nucleic Acids Res., 19:5227–32 (1991). The major differences in procedure are that the RNA is alkaline hydrolyzed after reverse transcription and RNA ligase is used to join a restriction site-containing anchor primer to the first-strand cDNA. This obviates the necessity for the dA-tailing reaction which results in a polyT stretch that is difficult to sequence past.

An alternative to generating 5' or 3' cDNA from RNA is to use cDNA library double-stranded DNA. An asymmetric PCR-amplified antisense cDNA strand is synthesized with an antisense cDNA-specific primer and a plasmid-anchored primer. These primers are removed and a symmetric PCR reaction is performed with a nested cDNA-specific antisense primer and the plasmid-anchored primer.

RNA Ligase Protocol for Generating the 5' or 3' End Sequences to Obtain Full Length Genes Once a gene of interest is identified, several methods are available for the identification of the 5' or 3' portions of the gene which may not be present in the original cDNA plasmid. These methods include, but are not limited to, filter probing, clone enrichment using specific probes and protocols similar and identical to 5' and 3'RACE. While the full length gene may be present in the library and can be identified by probing, a useful method for generating the 5' or 3' end is to use the existing sequence information from the original cDNA to generate the missing information. A method similar to 5'RACE is available for generating the missing 5' end of a desired full-length gene. (This method was published by Fromont-Racine et al., Nucleic Acids Res., 21(7):1683–1684 (1993)). Briefly, a specific RNA oligonucleotide is ligated to the 5' ends of a population of RNA presumably containing full-length gene RNA transcript and a primer set containing a primer specific to the ligated RNA oligonucleotide and a primer specific to a known sequence of the gene of interest, is used to PCR amplify the 5' portion of the desired full length gene which may then be sequenced and used to generate the full length gene. This method starts with total RNA isolated from the desired source, poly A RNA may be used but is not a prerequisite for this procedure. The RNA preparation may then be treated with phosphatase if necessary to eliminate 5' phosphate groups on degraded or damaged RNA which may interfere with the later RNA ligase step. The phosphatase if used is then inactivated and the RNA is treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase. This modified RNA preparation can then be used as a template for first strand cDNA synthesis using a gene specific olignucleotide. The first strand synthesis reaction can then be used as a template for PCR amplification of the desired 5' end using a primer specific to the ligated RNA oligonucleotide and a primer specific to the known sequence of the apoptosis related gene of interest. The resultant product is then sequenced and analyzed to confirm that the 5' end sequence belongs to the relevant apoptosis related gene.

Polynucleotide and Polypeptide Fragments

The present invention is also directed to polynucleotide fragments of the polynucleotides (nucleic acids) of the invention. In the present invention, a "polynucleotide fragment" refers to a polynucleotide having a nucleic acid sequencd which: is a portion of the cDNA contained in a cDNA plasmid:Z or encoding the polypeptide encoded by the cDNA contained in cDNA plasmid:Z; is a portion of the polynucleotide sequence in SEQ ID NO:X or the complementary strand thereto; is a polynucleotide sequence encoding a portion of the polypeptide of SEQ ID NO:Y; or is a polynucleotide sequence encoding a portion of a polypeptide encoded by SEQ ID NO:X. The nucleotide fragments of the invention are preferably at least about 15 nt, and more preferably at least about 20 nt, still more preferably at least about 30 nt, and even more preferably, at least about 40 nt, at least about 50 nt, at at least about 75 nt, at least about 100 nt, or at least about 150 nt in length. A fragment "at least 20 nt in length," for example, is intended to include 20 or more contiguous bases from, for example, the sequence contained in the cDNA in cDNA plasmid:Z, or the nucleotide sequence shown in SEQ ID NO:X or the complementary stand thereto. In this context "about" includes the particularly recited value, or a value larger or smaller by several (5, 4, 3, 2, or 1) nucleotides. These nucleotide fragments have uses that include, but are not limited to, as diagnostic probes and primers as discussed herein. Of course, larger fragments (e.g., at least 150, 175, 200, 250, 500, 600, 1000, or 2000 nucleotides in length) are also encompassed by the invention.

Moreover, representative examples of polynucleotide fragments of the invention, include, for example, fragments comprising, or alternatively consisting of, a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, 2001–2050, 2051–2100, 2101–2150, 2151–2200, 2201–2250, 2251–2300, 2301–2350, 2351–2400, 2401–2450, 2451–2500, 2501–2550, 2551–2600, 2601–2650, 2651–2700, 2701–2750, 2751–2800, 2801–2850, 2851–2900, 2901–2950, 2951–3000, 3001–3050, 3051–3100, 3101–3150, 3151–3200, 3201–3250, 3251–3300, 3301–3350, 3351–3400, 3401–3450, 3451–3500, 3501–3550, 3551–3600, 3601–3650, 3651–3700, 3701–3750, 3751–3800, 3801–3850, 3851–3900, 3901–3950, 3951–4000, 4001–4050, 4051–4100, 4101–4150, 4151–4200, 4201–4250, 4251–4300, 4301–4350, 4351–4400, and/or 4401–4415 of SEQ ID NO:X, or the complementary strand thereto. In this context "about" includes the particularly recited range or a range larger or smaller by several (5, 4, 3, 2, or 1) nucleotides, at either terminus or at both termini. Preferably, these fragments encode a polypeptide which has a functional activity (e.g. biological activity) of the polypeptide encoded by a polynucleotide of which the sequence is a portion. More preferably, these fragments can be used as probes or primers as discussed herein. Polynucleotides which hybridize to one or more of these fragments under stringent hybridization conditions or alternatively, under lower stringency conditions, are also encompassed by the invention, as are polypeptides encoded by these polynucleotides or fragments.

Moreover, representative of polynucleotide fragments of the invention, include, for example, fragments comprising, or alternatively consisting of, a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, 2001–2050, 2051–2100, 2101–2150, 2151–2200, 2201–2250, 2251–2300, 2301–2350, 2351–2400, 2401–2450, 2451–2500, 2501–2550, 2551–2600, 2601–2650, 2651–2700, 2701–2750, 2751–2800, 2801–2850, 2851–2900, 2901–2950, 2951–3000, 3001–3050, 3051–3100, 3101–3150, 3151–3200, 3201–3250, 3251–3300, 3301–3350, 3351–3400, 3401–3450, 3451–3500, 3501–3550, 3551–3600, 3601–3650, 3651–3700, 3701–3750, 3751–3800, 3801–3850, 3851–3900, 3901–3950, 3951–4000, 4001–4050, 4051–4100, 4101–4150, 4151–4200, 4201–4250, 4251–4300, 4301–4350, 4351–4400, and/or 4401–4415 of the cDNA nucleotide sequence contained in cDNA plasmid:Z, or the complementary strand thereto. In this context "about" includes the particularly recited range or a range larger or smaller by several (5, 4, 3, 2, or 1) nucleotides, at either terminus or at both termini. Preferably, these fragments encode a polypeptide which has a functional activity (e.g. biological activity) of the polypeptide encoded by a the cDNA nucleotide sequence contained in cDNA plasmid:Z. More preferably, these fragments can be used as probes or primers as discussed herein. Polynucleotides which hybridize to one or more of these fragments under stringent hybridization conditions or alternatively, under lower stringency conditions are also encompassed by the invention, as are polypeptides encoded by these polynucleotides or fragments.

In the present invention, a "polypeptide fragment" refers to an amino acid sequence which is a portion of that contained in SEQ ID NO:Y, a portion of an amino acid sequence encoded by the polynucleotide sequence of SEQ ID NO:X, and/or encoded by the cDNA in cDNA plasmid:Z. Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, an amino acid sequence from about amino acid number 1–20, 21–40, 41–60, 61–80, 81–100, 102–120, 121–140, 141–160, 161–180, 181–200, 201–220, 221–240, 241–260, 261–280, 281–300, 301–320, 321–340, 341–360, 361–380, 381–400, 401–420, 421–440, 441–460, 461–480, 481–500, 501–520, 521–540, 541–560, 561–580, 581–600, 601–620, 621–640, 641–660, 661–680, 681–700, 701–720, 721–740, 741–760, 761–780, 781–800, 801–840, 841–860, 861–880, 881–900, 901–920, 921–940, and/or 941–953 of the coding region of SEQ ID NO:Y. Moreover, polypeptide fragments of the invention may be at least about 10, 15, 20, 25, 30, 35, 40, 45, 50, 55, 60, 65, 70, 75, 80, 85, 90, 100, 110, 120, 130, 140, or 150 amino acids in length. In this context "about" includes the particularly recited ranges or values, or ranges or values larger or smaller by several (5, 4, 3, 2, or 1) amino acids, at either terminus or at both termini. Polynucleotides encoding these polypeptide fragments are also encompassed by the invention.

Even if deletion of one or more amino acids from the N-terminus of a protein results in modification of loss of one or more biological functions of the protein, other functional activities (e.g., biological activities, ability to multimerize, ability to bind a ligand) may still be retained. For example, the ability of shortened muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a mutein with a large number of deleted N-terminal amino acid residues may retain some biological or immunogenic activities. In fact, peptides composed of as few as six amino acid residues may often evoke an immune response.

Accordingly, polypeptide fragments of the invention include the secreted protein as well as the mature form. Further preferred polypeptide fragments include the secreted protein or the mature form having a continuous series of deleted residues from the amino or the carboxy terminus, or both. For example, any number of amino acids, ranging from 1–60, can be deleted from the amino terminus of either the secreted polypeptide or the mature form. Similarly, any number of amino acids, ranging from 1–30, can be deleted from the carboxy terminus of the secreted protein or mature form. Furthermore, any combination of the above amino and carboxy terminus deletions are preferred. Similarly, polynucleotides encoding these polypeptide fragments are also preferred.

The present invention further provides polypeptides having one or more residues deleted from the amino terminus of the amino acid sequence of a polypeptide disclosed herein (e.g., a polypeptide of SEQ ID NO:Y, a polypeptide encoded by the polynucleotide sequence contained in SEQ ID NO:X, and/or a polypeptide encoded by the cDNA contained in cDNA plasmid:Z). In particular, N-terminal deletions may be described by the general formula m–q, where q is a whole integer representing the total number of amino acid residues in a polypeptide of the invention (e.g., the polypeptide disclosed in SEQ ID NO:Y), and m is defined as any integer ranging from 2 to q-6. Polynucleotides encoding these polypeptides, including fragments and/or variants, are also encompassed by the invention.

Also as mentioned above, even if deletion of one or more amino acids from the C-terminus of a protein results in modification of loss of one or more biological functions of the protein, other functional activities (e.g., biological activities, ability to multimerize, ability to bind a ligand) may still be retained. For example the ability of the shortened mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a mutein with a large number of deleted C-terminal amino acid residues may retain some biological or immunogenic activities. In fact, peptides composed of as few as six amino acid residues may often evoke an immune response.

Accordingly, the present invention further provides polypeptides having one or more residues from the carboxy terminus of the amino acid sequence of a polypeptide disclosed herein (e.g., a polypeptide of SEQ ID NO:Y, a polypeptide encoded by the polynucleotide sequence contained in SEQ ID NO:X, and/or a polypeptide encoded by the cDNA contained in cDNA plasmid:Z). In particular, C-terminal deletions may be described by the general formula 1-n, where n is any whole integer ranging from 6 to q-1, and where n corresponds to the position of an amino acid residue in a polypeptide of the invention. Polynucleotides encoding these polypeptides, including fragments and/or variants, are also encompassed by the invention.

In addition, any of the above described N- or C-terminal deletions can be combined to produce a N- and C-terminal deleted polypeptide. The invention also provides polypeptides having one or more amino acids deleted from both the amino and the carboxyl termini, which may be described generally as having residues m–n of a polypeptide encoded by SEQ ID NO:X (e.g., including, but not limited to, the preferred polypeptide disclosed as SEQ ID NO:Y), and/or the cDNA in cDNA plasmid:Z, and/or the complement thereof, where n and m are integers as described above. Polynucleotides encoding these polypeptides, including fragments and/or variants, are also encompassed by the invention.

Any polypeptide sequence contained in the polypeptide of SEQ ID NO:Y, encoded by the polynucleotide sequences set forth as SEQ ID NO:XX, or encoded by the cDNA in cDNA plasmid:Z may be analyzed to determine certain preferred regions of the polypeptide. For example, the amino acid sequence of a polypeptide encoded by a polynucleotide sequence of SEQ ID NO:X or the cDNA in cDNA plasmid:Z may be analyzed using the default parameters of the DNASTAR computer algorithm (DNASTAR, Inc., 1228 S. Park St., Madison, Wis. 53715 USA; http://www.dnastar.com/).

Polypeptide regions that may be routinely obtained using the DNASTAR computer algorithm include, but are not limited to, Garnier-Robson alpha-regions, beta-regions, turn-regions, and coil-regions. Chou-Fasman alpha-regions, beta-regions, and turn-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index. Among highly preferred polynucleotides of the invention in this regard are those that encode polypeptides comprising regions that combine several structural features, such as several (e.g., 1, 2, 3 or 4) of the features set out above.

Additionally, Kyte-Doolittle hydrophilic regions and hydrophobic regions, Emini surface-forming regions, and Jameson-Wolf regions of high antigenic index (i.e., containing four or more contiguous amino acids having an antigenic index of greater than or equal to 1.5, as identified using the default parameters of the Jameson-Wolf program) can routinely be used to determine polypeptide regions that exhibit a high degree of potential for antigenicity. Regions of high antienicity are determined from data by DNASTAR analysis by choosing values which represent regions of the polypeptide which are likely to be exposed on the surface of the polypeptide in an environment in which antigen recognition may occur in the process of initiation of an immune response.

Preferred polypeptide fragments of the invention are fragments comprising, or alternatively, consisting of, an amino acid sequence that displays a functional activity (e.g. biological activity) of the polypeptide sequence of which the amino acid sequence is a fragment. By a polypeptide displaying a "functional activity" is meant a polypeptide capable of one or more known functional activities associated with a full-length protein, such as, for example, biological activity, antigenicity, immunogenicity, and/or multimerization, as described supra.

Other preferred polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity.

In preferred embodiments, polypeptides of the invention comprise, or alternatively consist of, one, two, three, four, five or more of the antigenic fragments of the polypeptide of SEQ ID NO:Y, or portions thereof. Polynucleotides encoding these polypeptides, including fragments and/or variants, are also encompassed by the invention.

The present invention encompasses polypeptides comprising, or alternatively consisting of, an epitope of the polypeptide sequence shown in SEQ ID NO:Y, or an epitope of the polypeptide sequence encoded by the cDNA in cDNA plasmid:Z, or encoded by a polynucleotide that hybridizes to the complement of an epitope encoding sequence of SEQ ID NO:X, or an epitope encoding sequence contained in cDNA plasmid:Z under stringent hybridization conditions, or alternatively, under lower stringency hybridization, as defined supra. The present invention further encompasses polynucleotide sequences encoding an epitope of a polypeptide sequence of the invention (such as, for example, the sequence disclosed in SEQ ID NO:X), polynucleotide sequences of the complementary strand of a polynucleotide sequence encoding an epitope of the invention, and polynucleotide sequences which hybridize to this complementary strand under stringent hybridization conditions, or alternatively, under lower stringency hybridization conditions, as defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, R. A., Proc. Natl. Acad. Sci. USA 82:5131–5135 (1985) further described in U.S. Pat. No. 4,631,211.)

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767–778 (1984); Sutcliffe et al., Science 219:660–666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention and immunogenic and/or antigenic epitope fragments thereof can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84–86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., J. Biochem., 270: 3958–3964 (1995).

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, may be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270: 9459–9471 (1995).)

Moreover, the polypeptides of the present invention can be fused to marker sequences, such as a peptide which facilitates purification of the fused polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the polynucleotides or the peptides of the present invention.

Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., Proc. Natl. Acad. Sci. USA 88:8972-897 (1991)). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605, 793; 5,811,238; 5,830,721; 5,834,252; and 5,837,458, and Patten et al., Curr. Opinion Biotechnol. 8:724–33 (1997); Harayama, Trends Biotechnol. 16(2):76–82 (1998); Hansson, et al., J. Mol. Biol. 287:265–76 (1999); and Lorenzo and Blasco, Biotechniques 24(2):308–13 (1998) (each of these patents and publications are hereby incorporated by reference in its entirety). In one embodiment, alteration of polynucleotides corresponding to SEQ ID NO:X and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Polynucleotide and Polypeptide Variants

The invention also encompasses apoptosis related variants. The present invention is directed to variants of the polynucleotide sequence disclosed in SEQ ID NO:X or the complementary strand thereto, and/or the cDNA sequence contained in cDNA plasmid:Z.

The present invention also encompasses variants of the polypeptide sequence disclosed in SEQ ID NO:Y, a polypeptide sequence encoded by the polynucleotide sequence in SEQ ID NO:X and/or a polypeptide sequence encoded by the cDNA in cDNA plasmid:Z.

"Variant" refers to a polynucleotide or polypeptide differing from the polynucleotide or polypeptide of the present invention, but retaining properties thereof. Generally, variants are overall closely similar, and, in many regions, identical to the polynucleotide or polypeptide of the present invention.

Thus, one aspect of the invention provides an isolated nucleic acid molecule comprising, or alternatively consisting of, a polynucleotide having a nucleotide sequence selected from the group consisting of: (a) a nucleotide sequence encoding a apoptosis related polypeptide having an amino acid sequence as shown in the sequence listing and described in SEQ ID NO:X or the cDNA in cDNA plasmid: Z; (b) a nucleotide sequence encoding a mature apoptosis related polypeptide having the amino acid sequence as shown in the sequence listing and described in SEQ ID NO:X or the cDNA in cDNA plasmid:Z; (c) a nucleotide sequence encoding a biologically active fragment of a apoptosis related polypeptide having an amino acid sequence shown in the sequence listing and described in SEQ ID NO:X or the cDNA in cDNA plasmid:Z; (d) a nucleotide sequence encoding an antigenic fragment of a apoptosis related polypeptide having an amino acid sequence shown in the sequence listing and described in SEQ ID NO:X or the cDNA in cDNA plasmid:Z; (e) a nucleotide sequence encoding a apoptosis related polypeptide comprising the complete amino acid sequence encoded by a human cDNA plasmid contained in SEQ ID NO:X or the cDNA in cDNA plasmid:Z; (f) a nucleotide sequence encoding a mature apoptosis related polypeptide having an amino acid sequence encoded by a human cDNA plasmid contained in SEQ ID NO:X or the cDNA in cDNA plasmid: Z; (g) a nucleotide sequence encoding a biologically active fragment of a apoptosis related polypeptide having an amino acid sequence encoded by a human cDNA plasmid contained in SEQ ID NO:X or the cDNA in cDNA plasmid:Z; (h) a nucleotide sequence encoding an antigenic fragment of a apoptosis related polypeptide having an amino acid sequence encoded by a human cDNA plasmid contained in SEQ ID NO:X or the cDNA in cDNA plasmid:Z; (i) a nucleotide sequence complementary to any of the nucleotide sequences in (a), (b), (c), (d), (e), (f), (g), or (h), above.

The present invention is also directed to nucleic acid molecules which comprise, or alternatively consist of, a nucleotide sequence which is at least 80%, 85%, 90%, 95%, 96%, 97%, 98%, 99%, or 100%, identical to, for example, any of the nucleotide sequences in (a), (b), (c), (d), (e), (f), (g), (h), or (i) above. Polypeptides encoded by these nucleic acid molecules are also encompassed by the invention. In another embodiment, the invention encompasses nucleic acid molecules which comprise, or alternatively, consist of a polynucleotide which hybridizes under stringent hybridization conditions, or alternatively, under lower stringency conditions, to a polynucleotide in (a), (b), (c), (d), (e), (f), (g), (h), or (i) above. Polynucleotides which hybridize to the complement of these nucleic acid molecules under stringent hybridization conditions or alternatively, under lower stringency conditions, are also encompassed by the invention, as are polypeptides encoded by these polynucleotides.

Another aspect of the invention provides an isolated nucleic acid molecule comprising, or alternatively consisting of, a polynucleotide having a nucleotide sequence selected from the group consisting of: (a) a nucleotide sequence encoding a apoptosis related polypeptide having an amino acid sequence as shown in the sequence listing and described in Table 1; (b) a nucleotide sequence encoding a mature apoptosis related polypeptide having the amino acid sequence as shown in the sequence listing and described in Table 1; (c) a nucleotide sequence encoding a biologically active fragment of a apoptosis related polypeptide having an amino acid sequence shown in the sequence listing and described in Table 1; (d) a nucleotide sequence encoding an antigenic fragment of a apoptosis related polypeptide having an amino acid sequence shown in the sequence listing and described in Table 1; (e) a nucleotide sequence encoding a apoptosis related polypeptide comprising the complete amino acid sequence encoded by a human cDNA in a cDNA plasmid contained in the ATCC Deposit and described in Table 1; (f) a nucleotide sequence encoding a mature apoptosis related polypeptide having an amino acid sequence encoded by a human cDNA in a cDNA plasmid contained in the ATCC Deposit and described in Table 1; (g) a nucleotide sequence encoding a biologically active fragment of a apoptosis related polypeptide having an amino acid sequence encoded by a human cDNA in a cDNA plasmid contained in the ATCC Deposit and described in Table 1; (h) a nucleotide sequence encoding an antigenic fragment of a apoptosis related polypeptide having an amino acid sequence encoded by a human cDNA in a cDNA plasmid contained in the ATCC Deposit and described in Table 1; (i) a nucleotide sequence complementary to any of the nucleotide sequences in (a), (b), (c), (d), (e), (f), (g), or (h), above.

The present invention is also directed to nucleic acid molecules which comprise, or alternatively consist of, a nucleotide sequence which is at least 80%, 85%, 90%, 95%, 96%, 97%, 98%, 99%, or 100%, identical to, for example, any of the nucleotide sequences in (a), (b), (c), (d), (e), (f), (g), (h), or (i) above. Polypeptides encoded by these nucleic acid molecules are also encompassed by the invention. In another embodiment, the invention encompasses nucleic acid molecules which comprise, or alternatively consist of a polynucleotide which hybridizes under stringent hybridization conditions, or alternatively, under lower stringency conditions, to a polynucleotide in (a), (b), (c), (d), (e), (f), (g), (h), or (i) above. Polynucleotides which hybridize to the complement of these nucleic acid molecules under stringent hybridization conditions or alternatively, under lower stringency conditions, are also encompassed by the invention, as are polypeptides encoded by these polynucleotides.

The present invention is also directed to polypeptides which comprise, or alternatively consist of, an amino acid sequence which is at least 80%, 85%, 90%, 95%, 96%, 97%, 98%, 99%, or 100% identical to, for example, the polypeptide sequence shown in SEQ ID NO:Y, a polypeptide sequence encoded by the nucleotide sequence in SEQ ID NO:X, a polypeptide sequence encoded by the cDNA in cDNA plasmid:Z, and/or polypeptide fragments of any of these polypeptides (e.g., those fragments described herein). Polynucleotides which hybridize to the complement of the nucleic acid molecules encoding these polypeptides under stringent hybridization conditions or alternatively, under lower stringency conditions are also encompassed by the invention, as are polypeptides encoded by these polynucleotides.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleoide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence referred to in Table 1, the ORF (open reading frame), or any fragment specified as described herein.

As a practical matter, whether any particular nucleic acid molecule or polypeptide is at least 80%, 85%, 90%, 95%, 96%, 97%, 98% or 99% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237–245 (1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identiy are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the lenght of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/aligned of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for examle, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, the amino acid sequence referred to in Table 1 or a fragment thereof, the amino acid sequence encoded by the nucleotide sequence in SEQ ID NO:X or a fragment thereof, or to the amino acid sequence encoded by the cDNA in cDNA plasmid:Z, or a fragment thereof, can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237–245(1990)). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty 0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequnce are manually corrected for. No other manual corrections are to made for the purposes of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which less than 50, less than 40, less than 30, less than 20, less than 10, or 5-50, 5-25, 5-10, 1-5, or 1-2 amino acids are substituted, deleted, or added in any combination are also preferred. Polynucleotide variants can be produced for a variety of reasons, e.g., to optimize codon expression for a particular host (change codons in the human mRNA to those preferred by a bacterial host such as E. coli).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, as discussed herein, one or more amino acids can be deleted from the N-terminus or C-terminus of the polypeptide of the present invention without substantial loss of biological function. The authors of Ron et al., J. Biol. Chem. 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein. (Dobeli et al., J. Biotechnology 7:199–216 (1988).)

Moreover, ample evidence demonstrates that variants often retain a biological activity similar to that of the naturally occurring protein. For example, Gayle and coworkers (J. Biol. Chem 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type.

Furthermore, as discussed herein, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes polypeptide variants which show a functional activity (e.g. biological activity) of the polypeptide of the invention, of which they are a variant. Such variants include deletions, insertions, inversions, repeats, and substitutions selected according to general rules known in the art so as have little effect on activity.

The present application is directed to nucleic acid molecules at least 80%, 85%, 90%, 95%, 96%, 97%, 98%, 99% or 100% identical to the nucleic acid sequences disclosed herein, (e.g., encoding a polypeptide having the amino acid sequence of an N and/or C terminal deletion), irrespective of whether they encode a polypeptide having functional activity. This is because even where a particular nucleic acid molecule does not encode a polypeptide having functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having functional activity include, inter alia, (1) isolating a gene or allelic or splice variants thereof in a cDNA library; (2) in situ hybridization (e.g., "FISH") to metaphase chromosomal spreads to provide precise chromosomal location of the gene, as described in Verma et al., Human Chromosomes: A Manual of Basic Techniques, Pergamon Press, New York (1988); and (3) Northern Blot analysis for detecting mRNA expression in specific tissues.

Preferred, however, are nucleic acid molecules having sequences at least 80%, 85%, 90%, 95%, 96%, 97%, 98%, 99% or 100% identical to the nucleic acid sequences disclosed herein, which do, in fact, encode a polypeptide having functional activity of a polypeptide of the invention.

Of course, due to the degeneracy of the genetic code, one of ordinary skill in the art will immediately recognize that a large number of the nucleic acid molecules having a sequence at least 80%, 85%, 90%, 95%, 96%, 97%, 98%, 99%, or 100% identical to, for example, the nucleic acid sequence of the cDNA in cDNA plasmid:Z, the nucleic acid sequence referred to in Table 1 (SEQ ID NO:X), or fragments thereof, will encode polypeptides "having functional activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having functional activity. This is because the skilled artisan is fully aware of amino acid substitutions that are either less likely or not likely to significantly effect protein function (e.g., replacing one aliphatic amino acid with a second aliphatic amino acid), as further described below.

For example, guidance concerning how to make phenotypically silent amino acid substitutions is provided in Bowie et al., "Deciphering the Message in Protein Sequences: Tolerance to Amino Acid Substitutions," Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly. Besides conservative amino acid substitution, variants of the present invention include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification or (v) fusion of the polypeptide with another compound, such as albumin (including but not limited to recombinant albumin (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)). Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340

(1967); Robbins et al., Diabetes 36: 838–845 (1987); Cleland et al., Crit. Rev. Therapeutic Drug Carrier Systems 10:307–377 (1993).)

A further embodiment of the invention relates to a polypeptide which comprises the amino acid sequence of a polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course it is highly preferable for a polypeptide to have an amino acid sequence which comprises the amino acid sequence of a polypeptide of SEQ ID NO:Y, an amino acid sequence encoded by SEQ ID NO:X, and/or the amino acid sequence encoded by the cDNA in cDNA plasmid:Z which contains, in order of ever-increasing preference, at least one, but not more than 10, 9, 8, 7, 6, 5, 4, 3, 2 or 1 amino acid substitutions. In specific embodiments, the number of additions, substitutions, and/or deletions in the amino acid sequence of SEQ ID NO:Y or fragments thereof (e.g., the mature form and/or other fragments described herein), an amino acid sequence encoded by SEQ ID NO:X or fragments thereof, and/or the amino acid sequence encoded by cDNA plasmid:Z or fragments thereof, is 1-5, 5-10, 5-25, 5-50, 10-50 or 50-150, conservative amino acid substitutions are preferable. As discussed herein, any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because secreted proteins target cellular locations based on trafficking signals, polypeptides of the present invention which are shown to be secreted can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

In certain preferred embodiments, proteins of the invention comprise fusion proteins wherein the polypeptides are N and/or C-terminal deletion mutants. In preferred embodiments, the application is directed to nucleic acid molecules at least 80%, 85%, 90%, 95%, 96%, 97%, 98% or 99% identical to the nucleic acid sequences encoding polypeptides having the amino acid sequence of the specific N- and C-terminal deletions mutants. Polynucleotides encoding these polypeptides, including fragments and/or variants, are also encompassed by the invention.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Also, peptide moieties may be added to the polypeptide to facilitate purification. Such regions may be removed prior to final preparation of the polypeptide. The addition of peptide moieties to facilitate handling of polypeptides are familiar and routine techniques in the art.

As one of skill in the art will appreciate, polypeptides of the present invention of the present invention and the epitope-bearing fragments thereof described above can be combined with heterologous polypeptide sequences. For example, the polypeptides of the present invention may be fused with heterologous polypeptide sequences, for example, the polypeptides of the present invention may be fused with the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature, 331:84–86 (1988).) Fusion proteins having disulfide-linked dimeric structures (due to the IgG) can also be more efficient in binding and neutralizing other molecules, than the monomeric protein or protein fragment alone. (Fountoulakis et al., J. Biochem., 270:3958–3964 (1995).)

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides of the invention may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells (e.g., Saccharomyces cerevisiae or Pichia pastoris (ATCC Accession No. 201178)); insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast *Pichia pastoris* is used to express polypeptides of the invention in a eukaryotic system. *Pichia pastoris* is a methylotrophic yeast which can metabolize methanol as its sole carbon source. A main step in the methanol metabolization pathway is the oxidation of methanol to formaldehyde using $O_2$. This reaction is catalyzed by the enzyme alcohol oxidase. In order to metabolize methanol as its sole carbon source, *Pichia pastoris* must generate high levels of alcohol oxidase due, in part, to the relatively low affinity of alcohol oxidase for $O_2$. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in *Pichia pastoris*. See, Ellis, S. B., et al., *Mol. Cell. Biol.* 5:1111–21 (1985); Koutz, P. J, et al., *Yeast* 5:167–77 (1989); Tschopp, J. F., et al., *Nucl. Acids Res.* 15:3859–76 (1987). Thus, a heterologous coding sequence, such as, for example, a polynucleotide of the present invention, under the transcriptional regulation of all or part of the AOX1 regulatory sequence is expressed at exceptionally high levels in Pichia yeast grown in the presence of methanol.

In one example, the plasmid vector pPIC9K is used to express DNA encoding a polypeptide of the invention, as set forth herein, in a Pichia yeast system essentially as described in "Pichia protocols: Methods in Molecular Biology," D. R. Higgins and J. Cregg, eds. The Humana Press, Totown, N.J., 1998. This expression vector allows expression and secretion of a polypeptide of the invention by virtue of the strong AOX1 promoter linked to the *Pichia pastoris* alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG as required.

In another embodiment, high-level expression of a heterologous coding sequence, such as, for example, a polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosure of each of which are incorporated by reference in their entireties).

In addition, polypeptides of the invention can be chemically synthesized using techniques known in the art (e.g., see Creighton, 1983, Proteins: Structures and Molecular Principles, W.H. Freeman & Co., N.Y., and Hunkapiller et al., *Nature,* 310:105–111 (1984)). For example, a polypeptide corresponding to a fragment of a polypeptide can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides of the present invention which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of efects on functional or antigenic domains of the protein. There are a number of attachment methods available for those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:Y or an amino acid sequence encoded by SEQ ID NO:X or the complement of SEQ ID NO:X, and/or an amino acid sequence encoded by cDNA plasmid:Z (including fragments, variants, splice variants, and fusion proteins, corresponding to these as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having idenical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/ or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in SEQ ID NO:Y, or contained in a polypeptide encoded by SEQ ID NO:X, and/or the cDNA plasmid:Z). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein. In one example, covalent associations are between the heterologous sequence contained in a fusion protein of the invention (see, e.g., U.S. Pat. No. 5,478,925). In a specific example, the covalent associations are between the heterologous sequence contained in a Fc fusion protein of the invention (as described herein). In another specific example, covalent associations of fusion proteins of the invention are between heterologous polypeptide sequence from another protein that is capable of forming covalently associated multimers, such as for example, osteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide seuqence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more intermolecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C-terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hydrophobic or signal peptide) and which can be incorporated by membrane reconstitution techniques Antibodies Further polypeptides of the invention relate to antibodies and T-cell antigen receptors (TCR) which immunospecifically bind a polypeptide, polypeptide fragment, or variant of SEQ ID NO:Y, and/or an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support mateial. See, e.g., PCT publications WO 93/17715; WO 92/08802; WO 91/00360; WO 92/05793; Tutt, et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, or by size in contiguous amino acid residues. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981–1988 (1998); Chen et al., Cancer Res. 58(16):3668–3678 (1998); Harrop et al., J. Immunol. 161 (4):1786–1794 (1998); Zhu et al., Cancer Res. 58(15): 3209–3214 (1998); Yoon et al., J. Immunol. 160(7):3170–3179 (1998); Prat et al., J. Cell. Sci. 111(Pt2): 237–247 (1998); Pitard et al., J. Immunol. Methods 205(2): 177–190 (1997); Liautard et al., Cytokine 9(4):233–241 (1997); Carlson et al., J. Biol. Chem. 272(17):11295–11301 (1997); Taryman et al., Neuron 14(4):755–762 (1995); Muller et al., Structure 6(9):1153–1167 (1998); Bartunek et al., Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/ blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and cornybacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182: 41–50 (1995); Ames et al., J. Immunol. Methods 184: 177–186 (1995); Kettleborough et al., Eur. J. Immunol. 24:952–958 (1994); Persic et al., Gene 187 9–18 (1997); burton et al., Advances in Immunology 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); and Sawai et al., AJRI 34:26–34 (1995); and Better et al., Science 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46–88 (1991); Shu et al., PNAS 90:7995–7999 (1993); and Skerra et al., Science 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; U.S. Pat. Nos. 5,807,715; 4,816,567; and 4,816,397, which are incorporated herein by reference in their entirety. Humanized antibodies are antibody molecules from non-human species antibody that binds the desired antigen having one or more comlementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530, 101; and 5,585,089), veneering or resurfacing (EP 592,106; EP 519,596; Padlan, Molecular Immunology 28(4/5): 489–498 (1991); Studnicka et al., Protein Engineering 7(6): 805–814 (1994); Roguska. et al., PNAS 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716, 111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "minic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or alternatively, under lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:Y.

The polynucleotides may be obtained, and the nucleotide sequence of the polynucleotides determines, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated form, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851–855 (1984); Neuberger et al., Nature 312:604–608 (1984); Takeda et al., Nature 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423–42 (1988); Huston et al., Proc. Natl. Acad.

Sci. USA 85:5879–5883 (1988); and Ward et al., Nature 334:544–54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242: 1038–1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem. 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355–359 (1984)).

Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be a variety of origins, both natural and synthetic. The efficiency of expression may be enhanced by the inclusion of appropriate transcription enhancer elements, transcription terminators, etc. (see Bittner et al., Methods in Enzymol. 153: 51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488–505; Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, 1993, TIB TECH 11(5): 155–215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a havey chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, proc. Natl. Acad. Sci. USA 77:2197 (1980)). The coding sequence for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specifid antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antiens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenzai et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides corresponding to a polypeptide, polypeptide fragment, or a variant of SEQ ID NO:Y may be fused or conjugated to the above antibody portions to increase the in vivo half life of the polypeptides or for use in immunoassays using methods known in the art. Further, the polypeptides corresponding to SEQ ID NO:Y may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52–58 (1995); Johanson et al., J. Biol. Chem. 270:9459–9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent mateials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahaski et al., *Int. Immunol.*, 6:1567–1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., *Cell*, 96:737–49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays For Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodoffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecule Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplememted with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., preclearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be adde to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecule Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions desribed herein. The treatment and/or prevention of diseases, disorders, or conditions associated with aberrant expression and/or activity of a polypeptide of the invention includes, but is not limited to, alleviating symptons associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 11(5):155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932–8935 (1989); Zijlstra et al., Nature 342: 435–438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932–8935 (1989); Zijlstra et al., Nature 342:435–438 (1989)).

In a specific embodiment, viral vectors that contains nucleic acid sequences encoding an antibody of the invention are used. For example, a retroviral vector can be used (see Miller et al., Meth. Enzymol. 217:581–599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291–302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644–651 (1994); Kiem et al., Blood 83:1467–1473 (1994); Salmons and Gunzberg, Human Gene Therapy 4:129–141 (1993); and Grossman and Wilson, Curr. Opin. in Genetics and Devel. 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499–503 (1993) present a review of adenovirus-based gene therapy. Bout et al., Human Gene Therapy 5:3–10 (1994) demonstrated the use of adenovirus vectors to transfer genes to the respiratory epithelia of rhesus monkeys. Other instances of the use of adenoviruses in gene therapy can be found in Rosenfeld et al., Science 252:431–434 (1991); Rosenfeld et al., Cell 68:143–155 (1992); Mastrangeli et al., J. Clin. Invest. 91:225–234 (1993); PCT Publication WO94/12649; and Wang, et al., Gene Therapy 2:775–783 (1995). In a preferred embodiment, adenovirus vectors are used.

Adeno-associated virus (AAV) has also been proposed for use in gene therapy (Walsh et al., Proc. Soc. Exp. Biol. Med. 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599–618 (1993); Cohen et al., Meth. Enzymol. 217:618–644 (1993); Cline, Pharmac. Ther. 29:69–92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973–985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably a polypeptide or antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among these described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429–4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J.Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can b dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976–985 (1985); Jalkanen, et al., J. Cell. Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid supprt, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each sequence is specifically targeted to and cay hybridize with a particular location on an individual human chromosome, thus each polynucleotide of the present invention can routinely be used as a chromosome marker using techniques known in the art.

Briefly, sequences can be mapped to chromosomes by preparing PCR primers (preferably at least 15 bp (e.g., 15–25 bp) from the sequences shown in SEQ ID NO:X. Primers can optionally be selected using computer analysis so that primers do not span more than one predicted exon in the genomic DNA. These primers are then used for PCR screening of somatic cell hybrids containing individual human chromosomes. Only those hybrids containing the human gene corresponding to SEQ ID NO:X will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, preselection by hybridization to construct chromosome specific-cDNA libraries, and computer mapping techniques (See, e.g., Shuler, Trends Biotechnol 16:456–459 (1998) which is hereby incorporated by reference in its entirety).

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes).

Thus, the present invention also provides a method for chromosomal localization which involves (a) preparing PCR primers from the polynucleotide sequences in Table 1 and SEQ ID NO:X and (b) screening somatic cell hybrids containing individual chromosomes.

The polynucleotides of the present invention would likewise be useful for radiation hybrid mapping, HAPPY mapping, and long range restriction mapping. For a review of these techniques and others known in the art, see, e.g., Dear, "Genome Mapping: A Practical Approach," IRL Press at Oxford University Press, London (1997); Aydin, J. Mol. Med. 77:691–694 (1999); Hacia et al., Mol. Psychiatry 3:483–492 (1998); Herrick et al., Chromosome Res. 7:409–423 (1999); Hamilton et al., Methods Cell Biol. 62:265–280 (2000); and/or Ott, J. Hered. 90:68–70 (1999) each of which is hereby incorporated by reference in its entirety.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library).) Assuming 1 megabase mapping resolution and one gene per 20 kg, a cDNA precisely localized to a chromosomal region associated with the disease could be one of 50–500 potential causative genes.

Thus, once coinheritance is established, differences in a polynucleotide of the invention and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using the polynucleotides of the invention. Any of these alterations (altered expression, chromosomal rearrangement, or mutation) can be used as a diagnostic or prognostic marker.

Thus, the invention also provides a diagnostic method useful during diagnosis of a disorder, involving measuring the expression level of polynucleotides of the present invention in cells or body fluid from an individual and comparing the measured gene expression level with a standard level of polynucleotide expression level, whereby an increase or decrease in the gene expression level compared to the standard is indicative of a disorder.

In still another embodiment, the invention includes a kit for analyzing samples for the presence of proliferative and/or cancerous polynucleotides derived from a test subject. In a general embodiment, the kit includes at least one polynucleotide probe containing a nucleotide sequence that will specifically hybridize with a polynucleotide of the invention and a suitable container. In a specific embodiment, the kit includes two polynucleotide probes defining an internal region of the polynucleotide of the invention, where each probe has one strand containing a 31'mer-end internal to the region. In a further embodiment, the probes may be useful as primers for polymerase chain reaction amplification.

Where a diagnosis of a related disorder, including, for example, diagnosis of a tumor, has already been made accordin to conventional methods, the present invention is useful as a prognostic indicator, whereby patients exhibiting enhanced or depressed polynucleotide of the invention expression will experience a worse clinical outcome relative to patients expressing the gene at a level nearer the standard level.

By "measuring the expression level of polynucleotides of the invention" is intended qualitatively or quantitatively measuring or estimating the level of the polypeptide of the invention or the level of the mRNA encoding the polypeptide of the invention in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or mRNA level, the standard being taken from a second biological sample obtained from an individual not having the related disorder or being determined by averaging levels from a population of individuals not having a related disorder. As will be appreciated in the art, once a standard polypeptide level or mRNA level is known, it can be used repeatedly as a standard for comparison.

By "biological sample" is intended any biological sample obtained from an individual, body fluid, cell line, tissue culture, or other source which contains polypeptide of the present invention or the corresponding mRNA. As indicated, biological samples include body fluids (such as semen, lymph, sera, plasma, urine, synovial fluid and spinal fluid) which contain the polypeptide of the present invention, and tissue sources found to express the polypeptide of the present invention. Methods for obtaining tissue biopsies and body fluids from mammals are well known in the art. Where the biological sample is to include mRNA, a tissue biopsy is the preferred source.

The method(s) provided above may preferably be applied in a diagnostic method and/or kits in which polynucleotides and/or polypeptides of the invention are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the invention attached may be used to identify polymorphisms between the isolated polynucleotide sequences of the invention, with polynucleotides isolated from a test subject. The knowledge of such polymorphisms (i.e. their location, as well as, their existence) would be beneficial in identifying disease loci for many disorders, such as for example, in neural disorders, immune system disorders, muscular disorders, reproductive disorders, gastrointestinal disorders, pulmonary disorders, cardiovascular disorders, renal disorders, proliferative disorders, and/or cancerous diseases and conditions. Such a method is described in U.S. Pat. Nos. 5,858,659 and 5,856,104. The U.S. patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides of the invention are incorporated onto a solid support, or gene chip. For the purposes of the present invention, a peptide nucleic acids (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, Science 254, 1497 (1991); and M. Egholm, O. Buchardt, L. Christensen, C. Behrens, S. M. Freier, D. A. Driver, R. H. Berg, S. K. Kim, B. Norden, and P. E. Nielsen, Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the strong binding. In addition, it is more likely that single base mismatches can be determined with PNA/DNA hybridization because a single mismatch in a PNA/DNA 15-mer lowers the melting point (T.sub.m) by 8°–20° C., vs. 4°–16° C. for the DNA/DNA 15-mer duplex. Also, the absence of charge groups in PNA means that hybridization can be done at low ionic strengths and reduce possible interference by salt during the analysis.

The present invention have uses which include, but are not limited to, detecting cancer in mammals. In particular the invention is useful during diagnosis of pathological cell proliferative neoplasias which include, but are not limited to: acute myelogenous leukemias including acute monocytic leukemia, acute myeloblastic leukemia, acute promyelocytic leukemia, acute myelomonocytic leukemia, acute erythroleukemia, acute megakaryocytic leukemia, and acute undifferentiated leukemia, etc.; and chronic myelogenous leukemias including chronic myelomonocytic leukemia, chronic granulocytic leukemia, etc. Preferred mammals include monkeys, apes, cats, dogs, cows, pigs, horses, rabbits and humans. Particularly preferred are humans.

Pathological cell proliferative disorders are often associated with inappropriate activation of proto-oncogenes. (Gelmann, E. P. et al., "The Etiology of Acute Leukemia: Molecular Genetics and Viral Oncology," in Neoplastic Diseases of the Blood, Vol 1., Wiernik, P. H. et al. eds., 161–182 (1985)). Neoplasias are now believed to result from the qualitative alteration of a normal cellular gene product, or from the quantitative modification of gene expression by insertion into the chromosome of a viral sequence, by chromosomal translocation of a gene to a more actively transcribed region, or by some other mechanism. (Gelmann et al., supra) It is likely that mutated or altered expression of specific genes is involved in the pathogenesis of some leukemias, among other tissues and cell types. (Gelmann et al., supra) Indeed, the human counterparts of the oncogenes involved in some animal neoplasias have been amplified or translocated in some cases of human leukemia and carcinoma. (Gelmann et al., supra)

For example, c-myc expression is highly amplified in the non-lymphoctic leukemia cell line HL-60. When HL-60 cells are chemically induced to stop proliferation, the level of c-myc is found to be downregulated. (International Publication Number WO 91/15580). However, it has been shown that exposure of HL-60 cells to a DNA construct that is complementary to the 5' end of c-myc or c-myb blocks translation of the corresponding mRNAs which downregulates expression of the c-myc or c-myb proteins and causes arrest of cell proliferation and differentiation of the treated cells. (International Publication Number WO 91/15580; Wickstrom et al., Proc. Natl. Acad. Sci. 85:1028 (1988); Anfossi et al., Proc. Natl. Acad. Sci. 86:3379 (1989)). However, the skilled artisan would appreciate the present invention's usefulness is not be limited to treatment of proliferative disorders of hematopoietic cells and tissues, in light of the numerous cells and cell types of varying origins which are known to exhibit proliferative phenotypes.

In addition to the foregoing, a polynucleotide of the present invention can be used to control gene expression through triple helix formation or through antisense DNA or RNA. Antisense techniques are discussed, for example, in Okano, J. Neurochem. 56: 560 (1991); "Oligodeoxynucleotides as Antisense Inhibitors of Gene Expression, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). Both methods rely on binding of the polynucleotide to a complementary DNA or RNA. For these techniques, preferred polynucleotides are usually oligonucleotides 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide.

The oligonucleotide described above can also be delivered to cells such that the antisense RNA or DNA may be expressed in vivo to inhibit production of polypeptide of the present invention antigens. Both techniques are effective in model systems, and the information disclosed herein can be used to design antisense or triple helix polynucleotides in an effort to treat disease, and in particular, for the treatment of proliferative diseases and/or conditions.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell.

The polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be ued as additional DNA markers for RFLP.

The polynucleotides of the present invention can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once an unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, synovial fluid, amniotic fluid, breast milk, lymph, pulmonary sputum or surfactant, urine, fecal matter, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, polynucleotides of the present invention can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers prepared from the sequences of the present invention. Panels of such reagents can identify tissue by species and/or by organ type. In a similar fashion, these reagents can be used to screen tissue cultures for contamination.

The polynucleotides of the present invention are also useful as hybridization probes for differential identification of the tissue(s) or cell type(s) present in a biological sample.

Similarly, polypeptides and antibodies directed to polypeptides of the present invention are useful to provide immunological probes for differential identification of the tissue(s) (e.g., immunohistochemistry assays) or cell type(s) (e.g., immunocytochemistry assays). In addition, for a number of disorders of the above tissues or cells, significantly higher or lower levels of gene expression of the polynucleotides/polypeptides of the present invention may be detected in certain tissues (e.g., tissues expressing polypeptides and/or polynucleotides of the present invention and/or cancerous and/or wounded tissues) or bodily fluids (e.g., serium, plasma, urine, synovial fluid or spinal fluid) taken from an individual having such a disorder, relative to a "standard" gene expression level, i.e., the expression level in healthy tissue from an individual not having the disorder.

Thus, the invention provides a diagnostic method of a disorder, which involves: (a) assaying the expression level in cells or body fluid of an individual; (b) comparing the gene expression level with a standard gene expression level, whereby an increase or decreas in the assayed gene expression level compared to the standard expression level is indicative of a disorder.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

Polypeptides and antibodies directed to polypeptides of the present invention are useful to provide immunological probes for differential identification of the tissue(s) (e.g., immunohistochemistry assays such as, for example, ABC immunoperoxidase (Hsu et al., J. Histochem. Cytochem. 29:577–580 (1981)) or cell type(s) (e.g., immunocytochemistry assays).

Antibodies can be used to assay levels of polypeptides encoded by polynucleotides of the invention in a biological sample using classical immunohistological methods known to those of skill in the art (e.g., see Jalkanen, et al., J. Cell. Biol. 101:976–985 (1985); Jalkanen, et al., J. Cell. Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru; luminescent labels, such as luminol; and fluorescent labels, such as fluorescein and rhodamine, and biotin.

In addition to assaying levels of polypeptide of the present invention in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, $^{131}$I, $^{112}$In, $^{99m}$Tc, ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which express the polypeptide encoded by a polynucleotide of the invention. In vivo tumor imaging is described in S. W. Burchiel et al., "Immunopharmacokinetics of Radiolabeled Antibodies and Their Fragments" (Chapter 13 to *Tumor Imaging: The Radiochemical Detection of Cancer*, S. W. Burchiel and B. A. Rhodes, eds., Masson Publishing Inc. (1982)).

In one embodiment, the invention provides a method for the specific delivery of compositions of the invention to cells by administering polypeptides of the invention (e.g., polypeptides encoded by polynucleotides of the invention and/or antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention in association with toxins or cytotoxic prodrugs.

By "toxin" is meant one or more compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, Psdueomonas exotoxin A, diphtheria toxin, saporin, momordin, gelonin, pokeweed antiviral protein, alpha-sarcin and cholera toxin. "Toxin" also includes a cytostatic or cytocidal agent, a therapeutic agent or a radioactive metal ion, e.g., alpha-emitters such as, for example, $^{213}$Bi, or other radioisotopes such as, for example, $^{103}$Pd, $^{133}$Xe, $^{131}$I, $^{68}$Ge, $^{57}$Co, $^{65}$Zn, $^{85}$Sr, $^{32}$P, $^{35}$S, $^{90}$Y, $^{153}$Gd, $^{169}$Yb, $^{51}$Cr, $^{54}$Mn, $^{75}$Se, $^{113}$Sn, $^{90}$Yttrium, $^{117}$Tin, $^{186}$Rhenium, $^{166}$Holmium, and $^{188}$Rhenium; luminescent labels, such as luminol; and fluorescent labels, such as fluorescein and rhodamine, and biotin.

Techniques known in the art may be applied to label polypeptides of the invention (including antibodies). Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety).

Thus, the invention provides a diagnostic method of a disorder, which involves (a) assaying the expression level of a polypeptide of the present invention in cells or body fluid of an individual; and (b) comparing assayed polypeptide expression level with a standard gene expression level, whereby an increase or decrease in the assayed polypeptide expression level compared to the standard expression level is indicative of a disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Moreover, polypeptides of the present invention can be used to treat or prevent diseases or conditions such as, for example, neural disorders, immune system disorders, muscular disorders, reproductive disorders, gastrointestinal disorders, pulmonary disorders, cardiovascular disorders, renal disorders, proliferative disorders, and/or cancerous diseases and conditions. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B, SOD, catalase, DNA repair proteins), to inhibit the activity of a polypeptide (e.g., an oncogene or tumor supressor), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth inhibition, enhancement of the immune response to proliferative cells or tissues).

Similarly, antibodies directed to a polypeptide of the present invention can also be used to treat disease (as described supra, and elsewhere herein). For example, administration of an antibody directed to a polypeptide of the present invention can bind, and/or neutralize the polypeptide, and/or reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Gene Therapy Methods

Another aspect of the present invention is to gene therapy methods for treating or preventing disorders, diseases and conditions. The gene therapy methods relate to the introduction of nucleic acid (DNA, RNA and antisense DNA or RNA) sequences into an animal to achieve expression of the polypeptide of the present invention. This method requires a polynucleotide which codes for a polypeptide of the present invention operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a polynucleotide of the present invention ex vivo, with the engineered cells then being provided to a patient to be treated with the polypeptide of the present invention. Such methods are well-known in the art. For example, see Belldegrun, A., et al., J. Natl. Cancer Inst. 85:207–216 (1993); Ferrantini, M. et al., Cancer Research 53: 1107–1112 (1993); Ferrantini, M. et al., J. Immunology 153: 4604–4615 (1994); Kaido, T., et al., Int. J. Cancer 60: 221–229 (1995); Ogura, H., et al., Cancer Research 50: 5102–5106 (1990); Santodonato, L., et al., Human Gene Therapy 7:1–10 (1996); Santodonato, L., et al., Gene Therapy 4:1246–1255 (1997); and Zhang, J.-F. et al., Cancer Gene Therapy 3: 31–38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the polypeptide constructs can be delivered by any method that delivers injectable materials to the cells of an animal, such as, injection into the interstitial space of tissues (heart, muscle, skin, lung, liver, and the like). The polynucleotide constructs may be delivered in a pharmaceutically acceptable liquid or aqueous carrier.

In one embodiment, the polynucleotide of the present invention is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the polynucleotide of the present invention can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The polynucleotide vector constructs used in the gene therapy method are preferably constructs that will not integrate into the host genome nor will they contain sequences that allow for replication. Appropriate vectors include pWL-NEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of the polynucleotide sequence. Suitable promoters include adenoviral promoters, such as the adenoviral major late promoter; or heterologous promoters, such as the cytomegalovirus (CMV) promoter;

the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for the polynucleotide of the present invention.

Unlike other gene therapy techniques, one major advantage of introducing naked nucleic acid sequences into target cells in the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, overy, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked nucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the polynucleotide constructs are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA (1987) 84:7413–7416, which is herein incorporated by reference); mRNA (Malone et al., Proc. Natl. Acad. Sci. USA (1989) 86:6077–6081, which is herein incorporated by reference); and purified transcription factors (Debs et al., J. Biol. Chem. (1990) 265:10189–10192, which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., Proc. Natl Acad. Sci. USA (1987) 84:7413–7416, which is herein incorporated by reference). Other commercially available liposomes include transfectate (DDAB/DOPE) and DOTAP/DOPE (Boehringer).

Other cationic liposomes can be prepared from readily available materials using techniques well known in the art. See, e.g. PCT Publication No. WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., P. Felgner et al., Proc. Natl. Acad. Sci. USA 84:7413–7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology (1983), 101:512–527, which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., Biochim. Biophys. Acta (1975) 394:483; Wilson et al., Cell (1979) 17:77); ether injection (Deamer, D. and Bangham, A., Biochim, Biophys. Acta (1976) 443:629; Ostro et al., Biochem. Biophys. Res. Commun. (1977) 76:836; Fraley et al., Proc. Natl. Acad. Sci. USA (1979) 76:3348); detergent dialysis (Enoch, H. and Strittmatter, P., Proc. Natl. Acad. Sci. USA (1979) 76:145); and reverse-phase evaporation (REV) (Fraley et al., J. Biol. Chem. (1980) 255:10431; Szoka, F. and Paphadjopoulos, D., Proc. Natl. Acad. Sci. USA (1978) 75:145; Schaefer-Ridder et al., Science (1982) 215:166), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication no. WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication no. WO 94/9469 (which are herein incorporated by reference) provide methods for delivering DNA-cationic lipid complexes to mammals.

In certain embodiments, cells are engineered, ex vivo or in vivo, using a retroviral particle containing RNA which comprises a sequence encoding a polypeptide of the present invention. Retriviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14X, VT-19-17-H2, RCRE, RCRIP, GP+E-86, GP+en-vAm12, and DAN cell lines as described in Miller, Human Gene Therapy 1:5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include polynucleotide encoding a polypeptide of the present invention. Such retroviral vector particles then may be employed, to transduce eukaryotic cells, either in vitro or in vivo. The transduced eukaryotic cells will express a polypeptide of the present invention.

In certain other embodiments, cells are engineered, ex vivo or in vivo, with polynucleotide contained in an adenovirus vector. Adenovirus can be manipulated such that it encodes and expresses a polypeptide of the present invention, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz, A. R. et al. (1974) Am. Rev. Respir. Dis. 109:233–238). Finally, adenovirus mediated gene transfer has been demonstrated in a number of instances including transfer of alpha-1-antitrypsin and CFTR to the lungs of cotton rats (Rosenfeld, M. A. et al. (1991) Science 252:431–434; Rosenfeld et al., (1992) Cell 68:143–155). Furthermore, extensive studies to attempt to establish adenovirus as a causative agent in human cancer were uniformly negative (Green, M. et al. (1979) Proc. Natl. Acad. Sci. USA 76:6606).

Suitable adenoviral vectors useful in the present invention are described, for example, in Kozarsky and Wilson, Curr. Opin. Genet. Devel. 3:499–503 (1993); Rosenfeld et al., Cell 68:143–155 (1992); Engelhardt et al., Human Genet. Ther. 4:759–769 (1993); Yang et al., Nature Genet. 7:362–369 (1994); Wilson et al., Nature 365:691–692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express Ela and Elb, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, N., Curr. Topics in Microbiol. Immunol. 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The polynucleotide construct is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the polynucleotide construct. These viral particles are then used to transduce eukaryotic cells, either ex vivo or in vivo. The transduced cells will contain the polynucleotide construct integrated into its genome, and will express a polypeptide of the invention.

Another method of gene therapy involves operably associating heterologous control regions and endogenous polynucleotide sequences (e.g. encoding a polypeptide of the present invention) via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous sequence is placed under the control of the promoter. The promoter then drives the expression of the endogenous sequence.

Preferably, the polynucleotide encoding a polypeptide of the present invention contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers (Kaneda et al., Science 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particle site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA 189:11277–11281, 1992, which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian.

Therapeutic compositions of the present invention can be administered to any animal, preferably to mammals and birds. Preferred mammals include humans, dogs, cats, mice, rats, rabbits sheep, cattle, horses and pigs, with humans being particularly preferred.

Biological Activities

Polynucleotide or polypeptides, or agonists or antagonists of the present invention, can be used in assays to test for one or more biological activities. If these polynucleotides or polypeptides, or agonists or antagonists of the present invention, do exhibit activity in a particular assay, it is likely that these molecules may be involved in the diseases associated with the biological activity. Thus, the polynucleotides and polypeptides, and agonists or antagonists could be used to treat the associated disease.

Apoptosis related proteins are believed to be involved in biological activities associated with activation, signaling, and facilitation of apoptosis. Accordingly, compositions of the invention (including polynucleotides, polypeptides and antibodies of the invention, and fragments and variants thereof) may be used in the diagnosis, detection and/or treatment of diseases and/or disorders associated with aberrant apoptosis activity. In preferred embodiments, compositions of the invention (including polynucleotides, polypeptides and antibodies of the invention, and fragments and variants thereof) may be used in the diagnosis, detection and/or treatment of diseases and/or disorders relating to apoptosis (e.g., apoptosis, and/or as described under "Immune activity" and "Hyperproliferative Disorders" below), neoplasias of the Immune system (e.g., Lymphomas, leukemias, and/or as described under "Immune Activity" and "Diseases at the Cellular Level" below), autoimmune disorders (e.g., rheumatoid arthritis, inflammatory disorders, and/or as described under "Immune Activity" below), and neural disorders (e.g., as described under "Neural Activity and Neurological Diseases" below). Thus, polynucleotides, translation products and antibodies of the invention are useful in the diagnosis, detection and/or treatment of diseases and/or disorders associated with activities that include, but are not limited to, apoptosis and apoptotic disorders, neoplasias, inflammation, autoimmune disorders, and neural disorders.

More generally, polynucleotides, translation products and antibodies corresponding to this gene may be useful for the diagnosis, detection and/or treatment of diseases and/or disorders associated with the following systems.

Immune Activity

Polynucleotides, polypeptides, antibodies, and/or agonists or antagonists of the present invention may be useful in treating, preventing, and/or diagnosing diseases, disorders, and/or conditions of the immune system, by, for example, activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune diseases, disorders, and/or conditions may be genetic, somatic, such as cancer and some autoimmune diseases, acquired (e.g., by chemotherapy or toxins), or infectious. Moreover, polynucleotides, polypeptides, antibodies, and/or agonists or antagonists of the present invention can be used as a marker or detector of a particular immune system disease or disorder.

Polynucleotides, polypeptides, antibodies, and/or agonists or antagonists of the present invention may be useful in treating, preventing, and/or diagnosing diseases, disorders, and/or conditions of hematopoietic cells. Polynucleotides, polypeptides, antibodies, and/or agonists or antagonists of the present invention could be used to increase differentiation and proliferation of hematopoietic cells, including the pluripotent stem cells, in an effort to treat or prevent those diseases, disorders, and/or conditions associated with a decrease in certain (or many) types hematopoietic cells. Examples of immunologic deficiency syndromes include, but are not limited to: blood protein diseases, disorders, and/or conditions (e.g., agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, polynucleotides, polypeptides, antibodies, and/or agonists or antagonists of the present invention could also be used to modulate hemostatic (the stopping of bleeding) or thrombolytic activity (clot formation). For example, by increasing hemostatic or thrombolytic activity, polynucleotides or polypeptides, and/or agonists or antagonists of the present invention could be used to treat or prevent blood coagulation diseases, disorders, and/or conditions (e.g., afibrinogenemia, factor deficiencies), blood platelet diseases, disorders, and/or conditions (e.g., thrombocytopenia), or wounds resulting from trauma, surgery, or other causes. Alternatively, polynucleotides, polypeptides, antibodies, and/or agonists or antagonists of the present invention that can decrease hemostatic or thrombolytic activity could be used to inhibit or dissolve clotting. These molecules could be important in the treatment or prevention of heart attacks (infarction), strokes, or scarring.

The polynucleotides, polypeptides, antibodies, and/or agonists or antagonists of the present invention may be useful in treating, preventing, and/or diagnosing autoimmune disorders. Many autoimmune disorders result from inappropriate recognition of self as foreign material by immune cells. This inappropriate recognition results in an immune response leading to the destruction of the host tissue. Therefore, the administration of polynucleotides and polypeptides of the invention that can inhibit an immune response, particularly the proliferation, differentiation, or chemotaxis of T-cells, may be an effective therapy in preventing autoimmune disorders.

Autoimmune diseases or disorders that may be treated, prevented, and/or diagnosed by polynucleotides, polypeptides, antibodies, and/or agonists or antagonists of the present invention include, but are not limited to, one or more of the following: autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (e.g, IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Autism, Guillain-Barre Syndrome, insulin dependent diabetes mellitus, and autoimmune inflammatory eye, autoimmune thyroiditis, hypothyroidism (i.e., Hashimoto's thyroiditis, systemic lupus erhythematosus, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, schleroderma with anti-collagen antibodies, missed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes millitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulamatosus, degenerative, and atrophic disorders.

Additional autoimmune disorders (that are probable) that may be treated, prevented, and/or diagnosed with the compositions of the invention include, but are not limited to, rheumatoid artiritis (often characterized, e.g., by immune complexes in joints), scleroderma with anti-collagen antibodies (often characterized, e.g., by nucleolar and other nuclear antibodies), mixed connective tissue disease (often characterized, e.g., by antibodies to extractable nuclear antigens (e.g., ribonucleoprotein)), polymyositis (often characterized, e.g., by nonhistone ANA), pernicious anemia (often characterized, e.g. by antiparietal cell, microsomes, and intrinsic factor antibodies), idiopathic Addison's disease (often characterized, e.g., by humoral and cell-mediated adrenal cytotoxicity, infertility (often characterized, e.g., by antispermatozoal antibodies), glomerulonephritis (often characterized, e.g., by glomerular basement membrane antibodies or immune complexes), bullous pemphigoig (often characterized, e.g., by IgG and complement in basement membrane), Sjogren's syndrome (often characterized, e.g., by multiple tissue antibodies, and/or a specific nonhistone ANA (SS-B)), diabetes millitus (often characterized, e.g., by cell-mediated and humoral islet cell antibodies), and adrenergic drug resistance (including adrenergic drug resistance with asthma or cystic fibrosis) (often characterized, e.g., by beta-adrenergic receptor antibodies).

Additional autoimmune disorders (that are possible) that may be treated, prevented, and/or diagnosed with the compostions of the invention include, but are not limited to, chronic active hepatitis (often characterized, e.g., by smooth muscle antibodies), primary biliary cirrhosis (often characterized, e.g., by mitochondrial antibodies), other endocrine gland failure (often characterized, e.g., by specific tissue antibodies in some cases), vitiligo (often characterized, e.g., by melanocyte antibodies), vasculitis (often characterized, e.g., by Ig and complement in vessel walls and/or low serum complement), post-MI (often characterized, e.g., by myocardial antibodies), cardiotomy syndrome (often characterized, e.g., by myocardial antibodies), urticaria (often characterized, e.g., by IgG and IgM antibodies to IgE), atopic dermatitis (often characterized, e.g., by IgG and IgM antibodies to IgE), asthma (often characterized, e.g., by IgG and IgM antibodies to IgE), and many other inflammatory, granulamatous, degenerative, and atrophic disorders.

In a preferred embodiment, the autoimmune diseases and disorders and/or conditions associated with the diseases and disorders recited above are treated, prevented, and/or diagnosed using for example, antagonists or agonists, polypeptides or polynucleotides, or antibodies of the present invention.

In a preferred embodiment polynucleotides, polypeptides, antibodies, and/or agonists or antagonists of the present invention could be used as an agent to boost immunoresponsiveness among B cell and/or T cell immunodeficient individuals.

B cell immunodeficiencies that may be ameliorated or treated by administering the polypeptides or polynucleotides of the invention, and/or agonists thereof, include, but are not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVI) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymophoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

T cell deficiencies that may be ameliorated or treated by administering the polypeptides or polynucleotides or the invention, and/or agonists thereof include, but are not limited to, for examle, DiGeorge anomaly, thymic hypoplasia, third and fourth pharyngeal pouch syndrome, 22q11.2 deletion, chronic mucocutaneous candidiasis, natural killer cell deficiency (NK), idiopathic CD4+ T-lymphocytopenia, immunodeficiency with predominant T cell defect (unspecified), and unspecified immunodeficiency of cell mediated immunity. In specific embodiments, DiGeorge anomaly or conditions associated with DiGeorge anomaly are ameliorated or treated by, for example, administering the polypeptides or polynucleotides of the invention, or antagonists or agonists thereof.

Other immunodeficiencies that may be ameliorated or treated by administering polypeptides or polynucleotides of the invention, and/or agonists thereof, but are not limited to, severe combined immunodeficiency (SCID; e.g., X-linked SCID, autosomal SCID, and adenosine deaminase deficiency), ataxia-telangiectasia, Wiskott-Aldrich syndrome, short-limber dwarfism, X-linked lymphoproliferative syndrome (XLP), Nezelof syndrome (e.g., purine nucleoside phosphorylase deficiency), MHC Class II deficiency. In specific embodiments, ataxia-telangiectasia or conditions associated with ataxia-telangiectasia are ameliorated or treated by administering the polypeptides or polynucleotides of the invention, and/or agonists thereof.

In a specific preferred embodiment, rheumatoid arthritis is treated, prevented, and/or diagnosed using polynucleotides, polypeptides, antibodies, and/or agonists or antagonists of the present invention. In another specific preferred embodiment, systemic lupus erythemosus is treated, prevented, and/or diagnosed using polynucleotides, polypeptides, antibodies, and/or agonists or antagonists of the present invention. In another specific preferred embodiment, idiopathic thrombocytopenia purpura is treated, prevented, and/or diagnosed using polynucleotides, polypeptides, antibodies, and/or agonists or antagonists of the present invention. In another specific preferred embodiment IgA nephropathy is treated, prevented, and/or diagnosed using polynucleotides, polypeptides, antibodies, and/or agonists or antagonists of the present invention. In a preferred embodiment, the autoimmune diseases and disorders and/or conditions associated with the diseases and disorders recited above are treated, prevented, and/or diagnosed using antibodies against the protein of the invention.

Similarly, allergic reactions and conditions, such as asthma (particularly allergic asthma) or other respiratory problems, may also be treated, prevented, and/or diagnosed using polypeptides, antibodies, or polynucleotides of the invention, and/or agonists or antagonists thereof. Moreover, these molecules can be used to treat, prevent, and/or diagnose anaphylaxis, hypersensitivity to an antigenic molecule, or blood group incompatibility.

Moreover, inflammatory conditions may also be treated, diagnosed, and/or prevented with polynucleotides, polypeptides, antibodies, and/or agonists or antagonists of the present invention. Such inflammatory conditions include, but are not limited to, for example, respiratory disorders (such as, e.g., asthma and allergy); gastrointestinal disorders (such as, e.g., inflammatory bowel disease); cancers (such as, e.g., gastric, ovarian, lung, bladder, liver, and breast); CNS disorders (such as, e.g., multiple sclerosis, blood-brain barrier permeability, ischemic brain injury and/or stroke, traumatic brain injury, neurodegenerative disorders (such as, e.g., Parkinson's disease and Alzheimer's disease), AIDS-related dementia, and prion disease); cardiovascular disorders (such as, e.g., atherosclerosis, myocarditis, cardiovascular disease, and cardiopulmonary bypass complications); as well as many additional diseases, conditions, and disorders that are characterized by inflammation (such as, e.g., chronic hepatitis (B and C), rheumatoid arthritis, gout, trauma, septic shock, pancreatitis, sarcoidosis, dermatitis, renal ischemia-reperfusion injury, Grave's disease, systemic lupus erythematosis, diabetes mellitus (i.e., type 1 diabetes), and allogenic transplant rejection).

In specific embodiments, polypeptides, antibodies, or polynucleotides of the invention, and/or agonists or antagonists thereof, are useful to treat, diagnose, and/or prevent transplantation rejections, graft-versus-host disease, autoimmune and inflammatory diseases (e.g., immune complex-induced vasculitis, glomerulonephritis, hemolytic anemia, myasthenia gravis, type II collagen-induced arthritis, experimental allergic and hyperacute xenograft rejection, rheumatoid arthritis, and systemic lupus erythematosus (SLE). Organ rejection occurs by host immune cell destruction of the transplanted tissue through an immune response. Similarly, an immune response is also involved in GVHD, but, in this case, the foreign transplanted immune cells destroy the host tissues. Polypeptides, antibodies, or polynucleotides of the invention, and/or agonists or antagonists thereof, that inhibit an immune response, particularly the activation, proliferation, differentiation, or chemotaxis of T-cells, may be an effective therapy in preventing organ rejection or GVHD.

Similarly, polynucleotides, polypeptides, antibodies, and/or agonists or antagonists of the present invention may also be used to modulate and/or diagnose inflammation. For example, since polypeptides, antibodies, or polynucleotides of the invention, and/or agonists or antagonists of the invention may inhibit the activation, proliferation and/or differentiation of cells involved in an inflammatory response, these molecules can be used to treat, diagnose, or prognose, inflammatory conditions, both chronic and acute conditions, including, but not limited to, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, and resulting from over production of cytokines (e.g., TNF or IL-1.).

Polypeptides, antibodies, polynucleotides and/or agonists or antagonists of the invention can be used to treat, detect, and/or prevent infectious agents. For example, by increasing the immune response, particularly increasing the proliferation activation and/or differentiation of B and/or T cells, infectious diseases may be treated, detected, and/or prevented. The immune response may be increased by either enhancing an existing immune response, or by initiating a new immune response. Alternatively, polynucleotides, polypeptides, antibodies, and/or agonists or antagonists of the present invention may also directly inhibit the infectious agent (refer to section of application listing infectious agents, etc), without necessarily eliciting an immune response.

Additional preferred embodiments of the invention include, but are not limited to, the use of polypeptides, antibodies, polynucleotides and/or agonists or antagonists in the following applications:

Administration to an animal (e.g., mouse, rat, rabbit, hamster, guinea pig, pigs, micro-pig, chicken, camel, goat, horse, cow, sheep, dog, cat, non-human primate, and human, most preferably human) to boost the immune system to produce increased quantities of one or more antibodies (e.g., IgG, IgA, IgM, and IgE), to induce higher affinity antibody production (e.g., IgG, IgA, IgM, and IgE), and/or to increase an immune response.

Administration to an animal (including, but not limited to, those listed above, and also including transgenic animals) incapable of producing functional endogenous antibody molecules or having an otherwise compromised endogenous immune system, but which is capable of producing human immunoglobulin molecules by means of a reconstituted or partially reconstituted immune system from another animal (see, e.g., published PCT Application Nos. WO98/24893, WO/9634096, WO/9633735, and WO/9110741.

A vaccine adjuvant that enhances immune responsiveness to specific antigen.

An adjuvant to enhance tumor-specific immune responses.

An adjuvant to enhance anti-viral immune responses. Anti-viral immune responses that may be enhanced using the compositions of the invention as an adjuvant, include virus and virus associated diseases or symptoms described herein or otherwise known in the art. In specific embodiments, the compositions of the invention are used as an adjuvant to enhance an immune response to a virus, disease, or symptom selected from the group consisting of: AIDS, memingitis, Dengue, EBV, and hepatitis (e.g., hepatitis B), In another specific embodiment, the compositions of the invention are used as an adjuvant to enhance an immune response to a virus, disease, or symptom selected from the group consisting of: HIV/AIDS, Respiratory syncytial virus, Dengue, Rotavirus, Japanese B encephalitis, Influenza A and B, Parainfluenza, Measles, Cytomegalovirus, Rabies, Junin, Chikungunya, Rift Valley fever, Herpes simplex, and yellow fever.

An adjuvant to enhance anti-bacterial or anti-fungal immune responses. Anti-bacterial or anti-fungal immune responses that may be enhanced using the compositions of the invention as an adjuvant, include bacteria or fungus and bacteria or fungus associated diseases or symptoms described herein or otherwise known in the art. In specific embodiments, the compositions of the invention are used as an adjuvant to enhance an immune response to a bacteria or fungus, disease, or symptom selected from the group consisting of: tetanus, Diphtheria, botulism, and meningitis type B. In another specific embodiment, the compositions of the invention are used as an adjuvant to enhance an immune response to a bacteria or fungus, disease, or symptom selected from the group consisting of: *Vibrio cholerae*, *Mycobacterium leprae*, *Salmonella typhi*, *Salmonella paratyphi*, *Meisseria meningitidis*, *Streptococcus pneumoniae*, Group B streptococcus, *Shigella* spp., Enterotoxigenic *Escherichia coli*, Enterohemorrhagic *E. coli*, *Borrelia burgdorferi*, and *Plasmodium* (malaria).

An adjuvant to enhance anti-parasitic immune responses. Anti-parasitic immune responses that may be enhanced using the compositions of the invention as an adjuvant, include parasite and parasite associated diseases or symptoms described herein or otherwise known in the art. In specific embodiments, the compositions of the invention are used as an adjuvant to enhance an immune response to a parasite. In another specific embodiment, the compositions of the invention are used as an adjuvant to enhance an immune respone to Plasmodium (malaria).

As a stimulator of B cell responsiveness to pathogens.

As an activator of T cells.

As an agent that elevates the immune status of an individual prior to their receipt of immunosuppressive therapies.

As an agent to induce higher affinity antibodies.

As an agent to increase serum immunoglobulin concentrations.

As an agent to accelerate recovery of immunocompromised individuals.

As an agent to boost immunoresponsive among aged populations.

As an immune system enhancer prior to, during, or after bone marrow transplant and/or other transplants (e.g., allogeneic or xenogeneic organ transplantation). With respect to transplantation, compositions of the invention may be administered prior to, concomitant with, and/or after transplantation. In a specific embodiment, compositions of the invention are administered after transplantation, prior to the beginning of recovery of T-cell populations. In another specific embodiment, compositions of the invention are first administered after transplantation after the beginning of recovery of T cell populations, but prior to full recovery of B cell populations.

As an agent to boost immunoresponsiveness among individuals having an acquired loss of B cell function. Conditions resulting in an acquired loss of B cell function that may be ameliorated or treated by administering the polypeptides, antibodies, polynucleotides and/or agonists or antagonists thereof, include, but are not limited to, HIV Infection, AIDS, bone marrow transplant, and B cell chronic lymphocytic leukemia (CLL).

As an agent to boost immunoresponsiveness among individuals having a temporary immune deficiency. Conditions resulting in a temporary immune deficiency that may be ameliorated or treated by administering the polypeptides, antibodies, polynucleotides and/or agonists or antagonists thereof, include, but are not limited to, recovery from viral infections (e.g., influenza), conditions associated with malnutrition, recovery from infectious mononucleosis, or conditions associated with stress, recovery from measles, recovery from blood transfusion, recovery from surgery.

As a regulator of antigen presentation by monocytes, dendritic cells, and/or B-cells. In one embodiment, polynucleotides, polypeptides, antibodies, and/or agonists or antagonists of the present invention enhance antigen presentation or antagonizes antigen presentation in vitro or in vivo. Moreover, in related embodiments, said enhancement or antagonization of antigen presentation may be useful as an anti-tumor treatment or to modulate the immune system.

As an agent to direct an individuals immune system towards development of a humoral response (i.e. TH2) as opposed to a TH1 cellular response.

As a means to induce tumor proliferation and thus make it more susceptible to anti-neoplastic agents. For example, multiple myeloma is a slowly dividing disease and is thus refractory to virtually all anti-neoplastic regimens. If these cells were forced to proliferate more rapidly their susceptibility profile would likely change.

As a stimulator of B cell production in pathologies such as AIDS, chronic lymphocute disorder and/or Common Variable Immunodificiency.

As a therapy for generation and/or regeneration of lymphoid tissues following surgery, trauma or genetic defect.

As a gene-based therapy for genetically inherited disorders resulting in immuno-incompetence such as observed among SCID patients.

As an antigen for the generation of antibodies to inhibit or enhance immune mediated responses against polypeptides of the invention.

As a means of activating T cells.

As a means of activating monocytes/macrophages to defend against parasitic diseases that effect monocytes such as Leshmania.

As pretreatment of bone marrow samples prior to transplant. Such treatment would increase B cell representation and thus accelerate recover.

As a means of regulating secreted cytokines that are elicited by polypeptides of the invention.

Additionally, polypeptides or polynucleotides of the invention, and/or agonists thereof, may be used to treat or prevent IgE-mediated allergic reactions. Such allergic reactions include, but are not limited to, asthma, rhinitis, and eczema.

All of the above described applications as they may apply to veterinary medicine.

Antagonists of the invention include, for example, binding and/or inhibitory antibodies, antisense nucleic acids, ribozymes or soluble forms of the immunoglobulin-like receptor(s) (e.g., a immunoglobulin-like-Fc fusion protein) (see e.g., Example 9). These would be expected to reverse many of the activities of the ligand described above as well as find clinical or practical application as:

A means of blocking various aspects of immune responses to foreign agents or self. Examples include autoimmune disorders such as lupus, and arthritis, as well as immunoresponsiveness to skin allergies, inflammation, bowel disease, injury and pathogens.

A therapy for preventing the B cell proliferation and Ig secretion associated with autoimmune diseases such as idiopathic thrombocytopenic purpura, systemic lupus erythramatosus and MS.

An inhibitor of B and/or T cell migration in endothelial cells. This activity disrupts tissue architecture or cognate responses and is useful, for example in disrupting immune responses, and blocking sepsis.

An inhibitor of graft versus host disease or transplant rejection.

A therapy for B cell and/or T cell malignancies such as ALL, Hodgkins disease, non-Hodgkins lymphoma, Chronic lymphocyte leukemia, plasmacytomas, multiple myeloma, Burkitt's lymphoma, and EBV-transformed diseases.

A therapy for chronic hypergammaglobulinemeia evident in such diseases as monoclonalgammopathy of undetermined significance (MGUS), Waldenstrom's disease, related idiopathic monoclonalgammopathies, and plasmacytomas.

A therapy for decreasing cellular proliferation of Large B-cell Lymphomas.

A means of decreasing the involvement of B cells and Ig associated with Chronic Myelogenous Leukemia.

An immunosuppressive agent(s).

Polynucleotides, polypeptides, antibodies, and/or agonists or antagonists of the present invention may be used to modulate IgE concentrations in vitro or in vivo.

In another embodiment, administration of polypeptides, antibodies, polynucleotides and/or agonists or antagonists of the invention, may be used to treat or prevent IgE-mediated allergic reactions including, but not limited to, asthma, rhinitis, and eczema.

The agonists and antagonists may be employed in a composition with a pharmaceutically acceptable carrier, e.g., as described herein.

The agonists or antagonists may be employed for instance to inhibit polypeptide chemotaxis and activation of macrophages and their precursors, and of neutrophils, basophils, B lymphocytes and some T-cell subsets, e.g., activated and CD8 cytotoxic T cells and natural killer cells, in certain auto-immune and chronic inflammatory and infective diseases. Examples of autoimmune diseases are described herein and include multiple sclerosis, and insulin-dependent diabetes. The antagonists or agonists may also be employed to treat infectious diseases including silicosis, sarcoidosis, idiopathic pulmonary fibrosis by, for example, preventing the recruitment and activation of mononuclear phagocytes. They may also be employed to treat idiopathic hyper-eosinophilic syndrome by, for example, preventing eosinophil production and migration. The antagonists or agonists or may also be employed for treating atherosclerosis, for example, by preventing monocyte infiltration in the artery wall.

Antibodies against polypeptides of the invention may be employed to treat ARDS.

Agonists and/or antagonists of the invention also have uses in stimulating wound and tissue repair, stimulating angiogenesis, stimulating the repair of vascular or lymphatic diseases or disorders. Additionally, agonists and antagonists of the invention may be used to stimulate the regeneration of mucosal surfaces.

In a specific embodiment, polynucleotides or polypeptides, and/or agonists thereof are used to treat or prevent a disorder characterized by primary or acquired immunodeficiency, deficient serum immunoglobulin production, recurrent infections, and/or immune system dysfunction. Moreover, polynucleotides or polypeptides, and/or agonists thereof may be used to treat or prevent infections of the joints, bones, skin, and/or parotid glands, blood-borne infections (e.g., sepsis, meningitis, septic arthritis, and/or osteomyelitis), autoimmune diseases (e.g., those disclosed herein), inflammatory disorders, and malignancies, and/or any disease or disorder or condition associated with these infections, diseases, disorders and/or malignancies) including, but not limited to, CVID, other primary immune deficiencies, HIV disease, CLL, recurrent bronchitis, sinusitis, otitis media, conjunctivitis, pneumonia, hepatitis, meningitis, herpes zoster (e.g., severe herpes zoster), and/or pneumocystis carnii.

In another embodiment, polynucleotides, polypeptides, antibodies, and/or agonists or antagonists of the present invention are used to treat, and/or diagnose an individual having common variable immunodeficiency disease ("CVID"; also known as "acquired agammaglobulinemia" and "acquired hypogammaglobulinemia") or a subset of this disease.

In a specific embodiment, polynucleotides, polypeptides, antibodies, and/or agonists or antagonists of the present invention may be used to treat, diagnose, and/or prevent (1) cancers or neoplasms and (2) autoimmune cell or tissue-related cancers or neoplasms. In a preferred embodiment, polynucleotides, polypeptides, antibodies, and/or agonists or antagonists of the present invention conjugated to a toxin or a radioactive isotope, as described herein, may be used to treat, diagnose, and/or prevent acute myelogeneous leukemia. In a further preferred embodiment, polynucleotides, polypeptides, antibodies, and/or agonists or antagonists of the present invention conjugated to a toxin or a radioactive isotope, as described herein, may be used to treat, diagnose, and/or prevent, chronic myelogeneous leukemia, multiple myeloma, non-Hodgkins lymphoma, and/or Hodgkins disease.

In another specific embodiment, polynucleotides or polypeptides, and/or agonists or antagonists of the invention may be used to treat, diagnose, prognose, and/or prevent selective IgA deficiency, myeloperoxidase deficiency, C2 deficiency, ataxia-telangiectasia, DeGeorge anomaly, common variable immunodeficiency (CVI), X-linked agammaglobulinemia, severe combined immunodeficiency (SCID), chronic gramulomatous disease (CGD), and Wiskott-Aldrish syndrome.

Examples of autoimmune disorders that can be treated or detected are described above and also include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

In a preferred embodiment, the autoimmune diseases and disorders and/or conditions associated with the diseases and disorders recited above are treated, prevented, and/or diagnosed using immunoglobulin-like antibodies and/or immunoglobulin-like antibodies and/or a soluble immunoglobulin-like polypeptide of the invention.

In specific embodiments, the compositions of the invention are used as an agent to boost immunoresponsiveness among B cell immunodeficient individuals, such as, for example, an individual who has undergone a partial or complete splenectomy.

Additionally, polynucleotides, polypeptides, and/or antagonists of the invention may affect apoptosis, and therefore, would be useful in treating a number of diseases associated with increased cell survival or the inhibition of apoptosis. For example, diseases associated with increased cell survival or the inhibition of apoptosis that could be treated or detected by polynucleotides, polypeptides, and/or antagonists of the invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, polynucleotides, polypeptides, and/or antagonists of the invention are used to inhibit growth, progression, and/or metasis of cancers, in particular those listed above.

Additional diseases or conditions associated with increased cell survival that could be treated or detected by polynucleotides, polypeptides, and/or antagonists of the invention, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated or detected by polynucleotides, polypeptides, and/or antagonists of the invention, include AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Hyperproliferative diseases and/or disorders that could be detected and/or treated by polynucleotides, polypeptides, and/or antagonists of the invention, include, but are not limited to neoplasms located in the: liver, abdomen, bone, breast, digestive system, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by polynucleotides, polypeptides, and/or antagonists of the invention. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Hyperproliferative Disorders

Polynucleotides or polypeptides, or agonists or antagonists of the present invention can be used to treat or detect hyperproliferative disorders, including neoplasms. Polynucleotides or polypeptides, or agonists or antagonists of the present invention may inhibit the proliferation of the disorder through direct or indirect interactions. Alternatively, Polynucleotides or polypeptides, or agonists or antagonists of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by Polynucleotides or polypeptides, or agonists or antagonists of the present invention include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by polynucleotidesor polypeptides, or agonists or antagonists of the present invention. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

One preferred embodiment utilizes polynucleotides of the present invention to inhibit aberrant cellular division, by gene therapy using the present invention, and/or protein fusions or fragments thereof.

Thus, the present invention provides a method for treating cell proliferative disorders by inserting into an abnormally proliferating cell a polynucleotide of the present invention, wherein said polynucleotide represses said expression.

Another embodiment of the present invention provides a method of treating cell-proliferative disorders in individuals comprising administration of one or more active gene copies of the present invention to an abnormally proliferating cell or cells. In a preferred embodiment, polynucleotides of the present invention is a DNA construct comprising a recombinant expression vector effective in expressing a DNA sequence encoding said polynucleotides. In another preferred embodiment of the present invention, the DNA construct encoding the polynucleotides of the present invention is inserted into cells to be treated utilizing a retrovirus, or more preferably an adenoviral vector (See G J. Nabel, et. al., PNAS 1999 96: 324–326, which is hereby incorporated by reference). In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e. magnetic, specific small molecule, chemical, or drug administration, etc.), which acts upon the promoter upstream of said polynucleotides to induce expression of the encoded protein product. As such the beneficial therapeutic affect of the present invention may be expressly modulated (i.e. to increase, decrease, or inhibit expression of the present invention) based upon said external stimulus.

The polynucleotides encoding a polypeptide of the present invention may be administered along with other polynucleotides encoding an angiogenic protein. Examples of angiogenic proteins include, but are not limited to, acidic and basic fibroblast growth factors, VEGF-1, VEGF-2, VEGF-3, epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Polynucleotides of the present invention may be useful in repressing expression of oncogenic genes or antigens. By "repressing expression of the oncogenic genes" is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to transfection, electroporation, microinjection of cells, or in vehicles such as liposomes, lipofectin, or as naked polynucleotides, or any other method described throughout the specification. The polynucleotide of the present invention may be delivered by known gene delivery systems such as, but not limited to, retroviral vectors (Gilboa, J. Virology 44:845 (1982); Hocke, Nature 320:275 (1986); Wilson, et al., Proc. Natl. Acad. Sci. U.S.A. 85:3014), vaccinia virus system (Chakrabarty et al., Mol. Cell Biol. 5:3403 (1985) or other efficient DNA delivery systems (Yates et al., Nature 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus, or adenovural (as described in the art and elsewhere herein) delivery system known to those of skill in the art. Since host DNA replication is required for retroviral DNA to integrate and the retrovirus will be unable to self replicate due to the lack of the retrovirus genes needed for its life cycle. Utilizing such a retroviral delivery system for polynucleotides of the present invention will target said gene and constructs to abnormally proliferating cells and will spare the non-dividing normal cells.

The polynucleotides of the present invention may be delivered directly to cell proliferative disorder/disease sites in internal organs, body cavities and the like by use of imaging devices used to guide an injecting needle directly to the disease site. the polynucleotides of the present invention may also be administered to disease sites at the time of surgical intervention.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells. Moreover, it is possible to administer more than one of the polynucleotide of the present invention simultaneously to the same site. By "biologically inhibiting" is meant partial or total growth inhibition as well as decreases in the rate of proliferation or growth of the cells. The biologically inhibitory dose may be determined by assessing the effects of the polynucleotides of the present invention on target malignant or abnormally proliferating cell growth in tissue culture, tumor growth in animals and cell cultures, or any other method known to one of ordinary skill in the art.

The present invention is further directed to antibody-based therapies which involve administering of anti-polypeptides and anti-polynucleotide antibodies to a mammalian, preferably human, patient for treating one or more of the described disorders. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

In particular, the antibodies, fragments and derivatives of the present invention are useful for treating a subject having or developing cell proliferative and/or differentiation disorders as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with lymphokines or hematopoietic growth factors, for example, which serve to increase the number or activity of effector cells which interact with the antibodies.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5 \times 10^{-6}$M, $10^{-6}$M, $5 \times 10^{-7}$M, $10^{-7}$M, $5 \times 10^{-8}$M, $10^{-8}$M, $5 \times 10^{-9}$M, $10^{-9}$M, $5 \times 10^{-10}$M, $10^{-10}$M, $5 \times 10^{-11}$M, $10^{-11}$M, $5 \times 10^{-12}$M, $10^{-12}$M, $5 \times 10^{-13}$M, $10^{-13}$M, $5 \times 10^{-14}$M, $10^{-14}$M, $5 \times 10^{-15}$M, and $10^{-15}$M.

Moreover, polypeptides of the present invention are useful in inhibiting the angiogenesis of proliferative cells or tissues, either alone, as a protein fusion, or in combination with other polypeptides directly or indirectly, as described elsewhere herein. In a most preferred embodiment, said anti-angiogenesis effect may be achieved indirectly, for example, through the inhibition of hematopoietic, tumor-specific cells, such as tumor-associated macrophages (See Joseph I B, et al. J Natl Cancer Inst, 90(21):1648–53 (1998), which is hereby incorporated by reference). Antibodies directed to polypeptides or polynucleotides of the present invention may also result in inhibition of angiogenesis directly, or indirectly (See Witte, L, et al., Cancer Metastasis Rev. 17(2):155–61 (1998), which is hereby incorporated by reference)).

Polypeptides, including protein fusions, of the present invention, or fragments thereof may be useful in inhibiting proliferative cells or tissues through the induction of apoptosis. Said polypeptides may act either directly, or indirectly to induce apoptosis of proliferative cells and tissues, for example in the activation of a death-domain receptor, such as tumor necrosis factor (TNF) receptor-1, CD95 (Fas/APO-1), TNF-receptor-related apoptosis-mediated protein (TRAMP) and TNF-related apoptosis-inducing ligand (TRAIL) receptor-1 and -2 (See Schulze-Osthoff K, et.al., Eur J Biochem 254(3):439–59 (1998), which is hereby incorporated by reference). Moreover, in another preferred embodiment of the present invention, said polypeptides may induce apoptosis through other mechanisms, such as in the activation of other proteins which will activate apoptosis, or through stimulating the expression of said proteins, either alone or in combination with small molecule drugs or adjuviants, such as apoptonin, galectins, thioredoxins, anti-inflammatory proteins (See for example, Mutat Res 400 (1–2):447–55 (1998), Med Hypotheses. 50(5):423–33 (1998), Chem Biol Interact. Apr 24;111–112:23–34 (1998), J Mol Med. 76(6):402–12 (1998), Int J Tissue React; 20(1): 3–15 (1998), which are all hereby incorporated by reference).

Polypeptides, including protein fusions to, or fragments thereof, of the present invention are useful in inhibiting the metastasis of proliferative cells or tissues. Inhibition may occur as a direct result of administering polypeptides, or antibodies directed to said polypeptides as described elsewhere herein, or indirectly, such as activating the expression of proteins known to inhibit metastasis, for example alpha 4 integrins, (See, e.g., Curr Top Microbiol Immunol 1998;231: 125–41, which is hereby incorporated by reference). Such thereapeutic affects of the present invention may be achieved either alone, or in combination with small molecule drugs or adjuvants.

In another embodiment, the invention provides a method of delivering compositions containing the polypeptides of the invention (e.g., compositions containing polypeptides or polypeptides antibodes associated with heterologous polypeptides, heterologous nucleic acids, toxins, or prodrugs) to targeted cells expressing the polypeptide of the present invention. Polypeptides or polypeptide antibodes of the invention may be associated with with heterologous polypeptides, heterologous nucleic acids, toxins, or prodrugs via hydrophobic, hydrophilic, ionic and/or covalent interactions.

Polypeptides, protein fusions to, or fragments thereof, of the present invention are useful in enhancing the immunogenicity and/or antigenicity of proliferating cells or tissues, either directly, such as would occur if the polypeptides of the present invention 'vaccinated' the immune response to respond to proliferative antigens and immunogens, or indirectly, such as in activating the expression of proteins known to enhance the immune response (e.g. chemokines), to said antigens and immunogens.

Cardiovascular Disorders

Polynucleotides or polypeptides, or agonists or antagonists of the present invention, may be used to treat cardiovascular disorders, including peripheral artery disease, such as limb ischemia.

Cardiovascular disorders include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular disorders also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, post-pericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hemotoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromboembolisms. Thrombosis include coronary thrombosis, hepatic vein thrombosis, retinal vein occlusion carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reprefusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

Polynucleotides or polypeptides, or agonists or antagonists of the present invention, are especially effective for the treatment of critical limb ischemia and coronary disease.

Polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pump, oral or suppositorial solid pharmaceutical formulations, decanting or topical applications during surgery, aerosol delivery. Such methods are known in the art. Polypeptides may be administered as part of a Therapeutic, described in more detail below. Methods of delivering polynucleotides are described in more detail herein.

Anti-Angiogenesis Activity

The naturally occurring balance between endogenous stimulators and inhibitors of angiogenesis is one in which inhibitory influences predominate. Rastinejad et al., *Cell* 56:345–355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., *Biotech.* 9:630–634 (1991); Folkman et al., *N. Engl. J. Med.*, 333:1757–1763 (1995); Auerbach et al., *J. Microvasc. Res.* 29:401–411 (1985); Folkman, Advances in Cancer Research, eds. Klein and Weinhouse, Academic Press, New York, pp. 175–203 (1985); Patz, *Am. J. Opthalmol.* 94:715–743 (1982); and Folkman et al., *Science* 221:719–725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442–447 (1987).

The present invention provides for treatment of diseases or disorders associated with neovascularization by administration of the polynucleotides and/or polypeptides of the invention, as well as agonists or antagonists of the present invention. Malignant and metastatic conditions which can be treated with the polynucleotides and polypeptides, of agonists or antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)). Thus, the present invention provides a method of treating an angiogenesis-related disease and/or disorder, comprising administering to an individual in need thereof a therapeutically effective amount of a polynucleotide, polypeptide, antagonist and/or agonist of the invention. For example, polynucleotides, polypeptides, antagonists and/or agonists may be utilized in a variety of additional methods in order to therapeutically treat a cancer or tumor. Cancers which may be treated with polynucleotides, polypeptides, antagonists and/or agonists include, but are not limited to solid tumors, including prostate, lung, breast, ovarian, stomach, pancrease, larynx, esophagus, testes, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non-small cell lung cancer; colorectal cancer; advanced malignancies; and blood born tumors such as leukemias. For example, polynucleotides, polypeptides, antagonists and/or agonists may be delivered topically, in order to treat cancers such as skin cancer, head and neck tumors, breast tumors, and Kaposi's sarcoma.

Within yet other aspects, polynucleotides, polypeptides, antagonists and/or agonists may be utilized to treat superficial forms of bladder cancer by, for example, intravesical administration. Polynucleotides, polypeptides, antagonists and/or agonists may be delivered directly into the tumor, or near the tumor site, via injection or a catheter. Of course, as the artisan of ordinary skill will appreciate, the appropriate mode of administration will vary according to the cancer to be treated. Other modes of delivery are discussed herein.

Polynucleotides, polypeptides, antagonists and/or agonists may be useful in treating other disorders, besides cancers, which involve angiogenesis. These disorders include, but are not limited to: benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration; corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Chrohn's disease; and atherosclerosis.

For example, within one aspect of the present invention methods are provided for treating hypertrophic scars and keloids, comprising the step of administering a polynucleotide, polypeptide, antagonist and/or agonist of the invention to a hypertrophic scar or keloid.

Within one embodiment of the present invention polynucleotides, polypeptides, antagonists and/or agonists are directly injected into a hypertrophic scar or keloid, in order to prevent the progression of these lesions. This therapy is of particular value in the prophylactic treatment of conditions which are known to result in the development of hypertrophic scars and keloids (e.g., burns), and is preferably initiated after the proliferative phase has had time to progress (approximately 14 days after the initial injury), but before hypertrophic scar or keloid development. As noted above, the present invention also provides methods for treating neovascular diseases of the eye, including for example, corneal neovascularization, neovascular glaucoma, proliferative diabetic retinopathy, retrolental fibroplasia and macular degeneration.

Moreover, Ocular disorders associated with neovascularization which can be treated with the polynucleotides and polypeptides of the present invention (including agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704–710 (1978) and Gartner et al., *Surv. Ophthal.* 22:291–312 (1978).

Thus, within one aspect of the present invention methods are provided for treating neovascular diseases of the eye such as corneal neovascularization (including corneal graft neovascularization), comprising the step of administering to a patient a therapeutically effective amount of a compound (as described above) to the cornea, such that the formation of blood vessels is inhibited. Briefly, the cornea is a tissue which normally lacks blood vessels. In certain pathological conditions however, capillaries may extend into the cornea from the pericorneal vascular plexus of the limbus. When the cornea becomes vascularized, it also becomes clouded, resulting in a decline in the patient's visual acuity. Visual loss may become complete if the cornea completely opacitates. A wide variety of disorders can result in corneal neovascularization, including for example, corneal infections (e.g., trachoma, herpes simplex keratitis, leishmaniasis and onchocerciasis), immunological processes (e.g., graft rejection amd Steves-Johnson's syndrome), alkali burns, trauma, inflammation (of any cause), toxic and nutritional deficiency states, and as a complication of wearing contact lenses.

Within particularly preferred embodiments of the invention, may be prepared for topical administration in saline (combined with any of the preservatives and antimicrobial agents commonly used in ocular preparations), and administered in eyedrop form. The solution or suspensions may be prepared in its pure form and administered several times daily. Alternatively, anti-angiogenic compositions, prepared as described above, may also be administered directly to the cornea. Within preferred embodiments, the anti-angiogenic composition is prepared with a muco-adhesive polymer which binds to cornea. Within further embodiments, the anti-angiogenic factors or anti-angiogenic compositions may be utilized as an adjunct to conventional steroid therapy. Topical therapy may also be useful prophylactically in corneal lesions which are known to have a high probability of inducing an angiogenic response (such as chemical burns). In these instances the treatment, likely in combination with steroids, may be instituted immediately to help prevent subsequent complications.

Within other embodiments, the compounds described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2–3 times per year. A steroid could also be added to the injection solution to reduce inflammation resulting from the injection itself.

Within another aspect of the present invention, methods are provided for treating neovascular glaucoma, comprising the step of administering to a patient a therapeutically effective amount of a polynucleotide, polypeptide, antagonist and/or agonist to the eye, such that the formation of blood vessels is inhibited. In one embodiment, the compound may be administered topically to the eye in order to treat early forms of neovascular glaucoma. Within other embodiments, the compound may be implanted by injection into the region of the anterior chamber angle. Within other embodiments, the compound may also be placed in any location such that the compound is continuously released into the aqueous humor. Within another aspect of the present invention, methods are provided for treating proliferative diabetic retinopathy, comprising the step of administering to a patient a therapeutically effective amount of a polynucleotide, polypeptide, antagonist and/or agonist to the eyes, such that the formation of blood vessels is inhibited.

Within the particularly preferred embodiments of the invention, proliferative diabetic retinopathy may be treated by injection into the aqueous humor or the vitreous, in order to increase the local concentration of the polynucleotide, polypeptide, antagonist and/or agonist in the retina. Preferably, this treatment should be initiated prior to the acquisition of severe disease requiring photocoagulation.

Within anothe aspect of the present invention, methods are provided for treating retrolental fibroplasia, comprising the step of administering to a patient a therapeutically effective amount of a polynucleotide, polypeptide, antagonist and/or agonist to the eye, such that the formation of blood vessels is inhibited. The compound may be administered topically, via intravitreous injection and/or via intraocular implants.

Additionally, disorders which can be treated with the polynucleotides, polypeptides, agonists and/or agonists include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, disorders and/or states, which can be treated with be treated with the the polynucleotides, polypeptides, agonists and/or agonists include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uvietis, delayed wound healing, endometriosis, vasculogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (Rochele minalia quintosa), ulcers (*Helicobacter pylori*), Bartonellosis and bacillary angiomatosis.

In one aspect of the birth control method, an amount of the compound sufficient to block embryo implantation is administered before or after intercourse and fertilization have occurred, thus providing an effective method of birth control, possibly a "morning after" method. Polynucleotides, polypeptides, agonists and/or agonists may also be used in controlling menstruation or administered as either a peritoneal lavage fluid or for peritoneal implantation in the treatment of endometriosis.

Polynucleotides, polypeptides, agonists and/or agonists of the present invention may be incorporated into surgical sutures in order to prevent stitch granulomas.

Polynucleotides, polypeptides, agonists and/or agonists may be utilized in a wide variety of surgical procedures. For example, within one aspect of the present invention a compositions (in the form of, for example, a spray or film) may be utilized to coat or spray an area prior to removal of a tumor, in order to isolate normal surrounding tissues from malignant tissue, and/or to prevent the spread of disease to surrounding tissues. Within other aspects of the present invention, compositions (e.g., in the form of a spray) may be delivered via endoscopic procedures in order to coat tumors, or inhibit angiogenesis in a desired locale. Within yet other aspects of the present invention, sugrical meshes which have been coated with anti-angiogenic compositions of the present invention may be utilized in any procedure wherein a surgical mesh might be utilized. For example, within one embodiment of the invention a surgical mesh laden with an anti-angiogenic composition may be utilized during abdominal cancer resection surgery (e.g., subsequent to colon resection) in order to provide support to the structure, and to release an amount of the anti-angiogenic factor.

Within further aspects of the present invention, methods are provided for treating tumor excision sites, comprising administering a polynucleotide, polypeptide, agonist and/or agonist to the resection margins of a tumor subsequent to excision, such that the local recurrence of cancer and the formation of new blood vessels at the site is inhibited. Within one embodiment of the invention, the anti-angiogenic compound is administered directly to the tumor excision site (e.g., applied by swabbing, brushing or otherwise coating the resection margins of the tumor with the anti-angiogenic compound). Alternatively, the anti-angiogenic compounds may be incorporated into known surgical pastes prior to administration. Within particularly preferred embodiments of the invention, the anti-angiogenic angiogenic compounds are applied after hepatic resections for malignancy, and after neurosurgical operations.

Within one aspect of the present invention, polynucleotides, polypeptides, agonists and/or agonists may be administered to the resection margin of a wide variety of tumors, including for example, breast, colon, brain and hepatic tumors. For example, within one embodiment of the invention, anti-angiogenic compounds may be administered to the site of a neurological tumor subsequent to excision, such that the formation of new blood vessels at the site are inhibited.

The polynucleotides, polypeptides, agonists and/or agonists of the present invention may also be administered along with other anti-angiogenic factors. Representative examples of other anti-angiogenic factors include: Anti-Invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammoniun tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include platelet factor 4; protamine sulphate; sulphated chitin derivatives (prepared from queen crab shells), (Murata et al., Cancer Res. 51:22–26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321–17326, 1992); Chymostatin (Tomkinson et al., Biochem J. 286:475–480, 1992); Cyclodextrin Tetradecasulfate; Eponemycin; Camptothecin; Fumagillin (Ingber et al., Nature 348:555–557, 1990); Gold Sodium Thiomalate ("GST"; Matsubara and Ziff, J. Clin. Invest. 79:1440–1446, 1987); anticollagenase-serum; alpha2-antiplasmin (Holmes et al., J. Biol. Chem. 262(4):1659–1664, 1987); Bisantrene (National Cancer Institute); Lobenzarit disodium (N-(2)-carboxyphenyl-4-chloroanthronilic acid disodium or "CCA"; Takeuchi et al., Agents Actions 36:312–316, 1992); Thalidomide; Angostatic steroid; AGM-1470; carboxynaminolmidazole; and metalloproteinase inhibitors such as BB94.

Diseases at the Cellular Level

Diseases associated with increased cell survival or the inhibition of apoptosis that could be treated or detected by polynucleotides or polypeptides, as well as antagonists or agonists of the present invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, polynucleotides, polypeptides, and/or antagonists of the invention are used to inhibit growth, progression, and/or metasis of cancers, in particular those listed above.

Additional diseases or conditions associated with increased cell survival that could be treated or detected by polynucleotides or polypeptides, or agonists or antagonists of the present invention include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated or detected by polynucleotides or polypeptides, as well as agonists or antagonists of the present invention include AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing polynucleotides or polypeptides, as well as agonists or antagonists of the present invention, for therapeutic purposes, for example, to stimulate epithelial cell proliferation and basal keratinocytes for the purpose of wound healing, and to stimulate hair follicle production and healing of dermal wounds. Polynucleotides or polypeptides, as well as agonists or antagonists of the present invention, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associated with systemic treatment with steroids, radiation therapy and antineoplastic drugs and antimetabolites. Polynucleotides or polypeptides, as well as agonists or antagonists of the present invention, could be used to promote dermal reestablishment subsequent to dermal loss Polynucleotides or polypeptides, as well as agonists or antagonists of the present invention, could be used to increase the adherence of skin grafts to a wound bed and to stimulate re-epithelialization from the wound bed. The following are types of grafts that polynucleotides or polypeptides, agonists or antagonists of the present invention, could be used to increase adherence to a wound bed: autografts, artificial skin, allografts, autodermic graft, autoepdermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, musocal graft, Ollier-Thiersch graft, omenpal graft, patch graft, pedicle graft, penetrating graft, split skin graft, thick split graft. Polynucleotides or polypeptides, as well as agonists or antagonists of the present invention, can be used to promote skin strength and to improve the appearance of aged skin.

It is believed that polynucleotides or polypeptides, as well as agonists or antagonists of the present invention, will also produce changes in hepatocyte proliferation, and epithelial cell proliferation in the lung, breast, pancreas, stomach, small intesting, and large intestine. Polynucleotides or polypeptides, as well as agonists or antagonists of the present invention, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. Polynucleotides or polypeptides, agonists or antagonists of the present invention, may promote proliferation of endothelial cells, keratinocytes, and basal keratinocytes.

Polynucleotides or polypeptides, as well as agonists or antagonists of the present invention, could also be used to reduce the side effects of gut toxicity that result from radiation, chemotherapy treatments or viral infections. Polynucleotides or polypeptides, as well as agonists or antagonists of the present invention, may have a cytoprotective effect on the small intestine mucosa. Polynucleotides or polypeptides, as well as agonists or antagonists of the present invention, may also stimulate healing of mucositis (mouth ulcers) that result from chemotherapy and viral infections.

Polynucleotides or polypeptides, as well as agonists or antagonists of the present invention, could further be used in full regeneration of skin in full and partial thickness skin defects, including burns, (i.e., repopulation of hair follicles, sweat glands, and sebaceous glands), treatment of other skin defects such as psoriasis. Polynucleotides or polypeptides, as well as agonists or antagonists of the present invention, could be used to treat epidermolysis bullosa, a defect in adherence of the epidermis to the underlying dermis which results in frequent, open and painful blisters by accelerating reepithelialization of these lesions. Polynucleotides or polypeptides, as well as agonists or antagonists of the present invention, could also be used to treat gastric and duodenal ulcers and help heal by scar formation of the mucosal lining and regeneration of glandular mucosa and duodenal musocal lining more rapidly. Inflammatory bowel diseases, such as Crohn's disease and ulcerative colitis, are diseases which result in destruction of the mucosal surface of the small or large intestine, respectively. Thus, polynucleotides or polypeptides, as well as agonists or antagonists of the present invention, could be used to promote the resurfacing of the mucosal surface to aid more rapid healing and to prevent progression of inflammatory bowel disease. Treatment with polynucleotides or polypeptides, agonists or antagonists of the present invention, is expected to have a significant effect on the production of mucus throughout the gastrointestinal tract and could be used to protect the intestinal mucosa from injurious substances that are ingested or following surgery. Polynucleotides or polypeptides, as well as agonists or antagonists of the present invention, could be used to treat diseases associate with the under expression.

Moreover, polynucleotides or polypeptides, as well as agonists or antagonists of the present invention, could be used to prevent and heal damage to the lungs due to various pathological states. Polynucleotides or polypeptides, as well as agonists or antagonists of the present invention, which could stimulate proliferation and differentiation and promote the repair of alveoli and brochiolar eqithelium to prevent or treat acute or chronic lung damage. For example, emphysema, which results in the progressive loss of aveoli, and inhalation injuries, i.e., resulting from smoke inhalation and burns, that cause necrosis of the bronchiolar epithelium and alveoli could be effectively treated using polynucleotides or polypeptides, as well as agonists or antagonists of the present invention, could be used to stimulate the proliferation of and differentiation of type II pneumocytes, which may help treat or prevent disease such as hyaline membrane diseases, such as infant respiratory distress syndrome and bronchopulmonary displasia, in premature infants.

Polynucleotides or polypeptides, as well as agonists or antagonists of the present invention, could stimulate the proliferation and differentiation of hepatocytes and, thus, could be used to alleviate or treat liver diseases and pathologies such as fulminant liver failure caused by cirrhosis, liver damage caused by viral hepatitis, and toxic substances (i.e., acetaminophen, carbon tetraholoride and other hepatotoxins known in the art).

In addition, polynucleotides or polypeptides, as well as agonists or antagonists of the present invention, could be used treat or prevent the onset of diabetes mellitus. In patients with newly diagnosed Types I and II diabetes, where some islet cell function remains, polynucleotides or polypeptides, as well as agonists or antagonists of the present invention, could be used to maintain the islet function so as to alleviate, delay or prevent permanent manifestation of the disease. Also, polynucleotides or polypeptides, as well as agonists or antagonists of the present invention, could be used as an auxiliary in islet cell transplantation to improve or promote islet cell function.

Neural Activity and Neurological Diseases

The polynucleotides, polypeptides and agonists or antagonists of the invention may be used for the diagnosis and/or treatment of diseases, disorders, damage or injury of the brain and/or nervous system. Nervous system disorders that can be treated with the compositions of the invention (e.g., immunoglobulin superfamily polypeptides, polynucleotides, and/or agonists or antagonists), include, but are not limited to, nervous system injuries, and diseases or disorders which result in either a disconnection of axons, a diminution or degeneration of neurons, or demyelination. Nervous system lesions which may be treated in a patient (including human and non-human mammalian patients) according to the methods of the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, or syphilis; (5) degenerative lesions, in which a portion of the nervous system is destroyed or injured as a result of a degenerative process including but not limited to, degeneration associated with Parkinson's disease, Alzheimer's disease, Huntington's chorea, or amyotrophic lateral sclerosis (ALS); (6) lesions associated with nutritional diseases or disorders, in which a portion of the nervous system is destroyed or injured by a nutritional disorder or disorder of metabolism including, but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In one embodiment, the polypeptides, polynucleotides, or agonists or antagonists of the invention are used to protect neural cells from the damaging effects of hypoxia. In a further preferred embodiment, the polypeptides, polynucleotides, or agonists or antagonists of the invention are used to protect neural cells from the damaging effects of cerebral hypoxia. According to this embodiment, the compositions of the invention are used to treat or prevent neural cell injury associated with cerebral hypoxia. In one non-exclusive aspect of this embodiment, the polypeptides, polynucleotides, or agonists or antagonists of the invention, are used to treat or prevent neural cell injury associated with cerebral ischemia. In another non-exclusive aspect of this embodiment, the polypeptides, polynucleotides, or agonists or antagonists of the invention are used to treat or prevent neural cell injury associated with cerebral infarction.

In another preferred embodiment, the polypeptides, polynucleotides, or agonists or antagonists of the invention are used to treat or prevent neural cell injury associated with a stroke. In a specific embodiment, the polypeptides, polynucleotides, or agonists or antagonists of the invention are used to treat or prevent cerebral neural cell injury associated with a stroke.

In another preferred embodiment, the polypeptides, polynucleotides, or agonists or antagonists of the invention are used to treat or prevent neural cell injury associated with a heart attack. In a specific embodiment, the polypeptides, polynucleotides, or agonists or antagonists of the invention are used to treat or prevent cerebral neural cell injury associated with a heart attack.

The compositions of the invention which are useful for treating or preventing a nervous system disorder may be selected by testing for biological activity in promoting the survival or differentiation of neurons. For example, and not by way of limitation, compositions of the invention which elicit any of the following effects may be useful according to the invention: (1) increased survival time of neurons in culture either in the presence or absence of hypoxia or hypoxic conditions; (2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In preferred, non-limiting embodiments, increased survival of neurons may routinely be measured using a method set forth erein or otherwise known in the art, such as, for example, in Zhang et al., *Proc Natl Acad Sci USA* 97:3637–42 (2000) or in Arakawa et al., *J. Neurosci.*, 10:3507–15 (1990); increased sprouting of neurons may be detected by methods known in the art, such as, for example, the methods set forth in Pestronk et al., *Exp. Neurol.*, 70:65–82 (1980), or Brown et al., *Ann. Rev. Neurosci.*, 4:17–42 (1981); increased production of neuron-associated molecules may be measured by bioassay, enzymatic assay, antibody binding, Northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

In specific embodiments, motor neuron disorders that may be treated according to the invention include, but are not limited to, disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

Further, polypeptides or polynucleotides of the invention may play a role in neuronal survival; synapse formation; conductance; neural differentiation, etc. Thus, compositions of the invention (including immunoglobulin superfamily polynucleotides, polypeptides, and agonists or antagonists) may be used to diagnose and/or treat or prevent diseases or disorders associated with these roles, including, but not limited to, learning and/or cognition disorders. The compositions of the invention may also be useful in the treatment or prevention of neurodegenerative disease states and/or behavioural disorders. Such neurodegenerative disease states and/or behavioral disorders include, but are not limited to, Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and preception. In addition, compositions of the invention may also play a role in the treatment, prevention and/or detection of developmental disorders associated with the developing embryo, or sexually-linked disorders.

Additionally, polypeptides, polynucleotides and/or agonists or antagonists of the invention may be useful in protecting neural cells from diseases, damage, disorders, or injury, associated with cerebrovascular disorders including, but not limited to, carotid artery diseases (e.g., carotid artery thrombosis, carotid stenosis, or Moyamoya Disease), cerebral amyloid angiopathy, cerebral aneurysm, cerebral anoxia, cerebral arteriosclerosis, cerebral arteriovenous malformations, cerebral artery diseases, cerebral embolism and thrombosis (e.g., carotid artery thrombosis, sinus thrombosis, or Wallenberg's Syndrome), cerebral hemorrhage (e.g., epidural or subdural hematoma, or subarachnoid hemorrhage), cerebral infarction, cerebral ischemia (e.g., transient cerebral ischemia, Subclavian Steal Syndrome, or vertebrobasilar insufficiency), vascular dementia (e.g., multi-infarct), leukomalacia, periventricular, and vascular headache (e.g., cluster headache or migraines).

In accordance with yet a further aspect of the present invention, there is provided a process for utilizing polynucleotides or polypeptides, as well as agonists or antagonists of the present invention, for therapeutic purposes, for example, to stimulate neurological cell proliferation and/or differentiation. Therefore, polynucleotides, polypeptides, agonists and/or antagonists of the invention may be used to treat and/or detect neurologic diseases. Moreover, polynucleotides or polypeptides, or agonists or antagonists of the invention, can be used as a marker or detector of a particular nervous system disease or disorder.

Examples of neurologic diseases which can be treated or detected with polynucleotides, polypeptides, agonists, and/or antagonists of the present invention include brain diseases, such as metabolic brain diseases which includes phenylketonuria such as maternal phenyketonuria, pyruvate carboxylase deficiency, pyruvate dehydrogenase complex deficiency, Wernicke's Encephalopathy, brain edema, brain neoplasms such as cerebellar neoplasms which include infratentorial neoplasms, cerebral ventricle neoplasms such as choroid plexus neoplasms, hypothalamic neoplasms, supratentorial neoplasms, canavan disease, cerebellar diseases such as cerebellar ataxia which include spinocerebellar degeneration such as ataxia telangiectasia, cerebellar dyssynergia, Friederich's Ataxia, Machado-Joseph Disease, olivopontocerebellar atrophy, cerebellar neoplasms such as infratentorial neoplasms, diffuse cerebral sclerosis such as encephalitis periaxialis, globoid cell leukodystrophy, metachromatic leukodystrophy and subacute sclerosing panencephalitis.

Additional neurologic diseases which can be treated or detected with polynucleotides, polypeptides, agonists, and/or antagonists of the present invention include cerebrovascular disorders (such as carotid artery diseases which include carotid artery thrombosis, carotid stenosis, or Moyamoya Disease), cerebral amyloid angiopathy, cerebral aneurysm, cerebral anoxia, cerebral arteriosclerosis, cerebral arteriovenous malformations, cerebral artery diseases, cerebral embolism and thrombosis such as carotid artery thromsosis, sinus thrombosis and Wallenberg's Syndrome, cerebral hemorrhage such as epidural hematoma, subdural hematoma and subarachnoid hemorrhage, cerebral infarction, cerebral ischemia such as transient cerebral ischemia, Subclavian Steal Syndrome and vertebrobasilar insufficiency, vascular dementia such as multi-infarct dementia, periventricular leukomalacia, vascular headache such as cluster headache and migraine.

Additional neurologic diseases which can be treated or detected with polynucleotides, polypeptides, agonists, and/or antagonists of the present invention include dementia such as AIDS Dementia Complex, presenile dementia such as Alzheimer's Disease and Creutzfeldt-Jakob Syndrome, senile dementia such as Alzheimer's Disease and progressive supranuclear palsy, vascular dementia such as multi-infarct dementia, encephalitis which include encephalitis periaxialis, viral encephalitis such as epidemic encephalitis, Japanese Encephalitis, St. Louis Encephalitis, tick-borne encephalitis and West Nile Fever, acute disseminated encephalomyelitis, meningoencephalitis such as uveomeningoencephalitis sydrome, Postencephalitis Parkinson Disease and subacute sclerosing panencephalitis, encephalomalacia such as periventricular leukomalacia, epilepsy such as generalized epilepsy which includes infantile spasms, absence epilepsy, myoclonic epilepsy which includes MERRF Syndrome, tonic-clonic epilepsy, partial epilepsy such as complex partial epilepsy, frontal lobe epilepsy and temporal lobe epilepsy, post-traumatic epilepsy, status epilepticus such as Epilepsia Partialis Continua, and Hallervorden-Spatz Syndrome.

Additional neurologic diseases which can be treated or detected with polynucleotides, polypeptides, agonists, and/or antagonists of the present invention include hydrocephalus such as Dandy-Walker Syndrome and normal pressure hydrocephalus, hypothalamic diseases such as hypothalamic neoplasms, cerebral malaria, narcolepsy which includes cataplexy, bulbar poliomyelitis, cerebri pseudotumor, Rett Syndrome, Reye's Syndrome, thalamic diseases, cerebral toxoplasmosis, intracranial tuberculoma and Zellweger Syndrome, Central nervous system infections such as AIDS Dementia Complex, Brain Abscess, subdural empyema, encephalomyelitis such as Equine Encephalomyelitis, Venezuelan Equine Encephalomyelitis, Necrotizing Hemorrhagic Encephalomyelitis, Visna, and cerebral malaria.

Additional neurologic diseases which can be treated or detected with polynucleotides, polypeptides, agonists, and/or antagonists of the present invention include meningitis such as arachnoiditis, aseptic meningtitis such as viral meningtitis which includes lymphocytic choriomeningitis, Bacterial meningtitis which includes Haemophilus Meningtitis, Listeria Meningtitis, Meningococcal Meningtitis such as Waterhouse-Friderichsen Syndrome, Pneumococcal Meningtitis and meningeal tuberculosis, fungal meningitis such as Cryptococcal Meningtitis, subdural effusion, meningoencephalitis such as uvemeningoencephalitic syndrome, myelitis such as transverse myelitis, neurosyphilis such as tabes dorsalis, poliomyelitis which includes bulbar poliomyelitis and postpoliomyelitis syndrome, prion diseases (such as Creutzfeldt-Jakob Syndrome, Bovine Spongiform Encephalopathy, Gerstmann-Starussler Syndrome, Kuru, Scrapie), and Cerebral Toxoplasmosis.

Additional neurologic diseases which can be treated or detected with polynucleotides, polypeptides, agonists, and/or antagonists of the present invention include central nervous system neoplasms such as brain neoplasms that include cerebellar neoplasms such as infratentorial neoplasms, cerebral ventricle neoplasms such as choroid plexus neoplasms, hypothalamic neoplasms and supratentorial neoplasms, meningeal neoplasms, spinal cord neoplasms which include epidural neoplasms, demyelinating diseases such as Canavan Disease, diffuse cerebral sceloris which includes adrenoleukodystrophy, encephalitis periaxialis, globoid cell leukodystrophy, diffuse cerebral sclerosis such as metachromic leukodystrophy, allergic encephalomyelitis, necrotizing hemorrhagic encephalomyelitis, progressive multifocal leukoencephalopathy, multiple sclerosis, central pontine myelinolysis, transverse myelitis, neuromyelitis optica, Scrapie, Swayback, Chronic Fatigue Syndrome, Visna, High Pressure Nervous Syndrome, Meningism, spinal cord diseases such as amyotonia congenita, amyotrophic lateral sclerosis, spinal muscular atrophy such as Werdnig-Hoffman Disease, spinal cord compression, spinal cord neoplasms such as epidural neoplasms. syringomyelia, Tabes Dorsalis, Stiff-Man Syndrome, mental retardation such as Angelman Syndrome, Cri-du-Chat Syndrome, De Lange's Syndrome, Down Syndrome, Gangliosidoses such as gangliosidoses G(M1), Sandhoff Disease, Tay-Sachs Disease, Hartnup Disease, homocystinuria, Laurence-Moon-Biedl Syndrome, Lesch-Nyhan Syndrome, Maple Syrup Urine Disease, mucolipidosis such as fucosidosis, neuronal ceroid-lipofuscinosis, oculocerebrorenal syndrome, phenylketonuria such as maternal phenylketonuria, Prader-Willi Syndrome, Rett Syndrome, Rubinstein-Taybi Syndrome, Tuberous Sclerosis, WAGR Syndrome, nervous system abnormalities such as holoprosencephaly, neural tube defects such as anencephaly which includes hydrangencephaly, Arnold-Chairi Deformity, encephalocele, meningocele, meningomyelocele, spinal dysraphism such as spina bifida cystica and spina bifida occulta.

Additional neurologic diseases which can be treated or detected with polynucleotides, polypeptides, agonists, and/or antagonists of the present invention include hereditary motor and sensory neuropathies which include Charcot-Marie Disease, Hereditary optic atrophy, Refsum's Disease, hereditary spastic paraplegia, Werdnig-Hoffmann Disease, Hereditary Sensory and Autonomic Neuropathies such as Congenital Analgesia and Familiar Dysautonomia, Neurologic manifestations (such as agnosia that include Gerstmann's Syndrome, Amnesia such as retrograde anmesia, apraxia, neurogenic bladder, cataplexy, communicative disorders such as hearing disorders that includes deafness, partial hearing loss, loudness recruitment and tinnitus, language disorders such as aphasia which include agraphia, anomia, broca aphasia, and Wernicke Aphasia, Dyslexia such as Acquired Dyslexia, language development disorders, speech disorders such as aphasia which includes anomia, broca aphasia and Wernicke Aphasia, articulation disorders, communicative disorders such as speech disorders which include dysarthria, echolalia, mutism and stuttering, voice disorders such as aphonia and hoarseness, decerebrate state, delirium, fasciculation, hallucinations, meningism, movement disorders such as angelman syndrome, ataxia, athetosis, chorea, dystonia, hypokinesia, muscle hypotonia, myoclonus, tic, torticollis and tremor, muscle hypertonia such as muscle rigidity such as stiff-man syndrome, muscle spasticity, paralysis such as facial paralysis which includes Herpes Zoster Oticus, Gastroparesis, Hemiplegia, ophthalmoplegia such as diplopia, Duane's Syndrome, Horner's Syndrome, Chronic progressive external ophthalmoplegia such as Kearns Syndrome, Bulbar Paralysis, Tropical Spastic Paraparesis, Paraplegia such as Brown-Sequard Syndrome, quadriplegia, respiratory paralysis and vocal cord paralysis, paresis, phantom limb, taste disorders such as ageusia and dysgeusia, vision disorders such as amblyopia, blindness, color vision defects, diplopia, hemianopsia, scotoma and subnormal vision, sleep disorders such as hypersomnia which includes Kleine-Levin Syndrome, insomnia, and somnambulism, spasm such as trismus, unconsciousness such as coma, persistent vegetative state and syncope and vertigo, neuromuscular diseases such as amyotonia congenita, amyotrophic lateral sclerosis, Lambert-Eaton Myasthenic Syndrome, motor neuron disease, muscular atrophy such as spinal muscular atrophy, Charcot-Marie Disease and Werdnig-Hoffmann Disease, Postpoliomyelitis Syndrome, Muscular Dystrophy, Myasthenia Gravis, Myotonia Atrophica, Myotonia Confenita, Nemaline Myopathy, Familial Perodic Paralysis, Multiplex Paramyloclonus, Tropical Spastic Paraparesis and Stiff-Man Syndrome, peripheral nervous system diseases such as acrodynia, amyloid neuropathies, autonomic nervous system diseases such as Adie's Syndrome, Barre-Lieou Syndrome, Familial Dysautonomia, Horner's Syndrome, Reflex Sympathetic Dystrophy and Shy-Drager Syndrome, Cranial Nerve Diseases such as Acoustic Nerve Disease such as Acoustic Neuroma which includes Neurofibromatosis 2, Facial Nerve Diseases such as Facial Neuralgia, Melkersson-Rosenthal Syndrome, ocular motility disorders which includes amblyopia, nystagmus, oculomotor nerve paralysis, ophthalmoplegia such as Duane's Syndrome, Horner's Syndrome, Chronic Progressive External Ophthalmoplegia which includes Kearns Syndrome, Strabismus such as Esotropia and Exotropia, Oculomotor Nerve Paralysis, Optic Nerve Diseases such as Optic Atrophy which includes Hereditary Optic Atrophy, Optic Disk Drusen, Optic Neuritis such as Neuromyelitis Optica, Papilledema, Trigeminal Neuralgia, Vocal Cord Paralysis, Demyelinating Diseases such as Neyromyelitis Optica and Swayback, and Diabetic neuropathies such as diabetic foot.

Additional neurologic diseases which can be treated or detected with polynucleotides, polypeptides, agonists, and/or antagonists of the present invention include nerve compression syndromes such as carpal tunnel syndrome, tarsal tunnel syndrome, thoracic outlet syndrome such as cervical rib syndrome, ulnar nerve compression syndrome, neuralgia such as causalgia, cervico-brachial neuralgia,, facial neuralgia and trigeminal neuralgia, neuritis such as experimental allergic neuritis, optic neuritis, polyneuritis, polyradiculoneuritis and radiculities such as polyradiculitis, hereditary motor and sensory neuropathies such as Charcot-Marie Disease, Hereditary Optic Atrophy, Refsum's Disease, Hereditary Spastic Paraplegia and Werdnig-Hoffmann Disease, Hereditary Sensory and Autonomic Neuropathies which include Congenital Analgesia and Familial Dysautonomia, POEMS Syndrome, Sciatica, Gustatory Sweating and Tetany).

Infectious Disease

Polynucleotides or polypeptides, as well as agonists or antagonists of the present invention can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, polynucleotides or polypeptides, as well as agonists or antagonists of the present invention may also directly inhibit the infectious agent, without necessarily eliciting an immune response.

Viruses are one example of an infectious agent that can cause disease or symptoms that can be treated or detected by a polynucleotide or polypeptide and/or agonist or antagonist of the present invention. Examples of viruses, include, but are not limited to Examples of viruses, include, but are not limited to the following DNA and RNA viruses and viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's warts), and viremia. polynucleotides or polypeptides, or agonists or antagonists of the invention, can be used to treat or detect any of these symptoms or diseases. In specific embodiments, polynucleotides, polypeptides, or agonists or antagonists of the invention are used to treat: meningitis, Dengue, EBV, and/or hepatitis (e.g., hepatitis B). In an additional specific embodiment polynucleotides, polypeptides, or agonists or antagonists of the invention are used to treat patients non-responsive to one or more other commercially available hepatitis vaccines. In a further specific embodiment polynucleotides, polypeptides, or agonists or antagonists of the invention are used to treat AIDS.

Similarly, bacterial or fungal agents that can cause disease or symptoms and that can be treated or detected by a polynucleotide or polypeptide and/or agonist or antagonist of the present invention include, but not limited to, include, but not limited to, the following Gram-Negative and Gram-positive bacteria and bacterial families and fungi: Actinomycetales (e.g., Corynebacterium, Mycobacterium, Norcardia), *Cryptococcus neoformans,* Aspergillosis, Bacillaceae (e.g., Anthrax, Clostridium), Bacteroidaceae, Blastomycosis, Bordetella, Borrelia (e.g., *Borrelia burgdorferi,* Brucellosis, Candidiasis, Campylobacter, Coccidioidomycosis, Cryptococcosis, Dermatocycoses, *E. coli* (e.g., Enterotoxigenic *E. coli* and Enterohemorrhagic *E. coli*), Enterobacteriaceae (Klebsiella, Salmonella (e.g., *Salmonella typhi,* and *Salmonella paratyphi*), Serratia, Yersinia), Erysipelothrix, Helicobacter, Legionellosis, Leptospirosis, Listeria, Mycopolasmatales, *Mycobacterium leprae, Vibrio cholerae,* Neisseriaceae (e.g., Acinetobacter, Gonorrhea, Menigococcal), *Meisseria meningitidis,* Pasteurellacea Infections (e.g., Actinobacillus, Heamophilus (e.g., Haemophilus influenza type B), Pasteurella), Pseudomonas, Rickettsiaceae, Chlamydiaceae, Syphilis, Shigella spp., Staphylococcal, Meningiococcal, Pneumococcal and Streptococcal (e.g., *Streptococcus pneumoniae* and Group B Streptococcus). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, Sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosos, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. Polynucleotides or polypeptides, agonists or antagonists of the invention, can be used to treat or detect any of these symptoms or diseases. In specific embodiments, Ppolynucleotides, polypeptides, agonists or antagonists of the invention are used to treat: tetanus, Diptheria, botulism, and/or meningitis type B.

Moreover, parasitic agents causing disease or symptoms that can be treated or detected by a polynucleotide or polypeptide and/or agonist or antagonist of the present invention include, but not limited to, the following families or class: Amebiasis, Babesiosis, Coccidiosis, Cryptosporidiosis, Dientamoebiasis, Duorine, Ectoparasitic, Giardiasis, Helminthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. polynucleotides or polypeptides, or agonists or antagonists of the invention, can be used to treat or detect any of these symptoms or diseases.

Polynucleotides or polypeptides, as well as agonists or antagonists of the present invention of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

Polynucleotides or polypeptides, as well as agonists or antagonists of the present invention can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g., osteoporisis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, polynucleotides or polypeptides, as well as agonists or antagonists of the present invention, may increase regeneration of tissues difficult to heal. For example, increased tendon/ligament regeneration would quicken recovery time after damage. Polynucleotides or polypeptides, as well as agonists or antagonists of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associatedwith vascular insufficiency, surgical, and traumatic wounds.

Similarly, nerve and brain tissue could also be regenerated by using polynucleotides or polypeptides, as well as agonists or antagonists of the present invention, to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the polynucleotides or polypeptides, as well as agonists or antagonists of the present invention.

Chemotaxis

Polynucleotides or polypeptides, as well as agonists or antagonists of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

Polynucleotides or polypeptides, as well as agonists or antagonists of the present invention may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other traums to tissues by attracting immune cells to the injured location. Chemotactic molecules of the present invention can also attract fibroblasts, which can be used to treat wounds.

It is also contemplated that polynucleotides or polypeptides, as well as agonists or antagonists of the present invention may inhibit chemotactic activity. These molecules could also be used to treat disorders. Thus, polynucleotides or polypeptides, as well as agonists or antagonists of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide. Preferred cells include cells from mammals, yeast, Drosophila, or $E.\ coli$. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

Additionally, the receptor to which the polypeptide of the present invention binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labelled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative recetors.

Moreover, the techniques of gene-shuffling, motif-shuffling, exon-shuffling, and/or codon-shuffling (collectively referred to as "DNA shuffling") may be employed to modulate the activities of the polypeptide of the present invention thereby effectively generating agonists and antagonists of the polypeptide of the present invention. See generally, U.S. Pat. Nos. 5,605,793, 5,811,238, 5,830,721, 5,834,252, and 5,837,458, and Patten, P. A., et al., Curr. Opinion Biotechnol. 8:724–33 (1997); Harayama, S. Trends Biotechnol. 16(2): 76–82 (1998); Hansson, L. O., et al., J. Mol. Biol. 287: 265–76 (1999), and Lorenzo, M. M. and Blasco, R. Biotechniques 24(2):308–13 (1998) (each of these patents and publications are hereby incorporated by reference). In one embodiment, alteration of polynucleotides and corresponding polypeptides may be achieved by DNA shuffling. DNA shuffling involves the assembly of two or more DNA segments into a desired molecule by homologous, or site-specific, recombination. In another embodiment, polynucleotides and corresponding polypeptides may be alterred by being subjected to random mutagenesis by error-prone PCR, random nucleotide insertion or other methods prior to recombination. In another embodiment, one or more components, motifs, sections, parts, domains, fragments, etc., of the polypeptide of the present invention may be recombined with one or more components, motifs, sections, parts, domains, fragments, etc. of one or more heterologous molecules. In preferred embodiments, the heterologous molecules are family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic (dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active fragments of the polypeptide of the present invention. Biologically active fragments are those exhibiting activity similar, but not necessarily identical, to an activity of the polypeptide of the present invention. The biological activity of the fragments may include an improved activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and $^3$[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of $^3$[H] thymidine in each case. The amount of fibroblast cell proliferation is measured by liquid scintillation chromatography which measures the incorporation of $^3$[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the receptor is measured and the ability of the compound to bind the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat disease or to bring about a particular result in a patient (e.g., blood vessel growth) by activating or inhibiting the polypeptide/molecule. Moreover, the assays can discover agents which may inhibit or enhance the production of the polypeptides of the invention from suitably manipulated cells or tissues.

Therefore, the invention includes a method of identifying compounds which bind to a polypeptide of the invention comprising the steps of: (a) incubating a candidate binding compound with a polypeptide of the present invention, and (b) determining if binding has occurred. Moreover, the invention includes a method of identifying agonists/antagonists comprising the steps of: (a) incubating a candidate compound with a polypeptide of the present invention, (b) assaying a biological activity, and (b) determining if a biological activity of the polypeptide has been altered.

Targeted Delivery

In another embodiment, the invention provides a method of delivering compositions to targeted cells expressing a receptor for a polypeptide of the invention, or cells expressing a cell bound form of a polypeptide of the invention.

As discussed herein, polypeptides or antibodies of the invention may be associated with heterologous polypeptides, heterologous nucleic acids, toxins, or prodrugs via hydrophobic, hydrophilic, ionic and/or covalent interactions. In one embodiment, the invention provides a method for the specific delivery of compositions of the invention to cells by administering polypeptides of the invention (including antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., polypeptides of the invention or antibodies of the invention) in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, Pseudomonas exotoxin A, diphtheria toxin, saporin momordin, gelonin, pokeweed antiviral protein, alpha-sarcin and cholera toxin. By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etopside or mitomycin C, cytosine arabinoside, daunorubisin, and phenoxyacetamide derivatives of doxorubicin.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

Antisense and Ribozyme (Antagonists)

In specific embodiments, antagonists according to the present invention are nucleic acids corresponding to the sequences contained in SEQ ID NO:X, or the complementary strand thereof, and/or to nucleotide sequences contained in the cDNA plasmid:Z identified in Table 1. In one embodiment, antisense sequence is generated internally, by the organism, in another embodiment, the antisense sequence is separately administered (see, for example, O'Connor, J., Neurochem. 56:560 (1991). Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251: 1300 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcoR1 site on the 5 end and a HindIII site on the 3 end. Next, the pair of oligonucleotides is heated at 90° C. for one minute and then annealed in 2× ligation buffer (20 mM TRIS HCl pH 7.5, 10 mM MgCl2, 10 MM dithiothreitol (DTT) and 0.2 mM ATP) and then ligated to the EcoR1/Hind III site of the retroviral vector PMV7 (WO 91/15580).

For example, the 5' coding portion of a polynucleotide that encodes the polypeptide of the present invention may be used to design an antisense RNA oliconucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding the polypeptide of the present invention or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature 29:304–310 (1981), the promoter contained in the 3' long terminal repeat of Rous sarcoma virus (Yamamoto et al., Cell 22:787–797 (1980), the herpes thymidine promoter (Wagner et al., Proc. Natl. Acad. Sci. U.S.A. 78:1441–1445 (1981), the regulatory sequences of the metallothionein gene (Brinster, et al., Nature 296:39–42 (1982)), etc.

The antisense nucleic acids of the invention comprise a sequence complementary to at least a portion of an RNA transcript of a gene of the present invention. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with a RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333–335. Thus, oligonucleotides complementary to either the 5'- or 3'-non-translated, non-coding regions of polynucleotide sequences described herein could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of mRNA of the present invention, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, or example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

While antisense nucleotides complementary to the coding region sequence could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al., Science 247:1222–1225 (1990). While ribozymes that cleave mRNA at site specific recognition sequences can be used to destroy mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585–591 (1988). There are numerous potential hammerhead ribozyme cleavage sites within the nucleotide sequence of SEQ ID NO:X. Preferably, the ribozyme is engineered so that the cleavage recognition site is located near the 5' end of the mRNA; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express polypeptides of the present invention in vivo. DNA constructs encoding the ribozyme may be introduced into the cell in the same manner as described above for the introduction of antisense encoding DNA. A preferred method of delivery involves using DNA reconstruct "encoding" the ribozyme under the control of a strong constitutive promoter, such as, for example, pol III or pol II promoter, so that transfected cells will produce sufficient quantities of the ribozyme to destroy endogenous messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat the diseases described herein.

Thus, the invention provides a method of treating disorders or diseases, including but not limited to the disorders or diseases listed throughout this application, associated with overexpression of a polynucleotide of the present invention by administering to a patient (a) an antisense molecule directed to the polynucleotide of the present invention, and/or (b) a ribozyme directed to the polynucleotide of the present invention.

Binding Peptides and Other Molecules

The invention also encompasses screening methods for identifying polypeptides and nonpolypeptides that bind apoptosis related polypeptides, and the apoptosis related binding molecules identified thereby. These binding molecules are useful, for example, as agonists and antagonists of the apoptosis related polypeptides. Such agonists and antagonists can be used, in accordance with the invention, in the therapeutic embodiments described in detail, below.

This method comprises the steps of:
a. contacting apoptosis related polypeptides or apoptosis related-like polypeptides with a plurality of molecules; and
b. identifying a molecule that binds the apoptosis related polypeptides or apoptosis related-like polypeptides.

The step of contacting the apoptosis related polypeptides or apoptosis related-like polypeptides with the plurality of molecules may be effected in a number of ways. For example, one may contemplate immobilizing the apoptosis related polypeptides or apoptosis related-like polypeptides on a solid support and bringing a solution of the plurality of molecules in contact with the immobilized apoptosis related polypeptides or apoptosis related-like polypeptides. Such a procedure would be akin to an affinity chromatographic process, with the affinity matrix being comprised of the immobilized apoptosis related polypeptides or apoptosis related-like polypeptides. The molecules having a selective affinity for the apoptosis related polypeptides or apoptosis related-like polypeptides can then be purified by affinity selection. The nature of the solid support, process for attachment of the apoptosis related polypeptides or apoptosis related-like polypeptides to the solid support, solvent, and conditions of the affinity isolation or selection are largely conventional and well known to those of ordinary skill in the art.

Alternatively, one may also separate a plurality of polypeptides into substantially separate fractions comprising a subset of or individual polypeptides. For instance, one can separate the plurality of polypeptides by gel electrophoresis, column chromatography, or like method known to those of ordinary skill for the separation of polypeptides. The individual polypeptides can also be produced by a transformed host cell in such a way as to be expressed on or about its outer surface (e.g., a recombinant phage). Individual isolates can then be "probed" by the apoptosis related polypeptides or apoptosis related-like polypeptides, optionally in the presence of an inducer should one be required for expression, to determine if any selective affinity interaction takes place between the apoptosis related polypeptides or apoptosis related-like polypeptides and the individual clone. Prior to contacting the apoptosis related polypeptides or apoptosis related-like polypeptides with each fraction comprising individual polypeptides, the polypeptides could first be transferred to a solid support for additional convenience. Such a solid support may simply be a piece of filter membrane, such as one made of nitrocellulose or nylon. In this manner, positive clones could be identified from a collection of transformed host cells of an expression library, which harbor a DNA construct encoding a polypeptide having a selective affinity for apoptosis related polypeptides or apoptosis related-like polypeptides. Furthermore, the amino acid sequence of the polypeptide having a selective affinity for the apoptosis related polypeptides or apoptosis realted-like polypeptides can be determined directly by conventional means or the boding sequence of the DNA encoding the polypeptide can frequently be determined more conveniently. The primary sequence can then be deduced from the corresponding DNA sequence. If the amino acid sequence is to be determined from the polypeptide itself, one may use microsequencing techniques. The sequencing technique may include mass spectroscopy.

In certain situations, it may be desirable to wash away any unbound apoptosis related polypeptides or apoptosis related-like polypeptides, or alternatively, unbound polypeptides, from a mixture of the apoptosis related polypeptides or apoptosis related-like polypeptides and a plurality of polypeptides prior to attempting to determine or to detect the presence of a selective affinity interaction. Such a wash step may be particularly desirable when the apoptosis related polypeptides or apoptosis related-like polypeptides or the plurality of polypeptides is bound to a solid support.

The plurality of molecules provided according to this method may be provided by way of diversity libraries, such as random or combinatorial peptide or nonpeptide libraries which can be screened for molecules that specifically bind apoptosis related polypeptides. Many libraries are known in the art that can be used, e.g., chemically synthesized libraries, recombinant (e.g., phage display libraries), and in vitro translation-based libraries. Examples of chemically synthesized libraries are described in Fodor et al., 1991, Science 251:767–773; Houghten et al., 1991, Nature 354:84–86; Lam et al., 1991, Nature 354:82–84; Medynski, 1994, Bio/Technology 12:709–710; Gallop et al., 1994, J. Medicinal Chemistry 37(9):1233–1251; Ohlmeyer et al., 1993, Proc. Natl. Acad. Sci. USA 90:10922–10926; Erb et al., 1994, Proc. Natl. Acad. Sci. USA 91:11422–11426; Houghten et al., 1991, Biotechniques 13:412; Jayawickreme et al., 1994, Proc. Natl. Acad. Sci. USA 91:1614–1618; Salmon et al., 1993, Proc. Natl. Acad. Sci. USA 90:11708–11712; PCT Publication No. WO 93/20242; and Brenner and Lerner, 1992, Proc. Natl. Acad. Sci. USA 89:5381–5383.

Examples of phage display libraries are described in Scott and Smith, 1990, Science 249:386–390; Devlin et al., 1990, Science, 249:404–406; Christian, R. B., et al., 1992, J. Mol. Biol. 227:711–718); Lenstra, 1992, J. Immunol. Meth. 152:149–157; Kay et al., 1993, Gene 128:59–65; and PCT Publication No. WO 94/18318 dated Aug. 18, 1994.

In vitro translation-based libraries include but are not limited to those described in PCT Publication No. WO 91/05058 dated Apr. 18, 1991; and Mattheakis et al., 1994, Proc. Natl. Acad. Sci. USA 91:9022–9026.

By way of examples of nonpeptide libraries, a benzodiazepine library (see e.g., Bunin et al., 1994, Proc. Natl. Acad. Sci. USA 91:4708–4712) can be adapted for use. Peptoid libraries (Simon et al., 1992, Proc. Natl. Acad. Sci. USA 89:9367–9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138–11142).

The variety of non-peptide libraries that are useful in the present invention is great. For example, Ecker and Crooke, 1995, Bio/Technology 13:351–360 list benzodiazepines, hydantoins, piperazinediones, biphenyls, sugar analogs, beta-mercaptoketones, arylacetic acids, acylpiperidines, benzopyrans, cubanes, xanthines, aminimides, and oxazolones as among the chemical species that form the basis of various libraries.

Non-peptide libraries can be classified broadly into two types: decorated monomers and oligomers. Decorated monomer libraries employ a relatively simple scaffold structure upon which a variety functional groups is added. Often the scaffold will be a molecule with a known useful pharmacological activity. For example, the scaffold might be the benzodiazepine structure.

Non-peptide oligomer libraries utilize a large number of monomers that are assembled together in ways that create new shapes that depend on the order of the monomers. Among the monomer units that have been used are carbamates, pyrrolinones, and morpholinos. Peptoids, peptide-like oligomers in which the side chain is attached to the alpha amino group rather than the alpha carbon, form the basis of another version of non-peptide oligomer libraries. The first non-peptide oligomer libraries utilized a single type of monomer and thus contained a repeating backbone. Recent libraries have utilized more than one monomer, giving the libraries added flexibility.

Screening the libraries can be accomplished by any of a variety of commonly known methods. See, e.g., the following references, which disclose screening of peptide libraries: Parmley and Smith, 1989, Adv. Exp. Med. Biol. 251:215–218; Scott and Smith, 1990, Science 249:386–390; Fowlkes et al., 1992; BioTechniques 13:422–427; Oldenburg et al., 1992, Proc. Natl. Acad. Sci. USA 89:5393–5397; Yu et al., 1994, Cell 76:933–945; Staudt et al., 1988, Science 241:577–580; Bock et al., 1992, Nature 355:564–566; Tuerk et al., 1992, Proc. Natl. Acad. Sci. USA 89:6988–6992; Ellington et al., 1992, Nature 355:850–852; U.S. Pat. No. 5,096,815, U.S. Pat. No. 5,223,409, and U.S. Pat. No. 5,198,346, all to Ladner et al.; Rebar and Pabo, 1993, Science 263:671–673; and CT Publication No. WO 94/18318.

In a specific embodiment, screening to identify a molecule that binds apoptosis related polypeptides can be carried out by contacting the library members with a apoptosis related polypeptides or apoptosis related-like polypeptides immobilized on a solid phase and harvesting those library members that bind to the apoptosis related polypeptides or apoptosis related-like polypeptides. Examples of such screening methods, termed "panning" techniques are described by way of example in Parmley and Smith, 1988, Gene 73:305–318; Fowlkes et al., 1992, BioTechniques 13:422–427; PCT Publication No. WO 94/18318; and in references cited herein.

In another embodiment, the two-hybrid system for selecting interacting proteins in yeast (Fields and Song, 1989, Nature 340:245–246; Chien et al., 1991, Proc. Natl. Acad. Sci. USA 88:9578–9582) can be used to identify molecules that specifically bind to apoptisis related polypeptides or apoptosis related-like polypeptides.

Where the apoptosis related binding molecule is a polypeptide, the polypeptide can be conveniently selected from any peptide library, including random peptide libraries, combinatorial peptide libraries, or biased peptide librarie. The term "biased" is used herein to mean that the method of generating the library is manipulated so as to restrict one or more parameters that govern the diversity of the resulting collection of molecules, in this case peptides.

Thus, a truly random peptide library would generate a collection of peptides in which the probability of finding a particular amino acid at a given position of the peptide is the same for all 20 amino acids. A bias can be introduced into the library, however, by specifying, for example, that a lysine occur every fifth amino acid or that positions 4, 8, and 9 of a decapeptide library be fixed to include only arginine. Clearly, many types of biases can be contemplated, and the present invention is not restricted to any particular bias. Furthermore, the present invention contemplates specific types of peptide libraries, such as phage displayed peptide libraries and those that utilize a DNA construct comprising a lambda phage fector with a DNA insert.

As mentioned above, in the case of a apoptosis related binding molecule that is a polypeptide, the polypeptide may have about 6 to less than about 60 amino acid residues, preferably about 6 to about 10 amino acid residues, and most preferably, about 6 to about 22 amino acids. In another embodiment, a apoptosis related binding polypeptide has in the range of 15–100 amino acids, or 20–50 amino acids.

The selected apoptosis related binding polypeptide can be obtained by chemical synthesis or recombinant expression.

Other Activities

A polypeptide, polynucleotide, agonist, or antagonist of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. The polypeptide, polynucleotide, agonist, or antagonist of the present invention may also be employed to stimulate angiogenesis and limb regeneration, as discussed above.

A polypeptide, polynucleotide, agonist, or antagonist of the present invention may also be employed for treating wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

A polypeptide, polynucleotide, agonist, or antagonist of the present invention may also be employed stimulate neuronal growth and to treat and prevent neuronal damage which occurs in certain neuronal disorders or neuro-degenerative conditions such as Alzheimer's disease, Parkinson's disease, and AIDS-related complex. A polypeptide, polynucleotide, agonist, or antagonist of the present invention may have the ability to stimulate chondrocyte growth, therefore, they may be employed to enhance bone and periodontal regeneration and aid in tissue transplants or bone grafts.

A polypeptide, polynucleotide, agonist, or antagonist of the present invention may be also be employed to prevent skin aging due to sunburn by stimulating keratinocyte growth.

A polypeptide, polynucleotide, agonist, or antagonist of the present invention may also be employed for preventing hair loss, since FGF family members activate hair-forming cells and promotes melanocyte growth. Along the same lines, a polypeptide, polynucleotide, agonist, or antagonist of the present invention may be employed to stimulate growth and differentiation of hematopoietic cells and bone marrow cells when used in combination with other cytokines.

A polypeptide, polynucleotide, agonist, or antagonist of the present invention may also be employed to maintain organs before transplantation or for supporting cell culture of primary tissues. A polypeptide, polynucleotide, agonist, or antagonist of the present invention may also be employed for inducing tissue of mesodermal origin to differentiate in early embryos.

A polypeptide, polynucleotide, agonist, or antagonist of the present invention may also increase or decrease the differentiation or proliferation of embryonic stem cells, besides, as discussed above, hematopoietic lineage.

A polypeptide, polynucleotide, agonist, or antagonist of the present invention may also be used to modulate mammalian characteristics, such as body height, weight, hair color, eye color, skin, percentage of adipose tissue, pigmentation, size, and shape (e.g., cosmetic surgery). Similarly, a polypeptide, polynucleotide, agonist, or antagonist of the present invention may be used to modulate mammalian metabolism affecting catabolism, anabolism, processing, utilization, and storage of energy.

A polypeptide, polynucleotide, agonist, or antagonist of the present invention may be used to change a mammal's metal state or physical state by influencing biorhythms, caricadic rhythms, depression (including depressive disorders), tendency for violence, tolerance for pain, reproductive capabilities (preferably by Activin or Inhibin-like activity), hormonal or endocrine levels, appetite, libido, memory, stress, or other cognitive qualities.

A polypeptide, polynucleotide, agonist, or antagonist of the present invention may also be used as a food additive or preservative, such as to increase or decrease storage capabilities, fat content, lipid, protein, carbohydrate, vitamins, minerals, cofactors or other nutritional components.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

OTHER PREFERRED EMBODIMENTS

Other preferred embodiments of the claimed invention include an isolated nucleic acid molecule comprising an nucleotide sequence which is at least 95% identical to a sequence of at least about 50 contiguous nucleotides in the nucleotide sequence of SEQ ID NO:X or the complementary strand thereto, and/or cDNA plasmid:Z.

Also preferred is a nucleic acid molecule wherein said sequence of contiguous nucleotides is included in the nucleotide sequence of SEQ ID NO:X in the range of positions identified for SEQ ID NO:X in Table 1.

Also preferred is an isolated nucleic acid molecule comprising a nucleotide sequence which is at least 95% identical to a sequence of at least about 150 contiguous nucleotides in the nucleotide sequence of SEQ ID NO:X or the complementary strand thereto, and/or cDNA plasmid:Z.

Further preferred is an isolated nucleic acid molecule comprising a nucleotide sequence which is at least 95% identical to a sequence of at least about 500 contiguous nucleotides in the nucleotide sequence of SEQ ID NO:X or the complementary strand thereto, and/or cDNA plasmid:Z.

A further preferred embodiment is a nucleic acid molecule comprising a nucleotide sequence which is at least 95% identical to the nucleotide sequence of SEQ ID NO:X in the range of positions identified for SEQ ID NO:X in Table 1.

A further preferred embodiment is an isolated nucleic acid molecule comprising a nucleotide sequence which is at least 95% identical to the complete nucleotide sequence of SEQ ID NO:X or the complementary strand thereto, and/or cDNA plasmid:Z.

Also preferred is an isolated nucleic acid molecule which hybridizes under stringent hybridization conditions to a nucleic acid molecule comprising a nucleotide sequence of SEQ ID NO:X or the complementary strand thereto and/or cDNA plasmid:Z, wherein said nucleic acid molecule which hybridizes does not hybridize under stringent hybridization conditions to a nucleic acid molecule having a nucleotide sequence consisting of only A residues or of only T residues.

Also preferred is a composition of matter comprising a DNA molecule which comprises cDNA plasmid:Z.

Also preferred is an isolated nucleic acid molecule comprising a nucleotide sequence which is at least 95% identical to a sequence of at least 50 contiguous nucleotides in the nucleotide sequence of cDNA plasmid:Z.

Also preferred is an isolated nucleic acid molecule, wherein said sequence of at least 50 contiguous nucleotides is included in the nucleotide sequence of an open reading frame sequence encoded by cDNA plasmid:Z.

Also preferred is an isolated nucleic acid molecule comprising a nucleotide sequence which is at least 95% identical to sequence of at least 150 contiguous nucleotides in the nucleotide sequence encoded by cDNA plasmid:Z.

A further preferred embodiment is an isolated nucleic acid molecule comprising a nucleotide sequence which is at least 95% identical to sequence of at least 500 contiguous nucleotides in the nucleotide sequence encoded by cDNA plasmid:Z.

A further preferred embodiment is an isolated nucleic acid molecule comprising a nucleotide sequence which is at least 95% identical to the complete nucleotide sequence encoded by cDNA plasmid:Z.

A further preferred embodiment is a method for detecting in a biological sample a nucleic acid molecule comprising a nucleotide sequence which is at least 95% identical to a sequence of at least 50 contiguous nucleotides in a sequence selected from the group consisting of: a nucleotide sequence of SEQ ID NO:X or the complementary strand thereto and a nucleotide sequence encoded by cDNA plasmid:Z; which method comprises a step of comparing a nucleotide sequence of at least one nucleic acid molecule in said sample with a sequence selected from said group and determining whether the sequence of said nucleic acid molecule in said sample is at least 95% identical to said selected sequence.

Also preferred is the above method wherein said step of comparing sequences comprises determining the extent of nucleic acid hybridization between nucleic acid molecules in said sample and a nucleic acid molecule comprising said sequence selected from said group. Similarly, also preferred is the above method wherein said step of comparing sequences is performed by comparing the nucleotide sequence determined from a nucleic acid molecule in said sample with said sequence selected from said group. The nucleic acid molecules can comprise DNA molecules or RNA molecules.

A further preferred embodiment is a method for identifying the species, tissue or cell type of a biological sample which method comprises a step of detecting nucleic acid molecules in said sample, if any, comprising a nucleotide sequence that is at least 95% identical to a sequence of at least 50 contiguous nucleotides in a sequence selected from the group consisting of: a nucleotide sequence of SEQ ID NO:X of the complementary strand thereto and a nucleotide sequence encoded by cDNA plasmid:Z.

The method for identifying the species, tissue or cell type of a biological sample can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a method for diagnosing in a subject a pathological condition associated with abnormal structure or expression of a nucleotide sequence of SEQ ID NO:X or the complementary strand thereto or cDNA plasmid:Z which encodes a protein, wherein the method comprises a step of detecting in a biological sample obtained from said subject nucleic acid molecules, if any, comprising a nucleotide sequence that is at least 95% identical to a sequence of at least 50 contiguous nucleotides in a sequence selected from the group consisting of: a nucleotide sequence of SEQ ID NO:X or the complementary strand thereto and a nucleotide sequence of cDNA plasmid:Z.

The method for diagnosing a pathological condition can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a composition of matter comprising isolated nucleic acid molecules wherein the nucleotide sequences of said nucleic acid molecules comprise a panel of at least two nucleotide sequences, wherein at least one sequence in said panel is at least 95% identical to a sequence of at least 50 contiguous nucleotides in a sequence selected from the group consisting of: a nucleotide sequence of SEQ ID NO:X or the complementary strand thereto and a nucleotide sequence encoded by cDNA plasmid:Z. The nucleic acid molecules can comprise DNA molecules or RNA molecules.

Also preferred is an isolated polypeptide comprising an amino acid sequence at least 90% identical to a sequence of at least about 10 contiguous amino acids in the polypeptide sequence of SEQ ID NO:Y; a polypeptide encoded by SEQ ID NO:X or the complementary strand thereto and/or a polypeptide encoded by cDNA plasmid:Z.

Also preferred is an isolated polypeptide comprising an amino acid sequence at least 95% identical to a sequence of at least about 30 contiguous amino acids in the amino acid sequence of SEQ ID NO:Y; a polypeptide encoded by SEQ ID NO:X or the complementary strand thereto and/or a polypeptide encoded by cDNA plasmid:Z.

Further preferred is an isolated polypeptide comprising an amino acid sequence at least 95% identical to a sequence of at least about 100 contiguous amino acids in the amino acid sequence of SEQ ID NO:Y; a polypeptide encoded by SEQ ID NO:X or the complementary strand thereto and/or a polypeptide encoded by cDNA plasmid:Z.

Further preferred is an isolated polypeptide comprising an amino acid sequence at least 95% identical to the complete amino acid sequence of SEQ ID NO:Y; a polypeptide encoded by SEQ ID NO:X or the complementary strand thereto and/or a polypeptide encoded by cDNA plasmid:Z.

Further preferred is an isolated polypeptide comprising an amino acid sequence at least 90% identical to a sequence of at least about 10 contiguous amino acids in the complete amino acid sequence of a polypeptide encoded by cDNA plasmid:Z.

Also preferred is a polypeptide wherein said sequence of contiguous amino acids is included in the amino acid sequence of a portion of said polypeptide encoded by cDNA plasmid:Z; a polypeptide encoded by SEQ ID NO:X or the complementary strand thereto and/or the polypeptide sequence of SEQ ID NO:Y.

Also preferred is an isolated polypeptide comprising an amino acid sequence at least 95% identical to a sequence of at least about 30 contiguous amino acids in the amino acid sequence of a polypeptide encoded by cDNA plasmid:Z.

Also preferred is an isolated polypeptide comprising an amino acid sequence at least 95% identical to a sequence of at least about 100 contiguous amino acids in the amino acid sequence of a polypeptide encoded by cDNA plasmid:Z.

Also preferred is an isolated polypeptide comprising an amino acid sequence at least 95% identical to the amino acid sequence of a polypeptide encoded by cDNA plasmid:Z.

Further preferred is an isolated antibody which binds specifically to a polypeptide comprising an amino acid sequence that is at least 90% identical to a sequence of at least 10 contiguous amino acids in a sequence selected from the group consisting of: a polypeptide sequence of SEQ ID NO:Y; a polypeptide encoded by SEQ ID NO:X or the complementary strand thereto and/or a polypeptide encoded by cDNA plasmid:Z.

Further preferred is a method for detecting in a biological sample a polypeptide comprising an amino acid sequence that is at least 90% identical to a sequence of at least 10 contiguous amino acids in a sequence selected from the group consisting of: a polypeptide sequence of SEQ ID NO:Y; a polypeptide encoded by SEQ ID NO:X or the complementary strand thereto and/or a polypeptide encoded by cDNA plasmid:Z; which method comprises a step of comparing an amino acid sequence of at least one polypeptide molecule in said sample with a sequence selected from said group and determining whether the sequence of said polypeptide molecule in said sample is at least 90% identical to said sequence of at least 10 contiguous amino acids.

Also preferred is the above method wherein said step of comparing an amino acid sequence of at least one polypeptide molecule in said sample with a sequence selected from said group comprises determining the extent of specific binding of polypeptides in said sample to an antibody which binds specifically to a polypeptide comprising an amino acid sequence that is at least 90% identical to said sequence of at least 10 contiguous amino acids in a sequence selected from the group consisting of: a polypeptide sequence of SEQ ID NO:Y; a polypeptide encoded by SEQ ID NO:X or the complementary strand thereto and a polypeptide encoded by cDNA plasmid:Z.

Also preferred is the above method wherein said step of comparing sequences is performed by comparing the amino acid sequence determined from a polypeptide molecule in said sample with said sequence selected from said group.

Also preferred is a method for identifying the species, tissue or cell type of a biological sample which method comprises a step of detecting polypeptide molecules in said sample, if any, comprising an amino acid sequence that is at least 90% identical to a sequence of at least 10 contiguous amino acids in a sequence selected from the group consisting of: polypeptide sequence of SEQ ID NO:Y; a polypeptide encoded by SEQ ID NO:X or the complementary strand thereto and a polypeptide encoded by cDNA plasmid:Z.

Also preferred is the above method for identifying the species, tissue or cell type of a biological sample, which method comprises a step of detecting polypeptide molecules comprising an amino acid sequence in a panel of at least two amino acid sequences, wherein at least one sequence in said panel is at least 90% identical to a sequence of at least 10 contiguous amino acids in a sequence selected from the above group.

Also preferred is a method for diagnosing in a subject a pathological condition associated with abnormal structure or expression of a nucleic acid sequence identified in Table 1 encoding a polypeptide, which method comprises a step of detecting in a biological sample obtained from said subject polypeptide molecules comprising an amino acid sequence in a panel of at least two amino acid sequences, wherein at least one sequence in said panel is at least 90% identical to a sequence of at least 10 contiguous amino acids in a sequence selected from the group consisting of: polypeptide sequence of SEQ ID NO:Y; a polypeptide encoded by SEQ ID NO:X or the complementary strand thereto and a polypeptide encoded by cDNA plasmid:Z.

In any of these methods, the step of detecting said polypeptide molecules includes using an antibody.

Also preferred is an isolated nucleoci acid molecule comprising a nucleotide sequence which is at least 95% identical to a nucleotide sequence encoding a polypeptide wherein said polypeptide comprises an amino acid sequence that is at least 90% identical to a sequence of at least 10 contiguous amino acids in a sequence selected from the group consisting of: polypeptide sequence of SEQ ID NO:Y; a polypeptide encoded by SEQ ID NO:X or the complementary strand thereto and a polypeptide encoded by cDNA plasmid:Z.

Also preferred is an isolated nucleic acid molecule, wherein said nucleotide sequence encoding a polypeptide has been optimized for expression of said polypeptide in a prokaryotic host.

Also preferred is an isolated nucleic acid molecule, wherein said polypeptide comprises an amino acid sequence selected from the group consisting of: polypeptide sequence of SEQ ID NO:Y; a polypeptide encoded by SEQ ID NO:X or the complementary strand thereto and a polypeptide encoded by cDNA plasmid:Z.

Further preferred is a method of making a recombinant vector comprising inserting any of the above isolated nucleic acid molecule into a vector. Also preferred is the recombinant vector produced by this method. Also preferred is a method of making a recombinant host cell comprising introducing the vector into a host cell, as well as the recombinant host cell produced by this method.

Also preferred is a method of making an isolated polypeptide comprising culturing this recombinant host cell under conditions such that said polypeptide is expressed and recovering said polypeptide. Also preferred is this method of making an isolated polypeptide, wherein said recombinant host cell is a eukaryotic cell and said polypeptide is a human protein comprising an amino acid sequence selected from the group consisting of: polypeptide sequence of SEQ ID NO:Y; a polypeptide encoded by SEQ ID NO:X or the complementary strand thereto and a polypeptide encoded by cDNA plasmid:Z. The isolated polypeptide produced by this method is also preferred.

Also preferred is a method of treatment of an individual in need of an increased level of a protein activity, which method comprises administering to such an individual a Therapeutic comprising an amount of an isolated polypeptide, polynucleotide, immunogenic fragment or analogue thereof, binding agent, antibody, or antigen binding fragment of the claimed invention effective to increase the level of said protein activity in said individual.

Also preferred is a method of treatment of an individual in need of a decreased level of a protein activity, which method comprised administering to such an individual a Therapeutic comprising an amount of an isolated polypeptide, polynucleotide, immunogenic fragment or analogue thereof, binding agent, antibody, or antigen binding fragment of the claimed invention effective to increase the level of said protein activity in said individual.

In specific embodiments of the invention, for each "Contig ID" listed in the fourth column of Table 2, preferably excluded are one or more polynucleotides comprising, or alternatively consisting of, a nucleotide sequence referenced in the fifth column of Table 2 and described by the general formula of a–b, whereas a and b are uniquely determined for the corresponding SEQ ID NO:X referred to in column 3 of Table 2. Further specific embodiments are directed to polynucleotide sequences excluding one, two, three, four, or more of the specific polynucleotide sequences referred to in the fifth column of Table 2. In no way is this listing meant to encompass all of the sequences which may be excluded by the general formula, it is just a representative example. All references available through these accessions are hereby incorporated by reference in their entirety.

TABLE 2

| Gene No. | cDNA Clone ID | NT SEQ ID NO: X | Contig ID | Public Accession Numbers |
|---|---|---|---|---|
| 1 | HLDOK36 | 2 | 846025 | AW245401, AA662107, AI523949, AW245758, AI031817, AA725300, AI359207, AW270125, AA293413, AI090434, AA568269, AW013988, AA708767, AA682427, AI376689, AI033528, AW449244, C01335, AW263988, AI343327, AI360743, T50230, AI992119, AA908655, AA318766, T50243, AA635978, AW204989, AA830678, AA047668, AA748433, AA383495, AI635643, AA862542, F35595, AA218681, AI358311, AA090354, AI432940, AW050934, AW362290, AI636445, AW075351, AI800433, AL135661, AI349957, AL044207, AI800453, AI343112, AI349598, AI345735, AW080079, AW268253, AW148320, AI281837, AL036980, AW089572, AW129171, AI597750, AI290154, AW149851, AI282281, AW090013, AI869367, AI340582, AW075413, AI500077, AI567612, AI572787, AW074993, AW302992, AI538790, AI500659, AL119457, AI312152, AW080279, AI571861, AI349614, AI440426, AI925156, AI801544, AI309401, AW075084, AI784252, AI270707, AI348897, AI307708, AI349937, AI567351, AI439089, AI439717, AI862144, AI758437, AI590128, AL036403, AI950664, AI282655, AW169653, AI634224, AL040243, AI279984, AI281779, AW193635, AI475134, AI620639, AI499463, AW071349, AI684265, AI349004, AI862142, AL036146, AW268220, AI445165, AI568855, AW301300, AW075207, AI349256, AA508692, AI343037, AI520862, AI648684, AL038778, AI349645, AI334884, AI632033, AL121014, AI569583, AI497733, AW274192, AI313352, AW301409, AI560099, AI857296, AI633073, AI312428, AI580927, AI274541, AW071417, AA225339, AI627893, AI828818, AI818206, AI436456, AI273142, AI571133, AI609190, AWl51485, AW008048, AI281773, AA470491, AI636183, AI636585, AI572569, AI819970, AI919058, AI274508, AI564247, AI699857, AW149287, AW183621, AW068845, AI783504, AI824764, AW302965, AI436644, AW074869, AW263453, AI680388, AI564992, AI269862, AI536638, AI702068, AI349226, AI627360, AI249257, AI491852, AI952360, AI249323, AI273048, AL043326, AW118512, AW131954, AI653836, AL036396, AW196141, AI612920, AI439478, AI269205, AI678989, AW104724, AI554484, AI349933, AI682841, AI624206, AI610756, AI811344, AL036361, AW087445, AI912866, AI571551, AI690312, AI275175, AI702406, AI637584, AI340603, AI570384, AI538716, AI690490, AW002342, AI475451, AI569616, AI872074, AI872711, AI702433, AW301505, AI224992, AI799199, AI679764, AI554427, AW082040, AIl815855, AW269097, AI926790, AI564719, AI653541, AI269696, AI889376, AI874109, AI499146, AI868831, AW103371, AI524671, AI521012, AI591073, AI633419, AI921248, AI307543, AI498579, AI590120, AI866002, AI619502, AI571909, AI433976, AI802542, AI866100, AI744923, AI922901, AI828731, AI917253, I48979, Y11587, I89947, I89931, AF090943, AF113699, AF113694, AF118064, AL049314, A08916, AF118070, A08913, L31396, L31397, AL049452, AF113013, AJ242859, AL110221, AL080124, U42766, AL133557, AL122093, AL050393, AF113691, AB019565, AF078844, AF113690, AF113677, AL137557, AL133093, Y11254, AL122050, AF111851, AL117460, AL050149, AL050116, AF125949, AL050146, AL133606, AF113689, AL122123, S68736, X84990, AF090900, AL133565, AL133640, AF113676, AF158248, AL050108, S78214, AF090903, AL080060, AF090896, AF091084, AF113019, E03348, AF090934, AL110196, AL049466, AR059958, I48978, AL133075, AL117457, AL133016, AF125948, AL080137, AF090901, AL137527, X63574, AL122121, AF106862, E07361, A93016, AF017152, AL133080, AF146568, AL049938, AL050277, AL137459, AL117394, X82434, AL110225, AF104032, AJ000937, AL096744, U91329, AL050138, AF079765, I49625, AF017437, AL137283, Y16645, AL049464, AL133560, AL117585, E02349, AR011880, AL137550, AJ238278, A65341, U00763, A08910, AL049300, AF177401, AF067728, A08912, AF097996, AL049430, E07108, AL117583, AL117435, AL049382, A58524, A58523, A08909, AL137521, |

TABLE 2-continued

| Gene No. | cDNA Clone ID | NT SEQ ID NO: X | Contig ID | Public Accession Numbers |
|---|---|---|---|---|
| | | | | AF118094, Z82022, AF183393, I03321, AL122098, AL137648, X96540, U72620, AL050024, X70685, A77033, A77035, AL137463, X72889, AL137271, AL137538, AL080127, U80742, AL133113, AI2297, U35846, I33392, A03736, AL122110, AL049283, AF087943, X93495, I09360, X65873, X98834, S61953, AL110197, I17767, AF061943, AL080159, E08263, E08264, AF026124, U67958, AC006336, I42402, Y09972, AL137560, AL133568, AL122049, AL133072, AR038969, E15569, AL133014, Y07905, AF095901, AL133098, AJ012755, AL137523, I66342, AR054984, AF111112, I26207, AL133077, M30514, I00734, AF026816, AF119337, AL110280, A93350, E00617, E00717, E00778, A08911, AR000496, U39656, Z37987, AL137556, AL137526, AL137429, AC004093, AF061573, U68387, AL133104, AF003737, A45787, AF000145, AL050172, Y14314, AF106827, AF057300, AF057299, AR013797, A90832, AL122111, U58996, A07647, AF079763, X83508, AF100931, Z72491, AF153205, AF185576, E08631, U78525, AR038854, AL137292, AF162270, AL133067, E04233, AL080074, AL117649, U96683, AL117440, AL137476, X87582, AF210052, L13297, AC006371, E05822, AF051325, L30117, AL137656, AL050092, AC002467, AL133081, AL137533, AJ006417, X92070, and AF091512. |
| 2 | HDPBW68 | 3 | 847093 | AI797914, AA232727, AI264354, AA242826, AI421l52, AI373844, AI693559, AA293798, AA242961, AI681069, AA987481, AA253496, AA394280, AA865918, AW193319, AA699441, AA534330, AI246675, AI690035, AI921391, AI696791, AI696792, AI962498, AA478182, AA845215, R02588, AA501984, AA253392, AA975909, AI141321, AI359321, R02707, AI370136, AI424757, AA236520, AA065210, AI369930, AA064845, AI217878, AI470976, AI640699, AF113925, AF126484, AF149774, AC006027, AF149773, and AC005154. |
| 2 | HDPBW68 | 10 | 835653 | |
| 3 | HHEFO24 | 4 | 846324 | AW410791, AI910444, AW410792, AW135479, AI609413, AI733753, AI479543, AA052898, AA053071, AA599894, AI651518, AI262133, AW206814, AW242057, N77940, AI741979, AA026620, AA026732, AI692702, AI690860, W06897, T84089, AW449583, AW206187, AA310890, AA047315, AI492080, AA334702, AA310840, AI572152, AA047316, T83444, AI525358, AW407496, H99721, AA334684, AA932181, AA236177, H63078, AA100344, and AB020694. |
| 4 | HEGAL46 | 5 | 839584 | AI951905, AI935307, AW293446, AI694308, AA631067, AA714504, N39432, AW450043, AI193673, AA642327, N50632, AI674982, AA507436, AA826605, AA598930, R13288, N55392, R45988, and AA377586. |
| 5 | HFOYC02 | 6 | 775677 | AA203338, AI693169, AW003902, AL135076, AI597610, AA716206, AI479987, AA582941, AI692611, AA485609, AI889044, D83867, N27871, AW080978, AI568020, AW316656, AI201938, AAI55950, AA490228, D55820, AI299131, H18712, AW069403, N40648, AA236975, AA305709, AA765761, AAI92998, AA946944, N33286, AA393877, AA252795, H59030, AA862222, T63672, AA261817, R52868, Z43502, AA211032, AI039732, AI198010, T09360, T17275, AA336378, AA360198, H59029, D82324, AA730251, AA545761, D55791, AAI93049, AW071584, T33758, R82391, N20127, R66449, AI880244, T32936, AA453221, AAI55905, AA235913, AI057001, N84480, T10639, AI458373, AA974036, AI884730, D55965, AA320670, AW403754, AI204172, AI873966, AA262514, Z42774, W01410, T11193, AA723391, AA887396, AA318022, M85632, AI470045, AI872411, AI289832, AA894810, AI052412, F02862, AA707555, AA485443, AA716192, AF077599, and AL080105. |
| 6 | HDABV82 | 7 | 828174 | AW069306, AI743175, AI803970, AI811472, AI027704, AA099277, AI168623, AI276150, AI824726, AA213703, AW243339, AA483707, AA213668, AI653168, AA371310, R38844, AI434885, AA342147, AA342146, AA828028, |

TABLE 2-continued

| Gene No. | cDNA Clone ID | NT SEQ ID NO: X | Contig ID | Public Accession Numbers |
|---|---|---|---|---|
| | | | | AI581083, AA099276, AB023172, AP000245, AP000127, and AP000205. |
| 7 | HSVAF16 | 8 | 845403 | AW027073, AL038494, AI888327, AI361046, AI953282, AW385192, AW385191, AW072643, P1675185, AW005989, AI193532, AI688965, AA568251, AA843521, AA766104, AI379780, AI934841, AI479734, N40017, AA588815, N27282, AA872441, AW194363, AA602586, AW305055, AA557627, AA854085, AA807817, AI357691, AA593135, AI948655, AI457174, W86872, AW082605, AA493327, W86823, AI631373, T51002, AA730909, AA507175, AA259062, AL038493, AA844181, AI280762, AA312467, AW105578, AL038837, AW371305, AL039074, AL039564, AL039128, AL039109, AL039108, AL037051, AL038531, AL039659, T39725, AL039625, AL039648, AL039629, AL039678, AL040992, AA844410, AL039156, AL037726, AL045337, AL042909, AL039386, AL039423, AL036973, AL044407, AL039410, AL045353, AL036725, AL039150, AL045341, AL044530, AA249773, AL039538, AL039566, AL039509, AL043422, AA259061, AL036196, AL039924, AL045794, T24119, T24112, AL037639, AL038025, AA323906, AL038821, AL037615, AL036767, AL043445, AL043423, AW013814, AL043441, AL039085, H00069, AL037526, AL036679, T23947, AI927577, AL036924, T02921, AA938071, AL036418, AL037027, AL036117, AL036733, AW451070, AL036158, AI535983, AL036765, AL036268, AL036964, AL036238, AI535783, D51250, AL037601, AL036998, AL037082, AL038851, R47228, AW452756, AL036190, AL037047, AL037643, AL037178, AL036191, D80253, AL037021, AL036167, AL037049, AL037085, AL037054, Z99396, AL037177, AL036227, D80043, AL036133, D59275, AL037124, D80219, AL036163, D59787, AL036207, AL037600, AL036132, AL036914, AL036139, T23659, D80227, AL036152, AL037679, AL036900, AL036228, D80240, D80134, AL036174, D51423, T11051, AL048425, AL036150, T48598, D80210, AL036858, D59619, AL036808, AL036953, AL037077, AA514190, G14227, AL037569, AW450376, D80193, AL037081, D80196, Z25782, D80391, AL038043, D80168, D59927, AL038447, D80949, AI557751, D80366, H00072, AL037002, AL119457, AL036630, AL119324, C75259, AL119399, D80045, AL042544, D81026, AA631969, AW135155, C14014, Z25783, AL043152, AA894816, AW392670, D59889, AL079794, AL036229, AL043168, AL037016, C14389, T11417, U46347, AI431323, AL036241, AA835947, D80038, D80022, AW451416, AL042866, AL041587, AI309306, AW025279, AW384394, AL119443, AI873638, X68127, A85477, AR025207, AR017907, A85396, AR062871, A25909, A84772, A84776, A84773, A84775, AR062872, A84774, AR062873, AR067731, AR037157, AR067732, A86792, A58522, A91750, I18371, A20702, A20700, A43189, A43188, AF118808, X73004, Z96142, A44171, V00745, AR036903, AI1245, I19517, A76773, E13740, A22413, I13349, A35536, A35537, A02135, A02136, A04663, A04664, I01992, I08051, A95051, AI0361, AR036905, A95117, AR031374, A49700, AR031375, A58521, AJ244003, AJ244004, AR020969, A38214, I56772, I95540, AR018924, A63067, A51047, A63064, AR018923, A48774, A63072, A48775, AR068507, AR068506, AR015960, AR000007, AR015961, I19516, E03165, AI8053, I06859, AR043602, A23334, A75888, I70384, AR043603, A60111, A23633, A23998, AR043601, A02712, A95052, AI8050, AR007512, A98767, A93963, A93964, I63120, I60241, I60242, AR054109, A58524, A58523, A64081, A24783, A24782, I03343, A81878, A97211, AR022240, A02710, E12615, AR035193, A92133, E14304, A07700, AI3392, AI3393, A27396, AR027100, I28266, I21869, A49045, E16678, E16636, A93016, A92636, A82653, D28584, I25027, I26929, I44515, I26928, I26930, I26927, A58525, E02221, E01614, E13364, A67220, A70040, AR038762, I49890, I44516, AF156296, AR000006, U87250, AR035975, AR035974, AR035977, AR035976, AR035978, A51384, A58526, A91753, I00079, |

TABLE 2-continued

| Gene No. | cDNA Clone ID | NT SEQ ID NO: X | Contig ID | Public Accession Numbers |
|---|---|---|---|---|
| | | | | E16590, AF156294, AJ230933, AJ244005, Y11923, Y11926, AR008430, I00074, AI5078, I03665, I03664, D88984, I66494, I66495, I66498, I66497, I66496, I66486, I66487, A91965, E00523, AR038286, I25041, I92483, I00077, D34614, A20701, AF156303, AR027069, A52326, AB012117, A04710, D14548, X13220, AF156299, I07429, I168636, A97221, AF156304, AF156302, AF019720, AR066482, AR028564, AR060673, AR060676, A49428, AI8722, S70644, M32676, AF096810, E06034, A91754, I69350, A08457, A08458, S65373, X58217, AI3038, A29289, Y17188, A60957, A00782, A02741, AI4595, AI8755, A25856, I12245, A49695, A49696, I84554, I84553, AF096793, A60968, A60985, A60990, A60987, D44443, AB007195, X15418, AF130655, AI0363, X73003, I08250, E04616, AR064706, S78798, X16234, A80951, I19525, I40851, A60983, I07888, AF156300, Y11920, I03663, S83538, and Y11449. |
| 8 | HSIFO61 | 9 | 859875 | AW194103, AA570483, AW247071, AL134627, AA532739, AI950034, AI831065, AI791597, AW025209, AI733101, AW072315, AW088486, AW250423, AW027992, AI872396, AI822039, AI978692, AA526905, AA004890, AI521711, AI859462, AI589001, AW062708, AI149487, AA932997, AI709015, AW269349, AW269185, AI140101, AA725306, AW002658, AA481316, AI554225, AA600310, AI352315, AA651838, AAI34415, AI635661, AI431710, AW235534, AI284946, AI753373, AA705577, H20713, AW269158, AI983743, AAI34414, AI248592, AI942429, AI873092, AA913640, AI933816, AI633977, H15546, AI360370, G04532, AA004615, AW401864, AI262449, H38876, AW269279, AW134805, AI685722, AA384219, H52328, AI701951, AAI12729, C03711, AA337888, H17067, AA299451, AA844628, AI628603, R23191, AI018039, AI767301, C04547, H15605, T99856, AA086474, AA846145, AA907827, AW050938, AA913178, T99761, AW021529, AW303950, AW269300, AI687274, AI547123, AW189104, AA496397, AA496496, AW408394, AA907899, AA496348, AA496621, AI834231, R23192, AW401626, AW059616, AF100928, AL049703, AF131759, ALF100927, AL049704, Z81364, and Z81370. |

TABLE 3

| Clone ID NO: Z | Library Code |
|---|---|
| HLDOK36 | H0012 H0013 H0014 H0015 H0024 H0038 H0039 H0045 H0046 H0051 H0056 H0059 H0063 H0069 H0074 H0083 H0087 H0090 H0123 H0130 H0135 H0156 H0163 H0166 H0188 H0213 H0222 H0250 H0261 H0264 H0265 H0266 H0271 H0294 H0295 H0309 H0316 H0333 H0341 H0351 H0370 H0390 H0393 H0411 H0416 H0421 H0422 H0423 H0424 H0427 H0428 H0431 H0435 H0436 H0441 H0444 H0445 H0457 H0478 H0484 H0486 H0494 H0497 H0510 H0519 H0520 H0521 H0522 H0530 H0539 H0543 H0545 H0546 H0547 H0549 H0551 H0556 H0574 H0575 H0576 H0580 H0581 H0584 H0585 H0587 H0594 H0595 H0597 H0598 H0613 H0617 H0618 H0624 H0625 H0633 H0634 H0635 H0638 H0646 H0648 H0649 H0650 H0652 H0659 H0661 H0662 H0665 H0668 H0672 H0684 H0695 H0702 L1290 S0002 S0003 S0007 S0011 S0026 S0028 S0031 S0032 S0036 S0040 S0045 S0046 S0049 S0050 S0052 S0114 S0116 S0126 S0132 S0142 S0144 S0150 S0192 S0194 S0206 S0210 S0212 S0214 S0218 S0222 S0276 S0278 S0280 S0306 S0320 S0322 S0330 S0344 S0348 S0350 S0354 S0356 S0358 S0360 S0372 S0374 S0376 S0378 S0380 S0382 S0384 S0388 S0392 S0422 S0424 S0426 S0432 S0448 S0450 S0460 S0472 S0474 S3012 S3014 S6022 T0002 T0003 T0006 T0039 T0042 T0048 T0049 T0109 |
| HDPBW68 | H0040 H0046 H0255 H0264 H0423 H0497 H0518 H0521 H0556 H0580 H0586 H0618 H0620 H0641 H0656 H0682 L1290 S0212 S0380 S0460 |
| HHEFO24 | H0002 H0083 H0519 H0521 H0561 H0581 L1290 S0426 S6014 |
| HEGAL46 | H0125 H0135 H0144 H0265 H0351 H0421 H0428 H0543 H0550 H0553 H0592 H0617 H0618 L1290 S0002 S0418 |

TABLE 3-continued

| Clone ID NO: Z | Library Code |
|---|---|
| HFOYC02 | H0009 H0013 H0024 H0025 H0031 H0038 H0046 H0050 H0052 H0097 H0099 H0123 H0224 H0261 H0264 H0265 H0268 H0284 H0341 H0412 H0413 H0486 H0497 H0520 H0529 H0550 H0551 H0556 H0595 H0599 H0616 H0637 H0638 H0658 H0688 L1290 S0002 S0010 S0026 S0027 S0037 S0038 S0044 S0045 S0049 S0126 S0142 S0150 S0206 S0222 S0276 S0278 S0344 S0360 S0388 S0418 S0420 S0426 S3014 T0010 T0060 T0082 T0114 |
| HDABV82 | H0014 H0032 H0038 H0040 H0046 H0057 H0087 H0090 H0171 H0255 H0264 H0266 H0268 H0327 H0328 H0341 H0375 H0421 H0422 H0423 H0449 H0483 H0518 H0521 H0529 H0580 H0586 H0587 H0616 H0618 H0620 H0641 H0644 H0656 H0657 H0672 H0682 L1290 S0003 S0045 S0176 S0212 S0214 S0222 S0356 S0380 S0460 S6028 |
| HSVAF16 | H0063 H0069 H0087 H0100 H0252 H0295 H0309 H0392 H0455 H0522 H0586 H0619 H0670 L1290 S0011 S0040 S0194 S0360 |
| HSIFO61 | H0004 H0012 H0013 H0036 H0038 H0046 H0059 H0090 H0134 H0135 H0144 H0196 H0266 H0286 H0318 H0341 H0351 H0373 H0393 H0409 H0431 H0435 H0497 H0510 H0521 H0522 H0529 H0542 H0543 H0551 H0556 H0561 H0590 H0592 H0638 H0644 H0650 H0658 H0670 L1290 S0002 S0003 S0028 S0046 S0132 S0150 S0182 S0278 S0374 T0067 |

TABLE 4

| SEQ ID NO: X | Cytologic Band or Chromosome: | OMIM I.D.: |
|---|---|---|
| 3 | 7p15-p14 | 107776 138079 139191 142959 153880 180104 203740 600994 601472 601649 |
| 6 | 12 | |
| 9 | Xq25-q26 | 300037 300076 300123 301201 301845 301900 304340 307150 307700 308000 308230 308240 309555 310490 312000 313350 313850 |

TABLE 5

| Library Code | Library Description |
|---|---|
| H0002 | Human Adult Heart |
| H0004 | Human Adult Spleen |
| H0009 | Human Fetal Brain |
| H0012 | Human Fetal Kidney |
| H0013 | Human 8 Week Whole Embryo |
| H0014 | Human Gall Bladder |
| H0015 | Human Gall Bladder, fraction II |
| H0024 | Human Fetal Lung III |
| H0025 | Human Adult Lymph Node |
| H0031 | Human Placenta |
| H0032 | Human Prostate |
| H0036 | Human Adult Small Intestine |
| H0038 | Human Testes |
| H0039 | Human Pancreas Tumor |
| H0040 | Human Testes Tumor |
| H0045 | Human Esophagus, Cancer |
| H0046 | Human Endometrial Tumor |
| H0050 | Human Fetal Heart |
| H0051 | Human Hippocampus |
| H0052 | Human Cerebellum |
| H0056 | Human Umbilical Vein, Endo. remake |
| H0057 | Human Fetal Spleen |
| H0059 | Human Uterine Cancer |
| H0063 | Human Thymus |
| H0069 | Human Activated T-Cells |
| H0074 | Human Platelets |
| H0083 | HUMAN JURKAT MEMBRANE BOUND POLYSOMES |
| H0087 | Human Thymus |
| H0090 | Human T-Cell Lymphoma |
| H0097 | Human Adult Heart, subtracted |
| H0099 | Human Lung Cancer, subtracted |
| H0100 | Human Whole Six Week Old Embryo |
| H0123 | Human Fetal Dura Mater |
| H0125 | Cem cells cyclohexamide treated |
| H0130 | LNCAP untreated |
| H0134 | Raji Cells, cyclohexamide treated |
| H0135 | Human Synovial Sarcoma |
| H0144 | Nine Week Old Early Stage Human |
| H0156 | Human Adrenal Gland Tumor |
| H0163 | Human Synovium |
| H0166 | Human Prostate Cancer, Stage B2 fraction |
| H0171 | 12 Week Old Early Stage Human, II |
| H0188 | Human Normal Breast |
| H0196 | Human Cardiomyopathy, subtracted |
| H0213 | Human Pituitary, subtracted |
| H0222 | Activated T-Cells, 8 hrs, subtracted |
| H0224 | Activated T-Cells, 12 hrs, subtracted |
| H0250 | Human Activated Monocytes |
| H0252 | Human Osteosarcoma |
| H0255 | breast lymph node CDNA library |
| H0261 | H. cerebellum, Enzyme subtracted |
| H0264 | human tonsils |
| H0265 | Activated T-Cell (12 hs)/Thiouridine labelledEco |
| H0266 | Human Microvascular Endothelial Cells, fract. A |
| H0268 | Human Umbilical Vein Endothelial Cells, fract. A |
| H0271 | Human Neutrophil, Activated |
| H0284 | Human OB MG63 control fraction I |
| H0286 | Human OB MG63 treated (10 nM E2) fraction I |
| H0294 | Amniotic Cells - TNF induced |
| H0295 | Amniotic Cells - Primary Culture |
| H0309 | Human Chronic Synovitis |
| H0316 | HUMAN STOMACH |
| H0318 | HUMAN B CELL LYMPHOMA |
| H0327 | human corpus colosum |
| H0328 | human ovarian cancer |
| H0333 | Hemangiopericytoma |
| H0341 | Bone Marrow Cell Line (RS4,11) |
| H0351 | Glioblastoma |
| H0370 | H. Lymph node breast Cancer |
| H0373 | Human Heart |
| H0375 | Human Lung |
| H0390 | Human Amygdala Depression, re-excision |
| H0392 | H. Meningima, M1 |
| H0393 | Fetal Liver, subtraction II |

TABLE 5-continued

| Library Code | Library Description |
|---|---|
| H0409 | H. Striatum Depression, subtracted |
| H0411 | H Female Bladder, Adult |
| H0412 | Human umbilical vein endothelial cells, IL-4 induced |
| H0413 | Human Umbilical Vein Endothelial Cells, uninduced |
| H0416 | Human Neutrophils, Activated, re-excision |
| H0421 | Human Bone Marrow, re-excision |
| H0422 | T-Cell PHA 16 hrs |
| H0423 | T-Cell PHA 24 hrs |
| H0424 | Human Pituitary, subt IX |
| H0427 | Human Adipose |
| H0428 | Human Ovary |
| H0431 | H. Kidney Medulla, re-excision |
| H0435 | Ovarian Tumor 10-3-95 |
| H0436 | Resting T-Cell Library, II |
| H0441 | H. Kidney Cortex, subtracted |
| H0444 | Spleen metastic melanoma |
| H0445 | Spleen, Chronic lymphocytic leukemia |
| H0449 | CD34 + cell, I |
| H0455 | H. Striatum Depression, subt |
| H0457 | Human Eosinophils |
| H0478 | Salivary Gland, Lib 2 |
| H0483 | Breast Cancer cell line, MDA 36 |
| H0484 | Breast Cancer Cell line, angiogenic |
| H0486 | Hodgkin's Lymphoma II |
| H0494 | Keratinocyte |
| H0497 | HEL cell line |
| H0510 | Human Liver, normal |
| H0518 | pBMC stimulated w/poly I/C |
| H0519 | NTERA2, control |
| H0520 | NTERA2 + retinoic acid, 14 days |
| H0521 | Primary Dendritic Cells, lib 1 |
| H0522 | Primary Dendritic cells, frac 2 |
| H0529 | Myoloid Progenitor Cell Line |
| H0530 | Human Dermal Endothelial Cells, untreated |
| H0539 | Pancreas Islet Cell Tumor |
| H0542 | T Cell helper I |
| H0543 | T cell helper II |
| H0545 | Human endometrial stromal cells-treated with progesterone |
| H0546 | Human endometrial stromal cells-treated with estradiol |
| H0547 | NTERA2 teratocarcinoma cell line + retinoic acid (14 days) |
| H0549 | H. Epididiymus, caput & corpus |
| H0550 | H. Epididiymus, cauda |
| H0551 | Human Thymus Stromal Cells |
| H0553 | Human Placenta |
| H0556 | Activated T-cell (12 h)/Thiouridine-re-excision |
| H0561 | L428 |
| H0574 | Hepatocellular Tumor, re-excision |
| H0575 | Human Adult Pulmonary, re-excision |
| H0576 | Resting T-Cell, re-excision |
| H0580 | Dendritic cells, pooled |
| H0581 | Human Bone Marrow, treated |
| H0584 | Activated T-cells, 24 hrs, re-excision |
| H0585 | Activated T-Cells, 12 hrs, re-excision |
| H0586 | Healing groin wound, 6.5 hours post incision |
| H0587 | Healing groin wound, 7.5 hours post incision |
| H0590 | Human adult small intestine, re-excision |
| H0592 | Healing groin wound - zero hr post-incision (control) |
| H0594 | Human Lung Cancer, re-excision |
| H0595 | Stomach cancer (human), re-excision |
| H0597 | Human Colon, re-excision |
| H0598 | Human Stomach, re-excision |
| H0599 | Human Adult Heart, re-excision |
| H0613 | H.Leukocytes, normalized cot 5B |
| H0616 | Human Testes, Reexcision |
| H0617 | Human Primary Breast Cancer Reexcision |
| H0618 | Human Adult Testes, Large Inserts, Reexcision |
| H0619 | Fetal Heart |
| H0620 | Human Fetal Kidney, Reexcision |
| H0624 | 12 Week Early Stage Human II, Reexcision |
| H0625 | Ku 812F Basophils Line |
| H0633 | Lung Carcinoma A549 TNFalpha activated |
| H0634 | Human Testes Tumor, re-excision |
| H0635 | Human Activated T-Cells, re-excision |
| H0637 | Dendritic Cells From CD34 Cells |
| H0638 | CD40 activated monocyte dendridic cells |
| H0641 | LPS activated derived dendritic cells |
| H0644 | Human Placenta (re-excision) |
| H0646 | Lung, Cancer (4005313 A3): Invasive Poorly Differentiated Lung Adenocarcinoma, |
| H0648 | Ovary, Cancer: (4004562 B6) Papillary Serous Cystic Neoplasm, Low Malignant Pot |
| H0649 | Lung, Normal: (4005313 B1) |
| H0650 | B-Cells |
| H0652 | Lung, Normal: (4005313 B1) |
| H0656 | B-cells (unstimulated) |
| H0657 | B-cells (stimulated) |
| H0658 | Ovary, Cancer (9809C332): Poorly differentiated adenocarcinoma |
| H0659 | Ovary, Cancer (15395A1F): Grade II Papillary Carcinoma |
| H0661 | Breast, Cancer: (4004943 A5) |
| H0662 | Breast, Normal: (4005522B2) |
| H0665 | Stromal cells 3.88 |
| H0668 | stromal cell clone 2.5 |
| H0670 | Ovary, Cancer (4004650 A3): Well-Differentiated Micropapillary Serous Carcinoma |
| H0672 | Ovary, Cancer: (4004576 A8) |
| H0682 | Ovarian cancer, Serous Papillary Adenocarcinoma |
| H0684 | Ovarian cancer, Serous Papillary Adenocarcinoma |
| H0688 | Human Ovarian Cancer (#9807G017) |
| H0695 | mononucleocytes from patient |
| H0702 | NK15 (IL2 treated for 48 hours) |
| L1290 | Stratagene HeLa cell s3 937216 |
| S0002 | Monocyte activated |
| S0003 | Human Osteoclastoma |
| S0007 | Early Stage Human Brain |
| S0010 | Human Amygdala |
| S0011 | STROMAL-OSTEOCLASTOMA |
| S0026 | Stromal cell TF274 |
| S0027 | Smooth muscle, serum treated |
| S0028 | Smooth muscle, control |
| S0031 | Spinal cord |
| S0032 | Smooth muscle-ILb induced |
| S0036 | Human Substantia Nigra |
| S0037 | Smooth muscle, IL1b induced |
| S0038 | Human Whole Brain #2 - Oligo dT > 1.5 Kb |
| S0040 | Adipocytes |
| S0044 | Prostate BPH |
| S0045 | Endothelial cells-control |
| S0046 | Endothelial-induced |
| S0049 | Human Brain, Striatum |
| S0050 | Human Frontal Cortex, Schizophrenia |
| S0052 | neutrophils control |
| S0114 | Anergic T-cell |
| S0116 | Bone marrow |
| S0126 | Osteoblasts |
| S0132 | Epithelial-TNFa and INF induced |
| S0142 | Macrophage-oxLDL |
| S0144 | Macrophage (GM-CSF treated) |
| S0150 | LNCAP prostate cell line |
| S0176 | Prostate, normal, subtraction I |
| S0182 | Human B Cell 8866 |
| S0192 | Synovial Fibroblasts (control) |
| S0194 | Synovial hypoxia |
| S0206 | Smooth Muscle-HASTE normalized |
| S0210 | Messangial cell, frac 2 |
| S0212 | Bone Marrow Stromal Cell, untreated |

TABLE 5-continued

| Library Code | Library Description |
|---|---|
| S0214 | Human Osteoclastoma, re-excision |
| S0218 | Apoptotic T-cell, re-excision |
| S0222 | H. Frontal cortex, epileptic, re-excision |
| S0276 | Synovial hypoxia-RSF subtracted |
| S0278 | H Macrophage (GM-CSF treated), re-excision |
| S0280 | Human Adipose Tissue, re-excision |
| S0306 | Larynx normal #10 261-273 |
| S0320 | Human Larynx |
| S0322 | Siebben Polyposis |
| S0330 | Palate normal |
| S0344 | Macrophage-oxLDL, re-excision |
| S0348 | Cheek Carcinoma |
| S0350 | Pharynx Carcinoma |
| S0354 | Colon Normal II |
| S0356 | Colon Carcinoma |
| S0358 | Colon Normal III |
| S0360 | Colon Tumor II |
| S0372 | Larynx carcinoma III |
| S0374 | Normal colon |
| S0376 | Colon Tumor |
| S0378 | Pancreas normal PCA4 No |
| S0380 | Pancreas Tumor PCA4 Tu |
| S0382 | Larynx carcinoma IV |
| S0384 | Tongue carcinoma |
| S0388 | Human Hypothalamus, schizophrenia, re-excision |
| S0392 | Salivary Gland |
| S0418 | CHME Cell Line, treated 5 hrs |
| S0420 | CHME Cell Line, untreated |
| S0422 | Mo7e Cell Line GM-CSF treated (1 ng/ml) |
| S0424 | TF-1 Cell Line GM-CSF Treated |
| S0426 | Monocyte activated, re-excision |
| S0432 | Sinus piriformis Tumour |
| S0448 | Larynx Normal |
| S0450 | Larynx Tumour |
| S0460 | Thyroid Tumour |
| S0472 | Lung Mesothelium |
| S0474 | Human blood platelets |
| S3012 | Smooth Muscle Serum Treated, Norm |
| S3014 | Smooth muscle, serum induced, re-exc |
| S6014 | H. hypothalamus, frac A |
| S6022 | H. Adipose Tissue |
| S6028 | Human Manic Depression Tissue |
| T0002 | Activated T-cells |
| T0003 | Human Fetal Lung |
| T0006 | Human Pineal Gland |
| T0010 | Human Infant Brain |
| T0039 | HSA 172 Cells |
| T0042 | Jurkat T-Cell, S phase |
| T0048 | Human Aortic Endothelium |
| T0049 | Aorta endothelial cells + TNF-a |
| T0060 | Human White Adipose |
| T0067 | Human Thyroid |
| T0082 | Human Adult Retina |
| T0109 | Human (HCC) cell line liver (mouse) metastasis, remake |
| T0114 | Human (Caco-2) cell line, adenocarcinoma, colon, remake |

TABLE 6

| OMIM ID | OMIM Description |
|---|---|
| 107776 | Colton blood group, 110450 (3) |
| 138079 | Hyperinsulinism, familial, 602485 (3) MODY, type 2, 125851 (3) |
| 139191 | Growth hormone deficient dwarfism (3) |
| 142959 | Hand-foot-uterus syndrome, 140000 (3) |
| 153880 | Macular dystrophy, dominant cystoid (2) |
| 180104 | Retinitis pigmentosa-9 (2) |
| 203740 | Alpha-ketoglutarate dehydrogenase deficiency (1) |

TABLE 6-continued

| OMIM ID | OMIM Description |
|---|---|
| 300037 | Simpson dysmorphia syndrome, 312870 (3) |
| 300076 | Wood neuroimmunologic syndrome (2) |
| 300123 | Mental retardation with isolated growth hormone deficiency (2) |
| 301201 | Amelogenesis imperfecta-3, hypoplastic type (2) (?) |
| 301845 | Bazex syndrome (2) |
| 301900 | Borjeson-Forssman-Lehmann syndrome (2) |
| 304340 | Mental retardation, X-linked, syndromic-5, with Dandy-Walker malformation, basal ganglia disease, and seizures (2) |
| 307150 | Hypertrichosis, congenital generalized (2) |
| 307700 | Hypoparathyroidism, X-linked (2) |
| 308000 | HPRT-related gout (3) Lesch-Nyhan syndrome (3) |
| 308230 | Immunodeficiency, X-linked, with hyper-IgM (3) |
| 308240 | Lymphoproliferative syndrome, X-linked (2) |
| 309555 | Gustavson syndrome (2) |
| 310490 | Cowchock syndrome (2) |
| 312000 | Panhypopituitarism, X-linked (2) |
| 313350 | Split hand/foot malformation, type 2 (2) |
| 313850 | Thoracoabdominal syndrome (2) |
| 600994 | Deafness, autosomal dominant 5 (2) |
| 601472 | Charcot-Marie-Tooth neuropathy-2D (2) |
| 601649 | Blepharophimosis, epicanthus inversus, and ptosis, type 2 (2) |

Having generally described the invention, the same will be more readily understood by reference to the following examples, which are provided by way of illustration and are not intended as limiting.

EXAMPLES

Example 1

Isolation of a Selected cDNA Clone from the Deposited Sample

Each cDNA clone in a cited ATCC deposit is contained in a plasmid vector. Table 1 identifies the vectors used to construct the cDNA library from which each clone was isolated. In many cases, the vector used to construct the library is a phage vector from which a plasmid has been excised. The table immediately below correlates the related plasmid for each phage vector used in constructing the cDNA library. For example, where a particular clone is identified in Table 1 as being isolated in the vector "Lambda Zap," the corresponding deposited clone is in "pBluescript."

| Vector Used to Construct Library | Corresponding Deposited Plasmid |
|---|---|
| Lambda Zap | pBluescript (pBS) |
| Uni-Zap XR | pBluescript (pBS) |
| Zap Express | pBK |
| lafmid BA | plafmid BA |
| pSport1 | pSport1 |
| pCMVSport 2.0 | pCMVSport 2.0 |
| pCMVSport 3.0 | pCMVSport 3.0 |
| pCR ® 2.1 | pCR ® 2.1 |

Vectors Lambda Zap (U.S. Pat. Nos. 5,128,256 and 5,286,636), Uni-Zap XR (U.S. Pat. Nos. 5,128,256 and 5,286,636), Zap Express (U.S. Pat. Nos. 5,128,256 and 5,286,636), pBluescript (pBS) (Short et al., *Nucleic Acids Res.*, 16:7583–7600 (1988); Alting-Mees et al., *Nucleic Acids Res.*, 17:9494 (1989)) and pBK (Alting-Mees et al., *Strategies*, 5:58–61 (1992)) are commercially available from Stratagene Cloning Systems, Inc., 11011 N. Torrey Pines Road, La Jolla, Calif., 92037. pBS contains an ampicillin resistance gene and pBK contains a neomycin resistance gene. Both can be transformed into *E. coli* strain XL-1 Blue, also available from Stratagene. pBS comes in 4 forms SK+, SK-, KS+ and KS. The S and K revers to the orientation of the polylinker to the T7 and T3 primer sequences which flank the polylinker region ("S" is for SacI and "K" is for KpnI which are the first sites on each respective end of the linker). "+" or "-" refer to the orientation of the f1 origin of replication ("ori"), such that in one orientation, single stranded rescue initiated from the f1 ori generates sense strand DNA and in the other, antisense.

Vectors pSport1, pCMV Sport 2.0 and pCMVSport 3.0, were obtained from Life Technologies, Inc., P. O. Box 6009, Gaithersburg, Md. 20897. All Sport vectors contain an ampicillin resistance gene and may be transformed into *E. coli* strain DH10B, also available from Life Technologies. (See, for instance, Gruber, C. E., et al., Focus 15:59 (1993).) Vector lafmid BA (Bento Soares, Columbia University, NY) contains an ampicillin resistance gene and can be transformed into *E. coli* strain XL-1 Blue. Vector pCR®2.1, which is available from Invitrogen, 1600 Faraday Avenue, Carlsbad, Calif. 92008, contains an ampicillin resistance gene and may be transformed into *E. coli* strain DH10B, available from Life Technologies. (See, for instance, Clark, *Nuc. Acids Res.*, 16:9677–9686 (1988) and Mead et al., *Bio/Technology*, 9 (1991).) Preferably, a polynucleotide of the present invention does not comprise the phage vector sequences identified for the particular clone in Table 1, as well as the corresponding plasmid vector sequences designated above.

The deposited material in the sample assigned the ATCC Deposit Number cited in Table 1 for any given cDNA clone also may contain one or more additional plasmids, each comprising a cDNA clone different from that given clone. Thus, deposits sharing the same ATCC Deposit Number contain at least a plasmid for each cDNA clone identified in Table 1. Typically, each ATCC deposit sample cited in Table 1 comprises a mixture of approximately equal amounts (by weight) of about 50 plasmid DNAs, each containing a different cDNA clone; but such a deposit sample may include plasmids for more or less than 50 cDNA clones, up to about 500 cDNA clones.

Two approaches can be used to isolate a particular clone from the deposited sample of plasmid DNAs cited for that clone in Table 1. First, a plasmid is directly isolated by screening the clones using a polynucleotide probe corresponding to SEQ ID NO:X.

Particularly, a specific polynucleotide with 30–40 nucleotides is synthesized using an Applied Biosystems DNA synthesizer according to the sequence reported. The oligonucleotide is labeled, for instance, with $^{32}$P-γ-ATP using T4 polynucleotide kinase and purified according to routine methods. (E.g., Maniatis et al., *Molecular Cloning: A Laboratory Manual*, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ ID NO:X (i.e., within the region of SEQ ID NO:X bounded by the 5' NT and the 3' NT of the clone defined in Table 1) are synthesized and used to amplify the desired cDNA using the deposited cDNA plasmid as a template. The polymerase chain reaction is carried out under routine conditions, for instance, in 25 μl of reaction mixture with 0.5 μg of the above cDNA template. A convenient reaction mixture is 1.5–5 mM $MgCl_2$, 0.01% (w/v) gelatin, 20 μM each of dATP, dCTP, dGTP, dTTP, 25 pmol of each primer and 0.25 Unit of Taq polymerase. Thirty five cycles of PCR (denaturation at 94° C. for 1 min; annealing at 55° C. for 1 min; elongation at 72° C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-docing portions of a gene which may not be present in the deposited clone. These methods include but are not limited, filter probing, clone enrichment using specific probes, and protocols similar ot identical to 5' and 3' "RACE" protocols which are well known in the art. For instance, a method similar to 5' RACE is available for generating the missing 5' end of a desired full-length transcript. (Fromont-Racine et al., *Nucleic Acids Res.*, 21(7): 1683–1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full length gene.

This above method starts with total RNA isolated from the desired source, although poly-A+ RNA can be used. The RNA preparation can then be treated with phosphatase if necessary to eliminate 5' phosphate groups on deraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene.

Example 2

Isolation of Genomic Clones Corresponding to a Polynucleotide

A human genomic P1 library (Genomic Systems, Inc.) is screened by PCR using primers selected for the cDNA sequence corresponding to SEQ ID NO:X., according to the method described in Example 1. (See also, Sambrook.)

Example 3

Tissue Distribution of Polypeptide

Tissue distribution of mRNA expression of polynucleotides of the present invention is determined using protocols for Northern blot analysis, described by, among others, Sambrook et al. For example, a cDNA probe produced by the method described in Example 1 is labeled with $P^{32}$ using the rediprime™ DNA labeling system (Amersham Life Science), according to manufacturer's instruction. After labeling, the probe is purified using CHROMA SPIN-100™ column (Clontech Laboratories, Inc.), according to manufacturer's protocol number PT1200-1. The purified labeled probe is then used to examine various human tissues for mRNA expression.

Multiple Tissue Northern (MTN) blots containing various human tissue (H) or human immune tissues (IM) (Clontech) are examined with the labeled probe using ExpressHyb™ hybridization solution (Clontech) according to manufacturer's protocol number PT1190-1. Following hybridization and washing, the blots are mounted and exposed to film at −70° C., overnight, and the films developed according to standard procedures.

Example 4

Chromosomal Mapping of the Polynucleotides

An oligonucleotide primer set is designed according to the sequence at the 5' end of SEQ ID NO:X. This primer preferably spans about 100 nucleotides. This primer set is then used in a polymerase chain reaction under the following set of conditions: 30 seconds, 95° C.; 1 minute, 56° C.; 1 minute, 70° C. This cycle is repeated 32 times followed by one 5 minute cycle at 70° C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 5

Bacterial Expression of a Polypeptide

A polynucleotide encoding a polypeptide of the present invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHI and XbaI and initiation/stop codons, if necessary, to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance ($Amp^r$), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the *E. coli* strain M15/rep4 (Qiagen, Inc.) which contains multiple copies of the plasmid pREP4, which expresses the lacI repressor and also confers kanamycin resistance ($Kan^r$). Transformants are identified by their ability to grow on LB plates and ampicillin/kanamycin resistant colonies are selected. Plasmid DNA is isolated and confirmed by restriction analys.s Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 2:250. The cells are grown to an optical density 600 ($O.D.^{600}$) of between 0.4 and 0.6. IPTG (Isopropyl-B-D-thiogalacto pyranoside) is then added to a final concentration of 1 mM. IPTG induces by inactivating the lacI repressor, clearing the P.O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3–4 hours at 4° C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIA expressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HLc pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

In addition to the above expression vector, the present invention further includes an expression vector comprising phage operator and promoter elements operatively linked to a polynucleotide of the present invention, called pHE4a. (ATCC Accession Number 209645, deposited on Feb. 25, 1998.) This vector contains: 1) a neomycinphosphotransferase gene as a selection marker, 2) an *E. coli* origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LT1, Gaithersburg, Md.). The promoter sequence and operator sequences are made synthetically.

DNA can be inserted into the pHEa by restricting the vector with NdeI and XbaI, BamHI, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

EXAMPLE 6

Purification of a Polypeptide from an Inclusion Body

The following alternative method can be used to purify a polypeptide expressed in E coli when it is present in the form of inclusion bodies. Unless otherwise specified, all of the following steps are conducted at 4–10° C.

Upon completion of the production phase of the E. coli fermentation, the cell culture is cooled to 4–10° C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4

The resulting washed inclusion bodies are solubilized with 1.5 M guanidine hydrochloride (GuHCl) for 2–4 hours. After 7000×g centrifugation for 15 min., the pellet is discarded and the polypeptide containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Commassie blue stained 16% SDS-PAGE gel when 5 μg of purified protein is loaded. The purified protein can also be tested for endotoxin/LPS contamination, and typically the LPS content is less than 0.1 ng/ml according to LAL assays.

EXAMPLE 7

Cloning and Expression of a Polypeptide in a Baculovirus Expression System

In this example, the plasmid shuttle vector pA2 is used to insert a polynucleotide into a baculovirus to express a polypeptide. This expression vector contains the strong polyhedrin promoter of the Autographa californica nuclear polyhedrosis virus (AcMNPV) followed by convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from E. coli under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

Specifically, the cDNA sequence contained in the deposited clone is amplified using the PCR protocol described in Example 1 using primers with appropriate restriction sites and initiation/stop codons. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin NO: 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. E. coli HB101 or other E. coli hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five µg of a plasmid containing the polynucleotide is co-transfected with 1.0 µg of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413–7417 (1987). One µg of BaculoGold™ virus DNA and 5 µg of the plasmid are mixed in a sterile well of a microtiter plate containing 50 µl of serum-free Grace's medium (Life Technologies, Inc., Gaithersburg, Md.). Afterwards, 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serm is added. Cultivation is then continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later the supernatants of these culture dishes are harvested and then they are stored at 4° C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 µCi of $^{35}$S-methionine and 5 µCi $^{35}$S-cysteine (available from Amersham) are added. The cells are further incubated for 16 hours and are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

EXAMPLE 8

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, moust NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful in developing cell lines that carry several hundred or even several thousand copies of the gene of interest. (See, e.g., Alt et al., J. Biol. Chem., 253:1357–1370 (1978); Hamlin et al., Biochem. et Biophys. Acta, 1097:107–143 (1990); Page et al., Biotechnology, 9:64–68 (1991)). Another useful selection marker is the enzyme glutamine synthase (GS) (Murphy et al., Biochem J., 227:277–279 (1991); Bebbington et al., Bio/Technology, 10:169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-dhfr (ATCC Accession No.: 37146), the expression vectors pC4 (ATCC Accession No.: 209646) and pC6 (ATCC Accession No.: 209647) contain the strong promoter (LTR) of the Rous Sarcoma Virus (Cullen et al., Molecular and Cellular Biology, 438–447 (March, 1985)) plus a fragment of the CMV-enhancer (Boshart et al., Cell, 41:521–530 (1985).) Multiple cloning sites, e.g., with the restriction enzyme cleavage sites BamHI, XbaI and Asp718, facilitate the cloning of the gene of interest. The vectors also contain the 3' intron, the polyadenylation and termination signal of the rat preproinsulin gene, and the mouse DHFR gene under control of the SV40 early promoter.

Specifically, the plasmid pC6, for example, is digested with appropriate restriction enzymes and then dephosphorylated using calf intestinal phosphates by procedures known in the art. The vector is then isolated from a 1% agarose gel.

A polynucleotide of the present invention is amplified according to the protocol outlined in Example 1 using primers with appropriate restrictions sites and initiation/stop codons, if necessary. The vector can be modified to include a heterologous signal sequence if necessary for secretion. (See, e.g., WO 96/34891.)

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. E. coli HB101 or XL-1 Blue cells are then transformed and bacteria are identified that contain the fragment inserted into plasmid pC6 using, for instance, restriction enzyme analysis.

Chinese hamster overy cells lacking an active DHFR gene is used for transfection. Five µg of the expression plasmid pC6 is cotransfected with 0.5 µg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 24, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 µM, 2 µM, 5µM, 10 mM, 20 mM). The same procedure is repeated until clones are obtained which grow at a concentration of 100–200 µM. Expression of the desired gene product is analyzed, for instance, by SDS-PAGE and Western blot or by reversed phase HPLC analysis.

EXAMPLE 9

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purifications. (See Example 5; see also EP A 394,827; Traunecker, et al., Nature, 331:84–86 (1988)) The polypeptides can also be fused to heterologous polypeptide sequences to facilitate secretion and intracellular trafficking (e.g., KDEL). Moreover, fusion to IgG-1, IgG-3, and albumin increases the halflife time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 5.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector, and initiation/stop codons, if necessary.

For example, if pC4 (Accession No.: 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide of the present invention, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc region:

GGGATCCGGAGCCCAAATCTTCTGACAAAACTCACACATGCCCACCGTGC

CCAGCACCTGAATTCGAGGGTGCACCGTCAGTCTTCCTCTTCCCCCCAAA

ACCCAAGGACACCCTCATGATCTCCCGGACTCCTGAGGTCACATGCGTGG

TGGTGGACGTAAGCCACGAAGACCCTGAGGTCAAGTTCAACTGGTACGTG

GACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

ACCCCCATCGAGAAAACCATCTCCAAAGCCAAAGGGCAGCCCCGAGAACC

ACAGGTGTACACCCTGCCCCCATCCCGGGATGAGCTGACCAAGAACCAGG

TCAGCCTGACCTGCCTGGTCAAAGGCTTCTATCCAAGCGACATCGCCGTG

GAGTGGGAGAGCAATGGGCAGCCGGAGAACAACTACAAGACCACGCCTCC

CGTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGG

TAAATGAGTGCGACGGCCGCGACTCTAGAGGAT (SEQ ID NO:1)

EXAMPLE 10

Formulating a Polypeptide

The polypeptide composition will be formulated and dosed in a fashion consistent with good medical practice, taking into account the clinical condition of the individual patient (especially the side effects of treatment with the secreted polypeptide alone), the site of delivery, the method of administration, the scheduling of administration, and other factors known to practitioners. The "effective amount" for purposes herein is thus determined by such considerations.

As a general proposition, the total pharmaceutically effective amount of polypeptide administered parenterally per dose will be in the range of about 1 µg/kg/day to 10 mg/kg/day of patient body weight, although, as noted above, this will be subject to herapeutic discretion. More preferably, this dose is at least 0.01 mg/kg/day, and most preferably for humans between about 0.01 and 1 mg/kg/day for the hormone. If given continuously, the polypeptide is typically administered at a dose rate of about 1 µg/kg/hour to about 50 µg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the polypeptide of the invention are administered orally, rectally, parenterally, intracisternally, intravaginally, interperitoneally, topically (as by powders, ointments, gels, drops or transdermal patch), bucally, or as an oral or nasal spray. "Pharmaceutically acceptable carrier" refers to a non-toxic solid, semi-solid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman et al., *Biopolymers,* 22:547–556 (1983)), poly (2-hydroxyethyl methacrylate) (Langer et al., *J. Biomed. Mater. Res.* 15:167–277 (1981), and Langer, *Chem. Tech.,* 12:98–105 (1982)), ethylene vinyl acetate (R. Langer et al.) or poly-D-(-)-3-hydroxybutyric acid (EP 133,988). Sustained-release compositions also include liposomally entrapped polypeptides. Liposomes containing the secreted polypeptide are prepared by methods known per se: DE 3,218,121; Epstein et al., *Proc. Natl. Acad. Sci, USA,* 82:3688–3692 (1985); Hwang et al., *Proc. Natl. Acad. Sci. USA,* 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal secreted polypeptide therapy.

For parenteral administration, in one embodiment, the polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinite, acetic acid, and other organic acids or their salts; antioxidants such as ascorbic acid; low molecular weight (less than about ten residues) polypeptides, e.g., polyarginine or tripeptides; proteins, such as serium albumin, geltain, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any polypeptide to be used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous bag or vial having a stopper pierceable by a hypodermic injection needle.

Polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous polypeptide solution, and the resulting mixture is lyophilized. The infusion solution is prepared by reconstituting the lyophilized polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

EXAMPLE 11

Method of Treating Decreased Levels of the Polypeptide

It will be appreciated that conditions caused by a decrease in the standard or normal expression level of a polypeptide in an individual can be treated by administering the polypeptide of the present invention, preferably in the secreted and/or soluble form. Thus, the invention also provides a method of treatment of an individual in need of an increased level of the polypeptide comprising administering to such an individual a pharmaceutical composition comprising an amount of the polypeptide to increase the activity level of the polypeptide in such an individual.

For example, a patient with decreased levels of a polypeptide receives a daily dose 0.1–100 ug/kg of the polypeptide for six consecutive days. Preferably, the polypeptide is in the secreted form. The exact details of the dosing scheme, based on administration and formulation, are provided in Example 10.

EXAMPLE 12

Method of Treating Increased Levels of the Polypeptide

Antisense technology is used to inhibit production of a polypeptide of the present invention. This technology is one example of a method of decreasing levels of a polypeptide, preferably a secreted form, due to a variety of ethiologies, such as cancer.

For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 10.

EXAMPLE 13

Method of Treatment Using Gene Therapy—Ex Vivo

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 1 using primers and having appropriate restriction sites and initiation/stop codons, if necessary. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a subconfluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

EXAMPLE 14

Gene Therapy Using Endogenous Apoptosis Related Genes

Another method of gene therapy according to the present invention involves operably associating the endogenous apoptosis related gene sequence with a promoter via homologous recombination as described, for example, in U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., *Proc. Natl. Acad. Sci. USA*, 86:8932–8935 (1989); and Zijlstra et al., *Nature*, 342:435–438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of the endogenous apoptosis related gene, flanking the promoter. The targeting sequence will be sufficiently near the 5' end of apoptosis related gene so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous apoptosis related gene sequence. This results in the expression of apoptosis related in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM $Na_2HPO_4$, 6 mM dextrose). The cells are recentrifuged, the supernatant aspirated, and the cells resuspended in electroporation buffer containing 1 mg/ml acetylated bovine serum albumin. The final cell suspension contains approximately $3\times10^6$ cells/ml. Electroporation should be performed immediately following resuspension.

Plasmid DNA is prepared according to standard techniques. For example, to construct a plasmid for targeting to the apoptosis related locus, plasmid pUC18 (MBI Fermentas, Amherst, N.Y.) is digested with HindIII. The CMV promoter is amplified by PCR with an XbaI site on the 5' end and a BamHI site on the 3'end. Two apoptosis related non-coding gene sequences are amplified via PCR: one apoptosis related non-coding sequence (apoptosis related fragment 1) is amplified with a HindIII site at the 5' end and an Xba site at the 3'end; the other apoptosis related non-coding sequence (apoptosis related fragment 2) is amplified with a BamHI site at the 5'end and a HindIII site at the 3'end. The CMV promoter and apoptosis related fragments are digested with the appropriate enzymes (CMV promoter—XbaI and BamHI; apoptosis related fragment 1—XbaI; apoptosis related fragment 2—BamHI) ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 μg/ml. 0.5 ml of the cell suspension (containing approximately $1.5.\times10^6$ cells) is then added to the cuvette, and the cell suspension and DNA solutions are gently mixed. Electroporation is performed with a Gene-Pulser apparatus (Bio-Rad). Capacitance and voltage are set at 960 μF and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

EXAMPLE 15

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) apoptosis related sequences into an animal to increase or decrease the expression of the apoptosis related polypeptide. The apoptosis related polynucleotide may be operatively linked to a promoter or any other genetic elements necessary for the expression of the apoptosis related polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata et al., *Cardiovasc. Res.* 35(3):470–479 (1997), Chao J et al., *Pharmacol. Res.,* 35(6):517–522 (1997), Wolff, *Neuromuscul. Disord.* 7(5): 314–318 (1997), Schwartz et al., *Gene Ther.,* 3(5):405–411 (1996), Tsurumi Y. et al., *circulation,* 94(12):3281–3290 (1996) (incorporated herein by reference).

The apoptosis related polynucleotide constructs may be delivered by any method that delivers injectable materials to the cells of an animal, such as, injection into the interstitial space of tissues (heart, muscle, skin, lung, liver, intestine and the like). The apoptosis related polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the apoptosis related polynucleotides may also be delivered in liposome formulations (sch as those taught in Felgner et al., *Ann. NY Acad. Sci.,* 772:126–139 (1995) and Abdallah et al., *Biol. Cell,* 85(1):1–7 (1995)) which can be prepared by methods well known to those skilled in the art.

The apoptosis related polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide constructs can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked apoptosis related polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked apoptosis related polynucleotide constructs can be delivered to arteries during angioplasty by the catheter used in the procedure.

The dose response effects of injected apoptosis related polynucleotide in muscle in vivo is determined as follows. Suitable apoptosis related template DNA for production of mRNA coding for apoptosis related polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The apoptosis related template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for apoptosis related protein expression. A time course for apoptosis related protein expression may be done in a similar fashion except that quadriceps from different mice are harvested at different times. Persistence of apoptosis related DNA in muscle following injection may be determined by Southern blot analysis after preparing total cellular DNA and HIRT supernatants from injected and control mice. The results of the above experimentation in mice can be used to extrapolate proper dosages and other treatment parameters in humans and other animals using apoptosis related naked DNA.

EXAMPLE 16

Production of an Antibody a) Hybridoma Technology

The antibodies of the present invention can be prepared by a variety of methods. (See, Current Protocols, Chapter 2.) As one example of such methods, cells expressing apoptosis related polypeptide(s) are administered to an animal to induce the production of sera containing polyclonal antibodies. In a preferred method, a preparation of apoptosis related polypeptide(s) is prepared and purified to render it substantially free of natural contaminants. Such a preparation is then introduced into an animal in order to produce polyclonal antisera of greater specific activity.

Monoclonal antibodies specific for apoptosis related polypeptide(s) are prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563–681 (1981)). In general, an animal (preferably a mouse) is immunized with apoptosis related polypeptide(s) or, more preferably, with a secreted apoptosis related polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the apoptosis related polypeptide(s).

Alternatively, additional antibodies capable of binding to apoptosis related polypeptide(s) can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the apoptosis related protein-specific antibody can be blocked by apoptosis related polypeptide(s). Such antibodies comprise anti-idiotypic antibodies to the apoptosis related protein-specific antibody and are used to immunize an animal to induce formation of further apoptosis related protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed herein. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

b) Isolation of Antibody Fragments Directed Against Apoptosis Related Polypeptide(s) From a Library of scFvs Naturally occurring V-genes isolated from human PBLs are constructed into a library of antibody fragments which contain reactivities against apoptosis related polypeptide(s) to which the donor may or may not have been exposed (see e.g., U.S. Pat. No. 5,885,793 incorporated herein by reference in its entirety).

Rescue of the Library

A library of scFvs is constructed from the RNA of human PBLs as described in PCT publication WO 92/01047. To rescue phage displaying antibody fragments, approximately 109 E. coli harboring the phagemid are used to inoculate 50 ml of 2×TY containing 1% glucose and 100 µg/ml of ampicillin (2×TY-AMP-GLU) and grown to an O.D. of 0.8 with shaking. Five ml of this culture is used to innoculate 50 ml of 2×TY-AMP-GLU, 2×108 TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 µg/ml ampicillin and 50 ug/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 µg ampicillin/ml and 25 µg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 µm filter (Minisart NML; Sartorius) to give a final concentration of approximately 1013 transducing units/ml (ampicillin-resistant clones).

Panning of the Library

Immunotubes (Nunc) are coated overnight in PBS with 4 ml of either 100 µg/ml or 10 µg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log E. coli TG1 by incubating eluted phage with bacteria for 30 minutes at 37° C. The E. coli are then plated on TYE plates containing 1% glucose and 100 µg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders

Eluted phage from the 3rd and 4th rounds of selection are used to infect E. coli HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

EXAMPLE 17

Identification of Binding Partners

The CARD and its structurally related death effector domain (DED) are peptide motifs that mediate interactions between apoptosis-regulatory proteins (Science 281:1301 (1998); Hofmann et al., Trends Biochem. Sci. 22:155 (1998)). To identify the binding partners of Nod1, the ability of Nod1 to associate with a panel of CARD and DED-containing proteins in 293T cells was tested. In these experiments, Nod1 is Myc- or HA-epitope-tagged and transiently expressed in 293T cells. Overexpressed Nod1 is a cytosolic protein. Co-immunoprecipitation assays with Nod1 and tagged proteins reveal that Nod1 preferentially interacts with several procaspases containing long prodomains with CARDs or DEDs including Caspase-1, Caspase-2, Caspase-4, Caspase-8 and Caspase-9, but not with short prodomains like Caspase-3 or Caspase-7 (Inohara, et al., J. Biol. Chem. 273:12296 (1998); Inohara et al., unpublished data)). In addition, Nod1 interacts with Nod1 itself, with RICK, ARC, IAP-1 and NIAP, but not with other CARD or DED-containing proteins including RAIDD, Apaf-1, Ced-4, FADD, PEA15, or DEDD. In addition, Nod1 does not associate with IAP1 or several TRAFs, nor with multiple regulators of the NF-kB activation including several TRAFs, IKKa, IKKb, N1K, or A20.

EXAMPLE 18

Functional Activity of Apoptosis Related Polypeptides

Modulation of Apoptosis

To determine the functional relevance of the above interactions, the ability of Nod1 to modulate the apoptosis regulatory function of binding proteins in 293T cells is tested (Inohara et al., J. Biol. Chem., 273:12296 (1998); McCarthy et al., J. Biol. Chem., 273:16968 (1998); Thorne et al., Curr. Biol., 8:885 (1998)). Nod1 does not activate apoptosis by itself, but significantly enhances apoptosis induced by Caspase-9, but not that induced by Caspase-4, Caspase-8, or CLARP. Consistent with its inability to modulate Caspase-8 mediated apoptosis, Nod1 does not affect apoptosis induced by FADD, CLARP, DR3/TRAMP and TNRF1, which induce apoptosis through Caspase-8 activation. (For review, see the special issue of Science 281:1301 (1998)). In addition, expression of Nod1 does not change the apoptosis regulatory function of Caspase-1, Caspase-2, RICK, ARC, IAP-1, and NIAP. These results indicate that the ability of Nod1 to regulate apoptosis is highly specific and limited so far to that activated by Caspase-9. The effect of Nod1 on Caspase-9-induced apoptosis is not due to increased expression of Caspase-9, as there is not alteration in the levels of this procaspase-9 in cells transfected with Nod1 plasmids compared to control plasmids. Production of enzymatically active caspases including Caspase-9, requires proteolytic processing of the immature form of the enzyme. (For review, see the special issue of Science 281:1301 (1998)). To determine if Nod1 enhances Caspase-9 processing, 293T cells are transiently expressed in the presence or absence of Nod1. (Total lysate from 293T cells transfected with 50 ng of pcDNA3-Caspase-9-Flag or pcCNA3-Caspase-8-HA in the presence of 100 ng of pcDNA3-HA or pcDNA3-Nod1-HA is prepared 24 hr post-transfection and is subject to 15% SDS polyacrylamide gel electrophoresis. Tagged Caspase-9 and Caspase-8 are detected by anti-Flag and anti-HA antibodies, respectively). Expression of Nod1 includes the proteolytic activation of procaspase-9, but not that of procaspase-8. Thus, the ability of Nod1 to enhance caspase-9 but not caspase-8-mediated apoptosis correlates with its ability to induce proteolytic processing of procaspase. By analogy with Nod1, Apaf-1 binds to several caspases with long prodomains, but only promotes activation of procaspase-9. (Hu et al., Proc. Natl. Acad. Sci. USA 95:4386 (1998)).

Identification of Functionally Important Residues

Mutant forms of Nod1 (polypeptides comprising residues 1–648, 649–953, and 126–953) are engineered to determine the regions of Nod1 that are required for caspase-9 activation. Expression of mutant containing the CARD and NBD (residues 1–648) retains its ability to enhance Caspase-9-induce apoptosis but the mutant containing the LRRs (residues 659–953) does not, indicating that Nod1 promotes Caspase-9 apoptosis through the CARD and/or NBD, as it was previously reported for Apaf-1 and Ced-4. (Zou et al., Cell, 90:405 (1997); Hu et al., Proc. Natl. Acad. Sci. USA, 95:4386 (1998); and Chinnaiyan et al., Nature, 388:728 (1997); Hu et al., Proc. Natl. Acad. Sci. USA, 95:4386 (1998); Srinivasula et al., Mol. Cell, 1:946 (1998); Chaudhary et al., J. Biol. Chem., 273:17708 (1998); Yang et al., Science, 281:1355 (1998)). The conserved lysine residue of P-loop of ced-4 and Apaf-1 are critical for both caspase activation and apoptosis enhancement (Hu et al., Proc. Natl. Acad. Sci. USA, 95:4386 (1998); and Chinnaiyan et al., Nature, 388:728 (1997); Hu et al., Proc. Natl. Acad. Sci. USA, 95:4386 (1998); Srinivasula et al., Mol. Cell, 1:946 (1998); Chaudhary et al., J. Biol. Chem., 273:17708 (1998); Yang et al., Science, 281:1355 (1998)) as well as the conserved residues in the CARD of RAIDD (Duan et al. Nature, 385:86 (1997): Chou et al., Cell, 94:171 (1998)). Therefore, point mutations are introduced in highly conserved residues of the CARD (V41Q) and in the P-loop of the NBD (K208R), whose corresponding mutation results in loss-of-function of RAIDD, Apaf-1/Ced-4, respectively. (Hu et al., Proc. Natl. Acad. Sci. USA, 95:4386 (1998); Chinnaiyan et al., Nature, 388:728 (1997); Hu et al., Proc. Natl. Acad. Sci. USA, 95:4386 (1998); Srinivasula et al., Mol. Cell, 1:946 (1998); Chaudhary et al., J. Biol. Chem., 273: 17708 (1998); Yang et al., Science, 281:1355 (1998); Duan et al. Nature, 385:86 (1997); Chou et al., Cell, 94:171 (1998)). Both V41Q and K208R mutations of Nod1 inhibit the ability of Nod1 to enhance Caspase-9-induced apoptosis and Caspase-9 maturation. Thus, the CARD and NBD appear essential for Nod1 to activate procaspas-9 and to promote apoptosis. These results suggest that Nod1 and Apaf-1 activate procaspase-9 by a similar mechanisms, which may involve conformation changes and NBD oligomerization of these caspase activators to bring in close proximity several molecules of procaspase-9 (Hu et al., Proc. Natl. Acad. Sci. USA, 95:4386 (1998); Chinnaiyan et al., Nature, 388:728 (1997); Hu et al., Proc. Natl. Acad. Sci. USA, 95:4386 (1998); Srinivasula et al., Mol. Cell, 1:946 (1998); Chaudhary et al., J. Biol. Chem., 273:17708 (1998); Yang et al., Science, 281:1355 (1998)).

Identification of Regions Interacting with Binding Partners

Both Ced-4 and Apaf-1 associate with their target caspases via their corresponding CARDs (Zou et al., Cell, 90:405 (1997); Hu et al., Proc. Natl. Acad. Sci. USA, 95:4386 (1998);); Chinnaiyan et al., Nature, 388:728 (1997); Hu et al., Proc. Natl. Acad. Sci. USA, 95:4386 (1998); Srinivasula et al., Mol. Cell, 1:946 (1998); Chaudhary et al., J. Biol. Chem., 273:17708 (1998); Yang et al., Science, 281:1355 (1998)). Therefore the regions of Nod1 that are required for association with procaspase-9 are determined. 293T cells are transiently co-transfected with expression plasmids producing Caspase-9 and wild-type or mutant forms of Nod1. Immunoblotting analysis of protein complexes reveals that residues 1–648 of Nod1 containing the CARD and NBD co-immunoprecipitates with Caspase-9 but the LRRs does not. The K208R mutant still binds to Caspase-9, although its binding is reduced when compared with wild-type Nod1. Nod1 with mutation in a highly conserved residue of the CARD (V41Q) fails to associate with Caspase-0 C287S. Another mutant lacking the CARD (residues 126–953) also fails to interact with and activate procaspase-9. Thus, the CARD is essential for Nod-1 to bind and to activate procaspase-9, as well as to promote apoptosis. These results are consistent with the analyses of the Apaf-1-Caspase-9 and CED-4-Ced-3 interactions that shows that the CARD of Apaf-1 and Ced-4 are involved in their interaction with Caspase-9 and Ced-3, respectively.

These results show that Nod1 also interacts with RICK, a serine-threonine kinase with a CARD that promotes apoptosis and NF-kB activation. (Inohara et al., J. Biol. Chem. 273:12296 (1998); McCarthy et al., J. Biol. Chem. 273: 16968 (1998); Thorne et al., Curr. Biol., 8:885 (1998)). Because RICK induces NF-kB activation, it is determined whether Nod-1 could activate NF-kB. To test if Nod1 activates NF-kB, a Nod1 expression plasmid is co-transfected with pBIIx-Luc, a luciferase NF-kB reported plasmid or pf-Luc control plasmid lacking NF-kB binding sites into 293T cells (Inohara et al., J. Biol. Chem. 273:12296 (1998); McCarthy et al., J. Biol. Chem. 273:16968 (1998); Thorne et al., Curr. Biol., 8:885 (1998); Saksela et al., Mol. Cell. Biol., 13:3698 (1993)). Nod1 induces activation of NF-kB in a dose-dependent manner, whereas Apaf-1 does not. It is also confirmed that Nod1 induces NF-kB activation in parenteral 293 cells and HeLa cells. RICK alone induces NF-kB activation as reported (Inohara et al., J. Biol. Chem., 273: 12296 (1998); McCarthy et al., J. Biol. Chem., 273:16968

(1998); Thorne et al., *Curr. Biol.*, 8:885 (1998)), but co-expression of RICK and Nod1 causes synergistic NF-kB activation.

Mapping of Site of Action in NF-kB Pathway

Several surface receptors and intracellular mediators use different transducing molecules to activate a common set of intracellular components that lead to degradation of I-kB and release of cytoplasmic NF-kB such as RIP, TRAF2 and TRAF6. (Baeuerle et al., *Cell*, 87:13 (1996); Stancovski et al., *Cell*, 91:299 (1997); Verma et al., *Proc. Natl. Acad. Sci. USA*, 94:11758 (1997); Arch et al., *Genes Dev.*, 12:2821 (1998); T. Maniatis, *Science*, 278:818 (1998)). Stimulation of these upstream components culminate in the activation of a common set of signaling molecules that include NIK and IKKs that lead to inactivation of I-kB. (Baeuerle et al., *Cell*, 87:13 (1996); Stancovski et al., *Cell*, 91:299 (1997); Verma et al., *Proc. Natl. Acad. Sci. USA*, 94:11758 (1997); Arch et al., *Genes Dev.*, 12:2821 (1998); T. Maniatis, *Science*, 278: 818 (1998)). Mutant forms of these signaling components are used to map the site of Nod1 action in the NF-kB activation pathway. The NF-kB activity of Nod1 is abolished or greatly inhibited by dominant negative forms of NIK, IKKα, IKKβ and I-kB, but not by mutant forms of TRAF2, TRAF6 or RIP which can inhibit NF-kB activation mediated by surface receptors. (Baeuerle et al., *Cell*, 87:13 (1996); Stancovski et al., *Cell*, 91:299 (1997); Verma et al., *Proc. Natl. Acad. Sci. USA*, 94:11758 (1997); Arch et al., *Genes Dev.*, 12:2821 (1998); T. Maniatis, *Science*, 278:818 (1998); Hsu et al., *Cell*, 84:299 (1996); Cao et al., *Nature*, 383:443 (1996); Hsa et al., *Immunity*, 4:387 (1996); Liu et al., *Cell*, 87:565 (1996)). To test if Nod-1 activates NF-kB independently of its ability to promote Caspase-9-induced apoptosis, a catalytically inactive mutant of caspase-9 that acts as a dominant negative is used. Pan et al., *J. Biol. Chem.*, 273:5841 (1998); Inohara et al., *J. Biol. Chem.*, 273:32479 (1998). Expression of mutant Caspase-9 does not inhibit the activation of NF-kB induced by Nod1. These results suggest that Nod1 acts upstream of NIK, IKKs and I-kB but in a different pathway, or downstream of TRAF2, TRAF6 or RIP. Moreover, the result with dominant negative Caspase-9 suggests that the NF-kB-inducing activity of Nod1 does not require Caspase-9 activity. To determine the regions of Nod1 and RICK involved in the interaction, 293T cells are transiently co-transfected with plasmids producing WT or mutant Nod1 and RICK. The analysis shows that the NH$_2$-terminal 1–648 amino acids, but not the LRRs of Nod1 mediates the interaction with RIC. The V41 Q point mutant in the CARD, but not the K208R P-loop mutant, abolishs the association with RICK. In addition, another Nod-1 mutant (residues 126–953) fails to associate with RICK. This result indicates that the CARD of Nod1 is critical for the Nod1-RICK interaction. Reciprocal experiments reveal that the CARD, but not the kinase domain of RICK, is required for the association with Nod1. Thus, without intending to be bound, these results suggest that the Nod1/RICK interaction is mediated via their corresponding CARDs.

Expression of Nod1 promotes both procaspase-9 activation and NF-kB activation and the latter may involve the association of Nod1 with RICK. To determine if the NF-kB-inducing activity of RICK requires Nod1 or Caspase-9 activity, 293T cells are co-transfected with plasmids expressing RICK and mutant forms of Nod1 or catalytically inactive Caspase-9 or Caspase-3 (as a control). Expression of Nod mutants lacking the CARD (residues 126–953) or containing only the LRRs (residues 649–953) inhibits RICK-mediated NF-kB activation but not that induced by tumor necrosis factor α (TNF α) stimulation. The results suggest that both RICK and Nod1 activate a TNF-a-independent pathway of NF-kB activation. In addition, the NF-kB-inducing activity of RICK is unaffected by mutant Caspase-9 or Caspase-3, but is inhibited by mutant I-kB. The latter result indicates that Caspase-9 activity is not required for Nod1 or RICK to activate NF-kB activation and further suggests that both TNFα and the RICK/Nod-1 signaling pathways use common downstream components such as NIK, IKKs and I-kB for activation of NF-kB.

The above examples using Nod1 polypeptides can similarly be used to identify binding partners and determine the functional activity of other apoptosis related polypeptides of the present invention.

Certain apoptosis related polynucleotides and polypeptides of the present invention, including antibodies, were disclosed in U.S. provisional application Ser. Nos. 60/126, 018, 60/139,638, and 60/149,449, as well as in International Application No. PCT/US00/06642, each of which is herein incorporated by reference in its entirety.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

What is claimed is:

1. An isolated nucleic acid molecule comprising a polynucleotide selected from the group consisting of:
   (a) a polynucleotide encoding amino acid residues 1 to 304 of SEQ ID NO:11; and
   (b) a polynucleotide comprising nucleotides 1 to 2045 of SEQ ID NO:2.

2. The isolated nucleic acid molecule of claim 1, wherein said polynucleotide is (a).

3. The isolated nucleic acid molecule of claim 1, wherein said polynucleotide is (b).

4. The isolated nucleic acid molecule of claim 1 wherein the polynucleotide further comprises a heterologous polynucleotide.

5. The isolated nucleic acid molecule of claim 4 wherein said heterologous polynucleotide encodes a heterologous polypeptide.

6. A vector comprising the isolated nucleic acid molecule of claim 1.

7. The vector of claim 6 wherein the nucleic acid molecule is operably associated with a heterologous regulatory sequence that controls gene expression.

8. An isolated recombinant host cell comprising the isolated nucleic acid molecule of claim 1.

9. The isolated recombinant host cell of claim 8 wherein the nucleic acid molecule is operably associated with a heterologous regulatory sequence that controls gene expression.

10. A method for producing a polypeptide, comprising:
(a) culturing the isolated recombinant host cell of claim 8 under conditions suitable to produce the polypeptide encoded by said polynucleotide; and
(b) recovering the polypeptide from the cell culture.

11. An isolated nucleic acid molecule comprising a polynucleotide selected from the group consisting of:
(a) a polynucleotide encoding the amino acid sequence of the full-length polypeptide encoded by the cDNA clone contained in plasmid HLDOK36 in ATCC Deposit No. PTA161; and
(b) a polynucleotide comprising the cDNA clone contained in plasmid HLDOK36 in ATCC Deposit No. PTA161.

12. The isolated nucleic acid molecule of claim 11, wherein said polynucleotide is (a).

13. The isolated nucleic acid molecule of claim 11, wherein said polynucleotide is (b).

14. The isolated nucleic acid molecule of claim 11 wherein the polynucleotide further comprises a heterologous polynucleotide.

15. The isolated nucleic acid molecule of claim 14 wherein said heterologous polynucleotide encodes a heterologous polypeptide.

16. A vector comprising the isolated nucleic acid molecule of claim 11.

17. The vector of claim 16 wherein the nucleic acid molecule is operably associated with a heterologous regulatory sequence that controls gene expression.

18. An isolated recombinant host cell comprising the isolated nucleic acid molecule of claim 11.

19. The isolated recombinant host cell of claim 18 wherein the nucleic acid molecule is operably associated with a heterologous regulatory sequence that controls gene expression.

20. A method for producing a polypeptide, comprising:
(a) culturing the isolated recombinant host cell of claim 18 under conditions suitable to produce the polypeptide encoded by said polynucleotide; and
(b) recovering the polypeptide from the cell culture.

* * * * *